United States Patent
Liao et al.

(10) Patent No.: US 11,974,999 B2
(45) Date of Patent: May 7, 2024

(54) BRUTON'S TYROSINE KINASE INHIBITORS

(71) Applicants: Xibin Liao, Edison, NJ (US); Suzhou Baijibugong Pharmaceutical Technology Co., Ltd., Suzhou (CN)

(72) Inventors: Xibin Liao, Edison, NJ (US); Jia Li, Shanghai (CN); Zhijian Lu, Plainfield, IN (US); Yubo Zhou, Shanghai (CN); Anhui Gao, Shanghai (CN)

(73) Assignees: Xibin Liao, Edison, NJ (US); Suzhou Baijibugong Pharmaceutical Technology Co., Ltd., Suzhou (CN)

( * ) Notice: Subject to any disclaimer, the term of this patent is extended or adjusted under 35 U.S.C. 154(b) by 688 days.

(21) Appl. No.: 17/140,025

(22) Filed: Jan. 1, 2021

(65) Prior Publication Data
US 2021/0121458 A1    Apr. 29, 2021

Related U.S. Application Data

(60) Division of application No. 16/420,148, filed on May 22, 2019, now Pat. No. 10,933,063, which is a continuation-in-part of application No. PCT/US2018/023455, filed on Mar. 21, 2018.

(60) Provisional application No. 62/474,686, filed on Mar. 22, 2017.

(51) Int. Cl.
  *C07D 487/04* (2006.01)
  *A61K 31/4985* (2006.01)
  *C07D 519/00* (2006.01)
  *A61K 45/06* (2006.01)

(52) U.S. Cl.
  CPC ........ *A61K 31/4985* (2013.01); *C07D 487/04* (2013.01); *C07D 519/00* (2013.01); *A61K 45/06* (2013.01)

(58) Field of Classification Search
  CPC . C07D 487/04; C07D 519/00; A61K 31/4985
  See application file for complete search history.

(56) References Cited

U.S. PATENT DOCUMENTS

| | | | |
|---|---|---|---|
| 7,514,444 B2 | 4/2009 | Honigberg et al. | |
| 8,481,733 B2 | 7/2013 | Crew et al. | |
| 11,554,118 B2 * | 1/2023 | Liao | C07D 519/00 |
| 2014/0155406 A1 * | 6/2014 | Man | A61P 35/00 514/249 |
| 2014/0221354 A1 | 8/2014 | Mulbaier et al. | |

FOREIGN PATENT DOCUMENTS

| WO | WO 2015/057992 | * | 4/2015 |
| WO | 2015165279 A1 | | 11/2015 |
| WO | 2017156495 A1 | | 9/2017 |

OTHER PUBLICATIONS

Bundgaard, Design of Prodrugs, p. 1, 1985.*
Silverman, Prodrugs and Drug Delivery Systems, The Organic Chemistry of Drug Design and Drug Action, pp. 352-399, 1992.*
Wolff, Some consideration for prodrug design, Burger's Medicinal Chemistry and Drug Discovery, 5th Edition, vol. 1: Principles and Practice, pp. 975-977, 1995.*
Tan, L et al. Structure-guided development of covalent TAK1 inhibitors. Bioorganic and Medicinal Chemistry, vol. 25, 2017, pp. 838-846.
Honigberg, LA et al. The Bruton tyrosine kinase inhibitor PCI-32765 blocks B-cell activation and is efficacious in models of autoimmune disease and B-cell malignancy. Proceedings of he National Academy of Sciences of the United States of America, vol. 107, No. 29, Jul. 20, 2010, pp. 13075-13080.
Burger's Medicinal Chemistry, edited by Manfred E. Wolff, 5th Ed. Part 1, pp. 975-977 (1995).
Banker et al. "Modern Pharmaceutics", 3rd Ed. p. 596 (1996).

* cited by examiner

*Primary Examiner* — Deepak R Rao
(74) *Attorney, Agent, or Firm* — SZDC Law PC

(57) ABSTRACT

Bruton's tyrosine kinase (Btk) inhibitors have the following Formula (I):

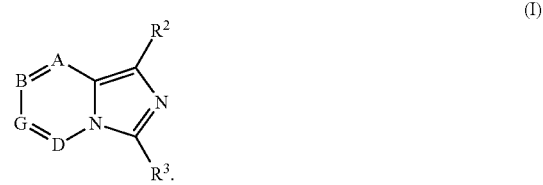

4 Claims, No Drawings

BRUTON'S TYROSINE KINASE INHIBITORS

This application is a divisional application of U.S. Ser. No. 16/420,148, filed on May 22, 2019, which is a continuation-in-part of PCT/US2018/023455, filed on Mar. 21, 2018, which claims the benefit of U.S. Provisional Application No. 62/474,686, filed on Mar. 22, 2017, which is incorporated by reference for all purposes as if fully set forth herein.

FIELD OF THE INVENTION

Described herein are Bruton's tyrosine kinase inhibitors, methods of making such inhibitors, and pharmaceutical compositions containing such inhibitors.

BACKGROUND OF THE INVENTION

Bruton's tyrosine kinase (Btk) plays an important role in signal transduction in B cells and is a factor that contributes to the survival, differentiation, proliferation, and activation of B cells. There is currently a need for methods of treating diseases in which B cells or mast cells participate. Btk is also known to participate in mast cell activation and in the physiological functions of platelets. Therefore, Btk inhibitors are effective for the treatment of diseases in which B cells or mast cells participate, for example, allergic diseases, autoimmune diseases, inflammatory diseases, thromboembolic diseases, and cancers.

SUMMARY OF THE INVENTION

The Btk inhibitors described herein have the following Formula (I):

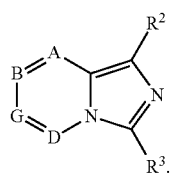

(I)

In Formula (I), A, B, G, and D are each independently N or $CR^1$, with the proviso that only one or two of A, B, G, and D can be N; $R^1$ is hydrogen, —$COOCH_3$, —$CH_2OH$, —$CH_2OCOCH_3$, $C_{1-6}$alkyl, $C_{1-6}$cycloalkyl, $C_{1-4}$alkoxy, —O—$C_{1-4}$alkoxy, $C_{1-6}$alkyl substituted with one to five fluorines, $C_{1-4}$alkoxy substituted with one to five fluorines, $C_{1-4}$alkoxy substituted with OH, $C_{1-4}$alkoxy substituted with $OCH_3$, $NH_2$ or $N(CH_3)_2$, or

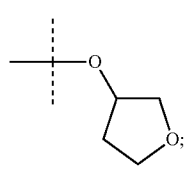

$R^2$ is

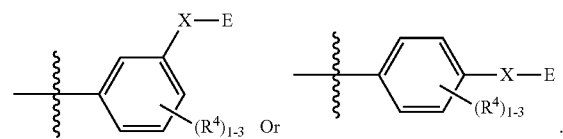

—X-E is one of the followings: (1) X is O, $OCR^aR^b$, $CR^aR^bO$, S(O), $S(O)_2$, $CR^aR^b$, $NR^c(C=O)$, C=$ONR^c$ or a bond; and E is a hydrogen, an aryl or a heteroaryl substituted with one to three $R^5$ substituents; or a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or (2) —X-E is hydrogen, halogen, —$OR^a$, —$O(CH_2)_{1-4}R^a$, —CN, —$NO_2$; $R^4$ and $R^5$ are each independently selected from the group consisting of hydrogen, halogen, hydroxy, cyano, $OCF_3$, $OCF_2H$, $C_{1-6}$ alkyl, optionally substituted with one to five fluorines, $C_{3-6}$ cycloalkyl, optionally substituted with one to five fluorines, $C_{1-4}$alkoxy, optionally substituted with one to five fluorines, $C_{1-4}$ alkylthio, optionally substituted with one to five fluorines, $C_{1-4}$ alkylsulfonyl, optionally substituted with one to five fluorines, carboxy, $C_{1-4}$ alkyloxycarbonyl, and $C_{1-4}$ alkylcarbonyl; $R^a$ and $R^b$ are each independently hydrogen, fluorine, or $C_{1-3}$ alkyl, optionally substituted with one to five fluorines; $R^c$ is hydrogen or $C_{1-3}$ alkyl, optionally substituted with one to five fluorines; and $R^3$ is a group having a double bond. Note in Formula (I), B can be N or C—H, and does not represent element boron; D can be N or C—H, and does not represent deuterium.

Further described is an isomer thereof, a tautomer thereof, a pharmaceutical acceptable solvate thereof, or a pharmaceutical acceptable prodrug thereof.

In one aspect, in Formula (I), E is selected from aryl, heteroaryl, carbocyclyl, heterocyclyl, any of which is optionally substituted with one to three $R^5$ substituents.

In one aspect, in Formula (I), $R^3$ is selected from the group consisting of:

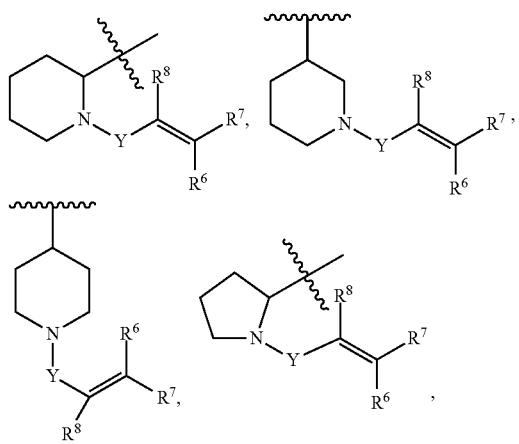

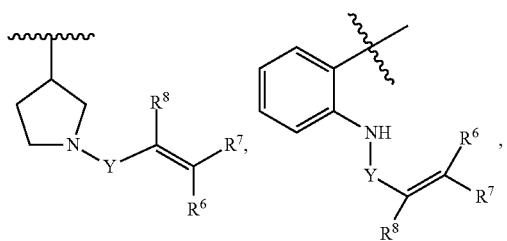

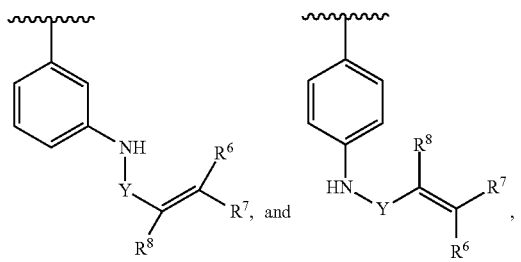

Y is C(=O), OC(=O), NHC(=O), S=O, S(=O)$_2$, or NHS(=O)$_2$; and R$^6$, R$^7$, R$^8$ are each independently hydrogen, halogen, CN, C$_{1-4}$ alkyl, C$_{1-6}$ alkoxyalkyl, C$_{1-8}$ alkylaminoalkyl, or C$_{1-4}$ alkylphenyl; or R$^7$ and R$^8$ taken together form a bond.

In one aspect, in Formula (I), R$^3$ is selected from the group consisting of

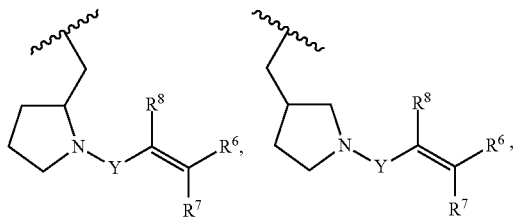

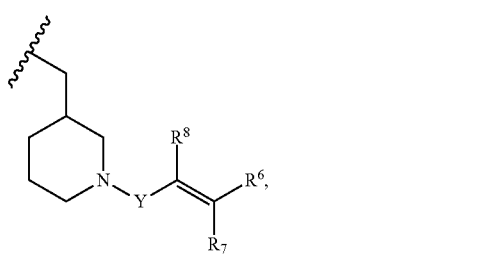

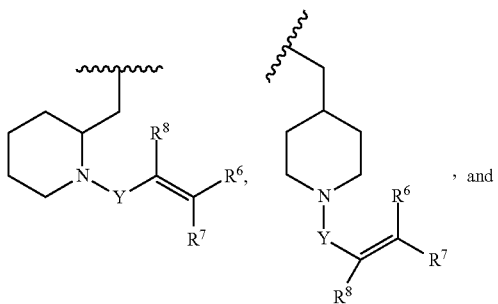

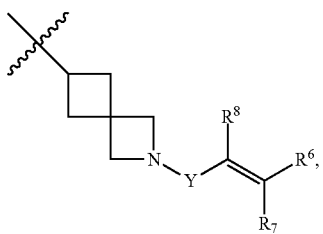

Y is C(=O), OC(=O), NHC(=O), S=O, S(=O)$_2$, or NHS(=O)$_2$; R$^6$, R$^7$, R$^8$ are each independently hydrogen, halogen, CN, C$_{1-4}$ alkyl, C$_{1-6}$ alkoxyalkyl, C$_{1-8}$ alkylaminoalkyl, or C$_{1-4}$ alkylphenyl; and R$^7$ and R$^8$ are optionally taken together form a bond.

In one aspect, in Formula (I), R$^3$ is selected from the group consisting of

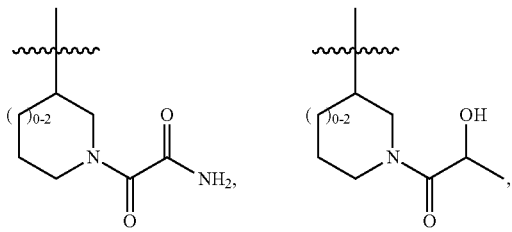

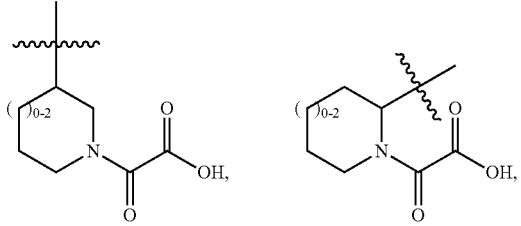

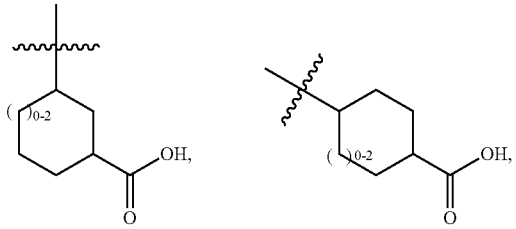

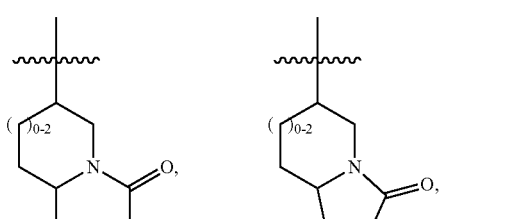

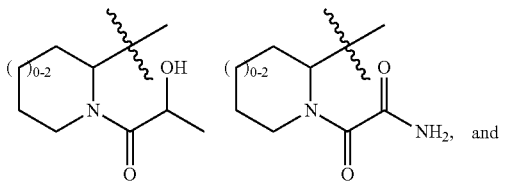

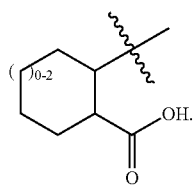

In one aspect, in Formula (I), A, G, and D are independently CR$^1$, and B is N.

In one aspect, in Formula (I), A is CR$^1$; G and D are CH; and B is N.

In one aspect, in Formula (I), G is CR$^1$; A and D are CH; and B is N.

In one aspect, in Formula (I), D is CR$^1$; A and G are CH; and B is N.

In one aspect, in Formula (I), R$^1$ is hydrogen, —COOCH$_3$, —CH$_2$OH, —CH$_2$OCOCH$_3$, —CH$_3$, —CH$_2$CH$_3$, —CH$_2$CH$_2$CH$_3$, —CH$_2$CH$_2$CH$_2$CH$_3$, —CH(CH$_3$)$_2$, —OCH$_3$, —OCH$_2$CH$_3$, —OCH$_2$CH$_2$CH$_3$, —OCH$_2$CH$_2$CH$_2$CH$_3$, —OCH(CH$_3$)$_2$, —CH$_2$F, —CF$_3$, —OCH$_2$CH$_2$OCH$_3$, —OCH$_2$CH$_2$N(CH$_3$)$_2$,

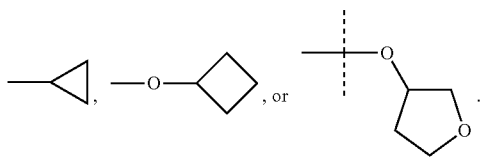

In one aspect, the compound of Formula (I) is selected from the group consisting of:

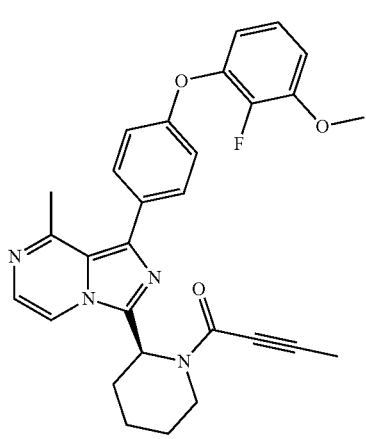

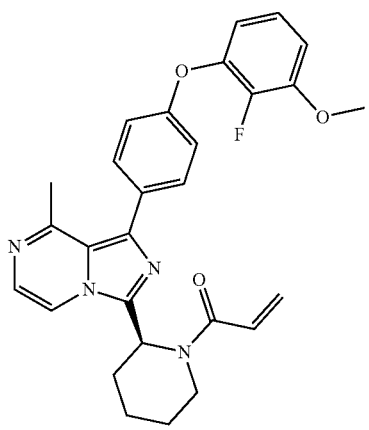

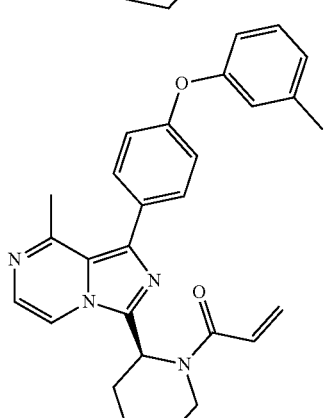

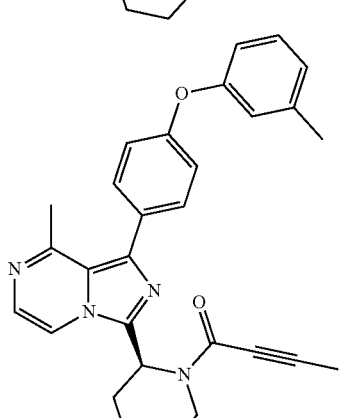

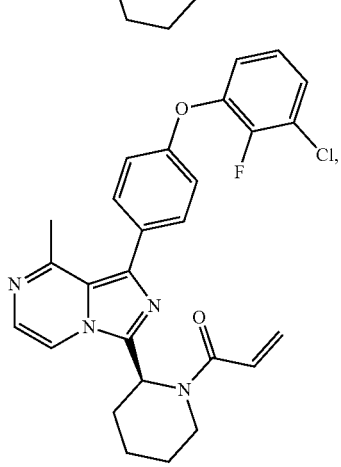

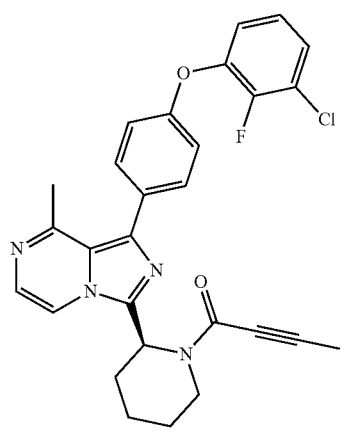,
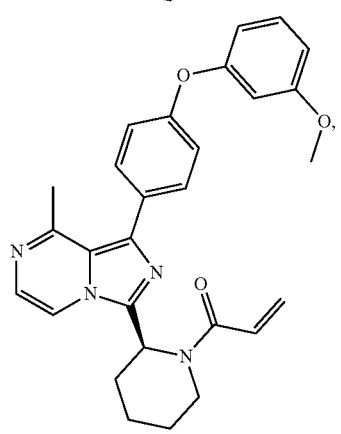,
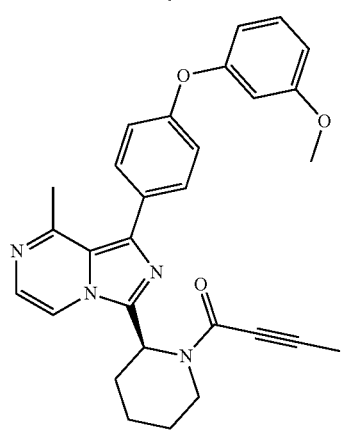,
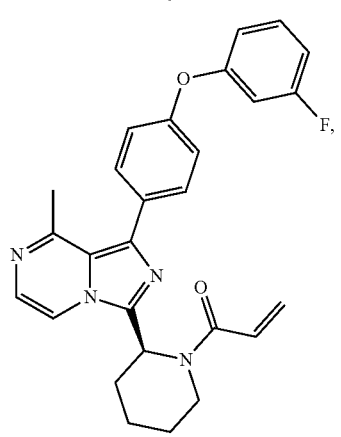,
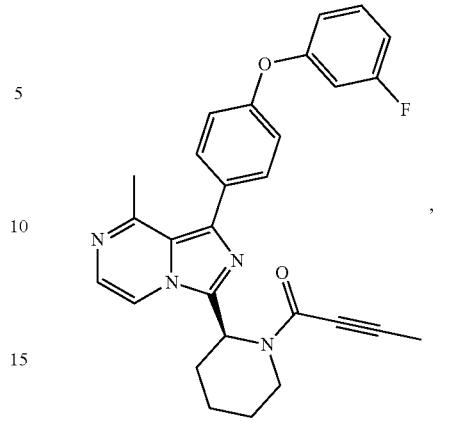,
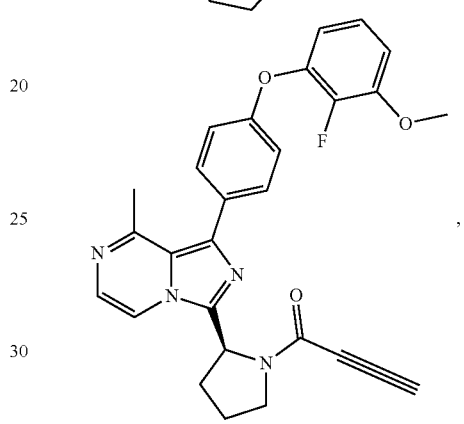,
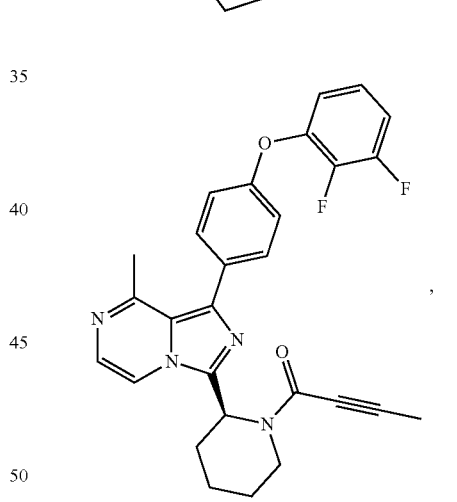,
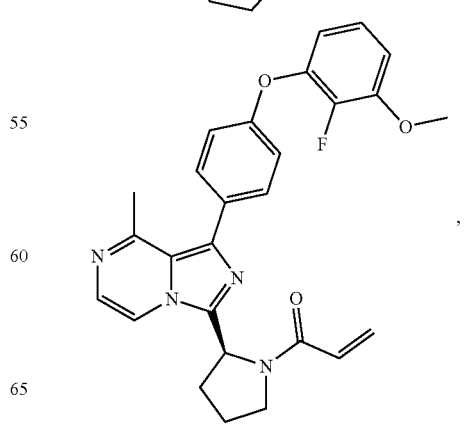, 9
-continued
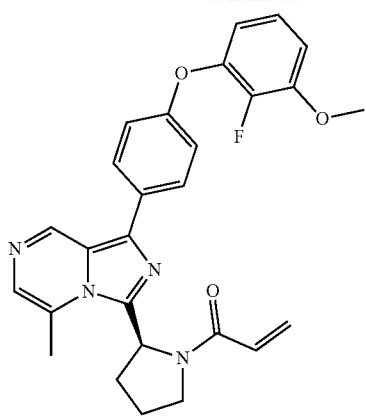
,
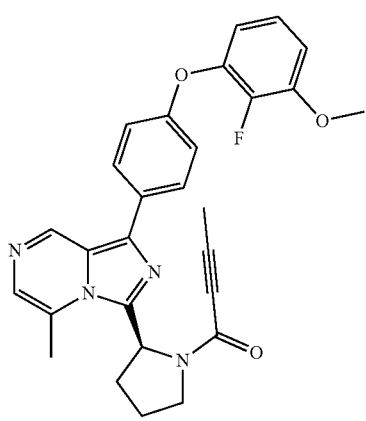
,
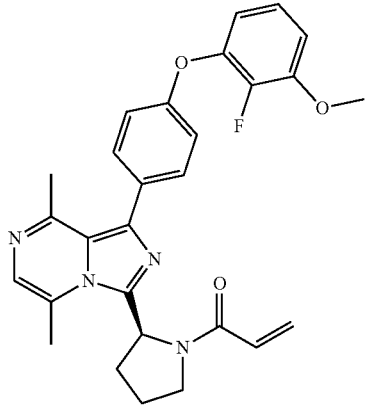
,
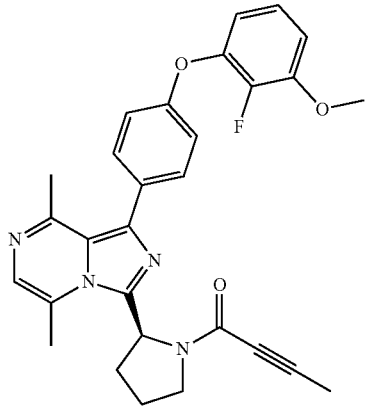
,
10
-continued
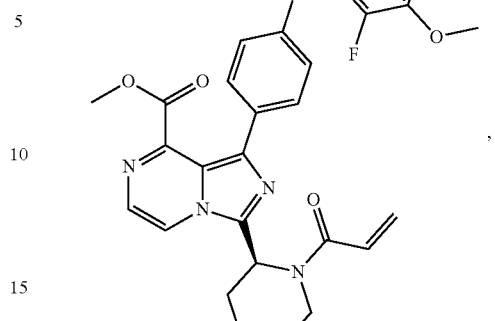
,
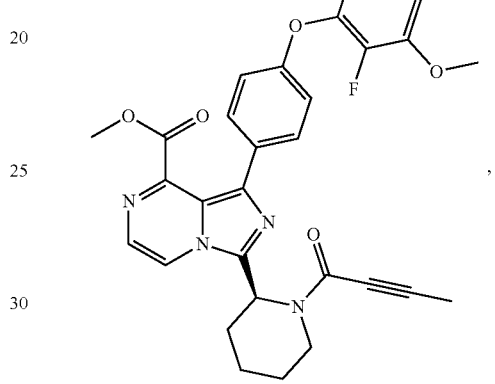
,
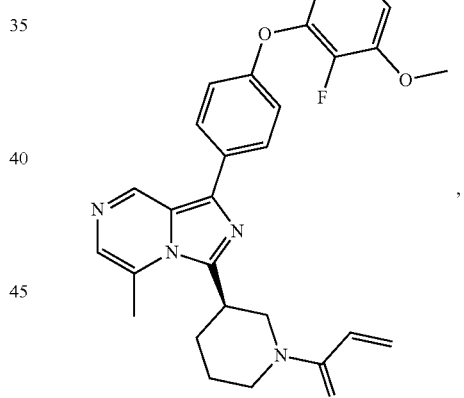
,
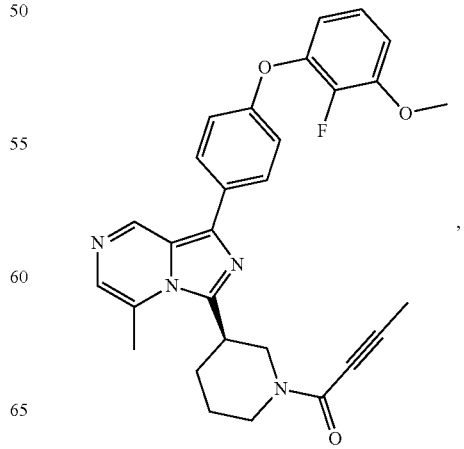
, 11
-continued
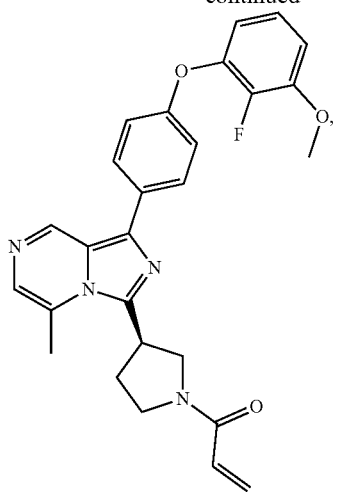
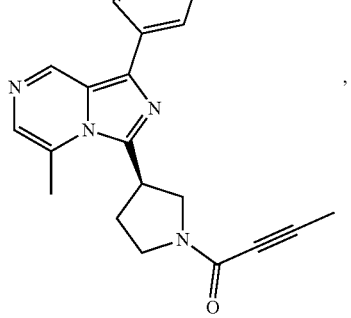
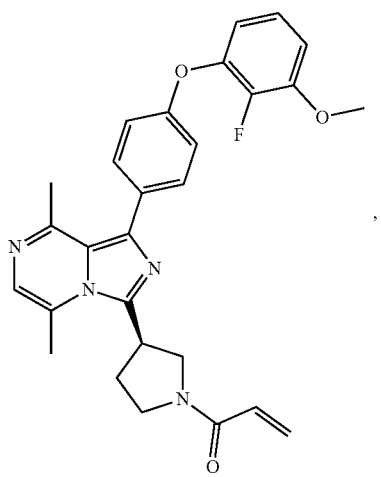
12
-continued
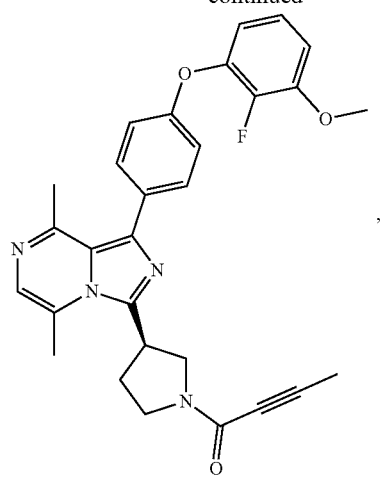
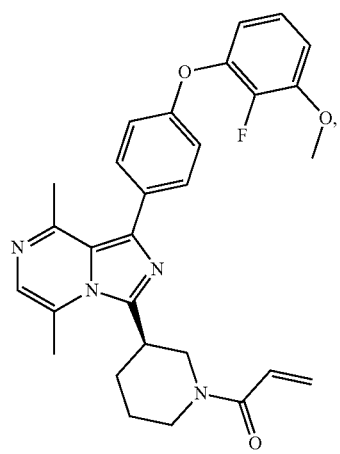
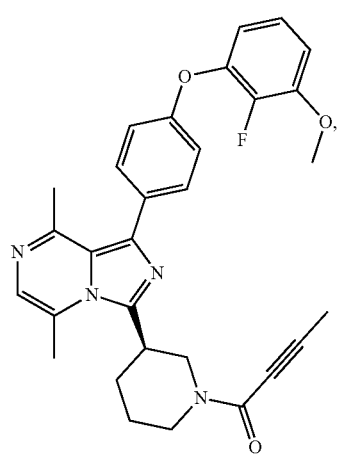

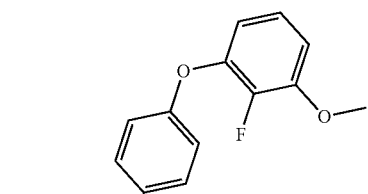
,
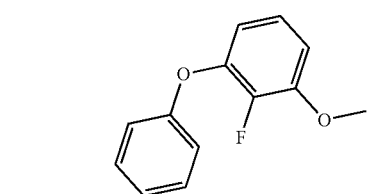
,
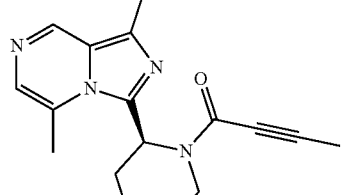
,
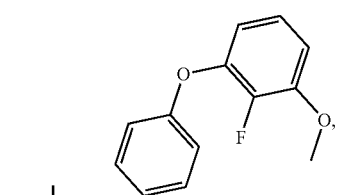
,
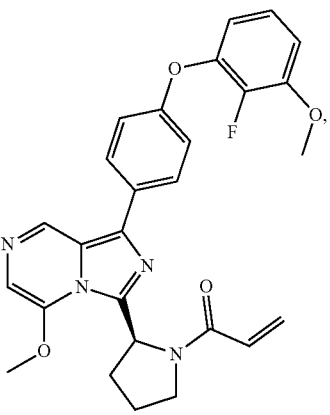
,
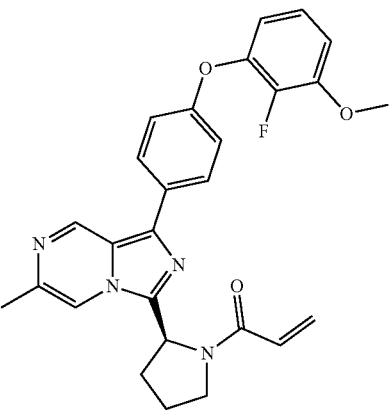
,
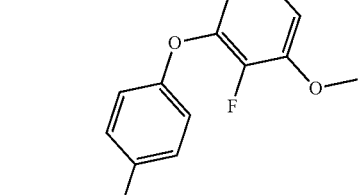
,
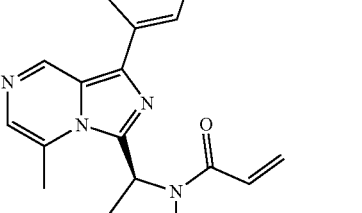
,
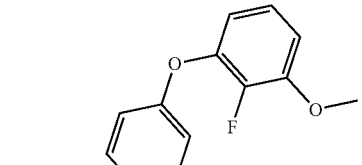
,

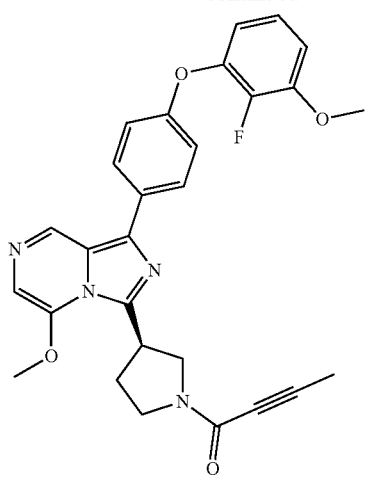
,
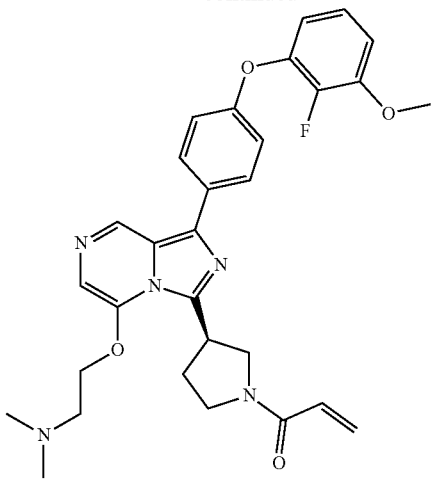
,
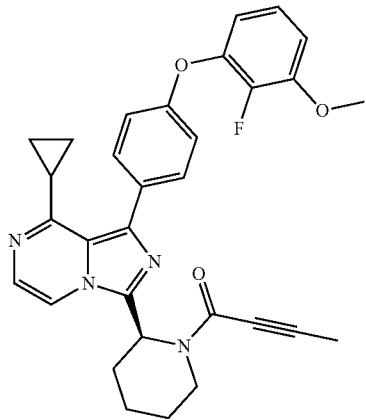
,
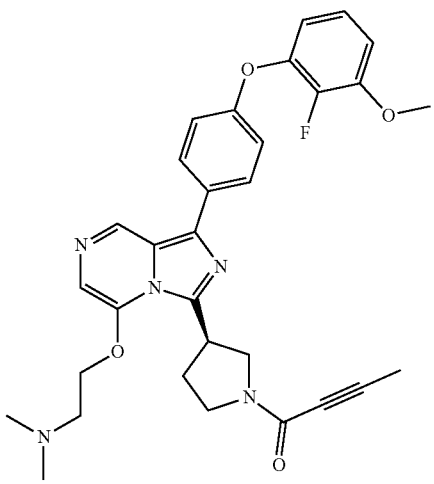
,
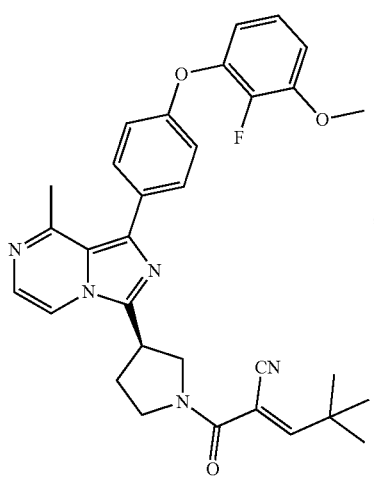
,
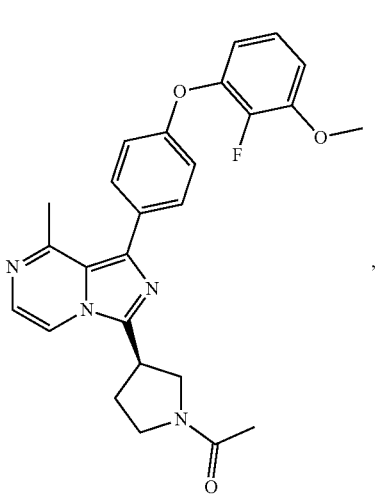
,

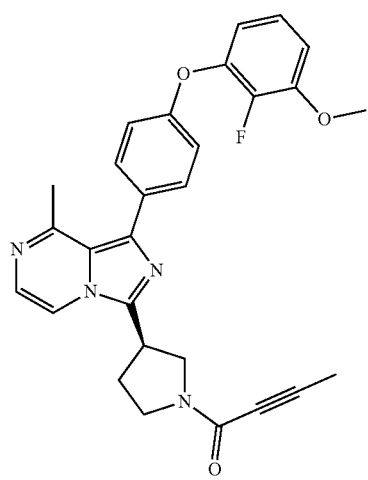
,
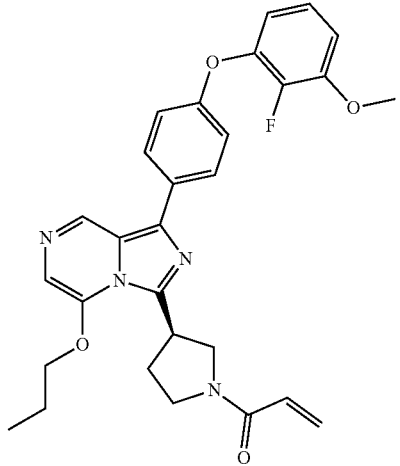
,
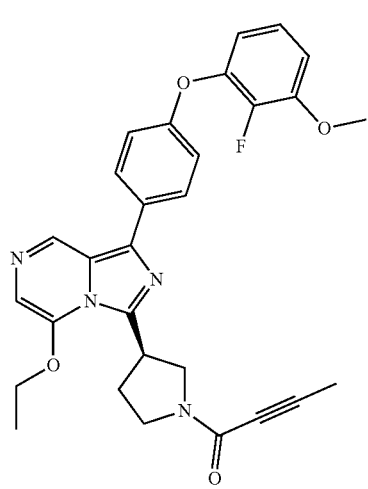
,
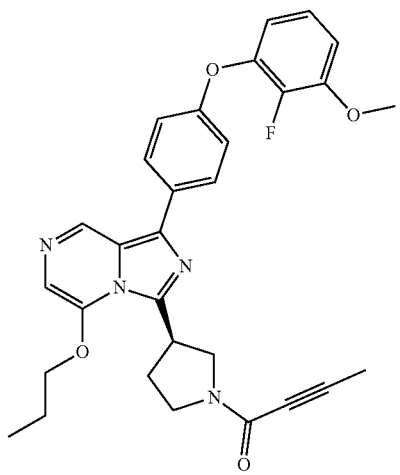
,
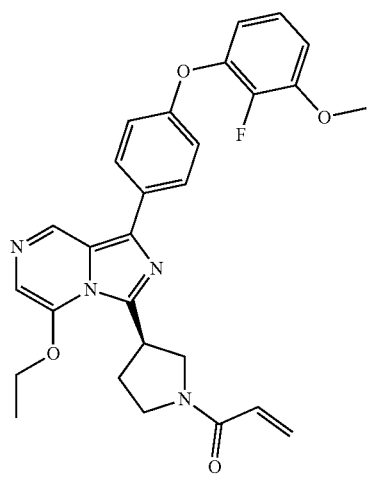
,
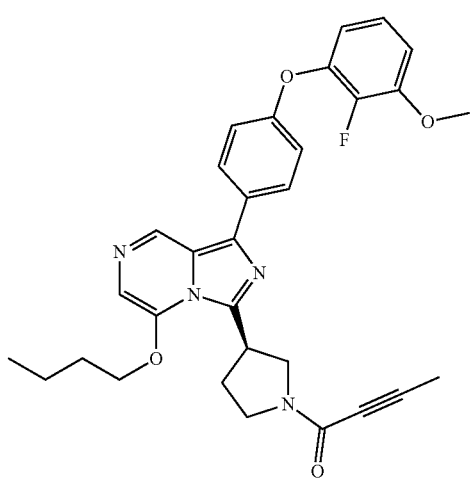
,

19
-continued
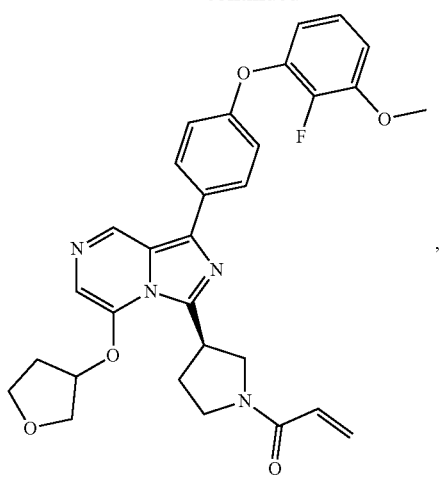
,
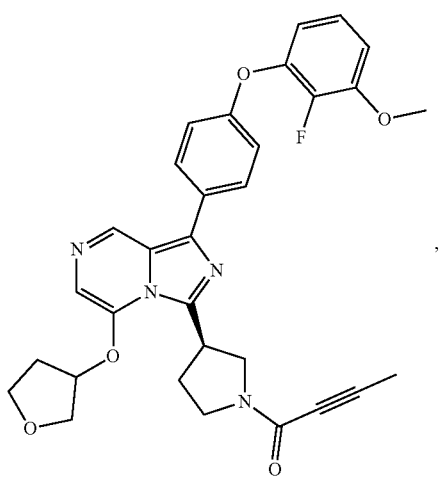
,
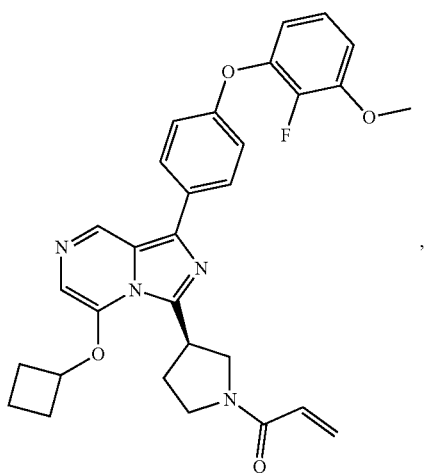
,
20
-continued
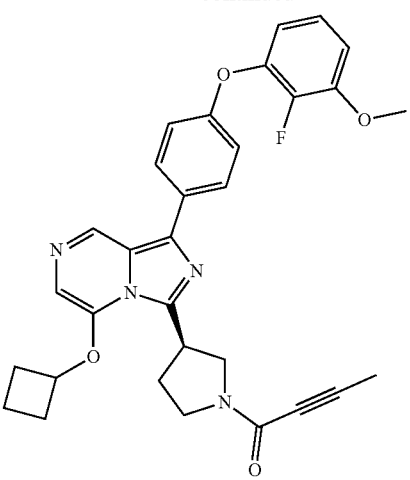
,
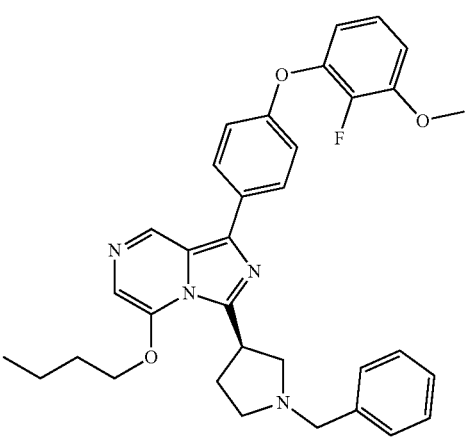
,
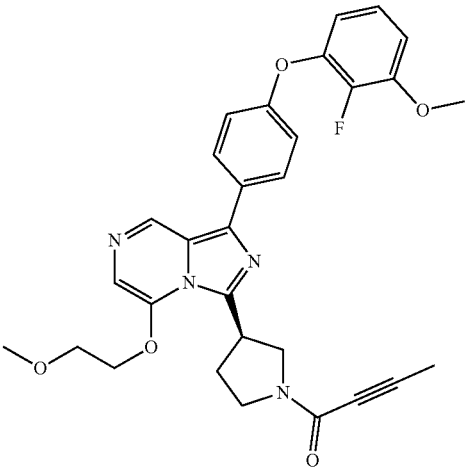
,

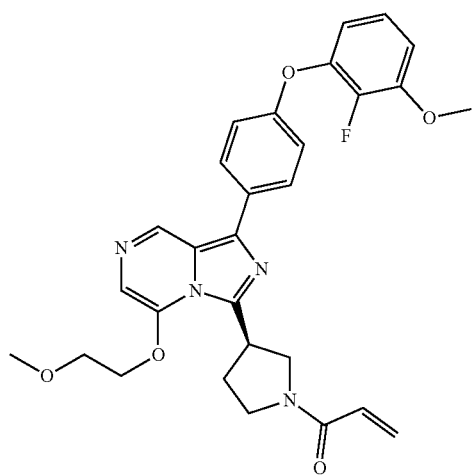
,
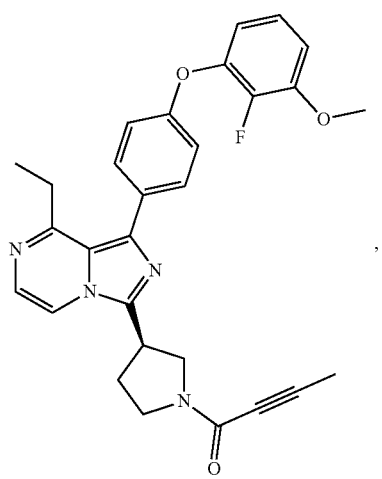
,
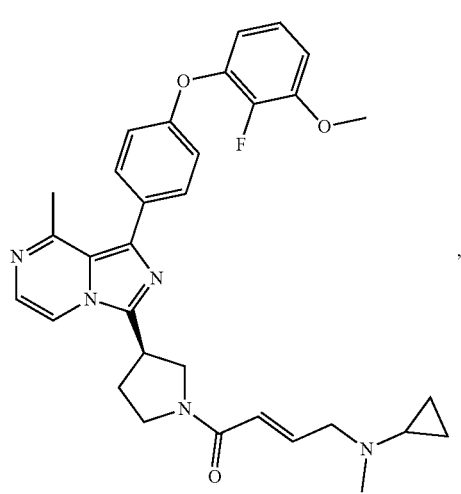
,
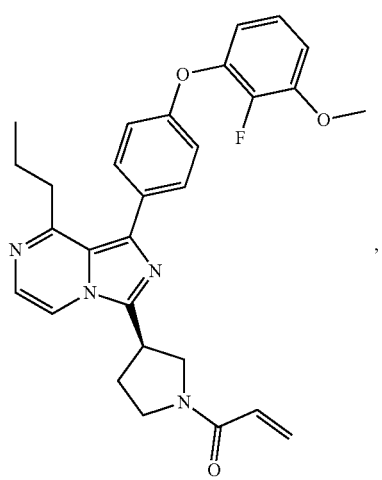
,

23
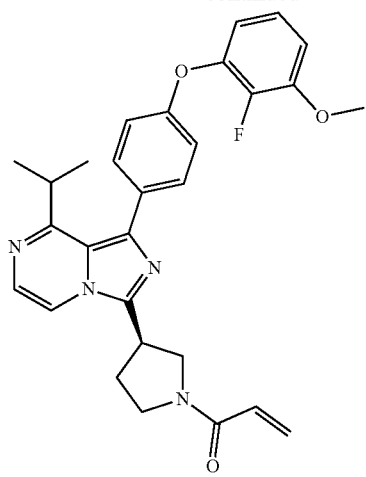
,
24
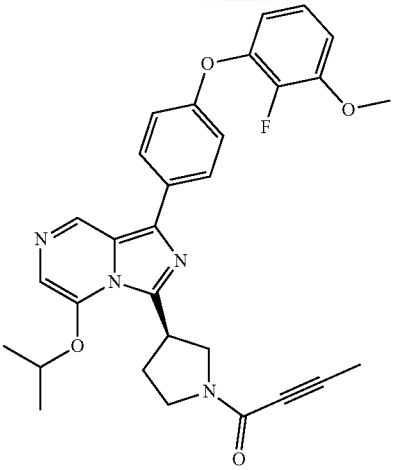
,
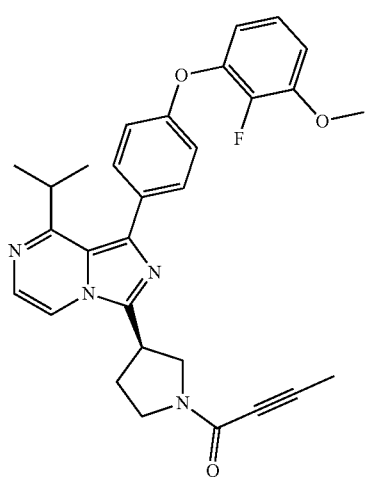
,
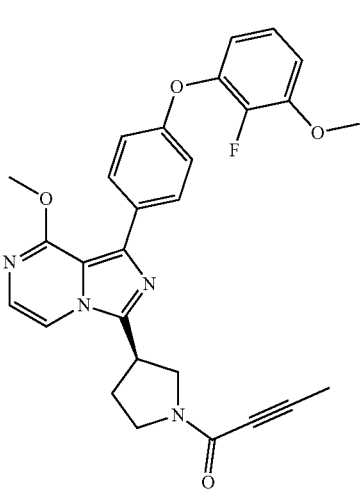
,
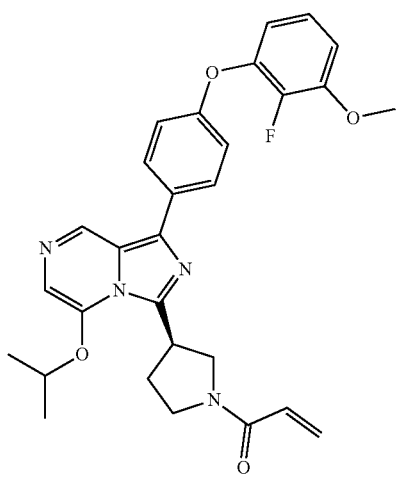
,
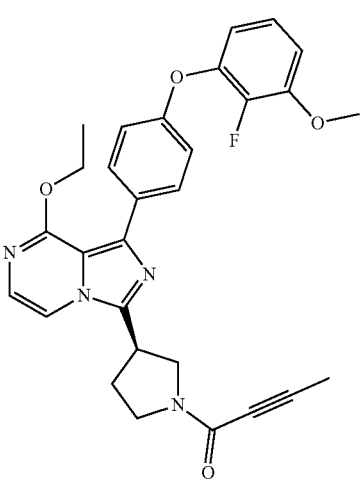
,

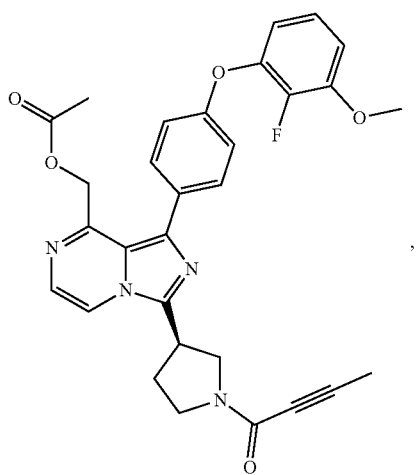
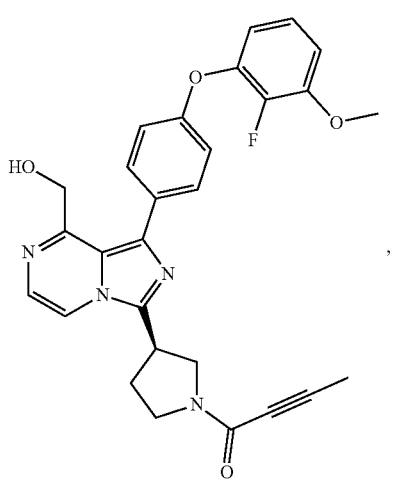
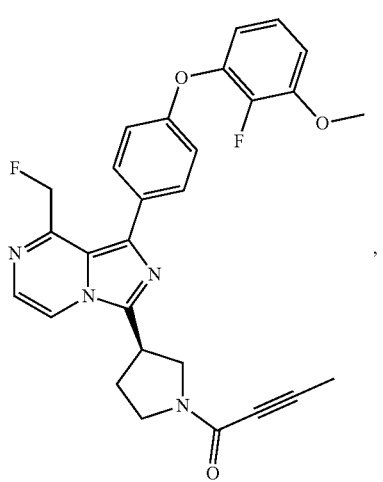
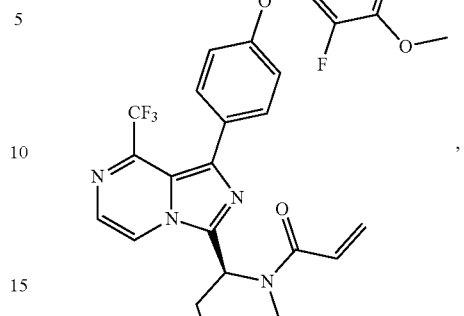
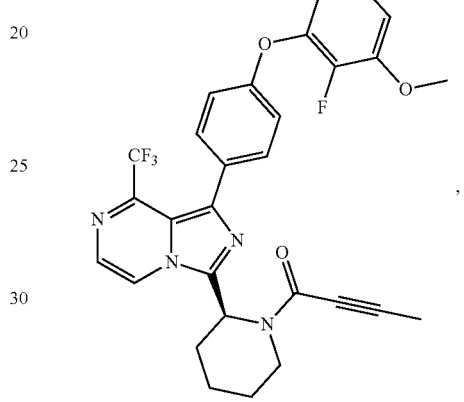
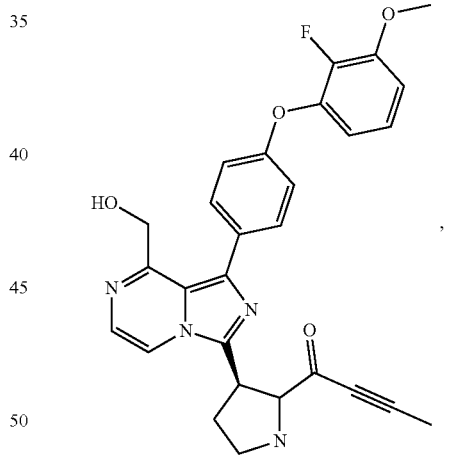
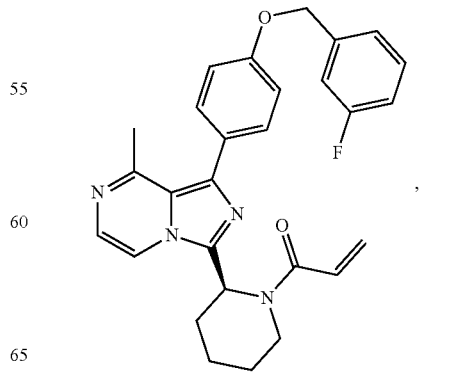

-continued
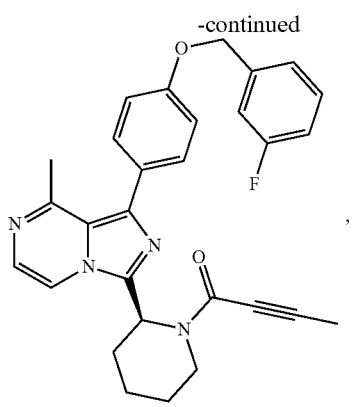
,
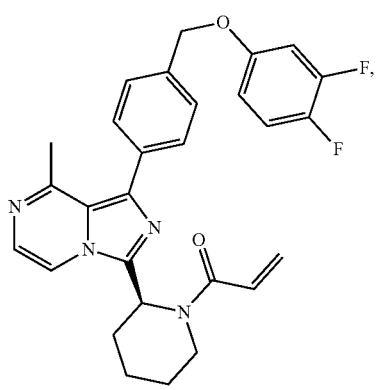
,
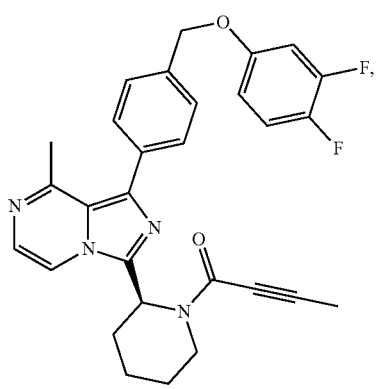
,
-continued
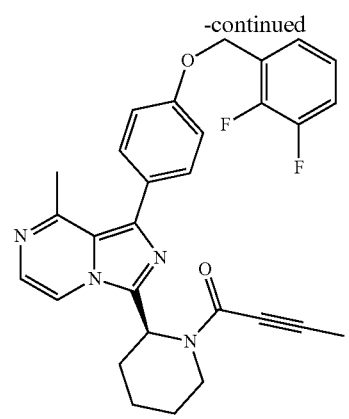
,
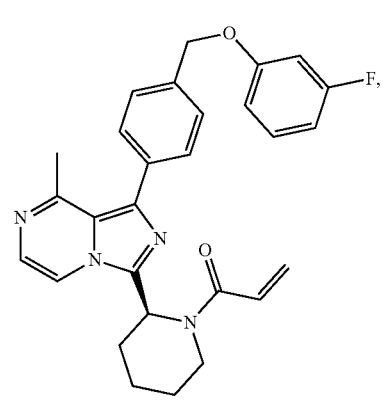
,
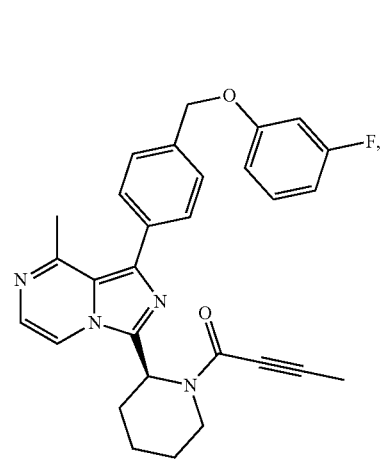
,
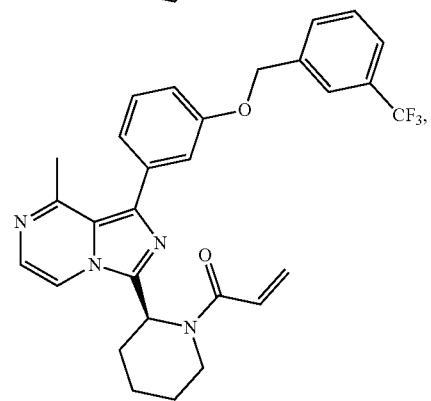

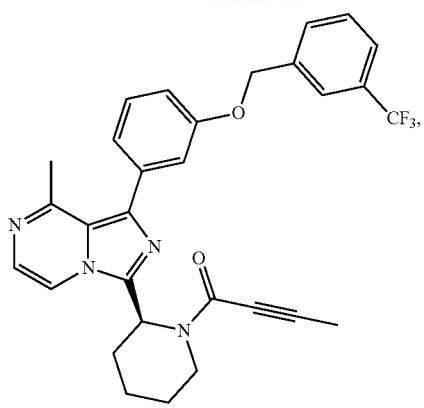
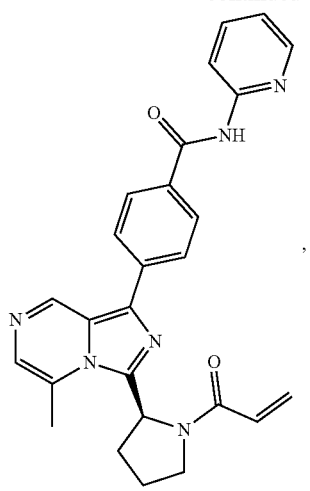
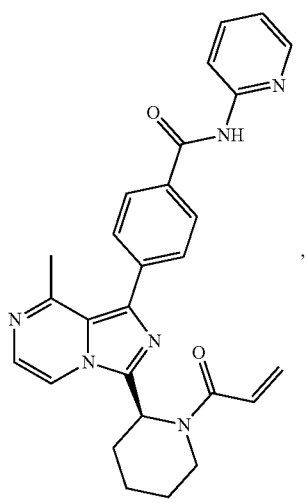
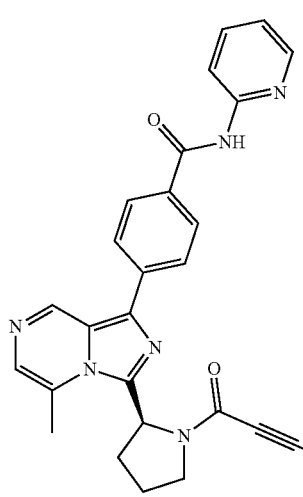
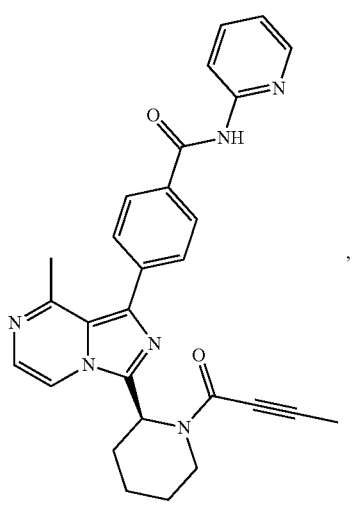
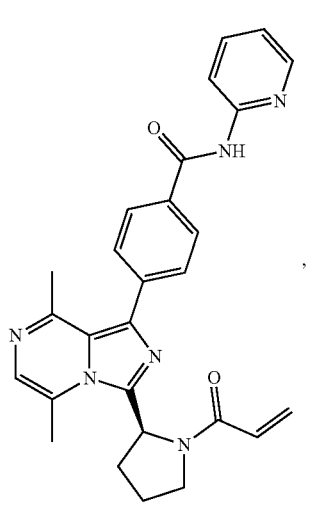

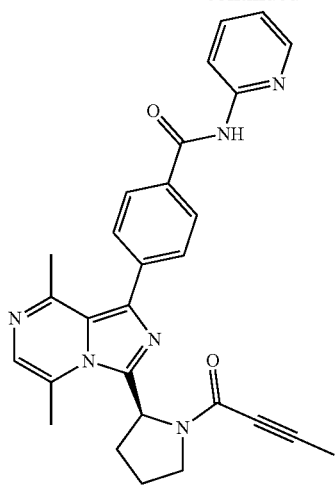
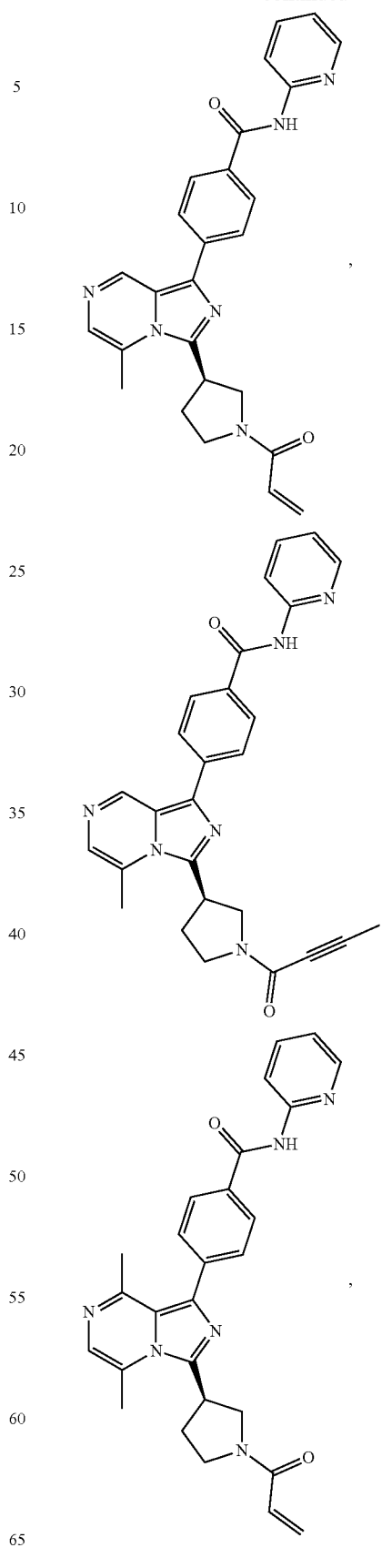

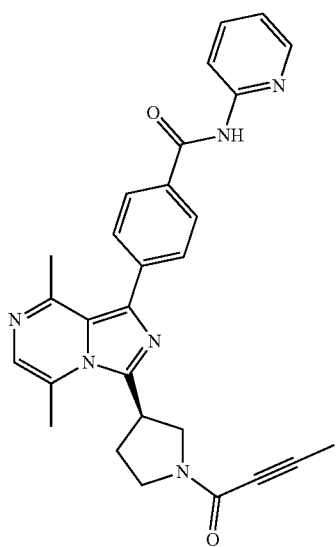
,
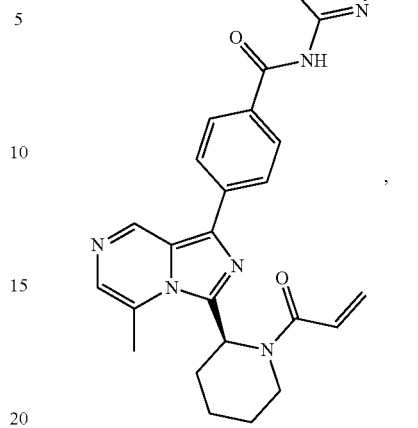
,
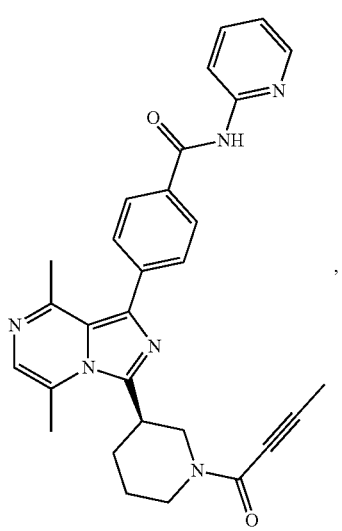
,
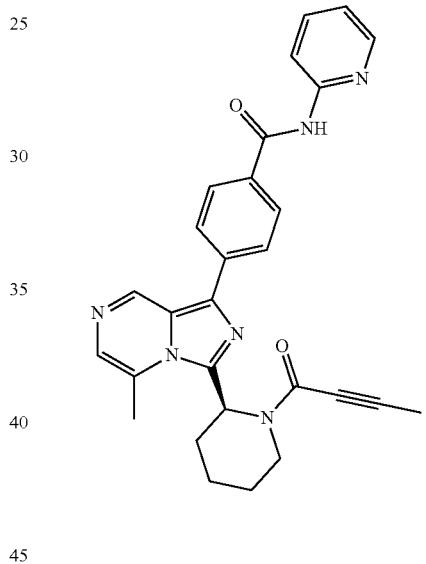
,
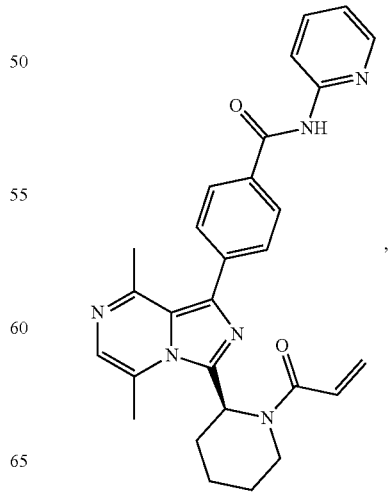
,

35
-continued
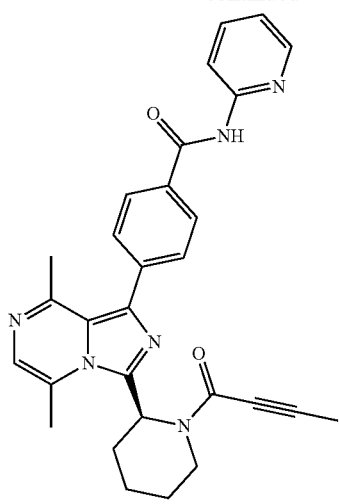
,
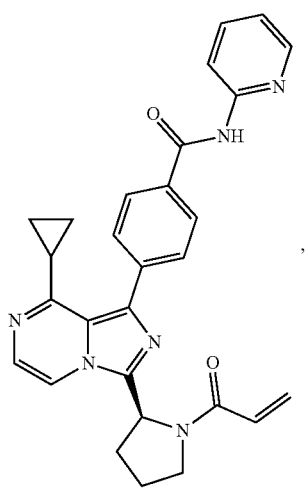
,
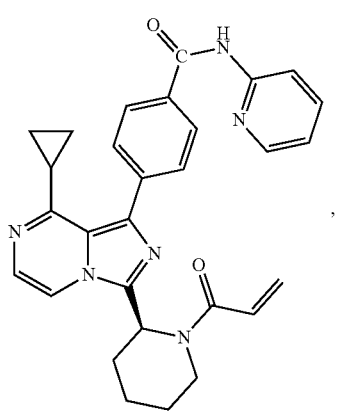
,
36
-continued
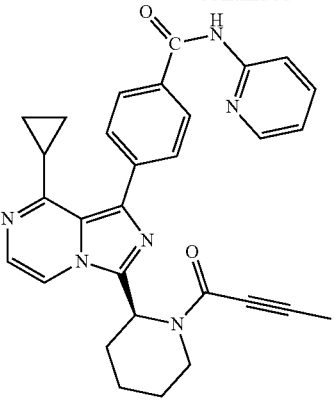
,
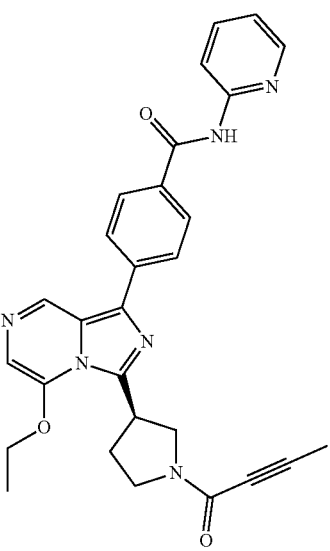
,
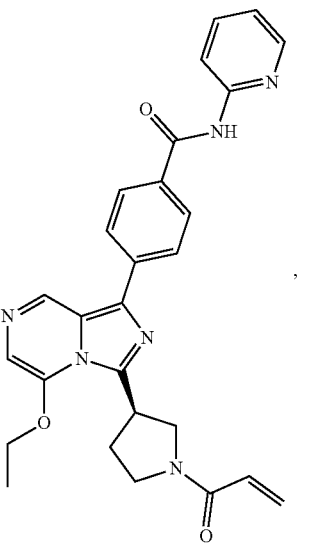
, -continued
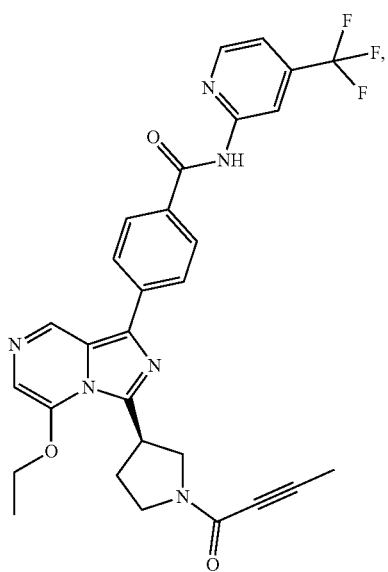
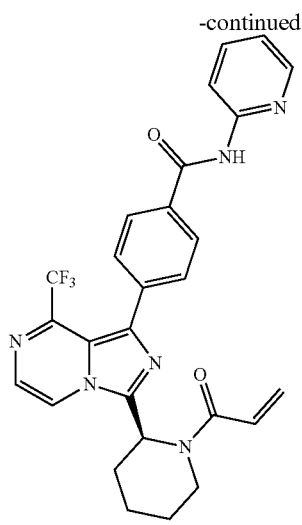
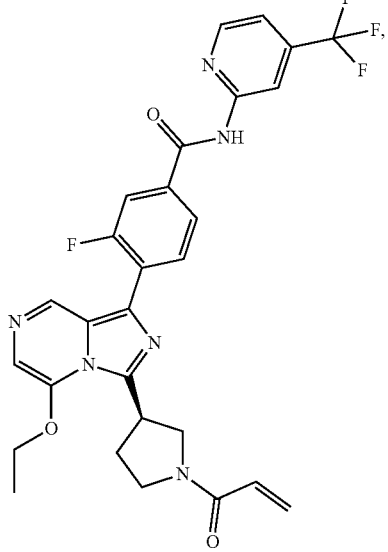
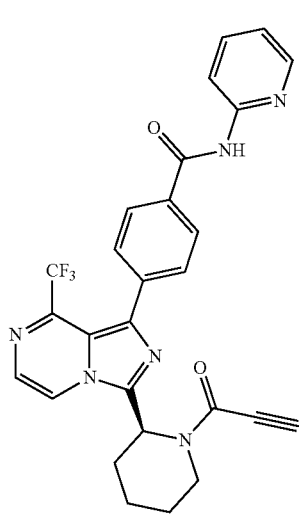
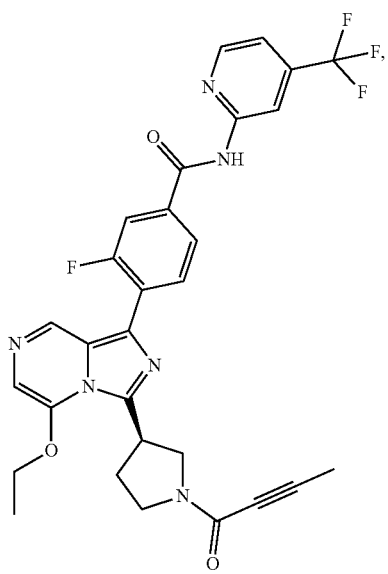
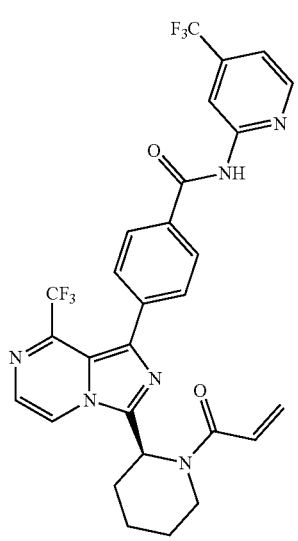

39
-continued
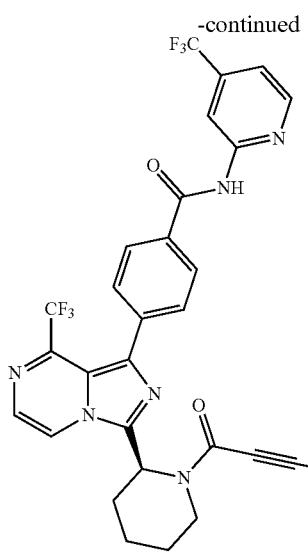
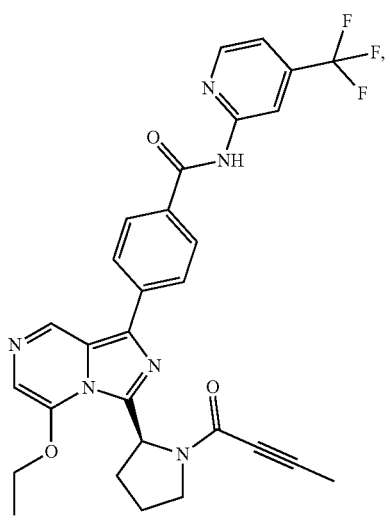
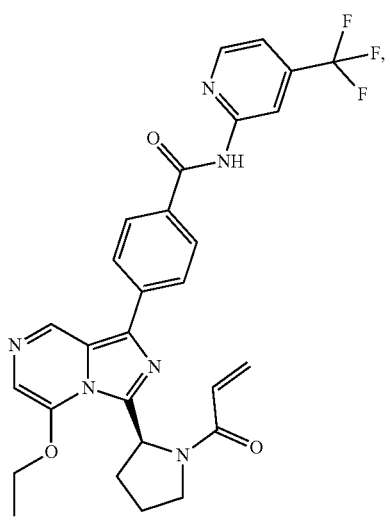
40
-continued
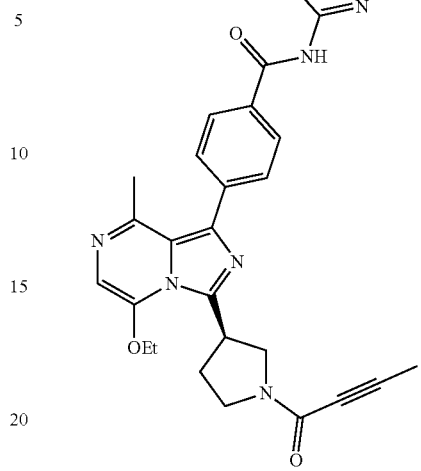
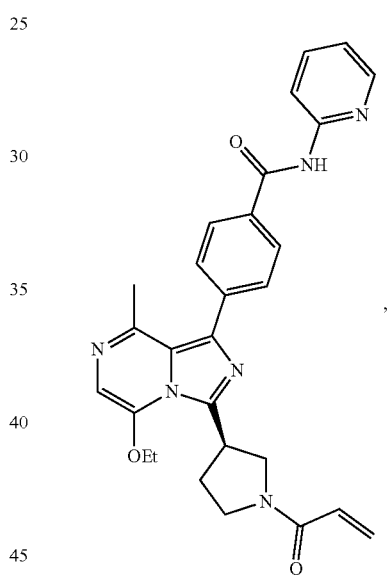
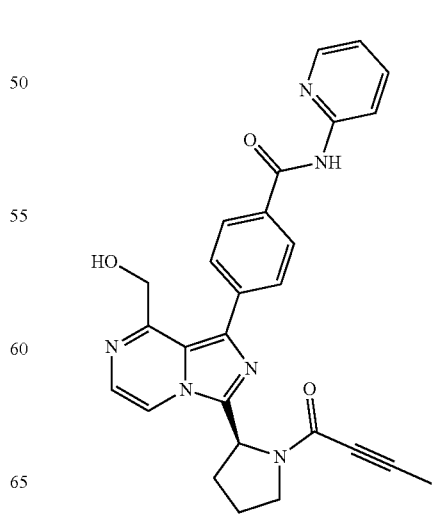

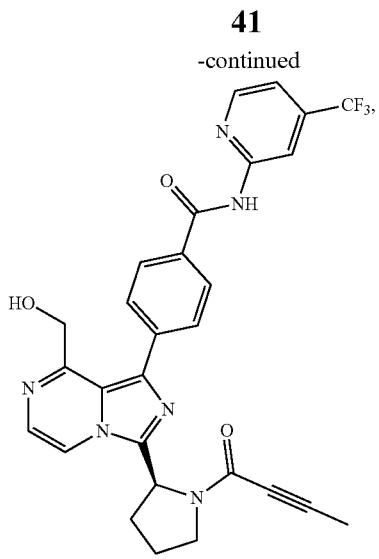

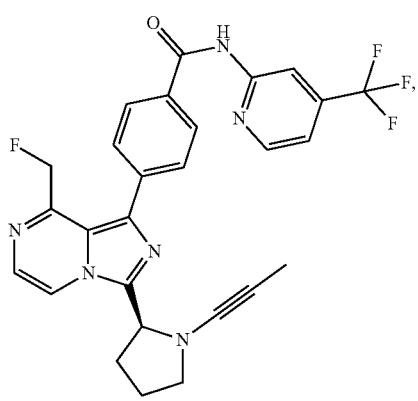

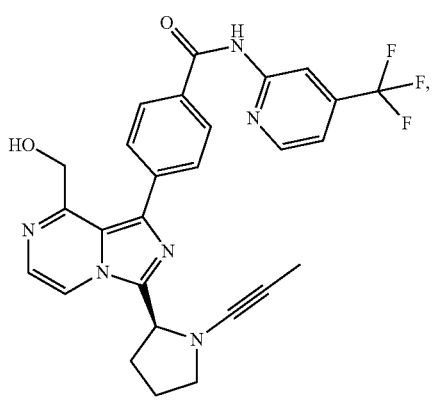

In another aspect, described herein is a pharmaceutical composition includes a therapeutically effective amount of the compound of Formula (I), and a pharmaceutically acceptable excipient.

In another aspect, described herein is a method for treating an autoimmune disease including administering to a subject in need thereof a composition containing a therapeutically effective amount of the compound of Formula (I).

In another aspect, in the method for treating an autoimmune disease, the composition is administered in combination with a therapeutic agent selected from the group consisting of: anticancer drugs, steroid drugs, methotrexates, leflunomides, anti-TNFa agents, calcineurin inhibitors, antihistaminic drugs, and a mixture thereof.

In another aspect, described herein is a pharmaceutical composition for preventing or treating cancers, tumors, inflammatory diseases, autoimmune diseases, or immunologically mediated disease including a therapeutically effective amount of the compound of Formula (I), and a pharmaceutically acceptable excipient.

In another aspect, described herein is a method for treating an autoimmune disease, cancers, tumors, inflammatory diseases, or immunologically mediated diseases including administering to a subject in need thereof a composition containing a therapeutically effective amount of the compound of Formula (I) and other therapeutic agents.

DETAILED DESCRIPTION OF THE INVENTION

The methods described herein include administering to a subject in need a composition containing a therapeutically effective amount of one or more Btk inhibitor compounds described herein.

Prodrugs means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs may be prepared by modifying functional groups present in the compounds in such a way that the modifications are cleaved, either in routine manipulation or in vivo, to the parent compounds.

Tautomers mean compounds produced by the phenomenon wherein a proton of one atom of a molecule shifts to another atom. Tautomers also refer to one of two or more structural isomers that exist in equilibrium and are readily converted from one isomeric form to another. One of ordinary skill in the art would recognize that other tautomeric ring atom arrangements are possible. All such isomeric forms of these compounds are expressly included in the present disclosure.

Isomers mean compounds having identical molecular formulae but differ in the nature or sequence of bonding of their atoms or in the arrangement of their atoms in space. Isomers that differ in the arrangement of their atoms in space are termed stereoisomers. Stereoisomers that are not mirror images of one another are termed diastereomers, and those that are non-superimposable mirror images of each other are termed enantiomers. When a compound has an asymmetric center, for example, it is bonded to four different groups, a pair of enantiomers is possible. A chiral compound can exist as either individual enantiomer or as a mixture thereof. Unless otherwise indicated, the description is intended to include individual stereoisomers as well as mixtures.

Certain compounds of the present disclosure can exist in unsolvated forms as well as solvated forms, including hydrated forms. Solvates refer to a complex formed by combination of solvent molecules with the compound of Formula I. The solvent can be an organic compound, an inorganic compound, or a mixture thereof.

Pharmaceutically acceptable salts represent those salts which are, within the scope of medical judgement, suitable for use in contact for the tissues of humans and lower animals without undue toxicity, irritation, allergic response and the like, and are commensurate with a reasonable benefit/risk ratio. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

Therapeutically effective amount means an amount of compound or a composition of the present invention effective in inhibiting Bruton's tyrosine kinase and thus producing the desired therapeutic effect.

As used herein, the term alkyl refers to a monovalent straight or branched chain, saturated aliphatic hydrocarbon radical having a number of carbon atoms in the specified range. For example, $C_{1-6}$ alkyl refers to any of the hexyl alkyl and pentyl alkyl isomers as well as n-, iso-, sec- and t-butyl, n- and iso-propyl, ethyl and methyl. Alkyl also includes saturated aliphatic hydrocarbon radicals wherein one or more hydrogens are replaced with deuterium, for example, $CD_3$.

The term branched alkyl refers to an alkyl group as defined above except that straight chain alkyl groups in the specified range are excluded. As defined herein, branched alkyl includes alkyl groups in which the alkyl is attached to the rest of the compound via a secondary or tertiary carbon. For example, isopropyl is a branched alkyl group.

The term cycloalkyl refers to any monocyclic ring of an alkane having a number of carbon atoms in the specified range. For example, $C_{3-6}$cycloalkyl refers to cyclopropyl, cyclobutyl, cyclopentyl, and cyclohexyl.

The term halogen refers to fluorine, chlorine, bromine and iodine (alternatively referred to as fluoro, chloro, bromo, and iodo).

The term haloalkyl refers to an alkyl group as defined above in which one or more of the hydrogen atoms have been replaced with a halogen (i.e., F, Cl, Br and/or I). For example, $C_{1-6}$ haloalkyl refers to a $C_1$ to $C_6$ linear or branched alkyl group as defined above with one or more halogen substituents. The term fluoroalkyl has an analogous meaning except that the halogen substituents are restricted to fluoro. Suitable fluoroalkyls include the series $(CH_2)_{0-4}CF_3$.

The term C(O) or CO refers to carbonyl. The terms $S(O)_2$ or $SO_2$ refers to sulfonyl. The term S(O) or SO refers to sulfinyl.

The term aryl refers to phenyl, naphthyl, tetrahydronaphthyl, idenyl, dihydroindenyl and the like. An aryl of particular interest is phenyl.

The term heteroaryl refers to (i) a 5- or 6-membered heteroaromatic ring containing from 1 to 4 heteroatoms independently selected from N, O and S, or (ii) is a heterobicyclic ring selected from quinolinyl, isoquinolinyl, and quinoxalinyl. Suitable 5- and 6-membered heteroaromatic rings include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. A class of heteroaryls of interest consists of (i) 5- and 6-membered heteroaromatic rings containing from 1 to 3 heteroatoms independently selected from N, O and S, and (ii) heterobicyclic rings selected from quinolinyl, isoquinolinyl, and quinoxalinyl. Heteroaryls of particular interest are pyrrolyl, imidazolyl, pyridyl, pyrazinyl, quinolinyl (or quinolyl), isoquinolinyl (or isoquinolyl), and quinoxalinyl.

Examples of 4- to 7-membered, saturated heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings which can be used in the present invention. These rings are merely representative.

Synthetic methods for preparing the compounds of the present invention are illustrated in the following Schemes, Methods, and Examples. Starting materials are commercially available or may be prepared according to procedures known in the art or as described herein. The compounds of the invention are illustrated by means of the specific examples shown below. However, these specific examples are not to be construed as forming the only genus that is considered as the invention. These examples further illustrate details for the preparation of the compounds of the present invention. Those skilled in the art will readily appreciate that known variations in the conditions and processes can be used to prepare such compounds.

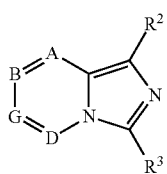

Formula (I)

In Formula (I), A, B, G, $R^2$, and $R^3$ are defined above in the Summary of the Invention section. The Btk inhibitor compounds of Formula (I) can be prepared by methods well known in the art of organic chemistry. The starting material used for the synthesis of these compounds can be either synthesized or obtained from commercial sources, such as, but not limited to, China chemical companies or Sigma-Aldrich Chemical Co. (St. Louis, Mo.) at China. The compounds described herein, and other related compounds having different substituents are optionally synthesized using techniques and materials, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). Other methods for the synthesis of compounds described herein may be found in international Application Publication No. WO 2013/010868 A1, Liu, J. et al. *ACS Medicinal Chemistry Letters* 10 (2016) 198-203. The definitions of chemistry terms used in this application may be found in these reference (if not otherwise defined herein). As a guide the following synthetic methods may be utilized.

During the synthetic sequences, it may be necessary and/or desirable to protect sensitive or reactive groups on any of the molecules concerned. This is achieved by means of conventional protecting groups, such as those described in T. W Greene and P. G. M. Wutts "Protective groups in Organic Synthesis" 3rd Edition, John Wiley and Sons, 1999. The protective groups are optionally removed at a convenient subsequent stage using methods well known in the art. The products of the reactions are optionally isolated and purified. If desired, using conventional techniques, but not limited to, filtration, distillation crystallization, chromatography and the like. Such materials are optionally characterized using conventional means, including physical constant and spectra data.

Compounds described herein may possess one or more sterocenters and each center may exist in the R or S configuration. The compounds presented herein include all diasterometic, enantiomeric, and epimeric forms as well as the appropriate mixtures thereof.

The Btk inhibitor compounds of Formula I can be, for example imidazo [1,5-a] pyrazine derivatives. Specifically, the Btk inhibitor compounds of Formula I can be, for example, compounds G, wherein $R_1$-$R_2$ have the previously defined meanings. A non-limiting example of a synthetic approach towards the preparation of compounds G can be prepared by the general synthetic route shown in Scheme I and Scheme II.

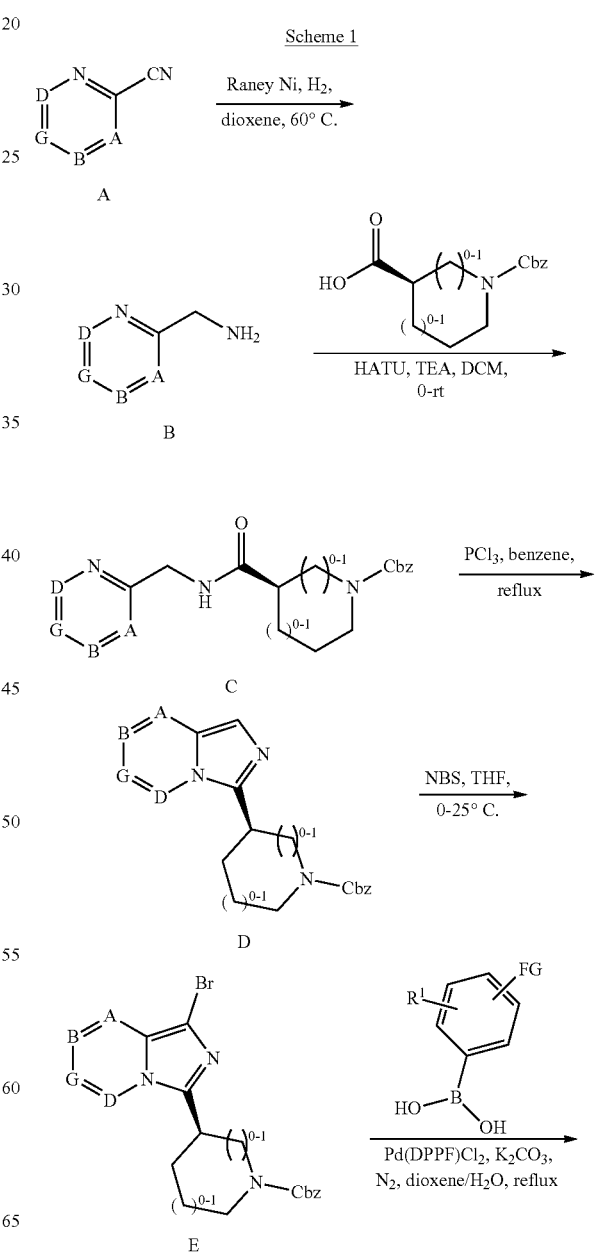

Scheme 1

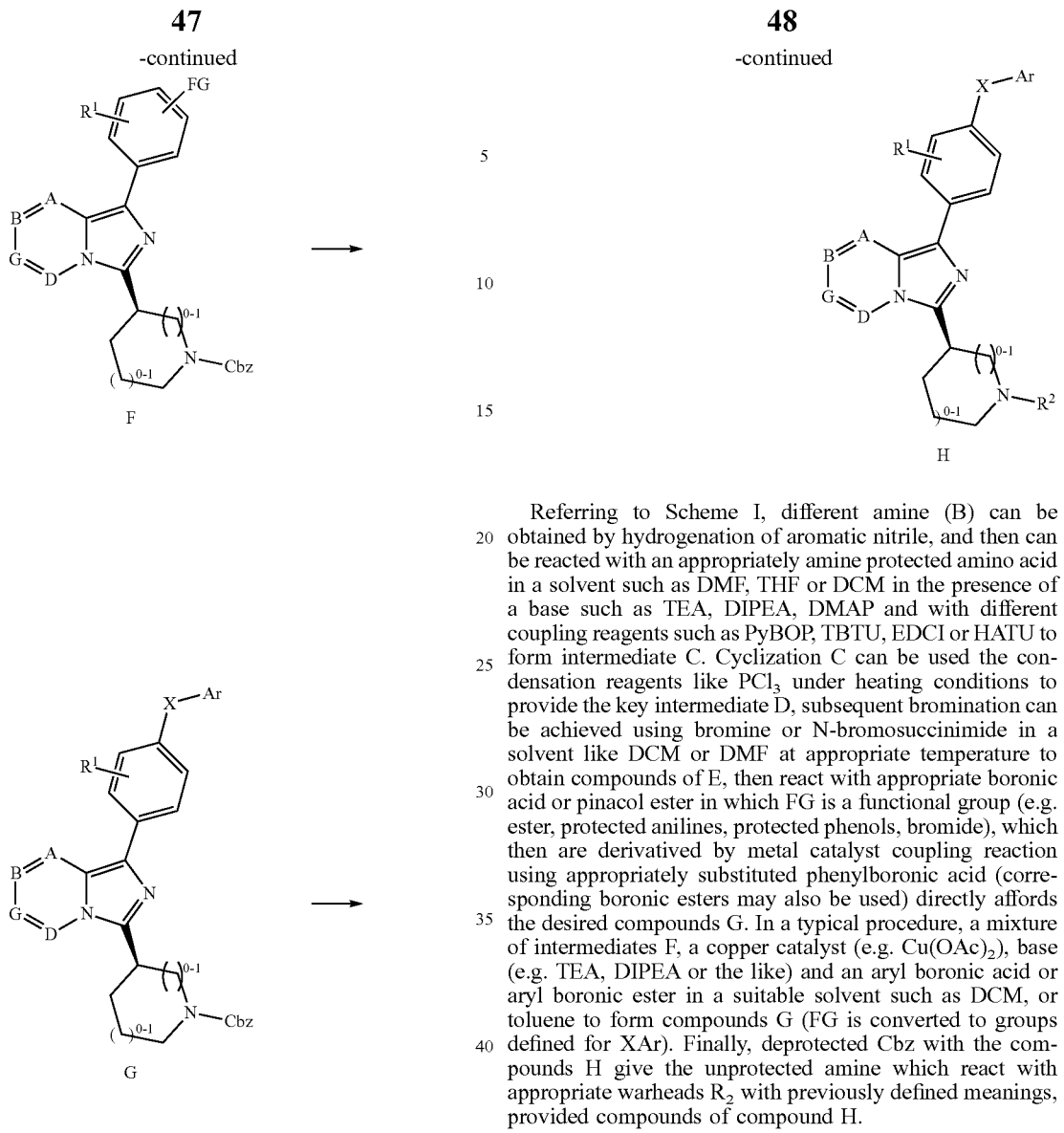

Referring to Scheme I, different amine (B) can be obtained by hydrogenation of aromatic nitrile, and then can be reacted with an appropriately amine protected amino acid in a solvent such as DMF, THF or DCM in the presence of a base such as TEA, DIPEA, DMAP and with different coupling reagents such as PyBOP, TBTU, EDCI or HATU to form intermediate C. Cyclization C can be used the condensation reagents like $PCl_3$ under heating conditions to provide the key intermediate D, subsequent bromination can be achieved using bromine or N-bromosuccinimide in a solvent like DCM or DMF at appropriate temperature to obtain compounds of E, then react with appropriate boronic acid or pinacol ester in which FG is a functional group (e.g. ester, protected anilines, protected phenols, bromide), which then are derivatived by metal catalyst coupling reaction using appropriately substituted phenylboronic acid (corresponding boronic esters may also be used) directly affords the desired compounds G. In a typical procedure, a mixture of intermediates F, a copper catalyst (e.g. $Cu(OAc)_2$), base (e.g. TEA, DIPEA or the like) and an aryl boronic acid or aryl boronic ester in a suitable solvent such as DCM, or toluene to form compounds G (FG is converted to groups defined for XAr). Finally, deprotected Cbz with the compounds H give the unprotected amine which react with appropriate warheads $R_2$ with previously defined meanings, provided compounds of compound H.

Scheme II

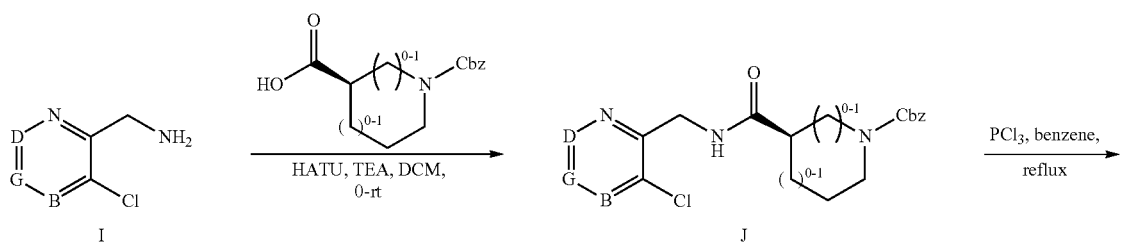

-continued
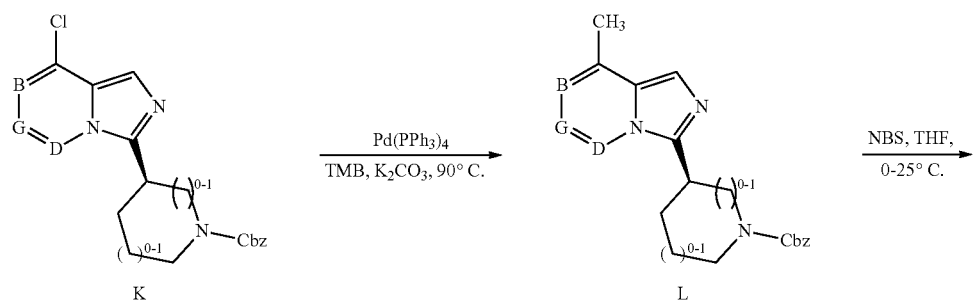
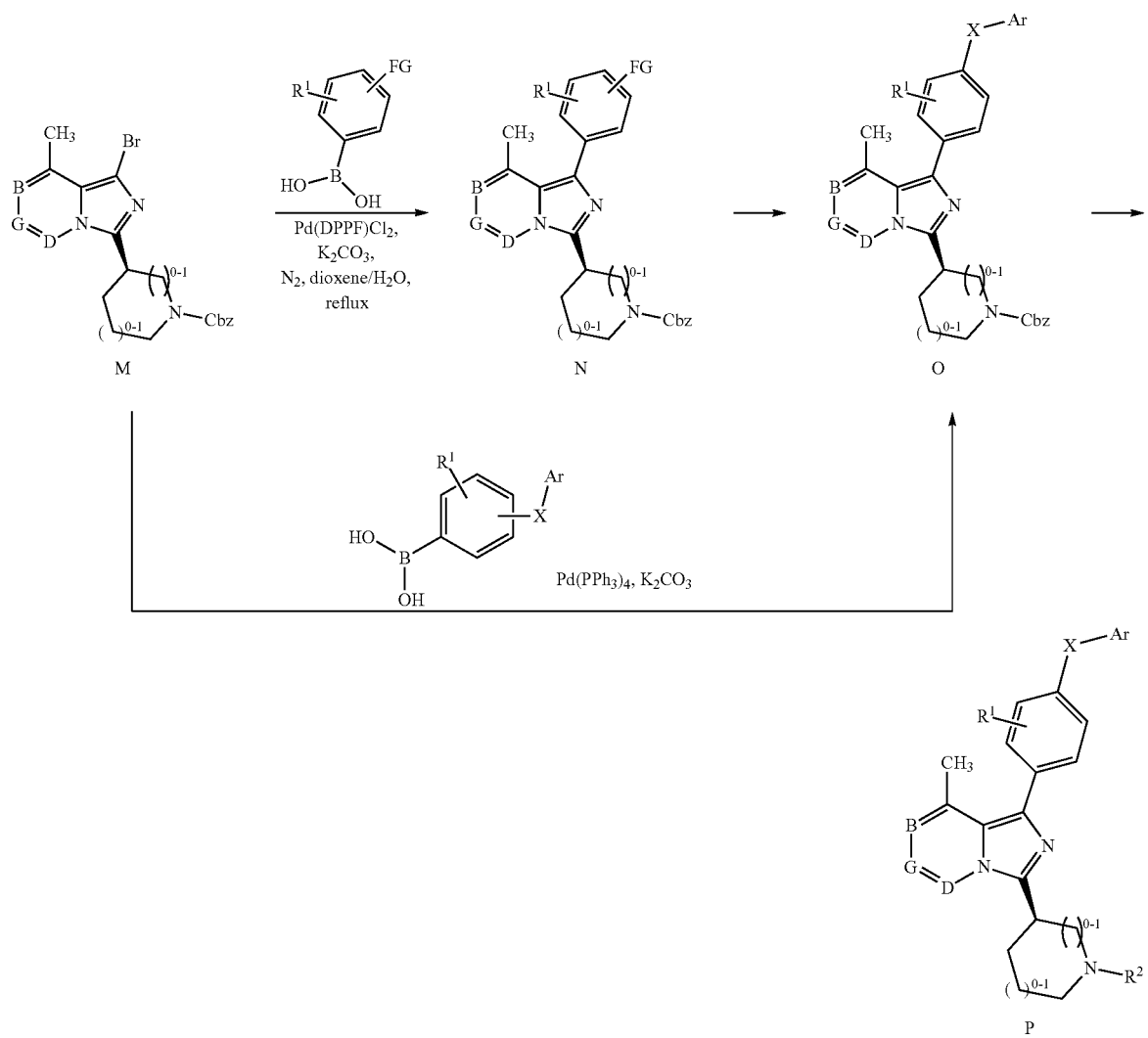

Referring to Scheme II, compounds P can be obtained from another substrate, and the chemistry is similar with Scheme I, Methyl derivatives L can be prepared using trimethylboroxin in the presence of a suitable palladium catalyst system and solvent, then key intermediates M was obtained by regioselective bromination or iodation with $Br_2/I_2$ or NBS/NIS, which then are derivatived by metal catalyst coupling reaction using appropriately substituted phenylboronic acid (corresponding boronic esters may also be used) affords a key intermediate N or directly affords the desired compounds O. The transformation from O to P is synthesized in a similar manner as before showed at Scheme I.

Alternatively, compound G (or O) can be obtained from compounds F (or N), in which FG is a functional group (e.g. ester, protected anilines, protected phenols, bromide) that can be easily converted to groups defined for XAr. Non-limiting examples of suitable functional groups in compounds F are a benzyl ether, dibenzyl anime, or methyl ester, which can be treated with base or $Pd/C/H_2$ to form the key intermediates F-1a, F-2a, F-3a (or N-1a, N-2a, N-3a), then form corresponding compounds G-1, G-2, G-3, G-4 (or O-1, O-2, O-3, O-4) at Scheme III.

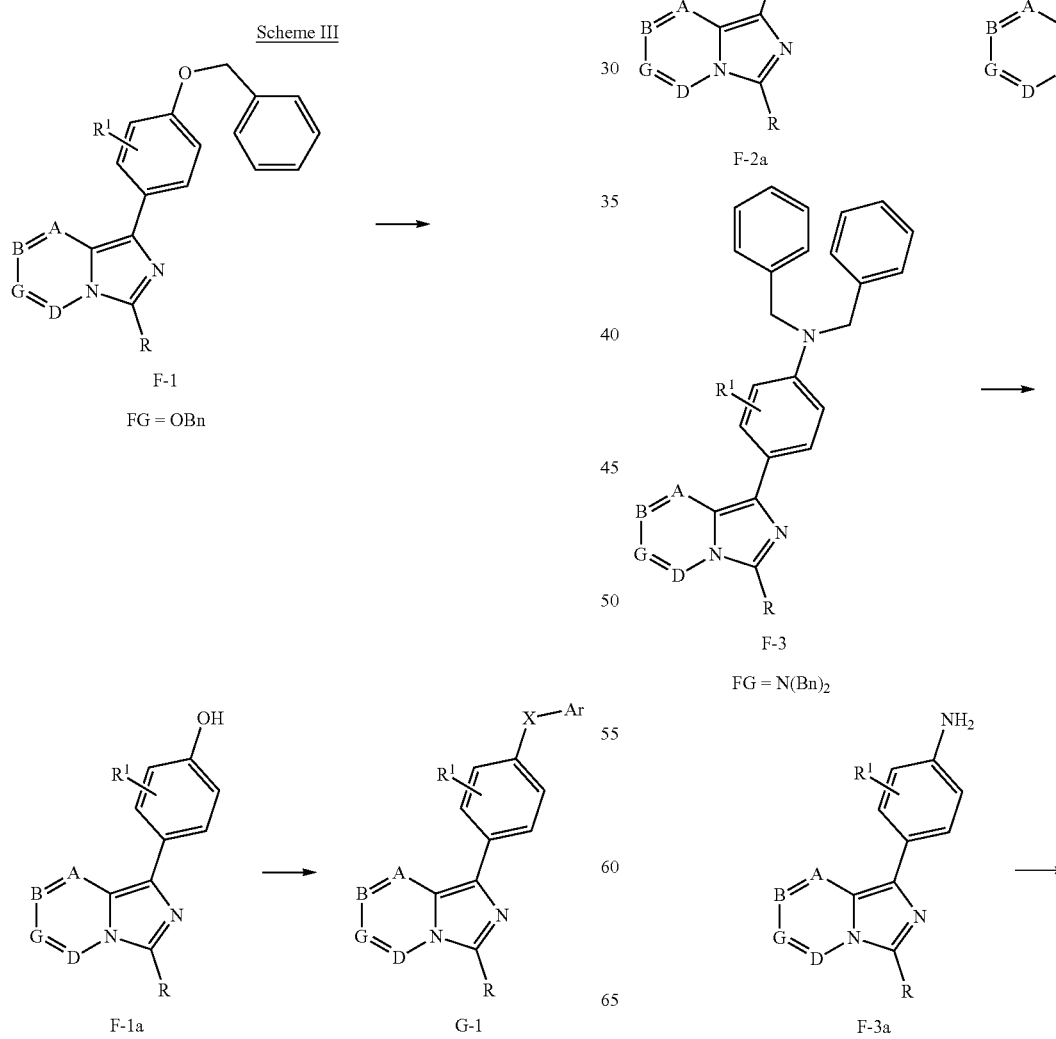

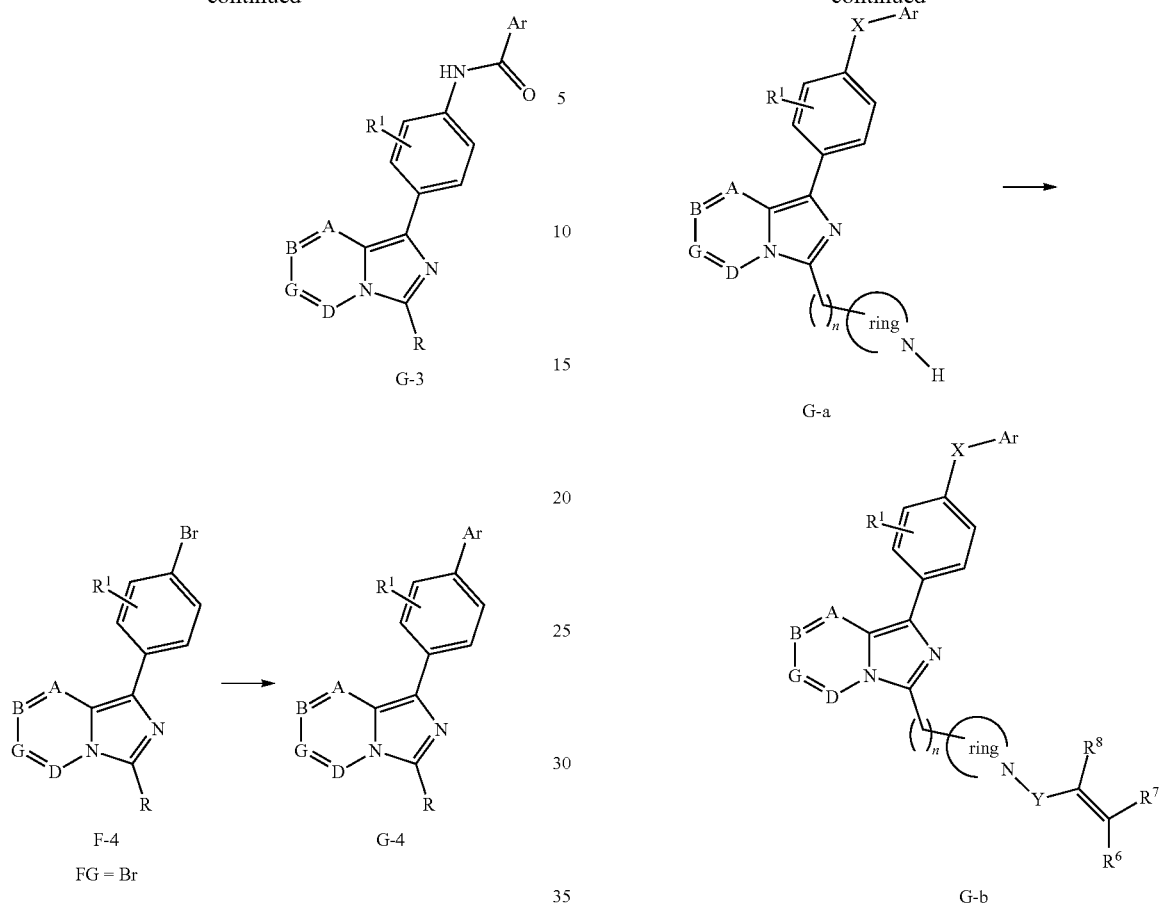

The deprotection reactions for the protective groups of compound G in Scheme IV are known and can be run by the methods described below. Examples here are (a) deprotection reaction under acid or basic conditions for Boc or Fmoc protecting group and (b) deprotection reactions based on hydrogenolysis for benzyl or Cbz protecting group. After deprotection with these conditions, coupling with, but not limited to, an acid chloride, such as, but not limited to, aryloyl chloride, completes the synthesis to provide compound G-b.

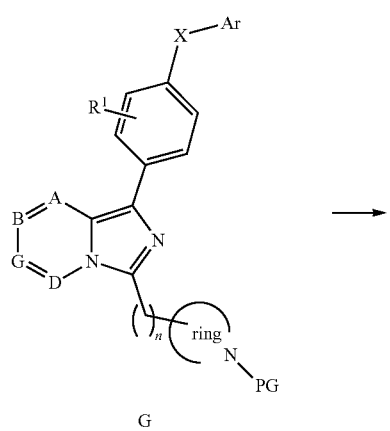

The present invention also embraces isotopically-labelled compounds of the present invention which are identical to those recited herein, but for the fact that one or more atoms are replaced by an atom having an atomic mass or mass number different from the atomic mass or number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{17}O$, $^{18}O$, $^{31}P$, $^{32}P$, $^{35}S$, $^{18}F$, and $^{36}Cl$ respectively.

Certain isotopically-labelled compounds of Formula I (e.g. those labeled with $^{3}H$ and $^{14}C$) are useful in compound and/or substrate tissue distribution assays. Tritiated and carbon-14 isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the schemes and/or in the examples herein below, by substituting and appropriate isotopically labeled reagent for a non-isotopically labeled reagent.

General experimental conditions: Preparative thin layer chromatography (PTLC) was performed on 20×20 cm plates (500 micron thick silica gel). Silica gel chromatography was performed on a Biotage Horizon flash chromatography system. $^{1}H$ NMR spectra were recorded on a Bruker Ascend™ 400 spectrometer at 400 MHz at 298° K, and the chemical shifts are given in parts per million (ppm) referenced to the residual proton signal of the deuterated solvents: CHCl$_3$ at δ=7.26 ppm and CH$_3$OH or CH$_3$OD at δ=3.30 ppm. LCMS spectra were taken on an Agilent Technologies 1260 Infinity or 6120 Quadrupole spectrometer. The mobile phase for the LC was acetonitrile (A) and water (B) with 0.01% formic acid, and the eluent gradient was from 5-95% A in 6.0 min, 60-95% A in 5.0 min, 80-100% A in 5.0 min and 85-100% A in 10 min using a SBC18 50 mm×4.6 mm× 2.7 μm capillary column. Mass spectra (MS) were measured by electrospray ion-mass spectroscopy (ESI). All temperatures are in degrees Celsius unless otherwise noted.

Analytical HPLC mass spectrometry conditions:

LC1: Column: SB-C18 50 mm×4.6 mm× 2.7 μm; Temperature: 50° C.; Eluent: 5:95 v/v acetonitrile/water+0.01% formic acid in 6 min; Flow Rate: 1.5 mL/min, Injection 5 μL; Detection: PDA, 200-600 nm; MS: mass range 150-750 amu; positive ion electrospray ionization.

LC2: Column: SB-C18 50 mm×4.6 mm× 2.7 μm; Temperature: 50° C.; Eluent: 5:95 to 95:5 v/v acetonitrile/water+ 0.05% TFA over 3.00 min; Flow Rate: 1.5 mL/min, Injection 5 μL; Detection: PDA, 200-600 nm; MS: mass range 150-750 amu; positive ion electrospray ionization.

LC3: Column: SB-C18 50 mm×4.6 mm× 2.7 μm; Temperature: 50° C.; Eluent: 10:90 to 98:2 v/v acetonitrile/ water+0.05% TFA over 3.75 min; Flow Rate: 1.0 mL/min, Injection 10 μL; Detection: PDA, 200-600 nm; MS: mass range 150-750 amu; positive ion electrospray ionization.

List of Abbreviations

AcOH=acetic acid; Alk=alkyl; Ar=aryl; Boc=tert-butyloxycarbonyl; bs=broad singlet; CH$_2$Cl$_2$=dichloromethane; d=doublet; dd=doublet of doublets; DBU=1,8-diazabicyclo-[5.4.0]undec-7-ene; DCM=dichloromethane; DEAD=diethyl azodicarboxylate; DMF=N,N-dimethylformamide; DMSO=dimethyl sulfoxide; EA=ethyl acetate; ESI=electrospray ionization; Et=ethyl; EtOAc=ethyl acetate; EtOH=ethyl alcohol; h=hours; HOAc=acetic acid; LiOH=lithium hydroxide; m=multiplet; Me=methyl; MeCN=acetonitrile; MeOH=methyl alcohol; MgSO$_4$=magnesium sulfate; min=minutes; MS=mass spectroscopy; NaCl=sodium chloride; NaOH=sodium hydroxide; Na$_2$SO$_4$=sodium sulfate; NMR=nuclear magnetic resonance spectroscopy; PE=petroleum ether; PG=protecting group; Ph=phenyl; rt=room temperature; s=singlet; t=triplet; TFA=trifluoroacetic acid; THF=tetrahydrofuran; Ts=p-toluenesulfonyl (tosyl).

The compounds of the present invention can be prepared following general methods detailed below. In certain embodiments, provided herein are methods of making the tyrosine kinase inhibitor compounds described herein. In certain embodiments, compounds described herein are synthesized using the following synthetic schemes. In other embodiments, compounds are synthesized using methodologies analogous to those described below by the use of appropriate alterative starting materials. All key intermediates were prepared according to the following methods.

Example 1

(R)-1-(3-(1-(4-(2-fluoro-3-methoxyphenoxy)phenyl) imidazo[1,5-a]pyrazin-3-yl)piperidin-1-yl)prop-2-en-1-one (7)

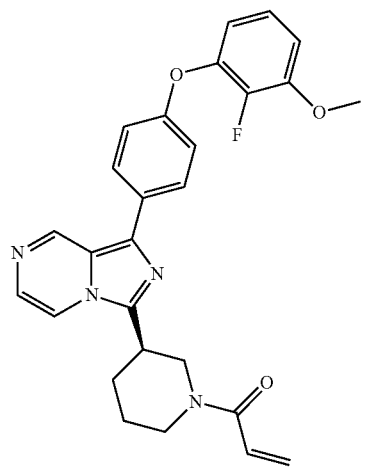 [SMILES: C=CC(=O)N1CCC[C@@H](c2nc(-c3ccc(Oc4cccc(OC)c4F)cc3)c3cnccn23)C1]

Scheme 1

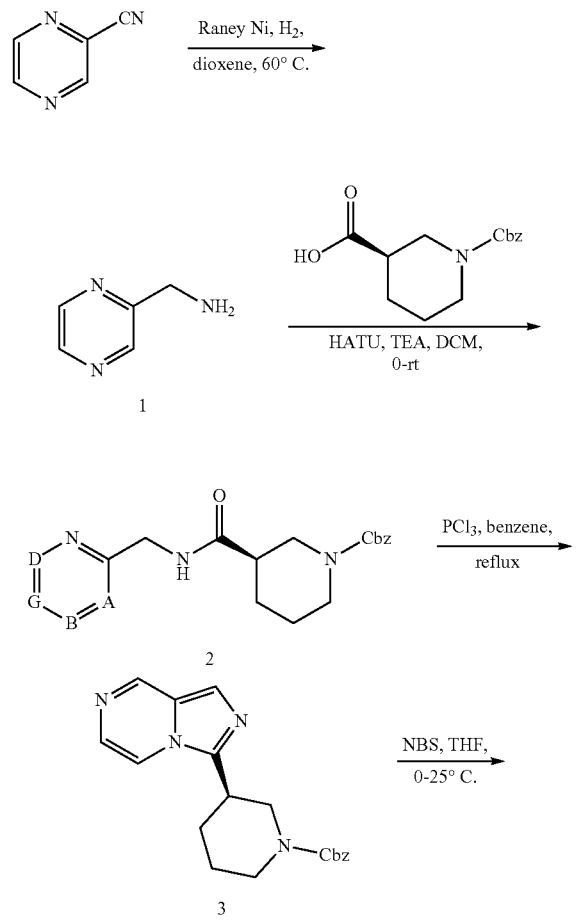

57

-continued

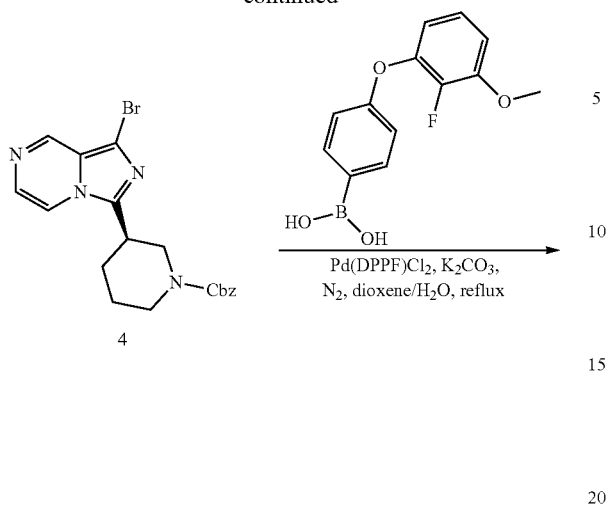

4

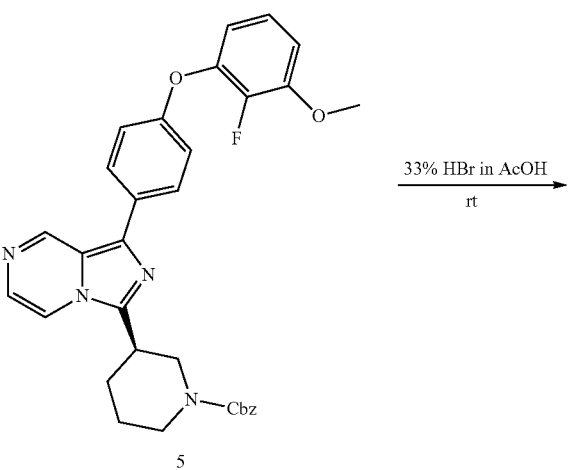

5

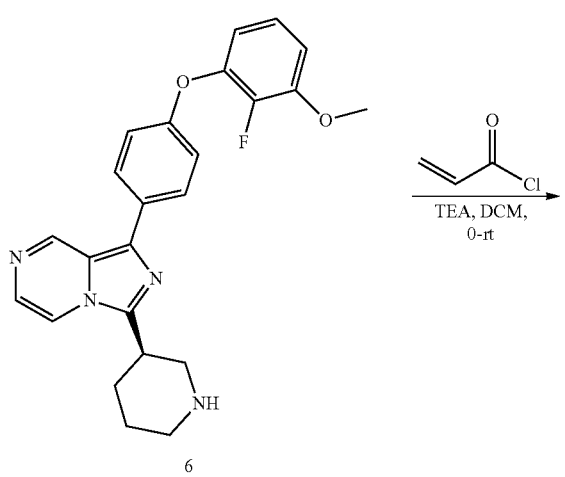

6

58

-continued

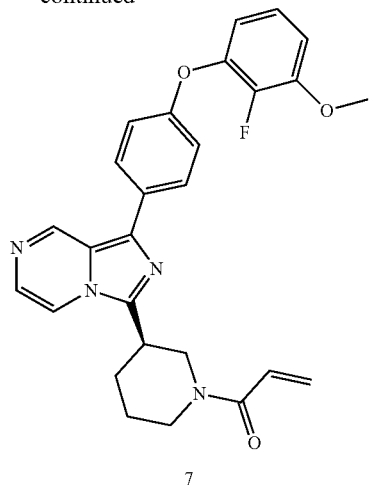

7

Step 1: Pyrazin-2-ylmethanamine (1)

Pyrazine-2-carbonitrile (19 g, 180 mmol) was dissolved in 1,4-dioxane (280 mL), and then Raney nickel (1.9 g) was added. The reaction mixture was reacted in hydrogen atmosphere at 60° C. for 48 hours. The mixture was filtered through Celite and the filtrate was concentrated under reduced pressure to obtain the title compound (1) (19 g, 98.9%) as a brown oil.

$^1$H NMR (400 MHz, DMSO-d$_6$): δ 871 (s, 1H), 8.54-8.53 (m, 2H), 8.48 (d, J=2.4 Hz, 1H), 3.86 (s, 2H), 1.97 (br, 2H).

Step 2: (R)-Benzyl 3-((pyrazin-2-ylmethyl)carbamoyl)piperidine-1-carboxylate (2)

To a solution of pyrazin-2-ylmethanamine (1, 5.0 g, 45.8 mmol), (R)-1-((benzyloxy)carbonyl)piperidine-3-carboxylic acid (12.6 g, 48.18 mmol) and HATU (20.8 g, 54.96 mmol) in dichloromethane (334 mL) was added TEA (25.4 mL, 183.2 mmol). The reaction mixture was stirred at 0° C. for 1 h and another 3 h at room temperature. The mixture was washed subsequently with 0.1 M HCl-solution, 5% NaHCO$_3$, water and brine. The organic layer was dried over anhydrous sodium sulfate and concentrated in vacuo. Purification by flash column chromatography on silica gel (D/M=100:1-25:1) gave 2 (14.5 g, 89.5%).

$^1$H NMR (400 MHz, CDCl$_3$): δ 8.58 (s, 1H), 8.49 (s, 1H), 7.36-7.28 (m, 5H), 5.17-5.12 (m, 2H), 4.60 (s, 1H), 4.01-3.93 (m, 2H), 3.26-3.21 (m, 2H), 2.41-2.39 (m, 1H), 1.95-1.79 (m, 4H).

Step 3: (R)-Benzyl-3-(imidazo[1,5-a]pyrazin-3-yl)piperidine-1-carboxylate (3)

A mixture of (R)-benzyl 3-((pyrazin-2-ylmethyl)carbamoyl)piperidine-1-carboxylate (2, 3.0 g, 8.47 mmol) and POCl$_3$ (4.2 mL) in benzene (15 mL) was refluxed for 2 h. The reaction was quenched by the addition of the water, and the mixture was made basic with sat. NaHCO$_3$. It was extracted with (DCM, 20 mL×3). The combined organic layers were washed with brine, dried over Na$_2$SO$_4$ and evaporated in vacuo. Purification by flash column chromatography on silica gel (D/M=100:1-50:1) gave 3 (0.4 g, 12.5%).

¹H NMR (400 MHz, CDCl₃): δ 8.84 (s, 1H), 7.65 (s, 1H), 7.30-7.26 (m, 1H), 7.25-7.19 (m, 6H), 5.22 (s, 2H), 5.14-5.08 (m, 2H), 4.36-4.21 (m, 2H), 3.05-2.86 (m, 3H), 2.18-2.10 (m, 2H), 1.96-1.90 (m, 1H), 1.83-1.80 (m, 1H). LCMS: m/z=337 [M+H]⁺.

Step 4: (R)-benzyl 3-(1-bromoimidazo[1,5-a]pyrazin-3-yl)piperidine-1-carboxylate (4)

To a solution of (R)-benzyl 3-(imidazo[1,5-a]pyrazin-3-yl)piperidine-1-carboxylate (3, 0.35 g, 1.04 mmol) in THF (6 mL) at 0° C., was added NBS (0.18 g, 1.04 mmol). The solution was stirred room temperature for 1 h. The reaction was quenched by the addition of water, and the mixture was made basic with sat. NaHCO₃. The mixture was extracted with (DCM, 20 mL×3). The combined organic layers were washed with brine, dried over Na₂SO₄ and evaporated in vacuo. Purification by flash column chromatography on silica gel (D/M=100:1-50:1) gave 4 (0.28 g, 63.8%).
¹H NMR (400 MHz, CDCl₃): δ 8.76 (s, 1H), 7.66-7.49 (m, 1H), 7.41-7.39 (m, 6H), 7.25-7.19 (m, 6H), 5.14-5.06 (m, 2H), 4.32-4.19 (m, 2H), 3.04-2.84 (m, 3H), 2.18-2.10 (m, 2H), 1.96-1.90 (m, 1H), 1.83-1.80 (m, 1H). LCMS: m/z=416, 417 [M+H]⁺.

Step 5: (R)-Benzyl 3-(1-(4-(2-fluoro-3-methoxyphenoxy)phenyl)imidazo[1,5-a]pyrazin-3-yl)piperidine-1-carboxylate (5)

A solution of (R)-benzyl 3-(1-bromoimidazo[1,5-a]pyrazin-3-yl)piperidine-1-carboxylate (4, 0.20 g, 0.48 mmol), (4-(2-fluoro-3-methoxyphenoxy)phenyl)boronic acid (0.16 g, 0.62 mmol), Pd(dppf)Cl₂ (35 mg, 0.048 mmol), and K₂CO₃ (0.13 g, 0.96 mmol) in dioxene/H₂O (=5/1, 6 mL) was heated to reflux for 5 h under nitrogen atmosphere. Water (10 mL) was added, and the mixture was extracted with EA (20 mL×3). The combined organic layers were washed with brine, dried over Na₂SO₄ and evaporated in vacuo. Purification by flash column chromatography on silica gel (D/M=50:1) gave 5 (0.21 g, 80.7%).
¹H NMR (400 MHz, CDCl₃): δ 9.07 (s, 1H), 7.76 (d, J=8 Hz, 2H), 7.41-7.39 (m, 6H), 7.03 (d, J=8 Hz, 2H), 6.96-6.92 (m, 1H), 6.74-6.70 (m, 1H), 6.63-6.60 (m, 1H), 5.14-5.06 (m, 2H), 4.32-4.19 (m, 2H), 3.04-2.84 (m, 3H), 2.18-2.10 (m, 2H), 1.96-1.90 (m, 1H), 1.83-1.80 (m, 1H). LCMS: m/z=553.1 [M+H]⁺.

Step 6: (R)-1-(4-(2-Fluoro-3-methoxyphenoxy)phenyl)-3-(piperidin-3-yl)imidazo[1,5-a]pyrazine (6)

A solution of (R)-benzyl 3-(1-(4-(2-fluoro-3-methoxyphenoxy)-phenyl)imidazo[1,5-a]pyrazin-3-yl)piperidine-1-carboxylate (5, 0.2 g, 0.36 mmol) in 33% HBr (in AcOH, 5 mL) was stirred at room temperature for 3 h. Water was added, and the mixture was extracted with EA (20 mL). The aqueous phase was neutralized using NH₃·H₂O, and then the mixture was extracted with DCM (10 mL×3). The combined organic layers were washed with brine, dried over Na₂SO₄ and evaporated in vacuo gave 6 (0.15 g, 99.3%). LCMS: m/z=419 [M+H]⁺.

Step 7: (R)-1-(3-(1-(4-(2-Fluoro-3-methoxyphenoxy)phenyl)imidazo[1,5-a]pyrazin-3-yl)piperidin-1-yl)prop-2-en-1-one (7)

A solution of acryloyl chloride (3.5 mg, 0.036 mmol) in DCM (1 mL) was added to a stirred solution of (R)-1-(4-(2-fluoro-3-methoxyphenoxy)phenyl)-3-(piperidin-3-yl)imidazo[1,5-a]pyrazine (6, 15 mg, 0.036 mmol), and TEA (0.1 mL) in DCM (5 mL) at 0° C. The reaction mixture was stirred for 1 h, and poured into brine. It was extracted with DCM. The organic layer was dried over Na₂SO₄ and evaporated in vacuo. Purification by TLC (D/M=20:1) gave 7 (7 mg, 41.4% 2 steps).
¹H NMR (400 MHz, CDCl₃): δ 9.16 (s, 1H), 7.85 (d, J=8 Hz, 2H), 7.54 (s, 1H), 7.11 (d, J=8 Hz, 2H), 7.03-7.01 (m, 1H), 6.75-6.72 (m, 1H), 6.71-6.68 (m, 2H), 6.39-6.28 (m, 1H), 5.71-5.69 (m, 1H), 4.91-4.88 (m, 1H), 4.70-4.68 (m, 0.5H), 4.22-4.20 (m, 0.5H), 4.12-4.09 (m, 1H), 3.93 (s, 3H), 3.28-3.18 (m, 2H), 2.97-2.91 (m, 1H), 2.34-2.28 (m, 2H), 2.02-1.93 (m, 2H). LCMS: m/z=553.1 [M+H]⁺.

Example 2

(R,E)-2-(3-(1-(4-(2-Fluoro-3-methoxyphenoxy)phenyl)imidazo[1,5-a]pyrazin-3-yl)piperidine-1-carbonyl)-4,4-dimethylpent-2-enenitrile (9)

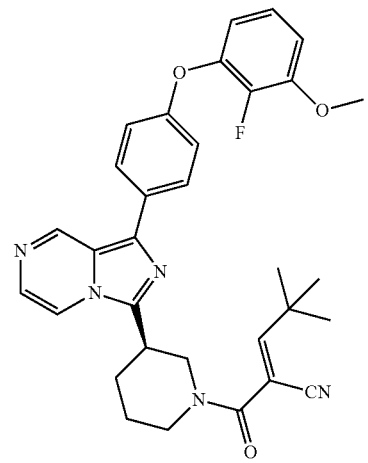 [SMILES: COc1cccc(Oc2ccc(-c3nc([C@@H]4CCCN(C(=O)/C(C#N)=C/C(C)(C)C)C4)n4ccncc34)cc2)c1F]

Scheme 2

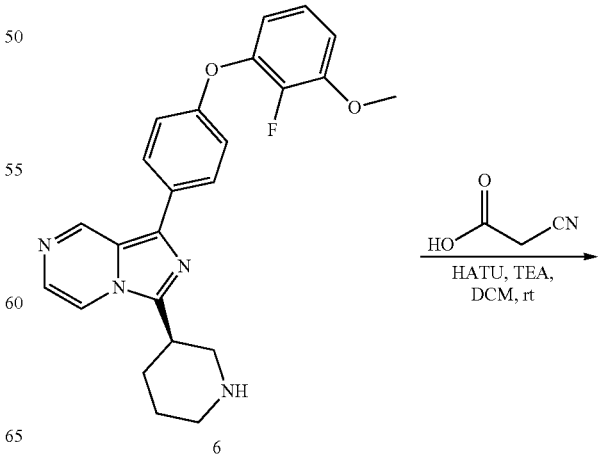

6

-continued

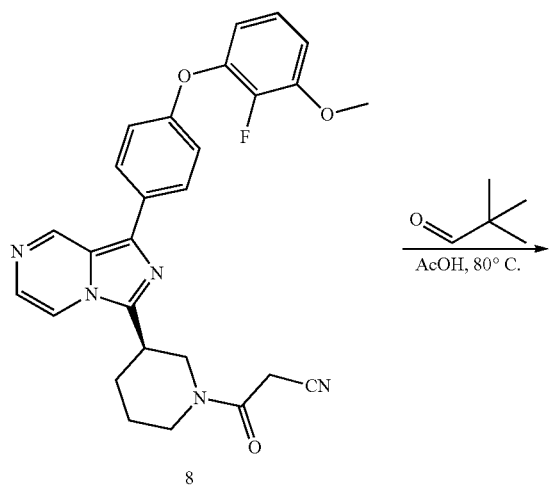

8

Step 1: (R)-3-(3-(1-(4-(2-Fluoro-3-methoxyphenoxy)phenyl)imidazo[1,5-a]pyrazin-3-yl)piperidin-1-yl)-3-oxopropanenitrile (8)

To a solution of (R)-1-(4-(2-fluoro-3-methoxyphenoxy)phenyl)-3-(piperidin-3-yl)imidazo[1,5-a]pyrazine (6.50 mg, 0.11 mmol), 2-cyanoacetic acid (14.5 mg, 0.17 mmol) and HATU (68 mg, 0.17 mmol) in dichloromethane (4 mL) was added TEA (44.4 mg, 0.44 mmol) and the reaction mixture was stirred at room temperature for 3 h. The organic layer was dried over anhydrous sodium sulfate and concentrated in vacuo. Purification by TLC (D/M=20:1) gave 8 (20 mg, 37.7%). LCMS: m/z=486 [M+H]$^+$.

Step 2: (R,E)-2-(3-(1-(4-(2-Fluoro-3-methoxyphenoxy)phenyl)imidazo[1,5-a]pyrazin-3-yl)piperidine-1-carbonyl)-4,4-dimethylpent-2-enenitrile (9)

A solution of (R)-3-(3-(1-(4-(2-fluoro-3-methoxyphenoxy)phenyl)imidazo[1,5-a]pyrazin-3-yl)piperidin-1-yl)-3-oxopropanenitrile (6, 10 mg, 0.02 mmol) and pivalaldehyde (0.17 mL) in acetic acid (2 mL) was stirred at 80° C. for 6 h. Water was added, and the mixture was extracted with EA (10 mL×3). The combined organic layers were washed with brine, dried over Na$_2$SO$_4$ and evaporated in vacuo. Purification by TLC (D/M=20:1) gave 9 (2.5 mg, 22.7%). LCMS: m/z=554 [M+H]$^+$.

Example 3

(R)-2-(3-(1-(4-(2-fluoro-3-methoxyphenoxy)phenyl)imidazo[1,5-a]pyrazin-3-yl)piperidin-1-yl)-2-oxoacetamide (11)

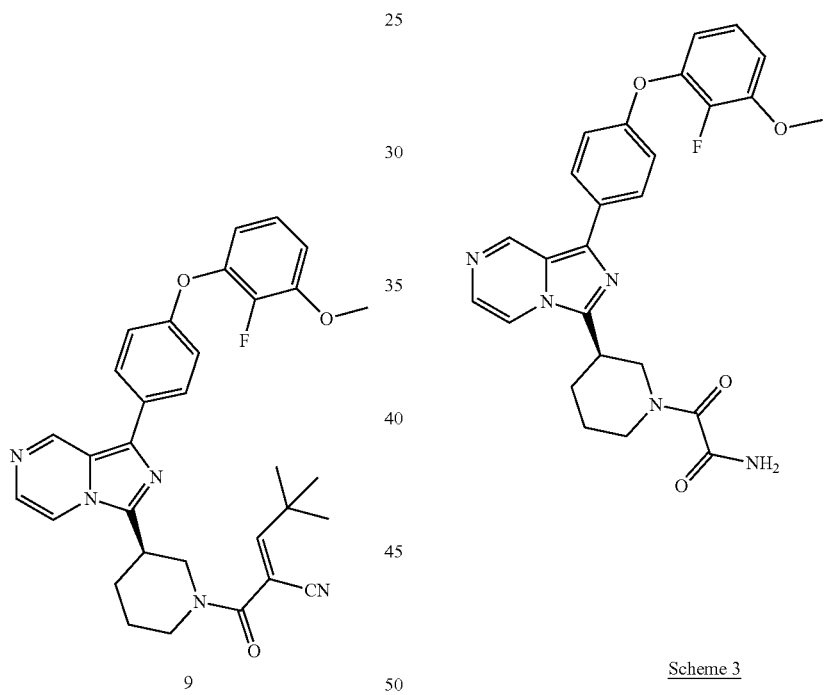

Scheme 3

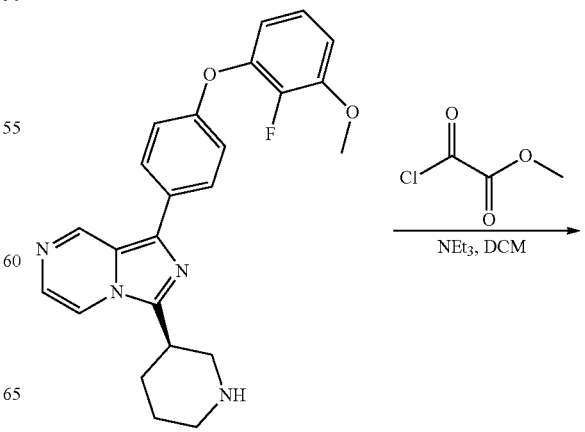

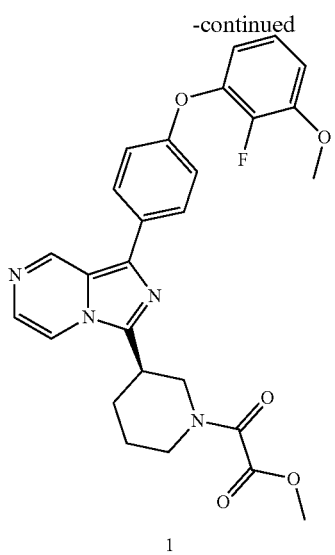

1

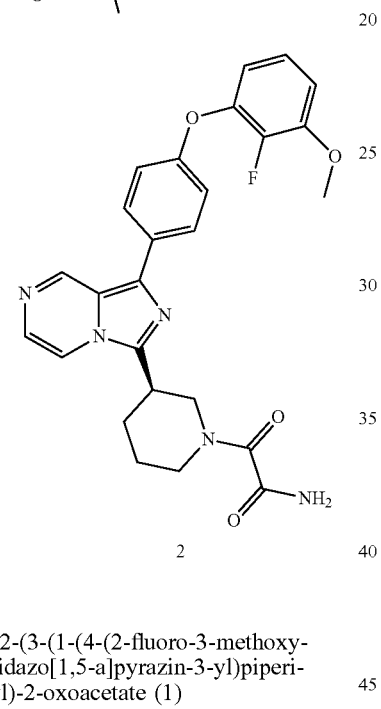

2

Step 1: (R)-Methyl 2-(3-(1-(4-(2-fluoro-3-methoxyphenyl)imidazo[1,5-a]pyrazin-3-yl)piperidin-1-yl)-2-oxoacetate (1)

To the solution of (S)-1-(4-(2-fluoro-3-methoxyphenoxy)phenyl)-3-(piperidin-3-yl)imidazo[1,5-a]pyrazine (crude, 0.12 mmol 1.0 eq) in DCM (5.0 mL) was added triethylamine (24 mg, 0.024 mmol). Then methyl 2-chloro-2-oxoacetate (18 mg, 0.12 mmol, 1.2 eq) was added dropwise under ice water bath and the mixture was stirred for 1 h. The mixture was quenched with MeOH and the mixture was evaporated to dryness to give the crude product. LCMS: m/z=505 [M+H]$^+$.

Step 2: (R)-2-(3-(1-(4-(2-Fluoro-3-methoxyphenoxy)phenyl)imidazo[1,5-a]pyrazin-3-yl)piperidin-1-yl)-2-oxoacetamide (2)

Compound 1 (10 mg, 0.02 mmol) was dissolved in NH$_3$/MeOH (7 M, 5.0 mL) and stirred at room temperature for 2 h. The solvent was removed and the residue was purified by prep-TLC to afford the titled product (8.3 mg, 80%).

$^1$H NMR (400 MHz, CDCl$_3$): δ 9.08 (s, 1H), 7.98-7.97 (m, 1H), 7.77-7.75 (m, 2H), 7.51-7.49 (m, 1H), 7.06-6.93 (m, 4H), 6.74-6.60 (m, 2H), 5.84 (s, 1H), 4.77-4.75 (m, 1H), 4.45-4.42 (m, 1H), 3.85 (s, 3H), 3.36-3.27 (m, 2H), 2.88-2.79 (m, 1H), 2.22-2.16 (m, 2H), 1.96-1.92 (m, 1H), 1.69-1.60 (m, 1H). LCMS: m/z=490 [M+H]$^+$.

Example 4

(S)-1-(2-(1-(6-Phenoxypyridin-3-yl)imidazo[1,5-a]pyrazin-3-yl)pyrrolidin-1-yl)prop-2-en-1-one (4)

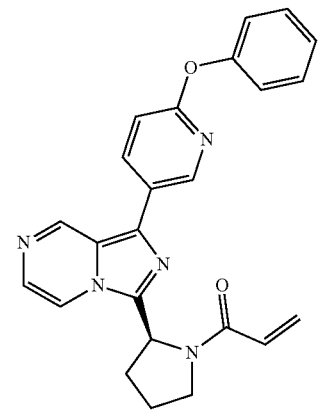 [SMILES: C=CC(=O)N1CCC[C@H]1c1nc(-c2ccc(Oc3ccccc3)nc2)c2cnccn12]

Scheme 4

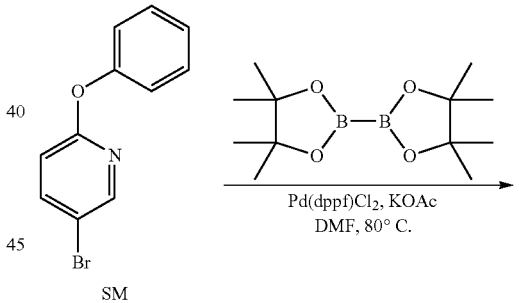

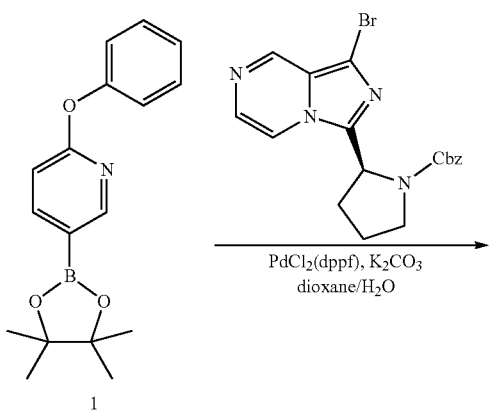

1

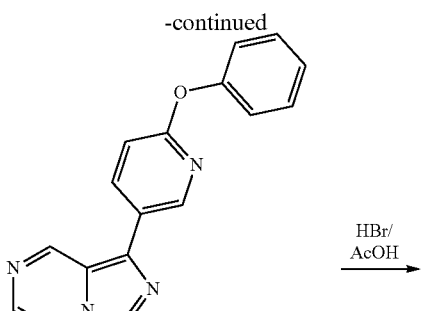

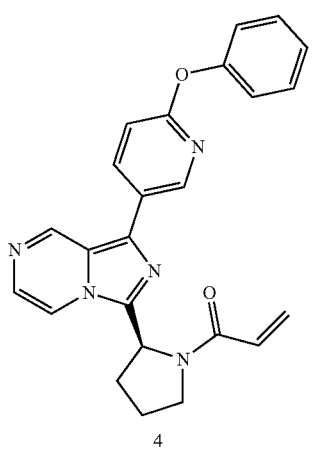 [SMILES: C=CC(=O)N1CCC[C@H]1c1nc(-c2ccc(Oc3ccccc3)nc2)c2cnccn12]

Step 1: 2-Phenoxy-5-(4,4,5,5-tetramethyl-1,3,2-dioxaborolan-2-yl)pyridine (1)

The suspension of SM (1.4 g, 5.6 mmol), 4,4,4',4',5,5,5',5'-octamethyl-2,2'-bi(1,3,2-dioxaborolane) (1.7 g, 6.7 mmol), PdCl$_2$(dppf) (245 mg, 0.3 mmol), and potassium acetate (1.6 g, 16.8 mmol) in DMF (20 mL) was stirred at 80° C. for 20 h. The mixture was then cooled to room temperature, diluted with water and extracted with EA. The combined organic layers were washed with water, brine, and dried over anhydrous sodium sulfate. The solvent was removed in vacuum and the residue was purified by silica gel column chromatography (PE) to afford the desired product (414 mg, yield 25%).

Step 2: (S)-benzyl-2-(1-(5-phenoxypyridin-2-yl)imidazo[1,5-a]pyrazin-3-yl)pyrrolidine-1-carboxylate (2)

The mixture of 1 (111 mg, 0.38 mmol), (S)-benzyl 2-(1-bromoimidazo[1,5-a]pyrazin-3-yl)pyrrolidine-1-carboxylate (100 mg, 0.25 mmol), PdCl$_2$(dppf) (15 mg), and potassium carbonate (69 mg, 0.50 mmol) in DMF (10 mL) was stirred at 80° C. for 21 h. The mixture was then cooled to room temperature, diluted water and extracted with EA. The combined organic layers were washed with water, brine, and dried over anhydrous sodium sulfate. The solvent was removed in vacuum and the residue was purified by silica gel column chromatography (PE/EA=10:1-6:1) to give the desired product (74 mg, yield 60%).

$^1$H NMR (400 MHz, CDCl$_3$): δ 9.05 (d, J=41.2 Hz, 1H), 8.69 (d, J=21.6 Hz, 1H), 8.28-8.17 (m, 1H), 7.66 (dd, J=12.0, 7.6 Hz, 1H), 7.57-7.53 (m, 1H), 7.50-7.38 (m, 4H), 7.25-7.15 (m, 4H), 7.15-7.09 (m, 1H), 7.05-7.00 (m, 1H), 6.88 (d, J=6.4 Hz, 1H), 5.35-5.20 (s, 1H), 5.18-4.96 (m, 2H), 3.83-3.59 (m, 2H), 2.68-2.4 (m, 2H), 2.15-2.00 (m, 2H). LCMS: m/z=492 [M+H]$^+$.

Step 3: (S)-1-(4-(Pyridin-3-yloxy)phenyl)-3-(pyrrolidin-2-yl)imidazo[1,5-a]pyrazine (3)

A mixture of 2 (68 mg, 0.14 mmol, 1.0 eq) in DCM (2.0 mL) and 33% HBr/acetic acid (2.0 mL) was stirred at room temperature (20° C.) for 0.5 h. It was then diluted with water, and extracted with DCM. The pH of aqueous phase was adjusted to 8 with ammonium hydroxide. The mixture was extracted with DCM. The combined organic layers were washed with water, brine, and dried over Na$_2$SO$_4$. The solution was filtered and the solvent was removed by rotary evaporation to give crude 3 (36 mg). LCMS: m/z=358 [M+H]$^+$.

Step 4: (S)-1-(2-(1-(4-(Pyridin-3-yloxy)phenyl)imidazo[1,5-a]pyrazin-3-yl)pyrrolidin-1-yl)prop-2-en-1-one (4):

To a solution of 3 (18 mg, 0.05 mmol) and TEA (0.05 mL) in DCM (20 mL), was added acryloyl chloride (5.0 mg, 0.05 mmol). The mixture was stirred at 10° C. for 10 min, and then the mixture solution was quenched with methanol (2.0 mL). The residue was purified with prep-TLC to give 4 (8.3 mg, 40%).

$^1$H NMR (400 MHz, CDCl$_3$): δ 9.09 (s, 1H), 8.71 (d, J=2.0 Hz, 1H), 8.35 (d, J=4.0 Hz, 1H), 8.20 (dd, J=8.4, 2.4 Hz, 1H), 7.59 (d, J=4.8 Hz, 1H), 7.42 (t, J=8.0 Hz, 2H), 7.24-7.15 (m, 3H), 7.02 (d, J=8.4 Hz, 1H), 6.45 (dd, J=16.4, 10.0 Hz, 1H), 6.32 (dd, J=16.8, 2.0 Hz, 1H), 5.68 (dd, J=10.0, 1.6 Hz, 1H), 5.53 (dd, J=8.0, 3.2 Hz, 1H), 3.95-3.84 (m, 1H), 3.75 (t, J=8.5 Hz, 1H), 2.88-2.73 (m, 1H), 2.61-2.44 (m, 1H), 2.42-2.24 (m, 1H), 2.19 (dd, J=7.2, 4.8 Hz, 1H). LCMS: m/z=412 [M+H]$^+$.

Example 5

(S)-1-(2-(1-(4-(2-Fluoro-3-methoxyphenoxy)phenyl)-8-methylimidazo[1,5-a]pyrazin-3-yl)piperidin-1-yl)but-2-yn-1-one (5)

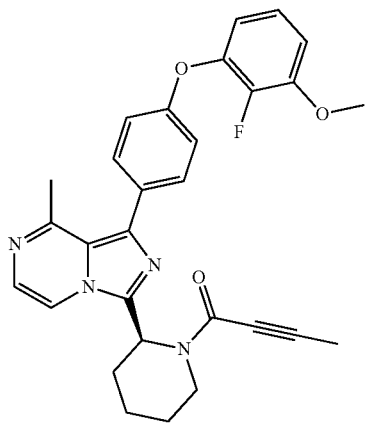 [SMILES: CC#CC(=O)N1CCCC[C@H]1c1nc(-c2ccc(Oc3cccc(OC)c3F)cc2)c2c(C)nccn12]

Scheme 5

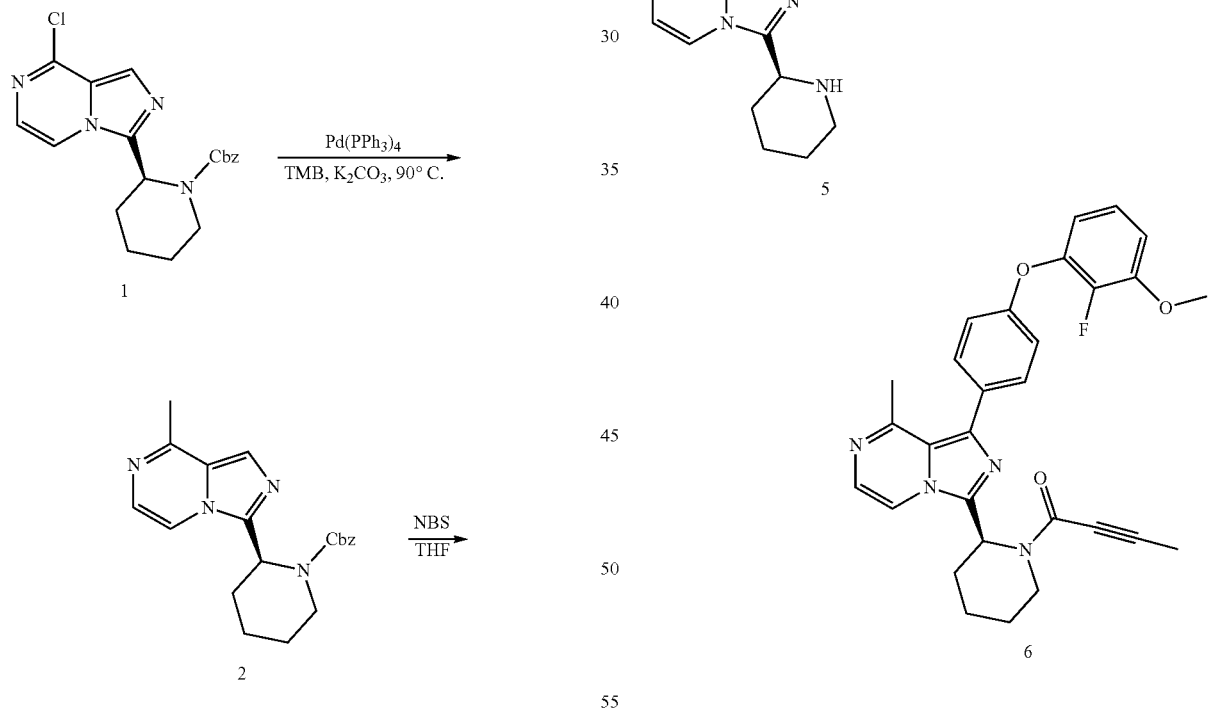

Step 1: Benzyl (S)-2-(8-methylimidazo[1,5-a]pyrazin-3-yl)piperidine-1-carboxylate (2)

A mixture of 1 (220 mg, 0.59 mmol, 1.0 eq), TMB (148 mg, 1.19 mmol, 2 eq), Pd(PPh$_3$)$_4$ (68 mg, 0.059 mmol, 0.1 eq), and potassium carbonate (164 mg, 1.19 mmol, 2.0 eq) in DMF (5 mL) was stirred at 90° C. overnight. Water was added and the mixture was extracted with EA. The combined organic layers were washed with water and brine. The solution was dried over anhydrous Na$_2$SO$_4$, filtered and concentrated. The residue was purified by silica gel column chromatography (DCM/MeOH=200:1-50:1) to give the desired product 2 (145 mg, yield=70%). LCMS: m/z=351 [M+H]⁺.

Step 2: Benzyl (S)- -2-(I-bromo-8-methylimidazo[1,5-a]pyrazin-3-yl)piperidine-1-carboxylate (3)

To a solution of 3 (145 mg, 0.41 mmol, 1.0 eq) in THF (2.5 mL) at 0° C., was added NBS (74 mg, 0.41 mmol, 1 eq). The mixture was stirred at 25° C. for 2 h. The mixture was diluted with water and the mixture was extracted with EA. The combined organic layers were washed with sodium bicarbonate, water and brine. The organic phase was dried over Na₂SO₄, and filtered. The solvent was removed by rotary evaporation. The residue was purified with silica gel column chromatography (DCM/MeOH=100:1-50:1) to give 3 (110 mg, yield 63%).

¹H NMR (400 MHz, CDCl₃): δ 7.84 (s, 1H), 7.36 (s, 5H), 5.76 (s, 1H), 5.19 (s, 2H), 4.12 (dd, J=13.4, 6.6 Hz, 1H), 3.99 (d, J=12.7 Hz, 1H), 2.89 (s, 3H), 2.73 (t, J=12.9 Hz, 1H), 2.46 (d, J=12.5 Hz, 1H), 2.35 (d, J=12.9 Hz, 1H), 2.05 (s, 1H), 1.97 (d, J=12.9 Hz, 1H), 1.79 (d, J=12.7 Hz, 1H), 1.71 (d, J=12.6 Hz, 1H), 1.54 (d, J=12.7 Hz, 1H). LCMS: m/z=429 [M+H]⁺.

Step 3: Benzyl (S)- -2-(1-(4-(2-fluoro-3-methoxyphenoxy)phenyl)-8-methylimidazo[1,5-a]pyrazin-3-yl)piperidine-1-carboxylate (4)

A mixture of 3 (110 mg, 0.26 mmol, 1.0 eq), (4-(2-fluoro-3-methoxyphenoxy)phenyl)boronic acid (101 mg, 0.39 mmol, 1.5 eq), PdCl₂(dppf) (19 mg, 0.026 mmol, 0.1 eq), and potassium carbonate (72 mg, 0.52 mmol, 2.0 eq) in dioxane (10.0 mL) and water (2.0 mL) was heated to reflux overnight. The mixture was allowed to cool to room temperature. Water was added and the mixture was extracted with EA. The combined organic layers were washed with water and brine. The organic phase was dried over anhydrous Na₂SO₄, filtered and concentrated. The residue was purified by silica gel column chromatography (DCM/MeOH=100:1) to give the desired product 4 (105 mg, yield 71.4%).

¹H NMR (400 MHz, CDCl₃): δ 7.83 (s, 1H), 7.51 (d, J=8.1 Hz, 2H), 7.37 (s, 5H), 7.05 (t, J=11.0 Hz, 3H), 6.81 (t, J=7.5 Hz, 1H), 6.72 (t, J=7.3 Hz, 1H), 5.85 (s, 1H), 5.22 (s, 2H), 4.12 (q, J=7.0 Hz, 3H), 4.01 (d, J=12.5 Hz, 1H), 3.93 (s, 3H), 2.80 (t, J=12.5 Hz, 1H), 2.66-2.35 (m, 5H), 2.01 (d, J=27.9 Hz, 5H), 1.79 (d, J=12.5 Hz, 2H), 1.70 (d, J=12.4 Hz, 1H), 1.56 (d, J=12.2 Hz, 1H). LCMS: m/z=567 [M+H]⁺.

Step 4: (S)-1-(4-(2-Fluoro-3-methoxyphenoxy)phenyl)-8-methyl-3-(piperidin-2-yl)imidazo[1,5-a]pyrazine (5)

A solution of 4 (105 mg, 0.19 mmol, 1.0 eq) in HBr/acetic acid (2.0 mL) was stirred at room temperature (22° C.) for 2 h. The solution was diluted with water, and the pH was adjusted to 7 with 2.0 M sodium hydroxide. The mixture was extracted with DCM, and the combined organic layers were washed with water and brine. The solution was dried over Na₂SO₄, filtered and concentrated to give crude 5 (82 mg, yield 100%). LCMS: m/z=433 [M+H]⁺.

Step 5: (S)-1-(2-(1-(4-(2-Fluoro-3-methoxyphenoxy)phenyl)-8-methylimidazo[1,5-a]pyrazin-3-yl)piperidin-1-yl)but-2-yn-1-one (6)

To a solution of 5 (25 mg, 0.06 mmol, 1.0 eq) and TEA (9 mg, 0.09 mmol, 1.5 eq) in DCM (2.0 mL), were added but-2-ynoic acid (5 mg, 0.06 mmol, 1.0 eq) and HATU (27 mg, 0.07 mmol, 1.2 eq). The mixture was stirred at room temperature (25° C.) for 1 h, and then the mixture solution was diluted with water. The mixture was extracted with DCM. The organic layer was washed with water and brine. It was dried over Na₂SO₄, filtered and concentrated. The residue was purified with prep-TLC to give 6 (5 mg, yield 16.7%).

¹H NMR (400 MHz, CDCl₃): δ 7.94 (s, 1H), 7.49 (t, J=22.0 Hz, 3H), 7.06 (t, J=11.5 Hz, 4H), 6.81 (t, J=7.3 Hz, 1H), 6.73 (t, J=7.1 Hz, 1H), 6.24 (d, J=3.9 Hz, 1H), 4.21 (d, J=11.1 Hz, 1H), 3.94 (s, 3H), 3.02 (t, J=13.1 Hz, 1H), 2.68 (dd, J=30.6, 12.2 Hz, 2H), 2.02 (s, 3H), 1.96 (d, J=13.8 Hz, 1H), 1.83 (d, J=11.0 Hz, 2H), 1.72-1.54 (m, 3H). LCMS: m/z=499 [M+H]⁺.

Example 6

(S)-1-(2-(1-(4-(2-Fluoro-3-methoxyphenoxy)phenyl)imidazo[1,5-a]pyrazin-3-yl)piperidin-1-yl)prop-2-en-1-one (6)

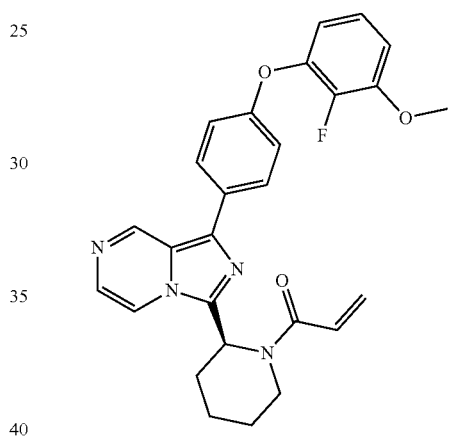

Scheme 6

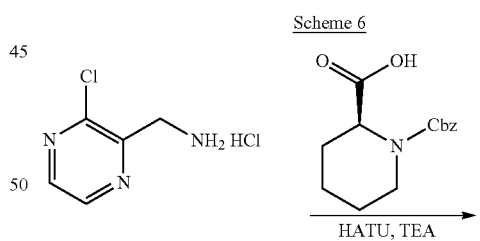

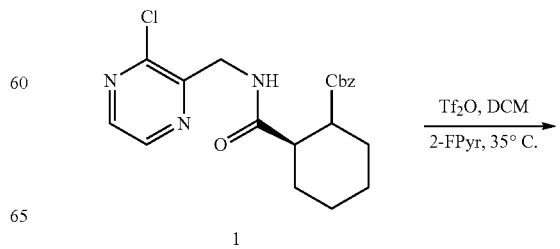

1

-continued

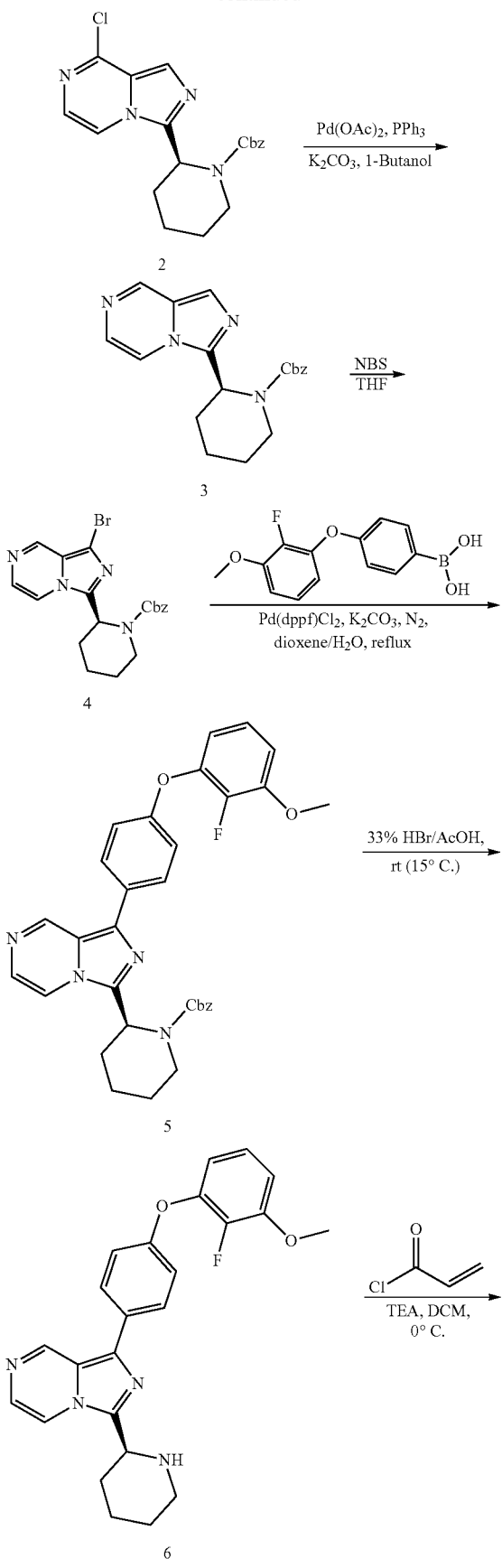

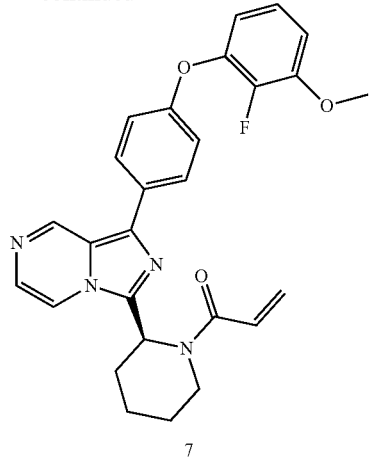 [SMILES: CC#CC(=O)N1CCCC[C@H]1c1nc(-c2ccc(Oc3cccc(OC)c3F)cc2)c2c(C)nccn12]

7

Step 1: (S)-Benzyl-2-(((3-chloropyrazin-2-yl)methyl)carbamoyl)piperidine-1-carboxylate (1)

To a mixture of (3-chloropyrazin-2-yl)methanamine hydrochloride (3.9 g, 21.8 mmol, 1 eq) and (S)-1-((benzyloxy)carbonyl)piperidine-2-carboxylic acid (5.73 g, 21.8 mmol, 1.0 eq) in DCM (50 mL), was added TEA (12.1 mL, 87.2 mmol, 4.0 eq). The reaction mixture was cooled to 0° C. After 10 min, HATU (9.94 g, 26.2 mmol, 1.2 eq) was added, and the reaction mixture was stirred at 0° C. for 1 h and then at room temperature overnight. The mixture was washed subsequently with 0.1 M HCl-solution, 5% NaHCO$_3$, water and brine. It was dried over anhydrous Na$_2$SO$_4$, filtered and concentrated. The residue was purified by silica gel column chromatography (DCM/MeOH=200:1-50:1) to afford the desired product 1 (7.13 g, yield 84.4%). LCMS: m/z=389 [M+H]$^+$.

Step 2: (S)-Benzyl-2-(8-chloroimidazo[1,5-a]pyrazin-3-yl)piperidine-1-carboxylate (2)

To a solution of compound 1 (1.0 g, 2.58 mmol, 1.0 eq) in DCM (6 mL), was added 2-fluoropyridine (276 mg, 2.84 mmol, 1.1 eq), followed by addition of Tf$_2$O (874 mg, 3.1 mmol) dropwise. The reaction mixture was stirred at 35° C. overnight. The reaction mixture was poured to H$_2$O, and the mixture was extracted with EA. The combined organic layers were washed with water and brine. The solution was dried over Na$_2$SO$_4$, filtered and concentrated. The residue was purified by silica gel column chromatography (DCM/MeOH=100:1-50:1) to give the desired product 2 (556 mg, yield 59%).

$^1$H NMR (400 MHz, CDCl$_3$): δ 7.93 (s, 1H), 7.79 (s, 1H), 7.36 (s, 5H), 7.19 (s, 1H), 5.82 (s, 1H), 5.19 (s, 2H), 4.01 (d, J=13.1 Hz, 1H), 2.70 (t, J=12.8 Hz, 1H), 2.42 (dd, J=30.5, 13.2 Hz, 2H), 2.01 (dd, J=23.4, 9.9 Hz, 1H), 1.83 (d, J=13.1 Hz, 1H), 1.76-1.44 (m, 3H). LCMS: m/z=371 [M+H]$^+$.

Step 3: (S)-Benzyl-2-(imidazo[1,5-a]pyrazin-3-yl)piperidine-1-carboxylate (3)

To a mixture of compound 2 (129 mg, 0.25 mmol, 1.0 eq), triphenylphosphine (18 mg, 0.07 mmol, 0.2 eq), Pd(OAc)$_2$ (8 mg, 0.035 mmol, 0.1 eq), and potassium carbonate (72 mg, 0.52 mmol, 2.0 eq) was added n-butyl alcohol (5 mL). The reaction mixture was stirred under reflux for 1 h, and then it was allowed to cool to room temperature. The mixture was filtered and concentrated. Water was added and the mixture was extracted with EA. The organic layer was washed with water and brine. The solution was dried over anhydrous $Na_2SO_4$, filtered and concentrated. The residue was purified by silica gel column chromatography (DCM/MeOH=200:1-50:1) to give product 3 (87 mg, yield=75%).

$^1$H NMR (400 MHz, CDCl$_3$): δ 8.93 (s, 1H), 7.97 (s, 1H), 7.75 (s, 1H), 7.37 (s, 5H), 5.85 (s, 1H), 5.20 (s, 2H), 4.01 (d, J=13.0 Hz, 1H), 2.70 (t, J=12.3 Hz, 1H), 2.44 (dd, J=33.6, 13.3 Hz, 2H), 1.98 (d, J=13.0 Hz, 1H), 1.83 (d, J=12.9 Hz, 1H), 1.71 (d, J=12.4 Hz, 1H), 1.64-1.48 (m, 1H). LCMS: m/z=337 [M+H]$^+$.

Step 4: (S)-Benzyl-2-(I-bromoimidazo[1,5-a]pyrazin-3-yl)piperidine-1-carboxylate (4)

To a solution of compound 3 (69 mg, 0.2 mmol, 1.0 eq) in THF (1.5 mL), was added NBS (36 mg, 0.2 mmol, 1 eq) at 0° C. The mixture was stirred at 25° C. for 1 h, and then the mixture was diluted with water. It was extracted with EA. The organic layer was washed with sodium bicarbonate, water and brine. The solution was dried over $Na_2SO_4$, filtered and concentrated. The residue was purified with silica gel column chromatography (DCM/MeOH=100:1-50:1) to give 4 (60 mg, yield 75%).

$^1$H NMR (400 MHz, CDCl$_3$): δ 8.85 (s, 1H), 7.92 (s, 1H), 7.36 (s, 5H), 5.80 (s, 1H), 5.19 (s, 2H), 4.00 (d, J=13.4 Hz, 1H), 2.72 (dd, J=18.9, 7.5 Hz, 1H), 2.41 (dd, J=41.3, 13.3 Hz, 2H), 2.09-1.87 (m, 1H), 1.76 (dd, J=36.0, 13.0 Hz, 3H), 1.55 (dd, J=25.9, 12.9 Hz, 1H). LCMS: m/z=415 [M+H]$^+$.

Step 5: (S)-Benzyl-2-(1-(4-(2-fluoro-3-methoxyphenoxy)phenyl)imidazo[1,5-a]pyrazin-3-yl)piperidine-1-carboxylate (5)

A mixture of 4 (60 mg, 0.15 mmol, 1.0 eq), (4-(2-fluoro-3-methoxyphenoxy)phenyl)boronic acid (57 mg, 0.22 mmol, 1.5 eq), PdCl$_2$(dppf) (11 mg, 0.015 mmol, 0.1 eq), and potassium carbonate (40 mg, 0.29 mmol, 2.0 eq) in dioxane (5.0 mL) and water (1.0 mL) was stirred under reflex overnight. The mixture was allowed to cool to room temperature. Water was added and the mixture was extracted with EA. The organic layer was washed with water and brine. The solution was dried over anhydrous $Na_2SO_4$, filtered and concentrated. He residue was purified by silica gel column chromatography (DCM/MeOH=100:1) to give the desired product 5 (66 mg, yield 82.5%).

$^1$H NMR (400 MHz, CDCl$_3$): δ 9.17 (s, 1H), 7.90 (d, J=7.1 Hz, 3H), 7.37 (s, 5H), 7.12 (d, J=7.1 Hz, 2H), 7.03 (t, J=8.2 Hz, 1H), 6.80 (t, J=7.4 Hz, 1H), 6.71 (t, J=6.9 Hz, 1H), 5.84 (s, 1H), 5.20 (s, 2H), 4.12 (d, J=5.6 Hz, 1H), 4.02 (d, J=12.7 Hz, 1H), 3.93 (s, 3H), 2.83 (t, J=13.0 Hz, 1H), 2.61 (s, 1H), 2.42 (d, J=12.5 Hz, 1H), 2.02 (d, J=17.3 Hz, 2H), 1.82 (d, J=12.5 Hz, 1H), 1.73 (d, J=9.0 Hz, 2H), 1.58 (d, J=12.0 Hz, 1H). LCMS: m/z=553 [M+H]$^+$.

Step 6: (S)-1-(4-(2-Fluoro-3-methoxyphenoxy)phenyl)-3-(piperidin-2-yl)imidazo[1,5-a]pyrazine (6)

Compound 5 (66 mg, 0.12 mmol, 1.0 eq) was mixed with HBr/acetic acid (2.0 mL), and the mixture was stirred at room temperature (22° C.) for 2 h. Water was added and the pH of solution was adjusted to 7 with 2.0 M sodium hydroxide. The mixture was extracted with DCM. The organic layer was washed with water and brine. The solution was dried over $Na_2SO_4$, filtered and concentrated to give the desired product 6 (50 mg, yield 100%). LCMS: m/z=419 [M+H]$^+$.

Step 7: (S)-1-(2-(1-(4-(2-Fluoro-3-methoxyphenoxy)phenyl)imidazo[1,5-a]pyrazin-3-yl)piperidin-J-yl)prop-2-en-1-one (7)

To a solution of compound 6 (25 mg, 0.06 mmol, 1.0 eq) and TEA (9 mg, 0.09 mmol, 1.5 eq) in DCM (2.0 mL), was added acryloyl chloride (6 mg, 0.0 6 mmol, 1 eq). The mixture was stirred at 15° C. for 20 min. The mixture was diluted with water and extracted with DCM. The organic layer was washed with water and brine. The solution was dried over $Na_2SO_4$, filtered and concentrated. The residue was purified with prep-TLC to give the desired product 7 (6 mg, yield 21.4%).

$^1$H NMR (400 MHz, CDCl$_3$): δ 9.19 (s, 1H), 8.10 (s, 1H), 7.91 (d, J=7.8 Hz, 2H), 7.50 (s, 1H), 7.12 (d, J=7.8 Hz, 2H), 7.03 (d, J=7.5 Hz, 1H), 6.81 (t, J=7.4 Hz, 1H), 6.72 (d, J=6.7 Hz, 1H), 6.67-6.51 (m, 1H), 6.38 (d, J=16.0 Hz, 2H), 5.77 (d, J=10.4 Hz, 1H), 3.94 (s, 3H), 3.78 (d, J=13.0 Hz, 1H), 3.09 (t, J=12.8 Hz, 1H), 2.81 (s, 1H), 2.47 (d, J=12.9 Hz, 1H), 2.02 (s, 1H), 1.84 (d, J=12.1 Hz, 2H), 1.76-1.50 (n, 3H). LCMS: m/z=473 [M+H]$^+$.

Examples 7 to 34 were prepared following the procedures described above from Examples 1 to 6:

| Entry | Structure | MS (cald.) [M + H]$^+$/ MS (found) | name |
|---|---|---|---|
| 7 | 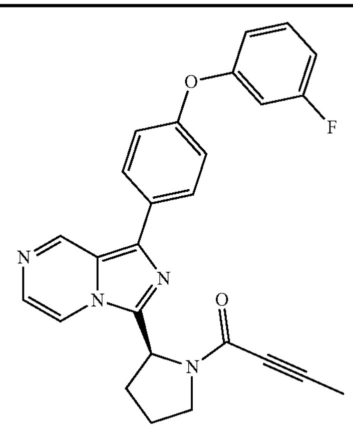 | 441.16/ 441.2 | (S)-1-(2-(1-(4-(3-fluorophenoxy)phenyl)imidazo[1,5-a]pyrazin-3-yl)pyrrolidin-1-yl)but-2-yn-1-one |

-continued

| Entry | Structure | MS (cald.) [M + H]+/ MS (found) | name |
|---|---|---|---|
| 8 | 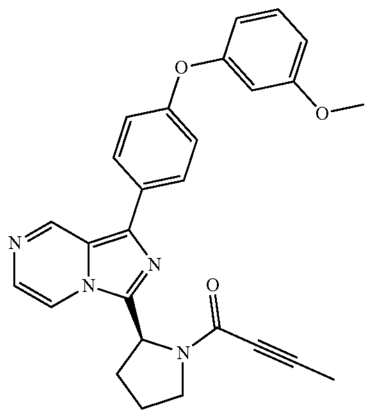 [SMILES: CC#CC(=O)N1CCC[C@H]1c1nc(-c2ccc(Oc3cccc(OC)c3)cc2)c2cnccn12] | 453.18/ 453.2 | (S)-1-(2-(1-(4-(3-methoxyphenoxy)phenyl)imidazo[1,5-a]pyrazin-3-yl)pyrrolidin-1-yl)but-2-yn-1-one |
| 9 | 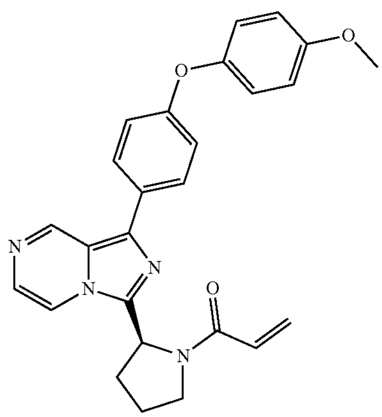 [SMILES: C=CC(=O)N1CCC[C@H]1c1nc(-c2ccc(Oc3ccc(OC)cc3)cc2)c2cnccn12] | 441.18/ 441.2 | (S)-1-(2-(1-(4-(4-methoxyphenoxy)phenyl)imidazo[1,5-a]pyrazin-3-yl)pyrrolidin-1-yl)prop-2-en-1-one |
| 10 | 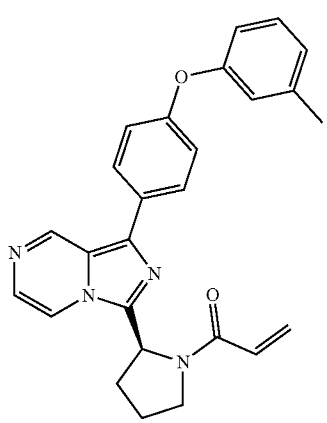 [SMILES: C=CC(=O)N1CCC[C@H]1c1nc(-c2ccc(Oc3cccc(C)c3)cc2)c2cnccn12] | 425.19/ 425.2 | (S)-1-(2-(1-(4-(m-tolyloxy)phenyl)imidazo[1,5-a]pyrazin-3-yl)pyrrolidin-1-yl)prop-2-en-1-one |

-continued

| Entry | Structure | MS (cald.) [M + H]+/ MS (found) | name |
|---|---|---|---|
| 11 | 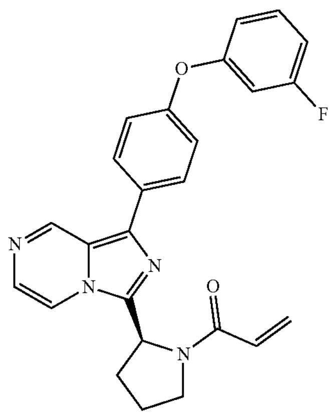 [SMILES: C=CC(=O)N1CCC[C@H]1c1nc(-c2ccc(Oc3cccc(F)c3)cc2)c2cnccn12] | 429.16/ 429.2 | (S)-1-(2-(1-(4-(3-fluorophenoxy)phenyl)imidazo[1,5-a]pyrazin-3-yl)pyrrolidin-1-yl)prop-2-en-1-one |
| 12 | 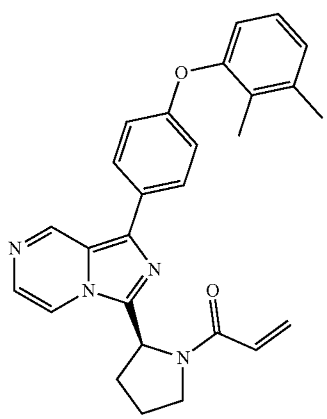 [SMILES: C=CC(=O)N1CCC[C@H]1c1nc(-c2ccc(Oc3cccc(C)c3C)cc2)c2cnccn12] | 439.21/ 439.2 | (S)-1-(2-(1-(4-(2,3-dimethylphenoxy)phenyl)imidazo[1,5-a]pyrazin-3-yl)pyrrolidin-1-yl)prop-2-en-1-one |
| 13 | 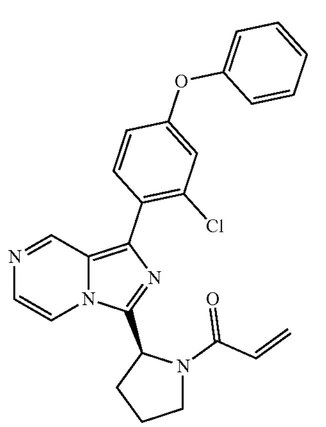 [SMILES: C=CC(=O)N1CCC[C@H]1c1nc(-c2ccc(Oc3ccccc3)cc2Cl)c2cnccn12] | 445.14/ 445.1 | (S)-1-(2-(1-(2-chloro-4-phenoxyphenyl)imidazo[1,5-a]pyrazin-3-yl)pyrrolidin-1-yl)prop-2-en-1-one |

-continued

| Entry | Structure | MS (cald.) [M + H]+/ MS (found) | name |
|---|---|---|---|
| 14 | 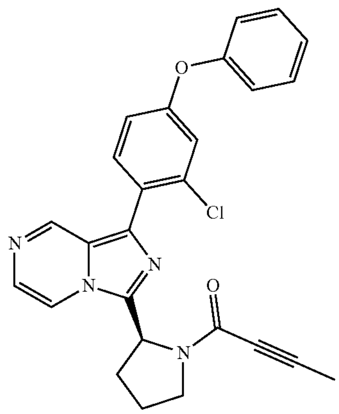 [SMILES: CC#CC(=O)N1CCC[C@H]1c1nc(-c2ccc(Oc3ccccc3)cc2Cl)c2cnccn12] | 457.14/ 457.1 | (S)-1-(2-(1-(2-chloro-4-phenoxyphenyl)imidazo[1,5-a]pyrazin-3-yl)pyrrolidin-1-yl)but-2-yn-1-one |
| 15 | 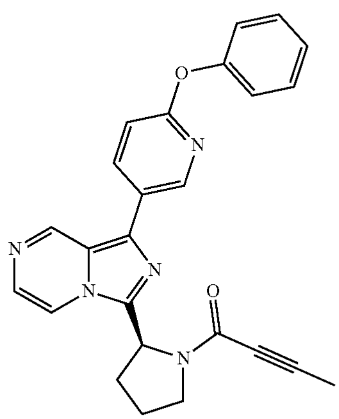 [SMILES: CC#CC(=O)N1CCC[C@H]1c1nc(-c2ccc(Oc3ccccc3)nc2)c2cnccn12] | 424.17/ 424.2 | (S)-1-(2-(1-(6-phenoxypyridin-3-yl)imidazo[1,5-a]pyrazin-3-yl)pyrrolidin-1-yl)but-2-yn-1-one |
| 16 | 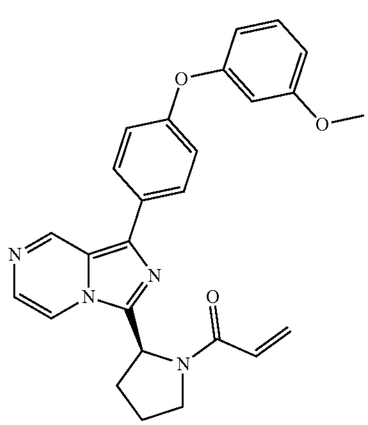 [SMILES: C=CC(=O)N1CCC[C@H]1c1nc(-c2ccc(Oc3cccc(OC)c3)cc2)c2cnccn12] | 441.18/ 441.2 | (S)-1-(2-(1-(4-(3-methoxyphenoxy)phenyl)imidazo[1,5-a]pyrazin-3-yl)pyrrolidin-1-yl)prop-2-en-1-one |

-continued

| Entry | Structure | MS (cald.) [M + H]+/ MS (found) | name |
|---|---|---|---|
| 17 | 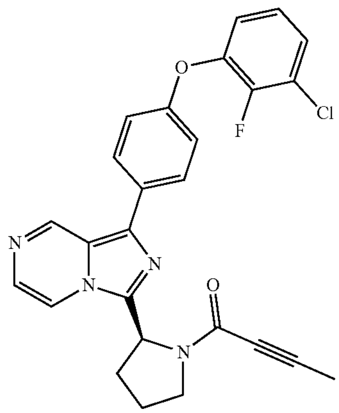 [SMILES: CC#CC(=O)N1CCC[C@H]1c1nc(-c2ccc(Oc3cccc(Cl)c3F)cc2)c2cnccn12] | 475.13/ 475.1 | (S)-1-(2-(1-(4-(3-chloro-2-fluorophenoxy)phenyl)imidazo[1,5-a]pyrazin-3-yl)pyrrolidin-1-yl)but-2-yn-1-one |
| 18 | 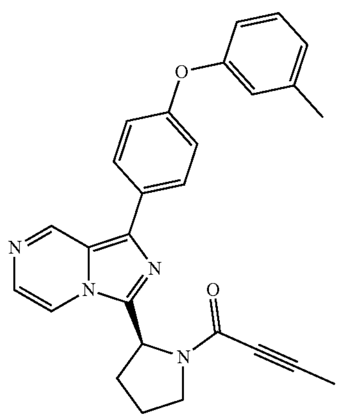 [SMILES: CC#CC(=O)N1CCC[C@H]1c1nc(-c2ccc(Oc3cccc(C)c3)cc2)c2cnccn12] | 437.19/ 437.2 | (S)-1-(2-(1-(4-(m-tolyloxy)phenyl)imidazo[1,5-a]pyrazin-3-yl)pyrrolidin-1-yl)but-2-yn-1-one |
| 19 | 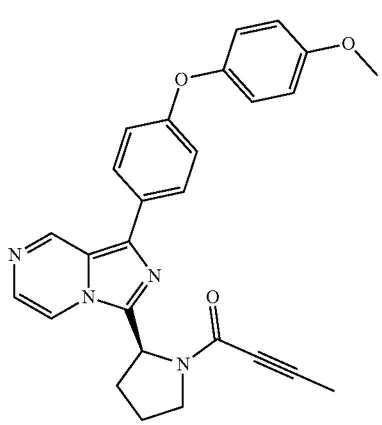 [SMILES: CC#CC(=O)N1CCC[C@H]1c1nc(-c2ccc(Oc3ccc(OC)cc3)cc2)c2cnccn12] | 453.18/ 453.2 | (S)-1-(2-(1-(4-(4-methoxyphenoxy)phenyl)imidazo[1,5-a]pyrazin-3-yl)pyrrolidin-1-yl)but-2-yn-1-one |

-continued

| Entry | Structure | MS (cald.) [M + H]+/ MS (found) | name |
|---|---|---|---|
| 20 | 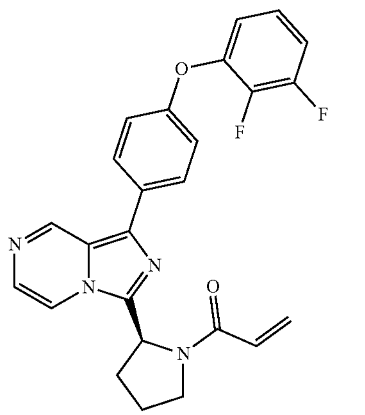 [SMILES: C=CC(=O)N1CCC[C@H]1c1nc(-c2ccc(Oc3cccc(F)c3F)cc2)c2cnccn12] | 447.16/ 447.2 | (S)-1-(2-(1-(4-(2,3-difluorophenoxy)phenyl)imidazo[1,5-a]pyrazin-3-yl)pyrrolidin-1-yl)prop-2-en-1-one |
| 21 | 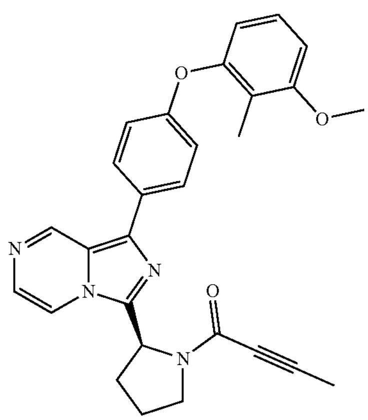 [SMILES: CC#CC(=O)N1CCC[C@H]1c1nc(-c2ccc(Oc3cccc(OC)c3C)cc2)c2cnccn12] | 467.20/ 467.2 | (S)-1-(2-(1-(4-(3-methoxy-2-methylphenoxy)phenyl)imidazo[1,5-a]pyrazin-3-yl)pyrrolidin-1-yl)but-2-yn-1-one |
| 22 | 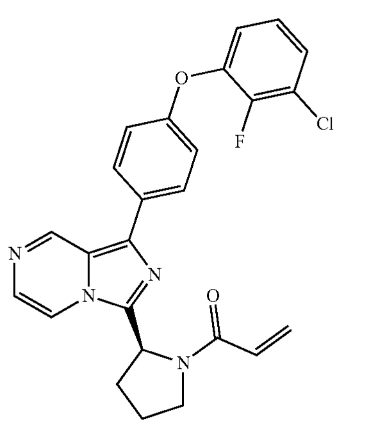 [SMILES: C=CC(=O)N1CCC[C@H]1c1nc(-c2ccc(Oc3cccc(Cl)c3F)cc2)c2cnccn12] | 463.13/ 463.1 | (S)-1-(2-(1-(4-(3-chloro-2-fluorophenoxy)phenyl)imidazo[1,5-a]pyrazin-3-yl)pyrrolidin-1-yl)prop-2-en-1-one |

-continued

| Entry | Structure | MS (cald.) [M + H]+/ MS (found) | name |
|---|---|---|---|
| 23 | 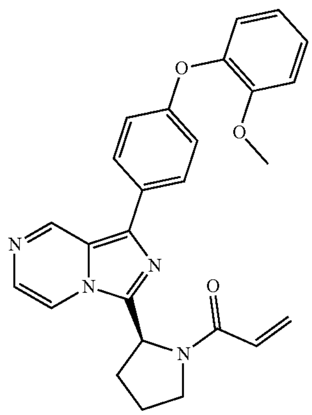 [SMILES: C=CC(=O)N1CCC[C@H]1c1nc(-c2ccc(Oc3ccccc3OC)cc2)c2cnccn12] | 441.18/ 441.2 | (S)-1-(2-(1-(4-(2-methoxyphenoxy)phenyl)imidazo[1,5-a]pyrazin-3-yl)pyrrolidin-1-yl)prop-2-en-1-one |
| 24 | 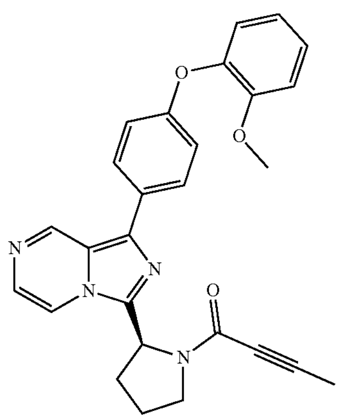 [SMILES: CC#CC(=O)N1CCC[C@H]1c1nc(-c2ccc(Oc3ccccc3OC)cc2)c2cnccn12] | 453.18/ 453.2 | (S)-1-(2-(1-(4-(2-methoxyphenoxy)phenyl)imidazo[1,5-a]pyrazin-3-yl)pyrrolidin-1-yl)but-2-yn-1-one |
| 25 | 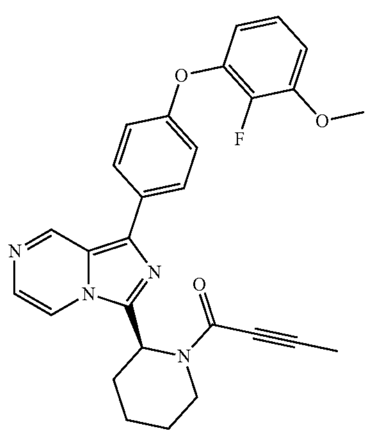 [SMILES: CC#CC(=O)N1CCCC[C@H]1c1nc(-c2ccc(Oc3cccc(OC)c3F)cc2)c2cnccn12] | 485.19/ 485.2 | (S)-1-(2-(1-(4-(2-fluoro-3-methoxyphenoxy)phenyl)imidazo[1,5-a]pyrazin-3-yl)piperidin-1-yl)but-2-yn-1-one |

-continued

| Entry | Structure | MS (cald.) [M + H]+/ MS (found) | name |
|---|---|---|---|
| 26 | 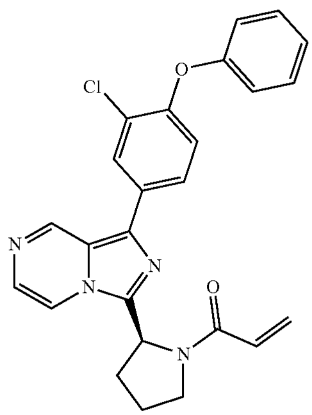 [SMILES: C=CC(=O)N1CCC[C@H]1c1nc(-c2ccc(Oc3ccccc3)c(Cl)c2)c2cnccn12] | 445.14/ 445.1 | (S)-1-(2-(1-(3-chloro-4-phenoxyphenyl)imidazo[1,5-a]pyrazin-3-yl)pyrrolidin-1-yl)prop-2-en-1-one |
| 27 | 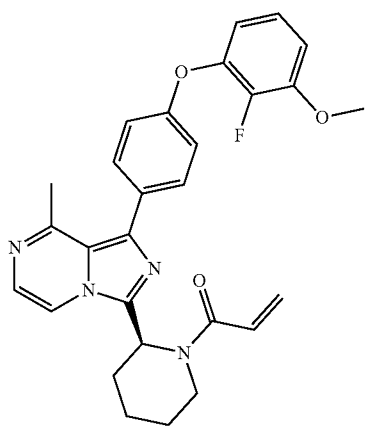 [SMILES: C=CC(=O)N1CCCC[C@H]1c1nc(-c2ccc(Oc3cccc(OC)c3F)cc2)c2c(C)nccn12] | 487.21/ 487.2 | (S)-1-(2-(1-(4-(2-fluoro-3-methoxyphenoxy)phenyl)-8-methylimidazo[1,5-a]pyrazin-3-yl)piperidin-1-yl)prop-2-en-1-one |
| 28 | 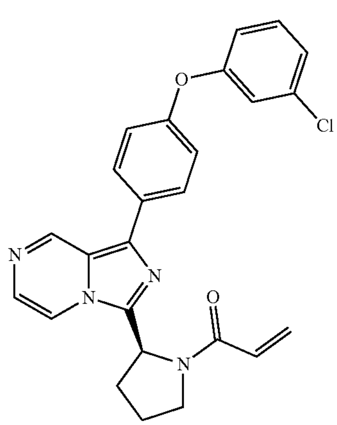 [SMILES: C=CC(=O)N1CCC[C@H]1c1nc(-c2ccc(Oc3cccc(Cl)c3)cc2)c2cnccn12] | 445.14/ 445.1 | (S)-1-(2-(1-(4-(3-chlorophenoxy)phenyl)imidazo[1,5-a]pyrazin-3-yl)pyrrolidin-1-yl)prop-2-en-1-one |

-continued

| Entry | Structure | MS (cald.) [M + H]+/ MS (found) | name |
|---|---|---|---|
| 29 | 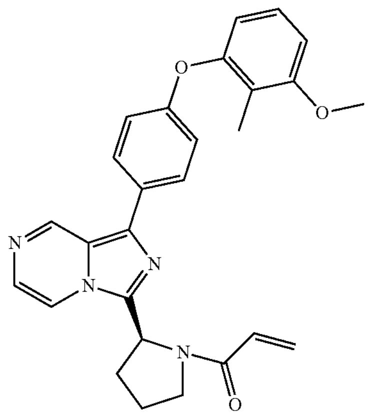 [SMILES: C=CC(=O)N1CCC[C@H]1c1nc(-c2ccc(Oc3cccc(OC)c3C)cc2)c2cnccn12] | 455.20/ 455.2 | (S)-1-(2-(1-(4-(3-methoxy-2-methylphenoxy)phenyl)imidazo[1,5-a]pyrazin-3-yl)pyrrolidin-1-yl)prop-2-en-1-one |
| 30 | 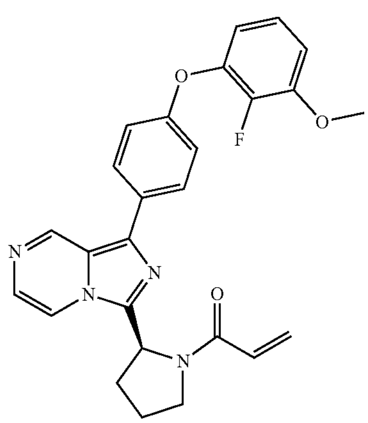 [SMILES: C=CC(=O)N1CCC[C@H]1c1nc(-c2ccc(Oc3cccc(OC)c3F)cc2)c2cnccn12] | 459.18/ 459.2 | (S)-1-(2-(1-(4-(2-fluoro-3-methoxyphenoxy)phenyl)imidazo[1,5-a]pyrazin-3-yl)pyrrolidin-1-yl)prop-2-en-1-one |
| 31 | 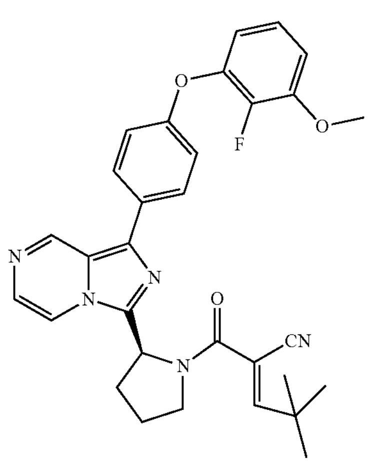 [SMILES: COc1cccc(Oc2ccc(-c3nc([C@@H]4CCCN4C(=O)/C(C#N)=C/C(C)(C)C)n4ccncc34)cc2)c1F] | 540.23/ 540.2 | (S,E)-2-(2-(1-(4-(2-fluoro-3-methoxyphenoxy)phenyl)imidazo[1,5-a]pyrazin-3-yl)pyrrolidine-1-carbonyl)-4,4-dimethylpent-2-enenitrile |

| Entry | Structure | MS (cald.) [M + H]+/ MS (found) | name |
|---|---|---|---|
| 32 | 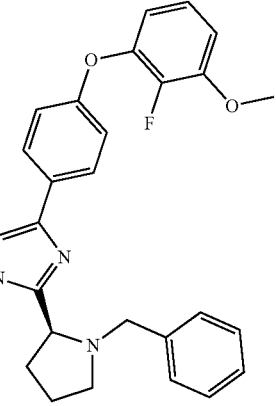 | 495.21/ 495.2 | (S)-3-(1-benzylpyrrolidin-2-yl)-1-(4-(2-fluoro-3-methoxyphenoxy)phenyl)imidazo[1,5-a]pyrazine |
| 33 | 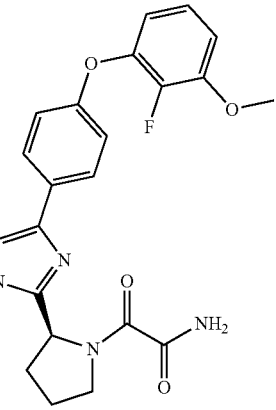 | 476.17/ 476.2 | (S)-2-(2-(1-(4-(2-fluoro-3-methoxyphenoxy)phenyl)imidazo[1,5-a]pyrazin-3-yl)pyrrolidin-1-yl)-2-oxoacetamide |
| 34 | 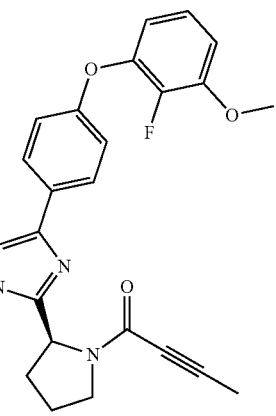 | 471.18/ 471.2 | (S)-1-(2-(1-(4-(2-fluoro-3-methoxyphenoxy)phenyl)imidazo[1,5-a]pyrazin-3-yl)pyrrolidin-1-yl)but-2-yn-1-one |

-continued

| Entry | Structure | MS (cald.) [M + H]+/ MS (found) | name |
|---|---|---|---|
| 35 | 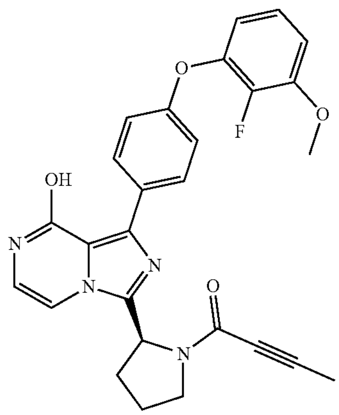 [SMILES: CC#CC(=O)N1CCC[C@H]1c1nc(-c2ccc(Oc3cccc(OC)c3F)cc2)c2c(O)nccn12] | 487.17/ 487.2 | (S)-1-(2-(1-(4-(2-fluoro-3-methoxyphenoxy)phenyl)-8-hydroxyimidazo[1,5-a]pyrazin-3-yl)pyrrolidin-1-yl)but-2-yn-1-one |
| 36 | 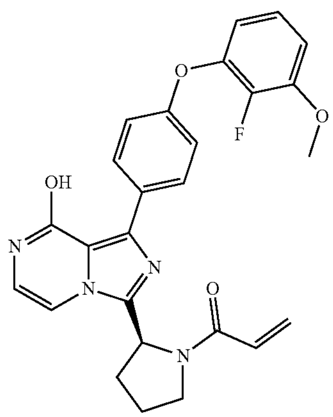 [SMILES: C=CC(=O)N1CCC[C@H]1c1nc(-c2ccc(Oc3cccc(OC)c3F)cc2)c2c(O)nccn12] | 475.17/ 475.2 | (S)-1-(2-(1-(4-(2-fluoro-3-methoxyphenoxy)phenyl)-8-hydroxyimidazo[1,5-a]pyrazin-3-yl)pyrrolidin-1-yl)prop-2-en-1-one |
| 37 | 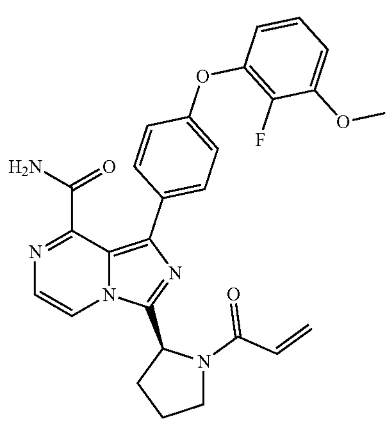 [SMILES: C=CC(=O)N1CCC[C@H]1c1nc(-c2ccc(Oc3cccc(OC)c3F)cc2)c2c(C(N)=O)nccn12] | 502.18/ 502.2 | (S)-3-(1-acryloylpyrrolidin-2-yl)-1-(4-(2-fluoro-3-methoxyphenoxy)phenyl)imidazo[1,5-a]pyrazine-8-carboxamide |

| Entry | Structure | MS (cald.) [M + H]+/ MS (found) | name |
|---|---|---|---|
| 38 | 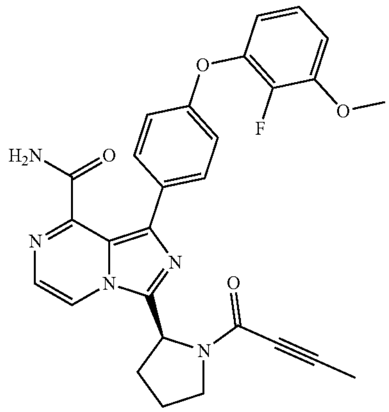 [SMILES: CC#CC(=O)N1CCC[C@H]1c1nc(-c2ccc(Oc3cccc(OC)c3F)cc2)c2c(C(N)=O)nccn12] | 514.18/ 514.2 | (S)-3-(1-(but-2-ynoyl)pyrrolidin-2-yl)-1-(4-(2-fluoro-3-methoxyphenoxy)phenyl)imidazo[1,5-a]pyrazine-8-carboxamide |
| 39 | 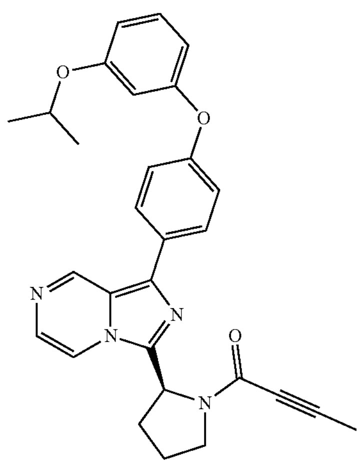 [SMILES: CC#CC(=O)N1CCC[C@H]1c1nc(-c2ccc(Oc3cccc(OC(C)C)c3)cc2)c2cnccn12] | 481.22/ 481.2 | (S)-1-(2-(1-(4-(3-isopropoxyphenoxy)phenyl)imidazo[1,5-a]pyrazin-3-yl)pyrrolidin-1-yl)but-2-yn-1-one |
| 40 | 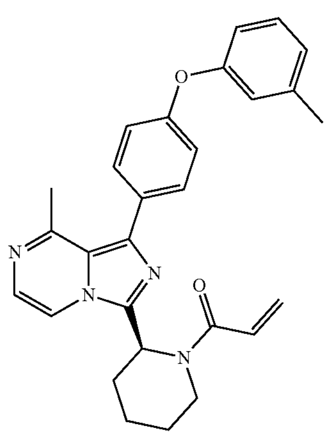 [SMILES: C=CC(=O)N1CCCC[C@H]1c1nc(-c2ccc(Oc3cccc(C)c3)cc2)c2c(C)nccn12] | 453.22/ 453.2 | (S)-1-(2-(8-methyl-1-(4-(m-tolyloxy)phenyl)imidazo[1,5-a]pyrazin-3-yl)piperidin-1-yl)prop-2-en-1-one |

-continued

| Entry | Structure | MS (cald.) [M + H]+/ MS (found) | name |
|---|---|---|---|
| 41 | 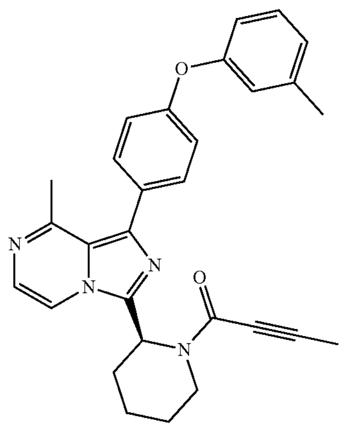 [SMILES: CC#CC(=O)N1CCCC[C@H]1c1nc(-c2ccc(Oc3cccc(C)c3)cc2)c2c(C)nccn12] | 465.22/ 465.2 | (S)-1-(2-(8-methyl-1-(4-(m-tolyloxy)phenyl)imidazo[1,5-a]pyrazin-3-yl)piperidin-1-yl)but-2-yn-1-one |
| 42 | 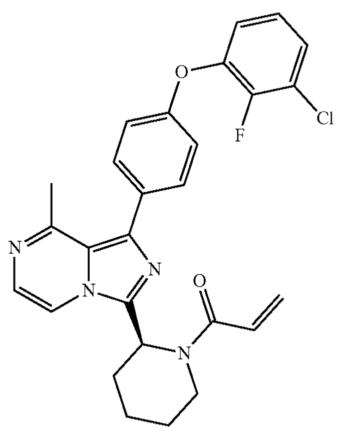 [SMILES: C=CC(=O)N1CCCC[C@H]1c1nc(-c2ccc(Oc3cccc(Cl)c3F)cc2)c2c(C)nccn12] | 491.16/ 491.2 | (S)-1-(2-(1-(4-(3-chloro-2-fluorophenoxy)phenyl)-8-methylimidazo[1,5-a]pyrazin-3-yl)piperidin-1-yl)prop-2-en-1-one |
| 43 | 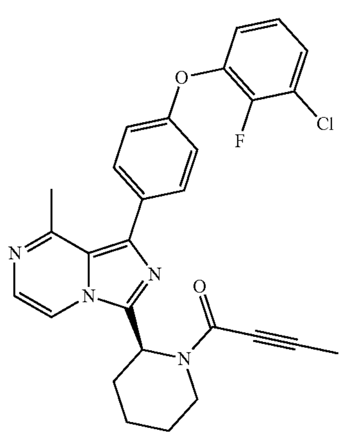 [SMILES: CC#CC(=O)N1CCCC[C@H]1c1nc(-c2ccc(Oc3cccc(Cl)c3F)cc2)c2c(C)nccn12] | 503.16/ 503.2 | (S)-1-(2-(1-(4-(3-chloro-2-fluorophenoxy)phenyl)-8-methylimidazo[1,5-a]pyrazin-3-yl)piperidin-1-yl)but-2-yn-1-one |

| Entry | Structure | MS (cald.) [M + H]+/ MS (found) | name |
|---|---|---|---|
| 44 | 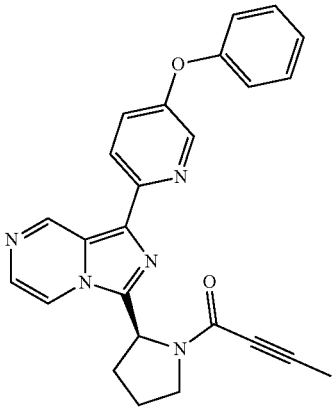 [SMILES: CC#CC(=O)N1CCC[C@H]1c1nc(-c2ccc(Oc3ccccc3)cn2)c2cnccn12] | 424.17/ 424.2 | (S)-1-(2-(1-(5-phenoxypyridin-2-yl)imidazo[1,5-a]pyrazin-3-yl)pyrrolidin-1-yl)but-2-yn-1-one |
| 45 | 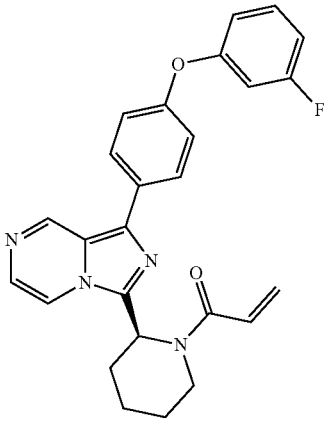 | 443.18/ 443.2 | (S)-1-(2-(1-(4-(3-fluorophenoxy)phenyl)imidazo[1,5-a]pyrazin-3-yl)piperidin-1-yl)prop-2-en-1-one |
| 46 | 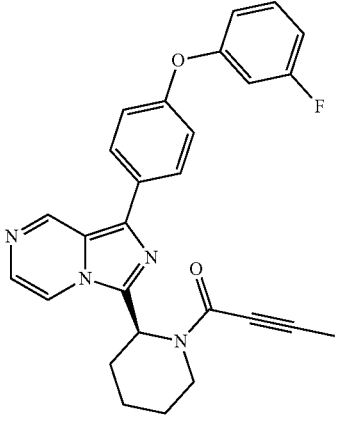 [SMILES: CC#CC(=O)N1CCCC[C@H]1c1nc(-c2ccc(Oc3cccc(F)c3)cc2)c2cnccn12] | 455.18/ 455.2 | (S)-1-(2-(1-(4-(3-fluorophenoxy)phenyl)imidazo[1,5-a]pyrazin-3-yl)piperidin-1-yl)but-2-yn-1-one |

-continued

| Entry | Structure | MS (cald.) [M + H]+/ MS (found) | name |
|---|---|---|---|
| 47 | 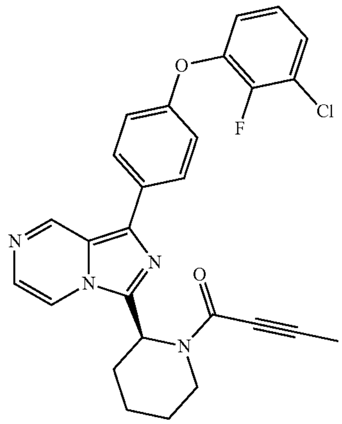 [SMILES: CC#CC(=O)N1CCCC[C@H]1c1nc(-c2ccc(Oc3cccc(Cl)c3F)cc2)c2cnccn12] | 489.14/ 489.1 | (S)-1-(2-(1-(4-(3-chloro-2-fluorophenoxy)phenyl)imidazo[1,5-a]pyrazin-3-yl)piperidin-1-yl)but-2-yn-1-one |
| 48 | 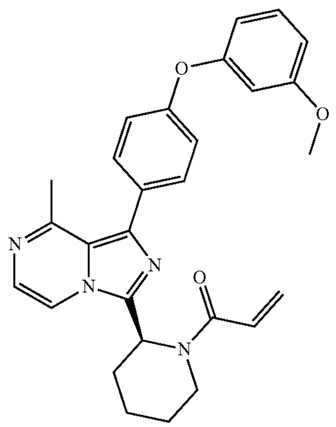 [SMILES: C=CC(=O)N1CCCC[C@H]1c1nc(-c2ccc(Oc3cccc(OC)c3)cc2)c2c(C)nccn12] | 469.22/ 469.2 | (S)-1-(2-(1-(4-(3-methoxyphenoxy)phenyl)-8-methylimidazo[1,5-a]pyrazin-3-yl)piperidin-1-yl)prop-2-en-1-one |
| 49 | 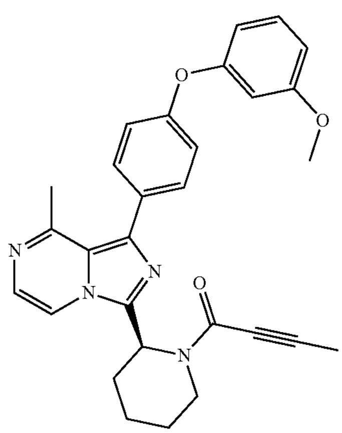 [SMILES: CC#CC(=O)N1CCCC[C@H]1c1nc(-c2ccc(Oc3cccc(OC)c3)cc2)c2c(C)nccn12] | 481.22/ 481.2 | (S)-1-(2-(1-(4-(3-methoxyphenoxy)phenyl)-8-methylimidazo[1,5-a]pyrazin-3-yl)piperidin-1-yl)but-2-yn-1-one |

-continued

| Entry | Structure | MS (cald.) [M + H]+/ MS (found) | name |
|---|---|---|---|
| 50 | 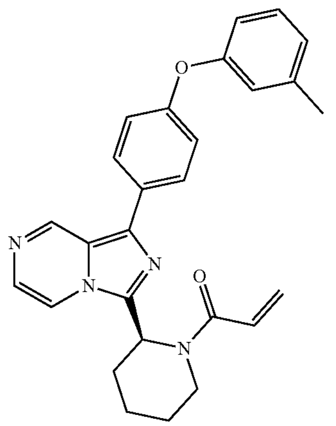 [SMILES: C=CC(=O)N1CCCC[C@H]1c1nc(-c2ccc(Oc3cccc(C)c3)cc2)c2cnccn12] | 439.21/ 439.2 | (S)-1-(2-(1-(4-(m-tolyloxy)phenyl)imidazo[1,5-a]pyrazin-3-yl)piperidin-1-yl)prop-2-en-1-one |
| 51 | 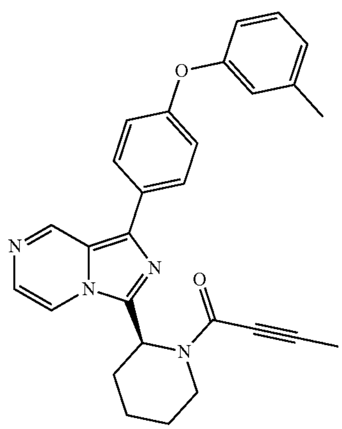 [SMILES: CC#CC(=O)N1CCCC[C@H]1c1nc(-c2ccc(Oc3cccc(C)c3)cc2)c2cnccn12] | 451.21/ 451.2 | (S)-1-(2-(1-(4-(m-tolyloxy)phenyl)imidazo[1,5-a]pyrazin-3-yl)piperidin-1-yl)but-2-yn-1-one |
| 52 | 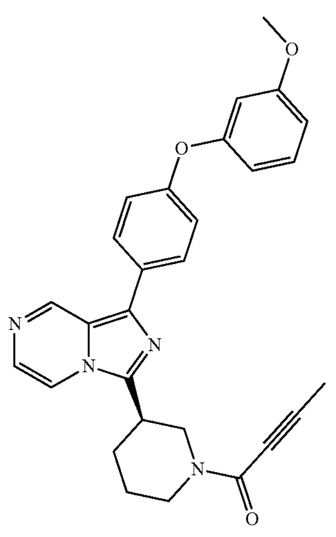 [SMILES: CC#CC(=O)N1CCC[C@@H](c2nc(-c3ccc(Oc4cccc(OC)c4)cc3)c3cnccn23)C1] | 467.20/ 467.2 | (R)-1-(3-(1-(4-(3-methoxyphenoxy)phenyl)imidazo[1,5-a]pyrazin-3-yl)piperidin-1-yl)but-2-yn-1-one |

-continued

| Entry | Structure | MS (cald.) [M + H]+/ MS (found) | name |
|---|---|---|---|
| 53 | 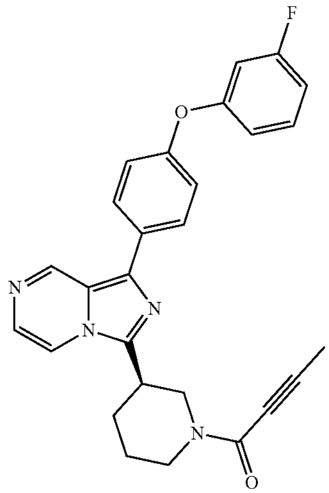 [SMILES: CC#CC(=O)N1CCC[C@@H](c2nc(-c3ccc(Oc4cccc(F)c4)cc3)c3cnccn23)C1] | 455.18/ 455.2 | (R)-1-(3-(1-(4-(3-fluorophenoxy)phenyl)imidazo[1,5-a]pyrazin-3-yl)piperidin-1-yl)but-2-yn-1-one |
| 54 | 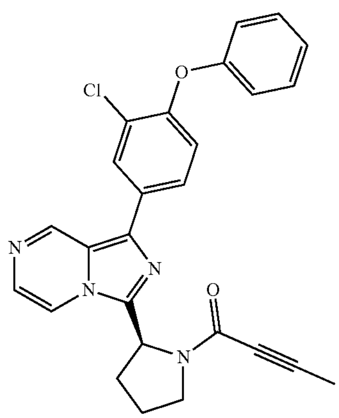 [SMILES: CC#CC(=O)N1CCC[C@H]1c1nc(-c2ccc(Oc3ccccc3)c(Cl)c2)c2cnccn12] | 457.14/ 457.1 | (S)-1-(2-(1-(3-chloro-4-phenoxyphenyl)imidazo[1,5-a]pyrazin-3-yl)pyrrolidin-1-yl)but-2-yn-1-one |
| 55 | 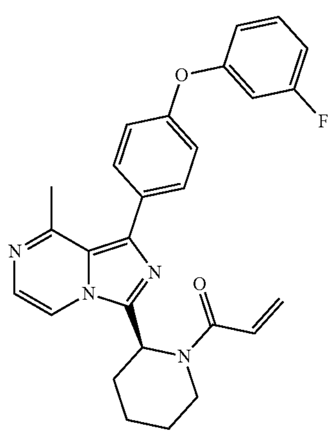 [SMILES: C=CC(=O)N1CCCC[C@H]1c1nc(-c2ccc(Oc3cccc(F)c3)cc2)c2c(C)nccn12] | 457.20/ 457.2 | (S)-1-(2-(1-(4-(3-fluorophenoxy)phenyl)-8-methylimidazo[1,5-a]pyrazin-3-yl)piperidin-1-yl)prop-2-en-1-one |

-continued

| Entry | Structure | MS (cald.) [M + H]+/ MS (found) | name |
|---|---|---|---|
| 56 | 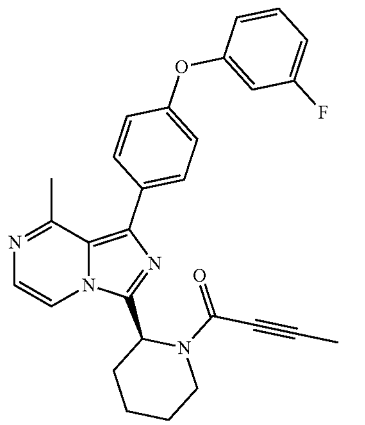 [SMILES: CC#CC(=O)N1CCCC[C@H]1c1nc(-c2ccc(Oc3cccc(F)c3)cc2)c2c(C)nccn12] | 469.20/ 469.2 | (S)-1-(2-(1-(4-(3-fluorophenoxy)phenyl)-8-methylimidazo[1,5-a]pyrazin-3-yl)piperidin-1-yl)but-2-yn-1-one |
| 57 | 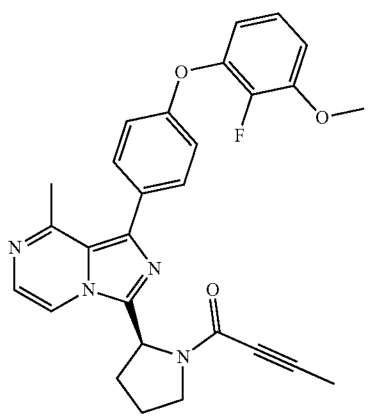 [SMILES: CC#CC(=O)N1CCC[C@H]1c1nc(-c2ccc(Oc3cccc(OC)c3F)cc2)c2c(C)nccn12] | 485.19/ 485.2 | (S)-1-(2-(1-(4-(2-fluoro-3-methoxyphenoxy)phenyl)-8-methylimidazo[1,5-a]pyrazin-3-yl)pyrrolidin-1-yl)but-2-yn-1-one |
| 58 | 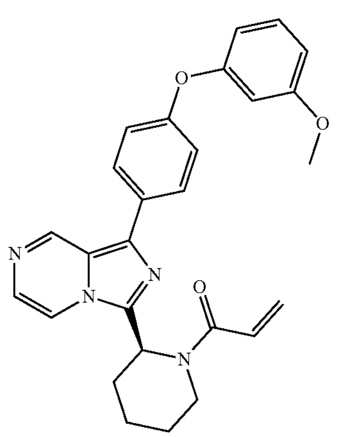 [SMILES: C=CC(=O)N1CCCC[C@H]1c1nc(-c2ccc(Oc3cccc(OC)c3)cc2)c2cnccn12] | 455.20/ 455.2 | (S)-1-(2-(1-(4-(3-methoxyphenoxy)phenyl)imidazo[1,5-a]pyrazin-3-yl)piperidin-1-yl)prop-2-en-1-one |

-continued

| Entry | Structure | MS (cald.) [M + H]+/ MS (found) | name |
|---|---|---|---|
| 59 | 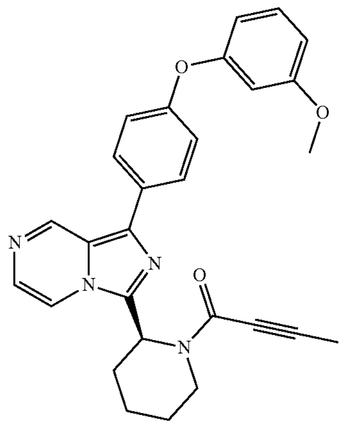 [SMILES: CC#CC(=O)N1CCCC[C@H]1c1nc(-c2ccc(Oc3cccc(OC)c3)cc2)c2cnccn12] | 467.20/ 467.2 | (S)-1-(2-(1-(4-(3-methoxyphenoxy)phenyl)imidazo[1,5-a]pyrazin-3-yl)piperidin-1-yl)but-2-yn-1-one |
| 60 | 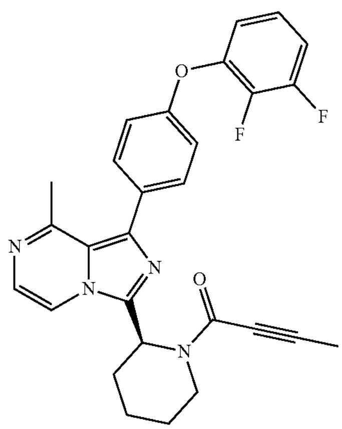 [SMILES: CC#CC(=O)N1CCCC[C@H]1c1nc(-c2ccc(Oc3cccc(F)c3F)cc2)c2c(C)nccn12] | 487.19/ 487.2 | (S)-1-(2-(1-(4-(2,3-difluorophenoxy)phenyl)-8-methylimidazo[1,5-a]pyrazin-3-yl)piperidin-1-yl)but-2-yn-1-one |
| 61 | 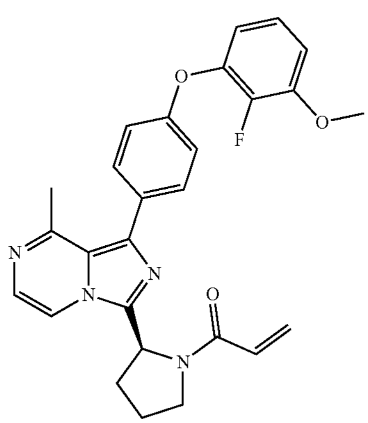 [SMILES: C=CC(=O)N1CCC[C@H]1c1nc(-c2ccc(Oc3cccc(OC)c3F)cc2)c2c(C)nccn12] | 473.19/ 473.2 | (S)-1-(2-(1-(4-(2-fluoro-3-methoxyphenoxy)phenyl)-8-methylimidazo[1,5-a]pyrazin-3-yl)pyrrolidin-1-yl)prop-2-en-1-one |

-continued

| Entry | Structure | MS (cald.) [M + H]+/ MS (found) | name |
|---|---|---|---|
| 62 | 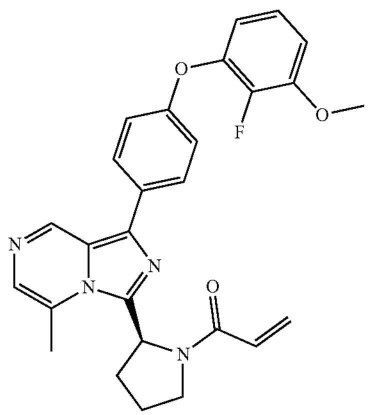 [SMILES: C=CC(=O)N1CCC[C@H]1c1nc(-c2ccc(Oc3cccc(OC)c3F)cc2)c2cncc(C)n12] | 473.19/ 473.2 | (S)-1-(2-(1-(4-(2-fluoro-3-methoxyphenoxy)phenyl)-5-methylimidazo[1,5-a]pyrazin-3-yl)pyrrolidin-1-yl)prop-2-en-1-one |
| 63 | 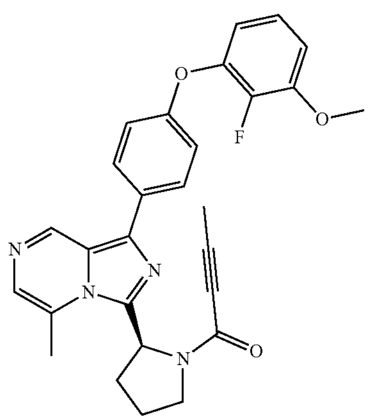 [SMILES: CC#CC(=O)N1CCC[C@H]1c1nc(-c2ccc(Oc3cccc(OC)c3F)cc2)c2cncc(C)n12] | 485.19/ 485.2 | (S)-1-(2-(1-(4-(2-fluoro-3-methoxyphenoxy)phenyl)-5-methylimidazo[1,5-a]pyrazin-3-yl)pyrrolidin-1-yl)but-2-yn-1-one |
| 64 | 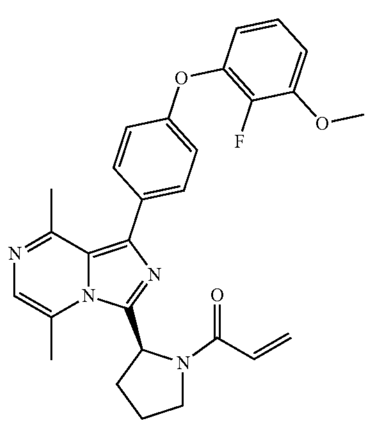 [SMILES: C=CC(=O)N1CCC[C@H]1c1nc(-c2ccc(Oc3cccc(OC)c3F)cc2)c2c(C)ncc(C)n12] | 487.21/ 487.2 | (S)-1-(2-(1-(4-(2-fluoro-3-methoxyphenoxy)phenyl)-5,8-dimethylimidazo[1,5-a]pyrazin-3-yl)pyrrolidin-1-yl)prop-2-en-1-one |

-continued
| Entry | Structure | MS (cald.) [M + H]+/ MS (found) | name |
|---|---|---|---|
| 65 | 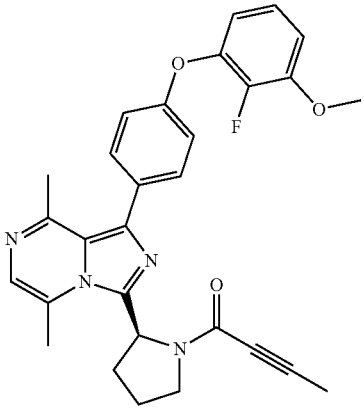 [SMILES: CC#CC(=O)N1CCC[C@H]1c1nc(-c2ccc(Oc3cccc(OC)c3F)cc2)c2c(C)ncc(C)n12] | 499.21/ 499.2 | (S)-1-(2-(1-(4-(2-fluoro-3-methoxyphenoxy)phenyl)-5,8-dimethylimidazo[1,5-a]pyrazin-3-yl)pyrrolidin-1-yl)but-2-yn-1-one |
| 66 | 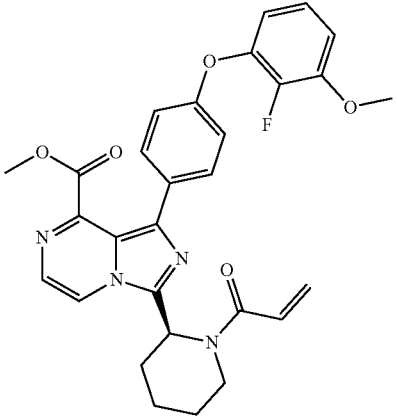 | 531.20/ 531.2 | methyl (S)-3-(1-acryloylpiperidin-2-yl)-1-(4-(2-fluoro-3-methoxyphenoxy)phenyl)imidazo[1,5-a]pyrazine-8-carboxylate |
| 67 | 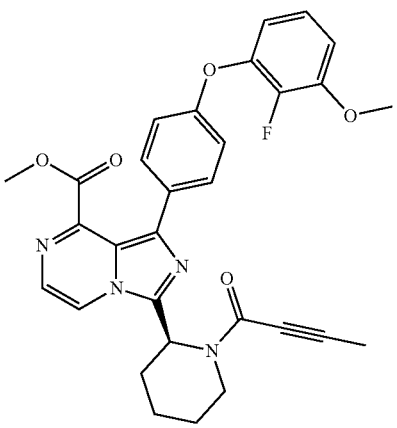 | 543.20/ 543.2 | methyl (S)-3-(1-(but-2-ynoyl)piperidin-2-yl)-1-(4-(2-fluoro-3-methoxyphenoxy)phenyl)imidazo[1,5-a]pyrazine-8-carboxylate |

-continued
| Entry | Structure | MS (cald.) [M + H]+/ MS (found) | name |
|---|---|---|---|
| 68 | 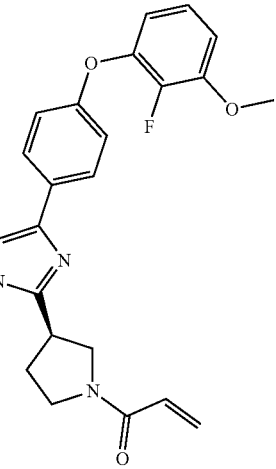 | 459.18/ 459.2 | (R)-1-(3-(1-(4-(2-fluoro-3-methoxyphenoxy)phenyl)imidazo[1,5-a]pyrazin-3-yl)pyrrolidin-1-yl)prop-2-en-1-one |
| 69 | 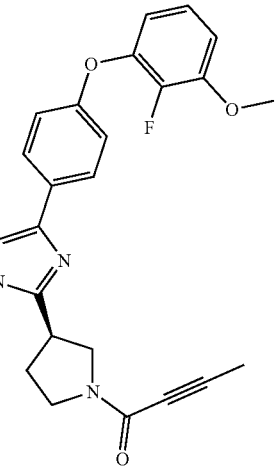 | 471.18/ 471.2 | (R)-1-(3-(1-(4-(2-fluoro-3-methoxyphenoxy)phenyl)imidazo[1,5-a]pyrazin-3-yl)pyrrolidin-1-yl)but-2-yn-1-one |
| 70 | 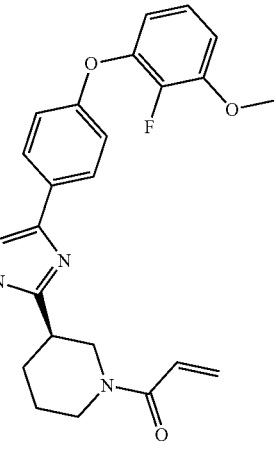 | 487.21/ 487.2 | (R)-1-(3-(1-(4-(2-fluoro-3-methoxyphenoxy)phenyl)-5-methylimidazo[1,5-a]pyrazin-3-yl)piperidin-1-yl)prop-2-en-1-one |

| Entry | Structure | MS (cald.) [M + H]+/ MS (found) | name |
|---|---|---|---|
| 71 | 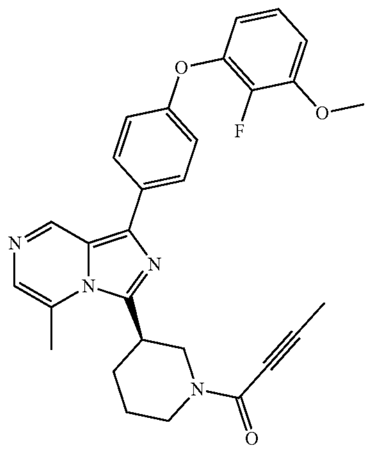 [SMILES: CC#CC(=O)N1CCC[C@@H](c2nc(-c3ccc(Oc4cccc(OC)c4F)cc3)c3cncc(C)n23)C1] | 499.21/ 499.2 | (R)-1-(3-(1-(4-(2-fluoro-3-methoxyphenoxy)phenyl)-5-methylimidazo[1,5-a]pyrazin-3-yl)piperidin-1-yl)but-2-yn-1-one |
| 72 | 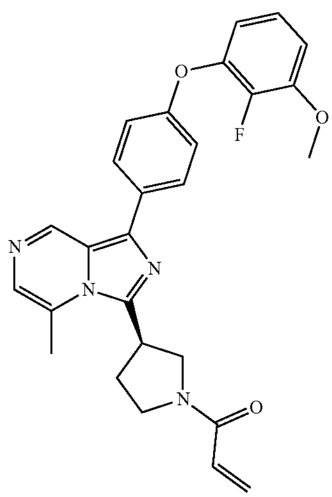 [SMILES: C=CC(=O)N1CC[C@@H](c2nc(-c3ccc(Oc4cccc(OC)c4F)cc3)c3cncc(C)n23)C1] | 473.19/ 473.2 | (R)-1-(3-(1-(4-(2-fluoro-3-methoxyphenoxy)phenyl)-5-methylimidazo[1,5-a]pyrazin-3-yl)pyrrolidin-1-yl)prop-2-en-1-one |
| 73 | 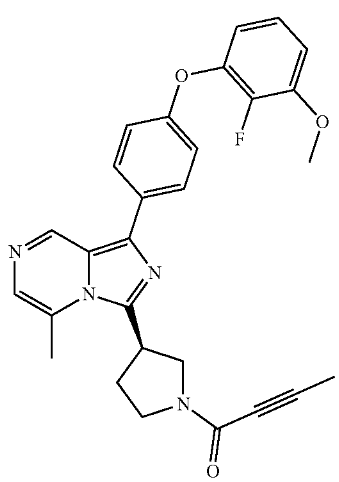 [SMILES: CC#CC(=O)N1CC[C@@H](c2nc(-c3ccc(Oc4cccc(OC)c4F)cc3)c3cncc(C)n23)C1] | 485.19/ 485.2 | (R)-1-(3-(1-(4-(2-fluoro-3-methoxyphenoxy)phenyl)-5-methylimidazo[1,5-a]pyrazin-3-yl)pyrrolidin-1-yl)but-2-yn-1-one |

| Entry | Structure | MS (cald.) [M + H]+/ MS (found) | name |
|---|---|---|---|
| 74 | 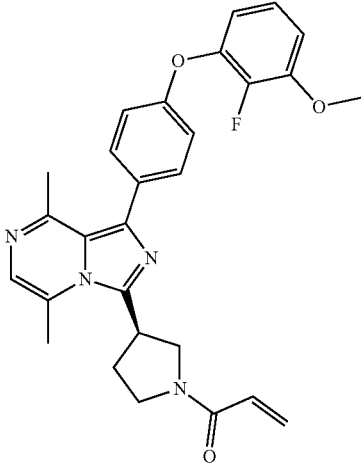 [SMILES: C=CC(=O)N1CC[C@@H](c2nc(-c3ccc(Oc4cccc(OC)c4F)cc3)c3c(C)ncc(C)n23)C1] | 487.20/ 487.2 | (R)-1-(3-(1-(4-(2-fluoro-3-methoxyphenoxy)phenyl)-5,8-dimethylimidazo[1,5-a]pyrazin-3-yl)pyrrolidin-1-yl)prop-2-en-1-one |
| 75 | 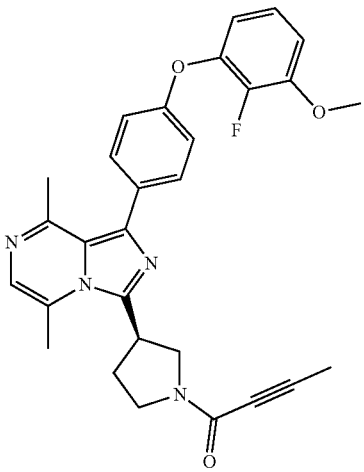 [SMILES: CC#CC(=O)N1CC[C@@H](c2nc(-c3ccc(Oc4cccc(OC)c4F)cc3)c3c(C)ncc(C)n23)C1] | 499.20/ 499.2 | (R)-1-(3-(1-(4-(2-fluoro-3-methoxyphenoxy)phenyl)-5,8-dimethylimidazo[1,5-a]pyrazin-3-yl)pyrrolidin-1-yl)but-2-yn-1-one |
| 76 | 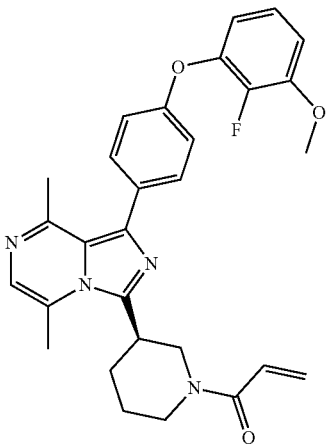 [SMILES: C=CC(=O)N1CCC[C@@H](c2nc(-c3ccc(Oc4cccc(OC)c4F)cc3)c3c(C)ncc(C)n23)C1] | 501.20/ 501.2 | (R)-1-(3-(1-(4-(2-fluoro-3-methoxyphenoxy)phenyl)-5,8-dimethylimidazo[1,5-a]pyrazin-3-yl)piperidin-1-yl)prop-2-en-1-one |

-continued

| Entry | Structure | MS (cald.) [M + H]+/ MS (found) | name |
|---|---|---|---|
| 77 | 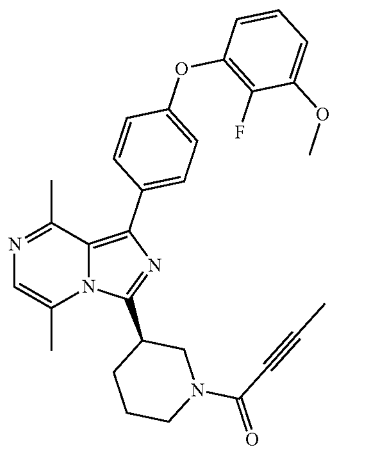 [SMILES: CC#CC(=O)N1CCC[C@@H](c2nc(-c3ccc(Oc4cccc(OC)c4F)cc3)c3c(C)ncc(C)n23)C1] | 413.20/ 413.2 | (R)-1-(3-(1-(4-(2-fluoro-3-methoxyphenoxy)phenyl)-5,8-dimethylimidazo[1,5-a]pyrazin-3-yl)piperidin-1-yl)but-2-yn-1-one |
| 78 | 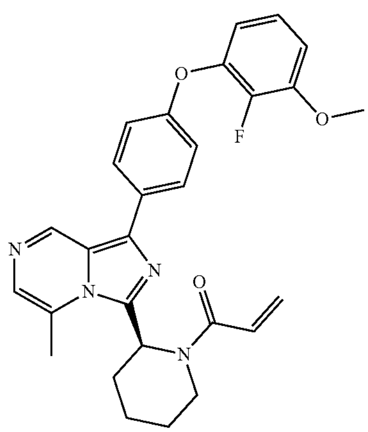 [SMILES: C=CC(=O)N1CCCC[C@H]1c1nc(-c2ccc(Oc3cccc(OC)c3F)cc2)c2cncc(C)n12] | 487.20/ 487.2 | (S)-1-(2-(1-(4-(2-fluoro-3-methoxyphenoxy)phenyl)-5-methylimidazo[1,5-a]pyrazin-3-yl)piperidin-1-yl)prop-2-en-1-one |
| 79 | 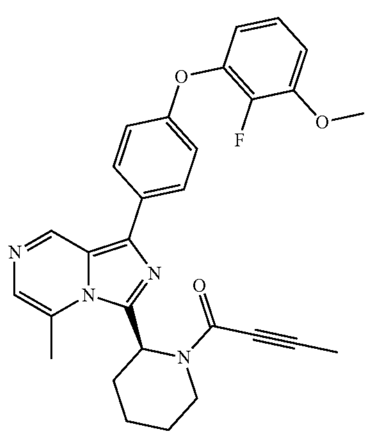 [SMILES: CC#CC(=O)N1CCCC[C@H]1c1nc(-c2ccc(Oc3cccc(OC)c3F)cc2)c2cncc(C)n12] | 499.20/ 499.2 | (S)-1-(2-(1-(4-(2-fluoro-3-methoxyphenoxy)phenyl)-5-methylimidazo[1,5-a]pyrazin-3-yl)piperidin-1-yl)but-2-yn-1-one |

-continued

| Entry | Structure | MS (cald.) [M + H]+/ MS (found) | name |
|---|---|---|---|
| 80 | 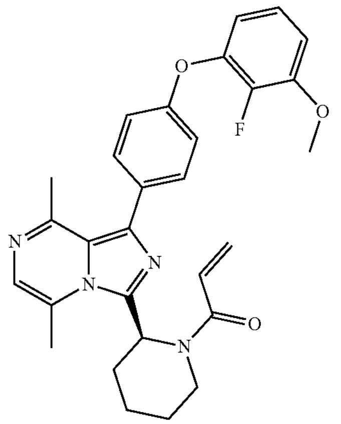 [SMILES: C=CC(=O)N1CCCC[C@H]1c1nc(-c2ccc(Oc3cccc(OC)c3F)cc2)c2c(C)ncc(C)n12] | 501.20/ 501.2 | (S)-1-(2-(1-(4-(2-fluoro-3-methoxyphenoxy)phenyl)-5,8-dimethylimidazo[1,5-a]pyrazin-3-yl)piperidin-1-yl)prop-2-en-1-one |
| 81 | 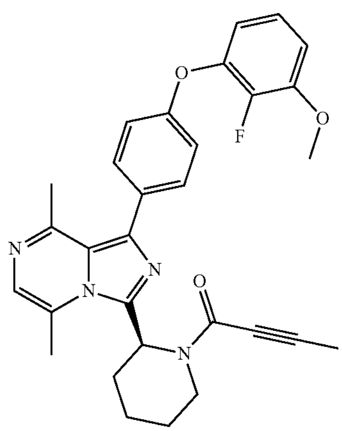 [SMILES: CC#CC(=O)N1CCCC[C@H]1c1nc(-c2ccc(Oc3cccc(OC)c3F)cc2)c2c(C)ncc(C)n12] | 513.20/ 513.2 | (S)-1-(2-(1-(4-(2-fluoro-3-methoxyphenoxy)phenyl)-5,8-dimethylimidazo[1,5-a]pyrazin-3-yl)piperidin-1-yl)but-2-yn-1-one |
| 82 | 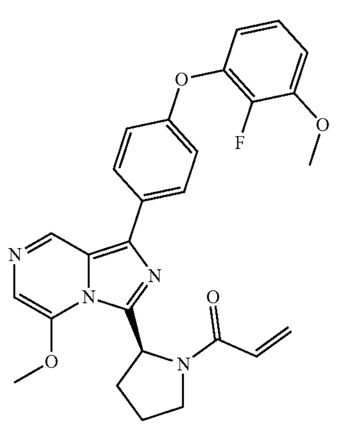 [SMILES: C=CC(=O)N1CCC[C@H]1c1nc(-c2ccc(Oc3cccc(OC)c3F)cc2)c2cncc(OC)n12] | 489.20/ 489.2 | (S)-1-(2-(1-(4-(2-fluoro-3-methoxyphenoxy)phenyl)-5-methoxyimidazo[1,5-a]pyrazin-3-yl)pyrrolidin-1-yl)prop-2-en-1-one |

| Entry | Structure | MS (cald.) [M + H]+/ MS (found) | name |
|---|---|---|---|
| 83 | 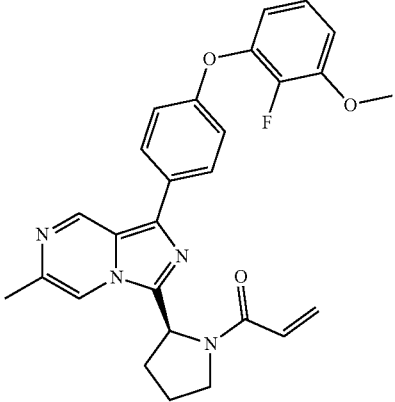 | 473.20/ 473.2 | (S)-1-(2-(1-(4-(2-fluoro-3-methoxyphenoxy)phenyl)-6-methylimidazo[1,5-a]pyrazin-3-yl)pyrrolidin-1-yl)prop-2-en-1-one |
| 84 | 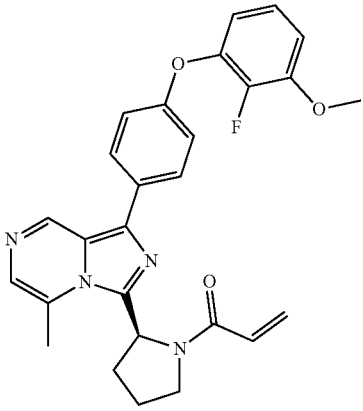 [SMILES: C=CC(=O)N1CCC[C@H]1c1nc(-c2ccc(Oc3cccc(OC)c3F)cc2)c2cncc(C)n12] | 473.20/ 473.2 | (S)-1-(2-(1-(4-(2-fluoro-3-methoxyphenoxy)phenyl)-5-methylimidazo[1,5-a]pyrazin-3-yl)pyrrolidin-1-yl)prop-2-en-1-one |
| 85 | 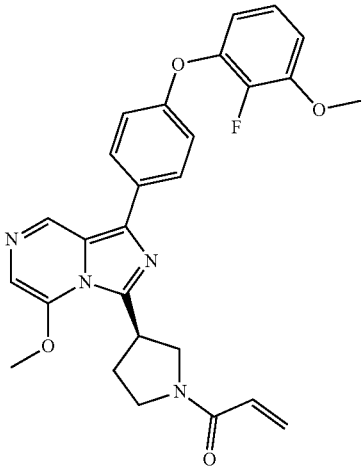 | 489.19/ 489.2 | (R)-1-(3-(1-(4-(2-fluoro-3-methoxyphenoxy)phenyl)-5-methoxyimidazo[1,5-a]pyrazin-3-yl)pyrrolidin-1-yl)prop-2-en-1-one |

| Entry | Structure | MS (cald.) [M + H]+/ MS (found) | name |
|---|---|---|---|
| 86 | 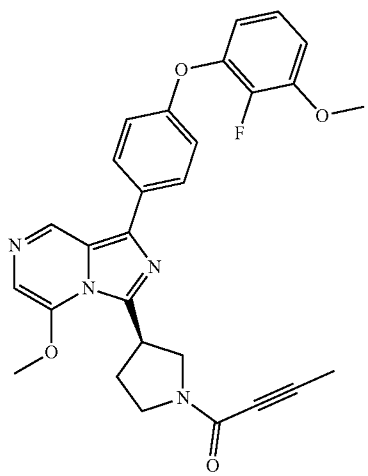 | 501.19/ 501.2 | (R)-1-(3-(1-(4-(2-fluoro-3-methoxyphenoxy)phenyl)-5-methoxyimidazo[1,5-a]pyrazin-3-yl)pyrrolidin-1-yl)but-2-yn-1-one |
| 87 | 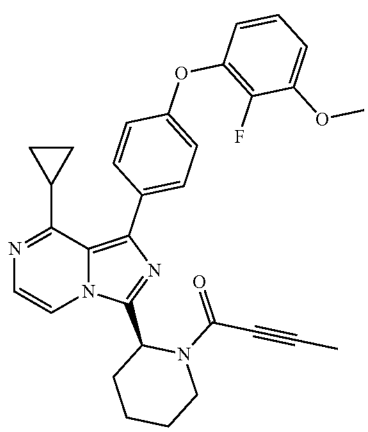 [SMILES: CC#CC(=O)N1CCCC[C@H]1c1nc(-c2ccc(Oc3cccc(OC)c3F)cc2)c2c(C3CC3)nccn12] | 425.22/ 425.2 | (S)-1-(2-(8-cyclopropyl-1-(4-(2-fluoro-3-methoxyphenoxy)phenyl)imidazo[1,5-a]pyrazin-3-yl)piperidin-1-yl)but-2-yn-1-one |
| 88 | 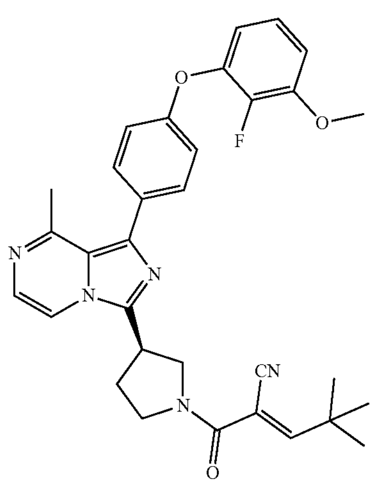 [SMILES: COc1cccc(Oc2ccc(-c3nc([C@@H]4CCN(C(=O)/C(C#N)=C/C(C)(C)C)C4)n4ccnc(C)c34)cc2)c1F] | 554.25/ 554.2 | (R,E)-2-(3-(1-(4-(2-fluoro-3-methoxyphenoxy)phenyl)-8-methylimidazo[1,5-a]pyrazin-3-yl)pyrrolidine-1-carbonyl)-4,4-dimethylpent-2-enenitrile |

-continued

| Entry | Structure | MS (cald.) [M + H]+/ MS (found) | name |
|---|---|---|---|
| 89 | 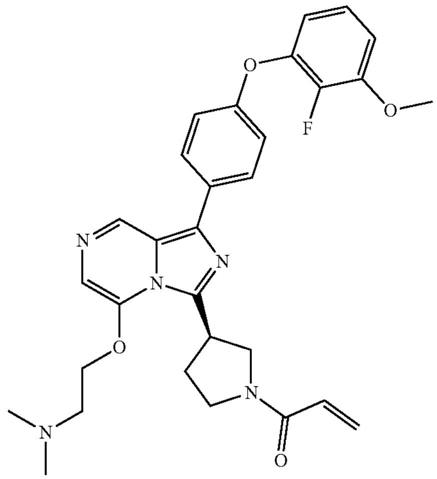 | 546.24/ 546.2 | (R)-1-(3-(5-(2-(dimethylamino)ethoxy)-1-(4-(2-fluoro-3-methoxyphenoxy)phenyl)imidazo[1,5-a]pyrazin-3-yl)pyrrolidin-1-yl)prop-2-en-1-one |
| 90 | 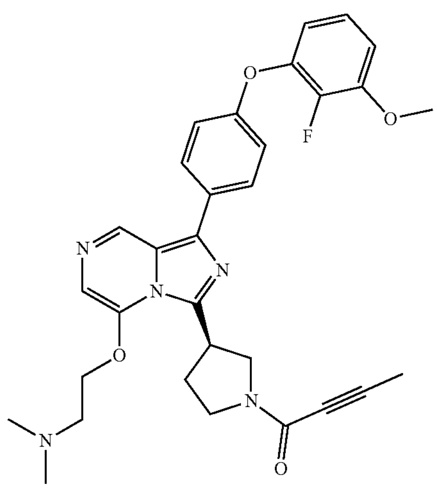 | 558.24/ 558.2 | (R)-1-(3-(5-(2-(dimethylamino)ethoxy)-1-(4-(2-fluoro-3-methoxyphenoxy)phenyl)imidazo[1,5-a]pyrazin-3-yl)pyrrolidin-1-yl)but-2-yn-1-one |
| 91 | 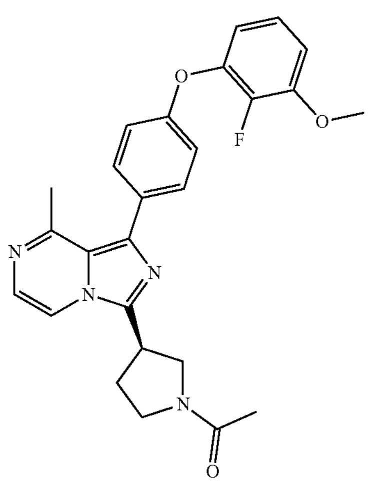 [SMILES: COc1cccc(Oc2ccc(-c3nc([C@@H]4CCN(C(C)=O)C4)n4ccnc(C)c34)cc2)c1F] | 461.19/ 461.2 | (R)-1-(3-(1-(4-(2-fluoro-3-methoxyphenoxy)phenyl)-8-methylimidazo[1,5-a]pyrazin-3-yl)pyrrolidin-1-yl)ethan-1-one |

-continued

| Entry | Structure | MS (cald.) [M + H]+/ MS (found) | name |
|---|---|---|---|
| 92 | 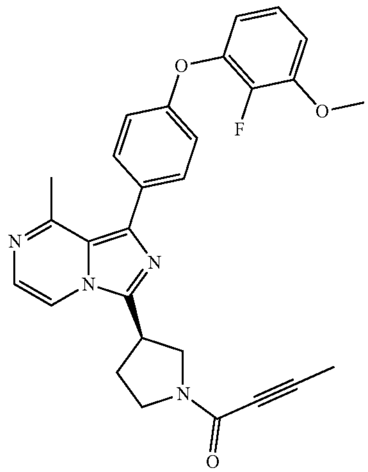 [SMILES: CC#CC(=O)N1CC[C@@H](c2nc(-c3ccc(Oc4cccc(OC)c4F)cc3)c3c(C)nccn23)C1] | 485.19/ 485.2 | (R)-1-(3-(1-(4-(2-fluoro-3-methoxyphenoxy)phenyl)-8-methylimidazo[1,5-a]pyrazin-3-yl)pyrrolidin-1-yl)but-2-yn-1-one |
| 93 | 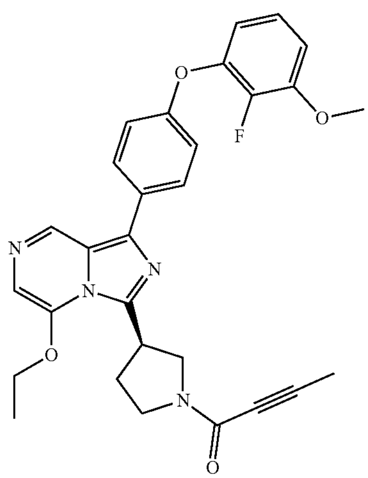 [SMILES: CC#CC(=O)N1CC[C@@H](c2nc(-c3ccc(Oc4cccc(OC)c4F)cc3)c3cncc(OCC)n23)C1] | 515.20/ 515.2 | (R)-1-(3-(5-ethoxy-1-(4-(2-fluoro-3-methoxyphenoxy)phenyl)imidazo[1,5-a]pyrazin-3-yl)pyrrolidin-1-yl)but-2-yn-1-one |
| 94 | 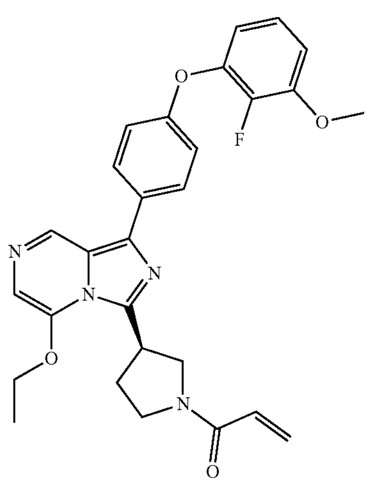 [SMILES: C=CC(=O)N1CC[C@@H](c2nc(-c3ccc(Oc4cccc(OC)c4F)cc3)c3cncc(OCC)n23)C1] | 503.20/ 503.2 | (R)-1-(3-(5-ethoxy-1-(4-(2-fluoro-3-methoxyphenoxy)phenyl)imidazo[1,5-a]pyrazin-3-yl)pyrrolidin-1-yl)prop-2-en-1-one |

| Entry | Structure | MS (cald.) [M + H]+/ MS (found) | name |
|---|---|---|---|
| 95 | 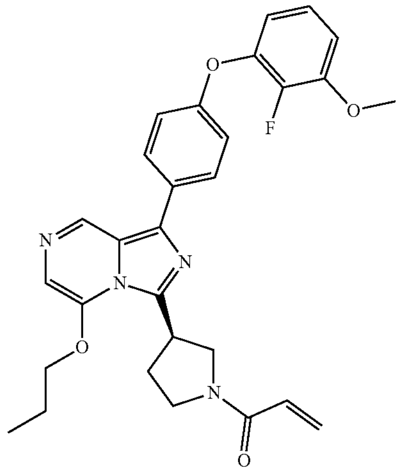 [SMILES: C=CC(=O)N1CC[C@@H](c2nc(-c3ccc(Oc4cccc(OC)c4F)cc3)c3cncc(OCCC)n23)C1] | 517.22/ 517.2 | (R)-1-(3-(1-(4-(2-fluoro-3-methoxyphenoxy)phenyl)-5-propoxyimidazo[1,5-a]pyrazin-3-yl)pyrrolidin-1-yl)prop-2-en-1-one |
| 96 | 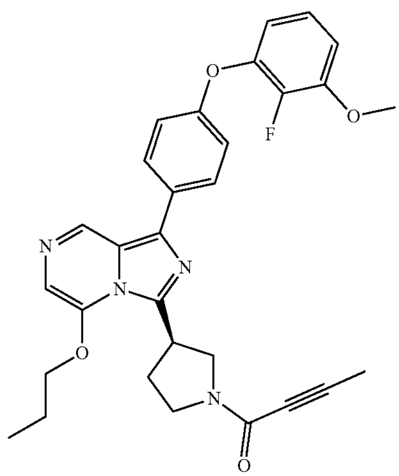 [SMILES: CC#CC(=O)N1CC[C@@H](c2nc(-c3ccc(Oc4cccc(OC)c4F)cc3)c3cncc(OCCC)n23)C1] | 529.22/ 529.2 | (R)-1-(3-(1-(4-(2-fluoro-3-methoxyphenoxy)phenyl)-5-propoxyimidazo[1,5-a]pyrazin-3-yl)pyrrolidin-1-yl)but-2-yn-1-one |
| 97 | 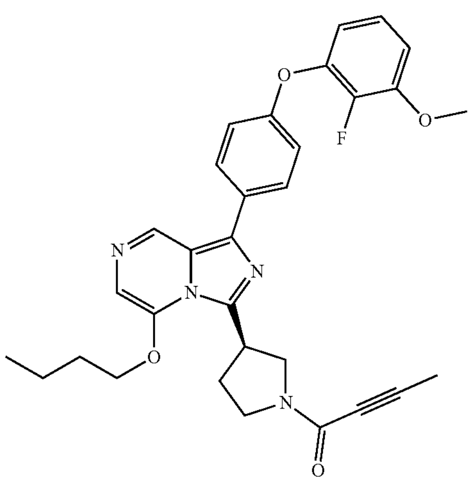 [SMILES: CC#CC(=O)N1CC[C@@H](c2nc(-c3ccc(Oc4cccc(OC)c4F)cc3)c3cncc(OCCCC)n23)C1] | 543.23/ 543.2 | (R)-1-(3-(5-butoxy-1-(4-(2-fluoro-3-methoxyphenoxy)phenyl)imidazo[1,5-a]pyrazin-3-yl)pyrrolidin-1-yl)but-2-yn-1-one |

-continued

| Entry | Structure | MS (cald.) [M + H]+/ MS (found) | name |
|---|---|---|---|
| 98 | 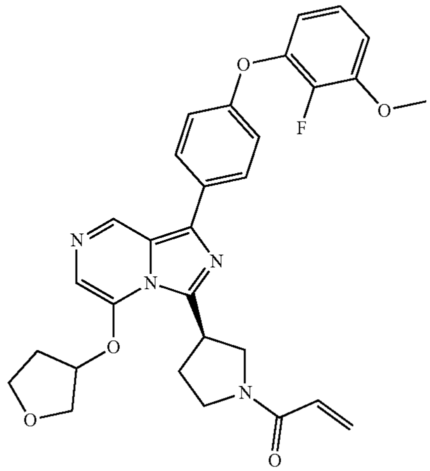 [SMILES: C=CC(=O)N1CC[C@@H](c2nc(-c3ccc(Oc4cccc(OC)c4F)cc3)c3cncc(OC4CCOC4)n23)C1] | 545.21/ 545.2 | 1-((3R)-3-(1-(4-(2-fluoro-3-methoxyphenoxy)phenyl)-5-((tetrahydrofuran-3-yl)oxy)imidazo[1,5-a]pyrazin-3-yl)pyrrolidin-1-yl)prop-2-en-1-one |
| 99 | 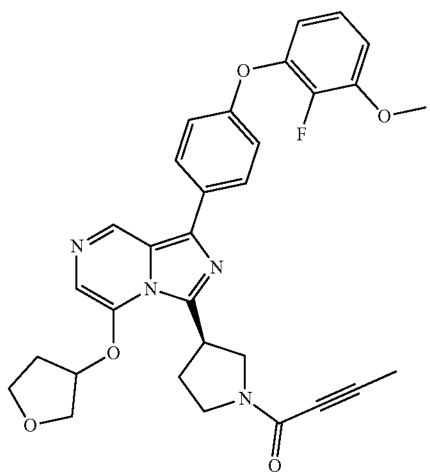 [SMILES: CC#CC(=O)N1CC[C@@H](c2nc(-c3ccc(Oc4cccc(OC)c4F)cc3)c3cncc(OC4CCOC4)n23)C1] | 557.21/ 557.2 | 1-((3R)-3-(1-(4-(2-fluoro-3-methoxyphenoxy)phenyl)-5-((tetrahydrofuran-3-yl)oxy)imidazo[1,5-a]pyrazin-3-yl)pyrrolidin-1-yl)but-2-yn-1-one |
| 100 | 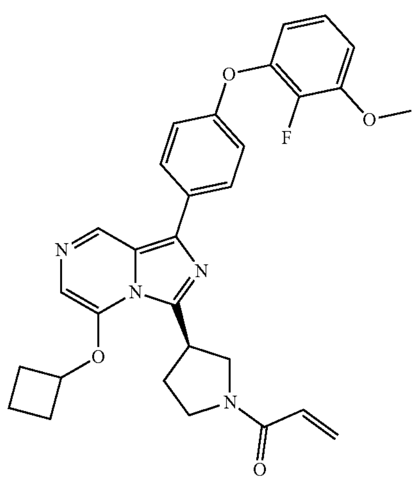 [SMILES: C=CC(=O)N1CC[C@@H](c2nc(-c3ccc(Oc4cccc(OC)c4F)cc3)c3cncc(OC4CCC4)n23)C1] | 529.22/ 529.2 | (R)-1-(3-(5-cyclobutoxy-1-(4-(2-fluoro-3-methoxyphenoxy)phenyl)imidazo[1,5-a]pyrazin-3-yl)pyrrolidin-1-yl)prop-2-en-1-one |

-continued

| Entry | Structure | MS (cald.) [M + H]+/ MS (found) | name |
|---|---|---|---|
| 101 | 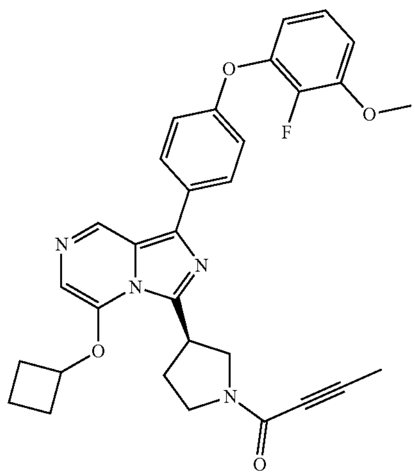 [SMILES: CC#CC(=O)N1CC[C@@H](c2nc(-c3ccc(Oc4cccc(OC)c4F)cc3)c3cncc(OC4CCC4)n23)C1] | 541.22/ 541.2 | (R)-1-(3-(5-cyclobutoxy-1-(4-(2-fluoro-3-methoxyphenoxy)phenyl)imidazo[1,5-a]pyrazin-3-yl)pyrrolidin-1-yl)but-2-yn-1-one |
| 102 | 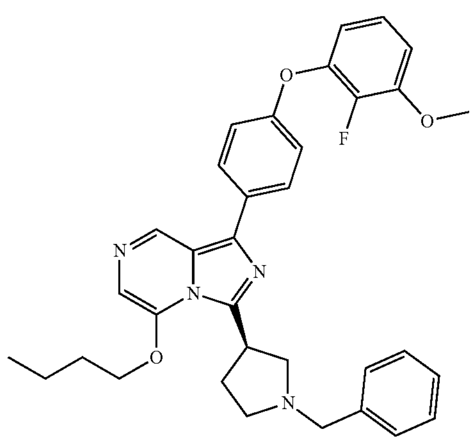 [SMILES: CCCCOc1cncc2c(-c3ccc(Oc4cccc(OC)c4F)cc3)nc([C@@H]3CCN(Cc4ccccc4)C3)n12] | 567.27/ 567.2 | (R)-3-(1-benzylpyrrolidin-3-yl)-5-butoxy-1-(4-(2-fluoro-3-methoxyphenoxy)phenyl)imidazo[1,5-a]pyrazine |
| 103 | 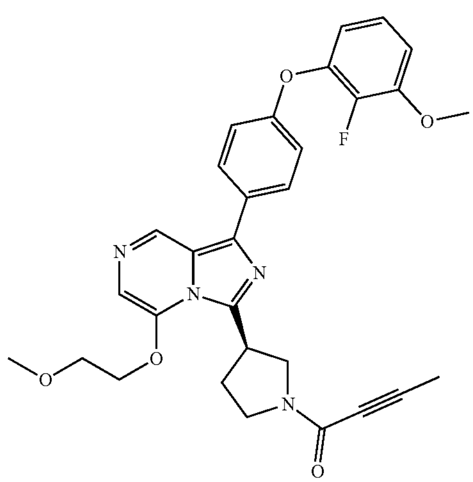 | 545.21/ 545.2 | (R)-1-(3-(1-(4-(2-fluoro-3-methoxyphenoxy)phenyl)-5-(2-methoxyethoxy)imidazo[1,5-a]pyrazin-3-yl)pyrrolidin-1-yl)but-2-yn-1-one |

-continued

| Entry | Structure | MS (cald.) [M + H]+/ MS (found) | name |
|---|---|---|---|
| 104 | 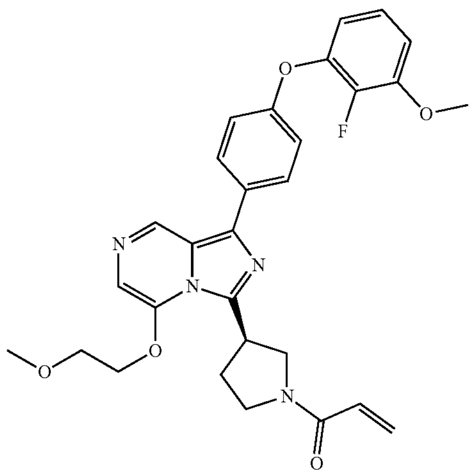 | 533.21/ 533.2 | (R)-1-(3-(1-(4-(2-fluoro-3-methoxyphenoxy)phenyl)-5-(2-methoxyethoxy)imidazo[1,5-a]pyrazin-3-yl)pyrrolidin-1-yl)prop-2-en-1-one |
| 105 | 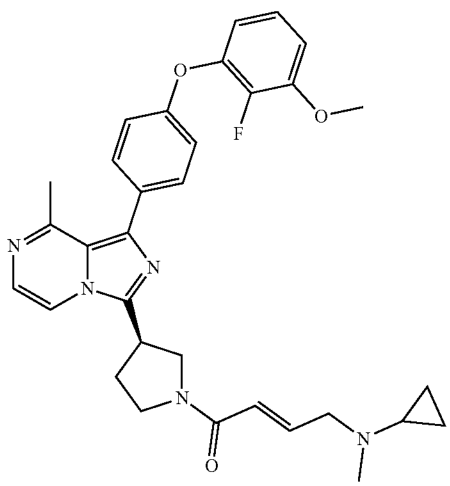 [SMILES: COc1cccc(Oc2ccc(-c3nc([C@@H]4CCN(C(=O)/C=C/CN(C)C5CC5)C4)n4ccnc(C)c34)cc2)c1F] | 556.26/ 556.2 | (R,E)-4-(cyclopropyl(methyl)amino)-1-(3-(1-(4-(2-fluoro-3-methoxyphenoxy)phenyl)-8-methylimidazo[1,5-a]pyrazin-3-yl)pyrrolidin-1-yl)but-2-en-1-one |
| 106 | 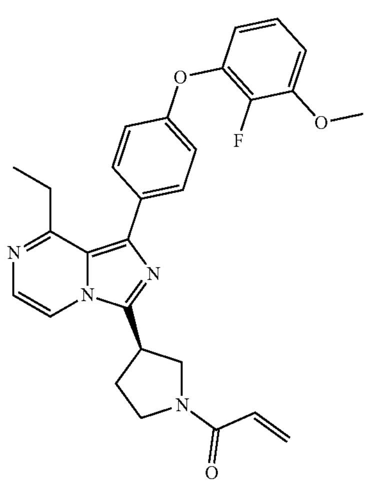 [SMILES: C=CC(=O)N1CC[C@@H](c2nc(-c3ccc(Oc4cccc(OC)c4F)cc3)c3c(CC)nccn23)C1] | 487.21/ 487.2 | (R)-1-(3-(8-ethyl-1-(4-(2-fluoro-3-methoxyphenoxy)phenyl)imidazo[1,5-a]pyrazin-3-yl)pyrrolidin-1-yl)prop-2-en-1-one |

-continued

| Entry | Structure | MS (cald.) [M + H]⁺/ MS (found) | name |
|---|---|---|---|
| 107 | 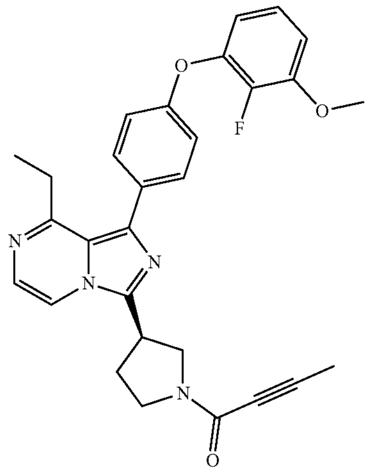 [SMILES: CC#CC(=O)N1CC[C@@H](c2nc(-c3ccc(Oc4cccc(OC)c4F)cc3)c3c(CC)nccn23)C1] | 499.21/ 499.2 | (R)-1-(3-(8-ethyl-1-(4-(2-fluoro-3-methoxyphenoxy)phenyl)imidazo[1,5-a]pyrazin-3-yl)pyrrolidin-1-yl)but-2-yn-1-one |
| 108 | 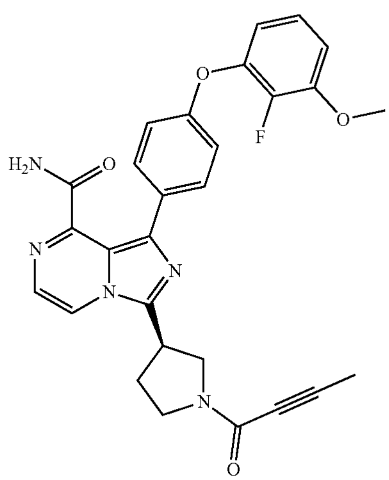 [SMILES: CC#CC(=O)N1CC[C@@H](c2nc(-c3ccc(Oc4cccc(OC)c4F)cc3)c3c(C(N)=O)nccn23)C1] | 514.18/ 514.2 | (R)-3-(1-(but-2-ynoyl)pyrrolidin-3-yl)-1-(4-(2-fluoro-3-methoxyphenoxy)phenyl)imidazo[1,5-a]pyrazine-8-carboxamide |
| 109 | 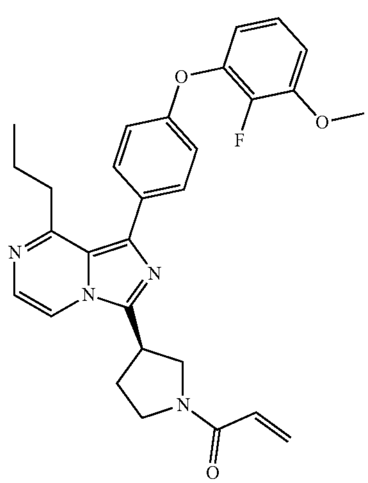 [SMILES: C=CC(=O)N1CC[C@@H](c2nc(-c3ccc(Oc4cccc(OC)c4F)cc3)c3c(CCC)nccn23)C1] | 501.22/ 501.2 | (R)-1-(3-(1-(4-(2-fluoro-3-methoxyphenoxy)phenyl)-8-propylimidazo[1,5-a]pyrazin-3-yl)pyrrolidin-1-yl)prop-2-en-1-one |

| Entry | Structure | MS (cald.) [M + H]+/ MS (found) | name |
|---|---|---|---|
| 110 | 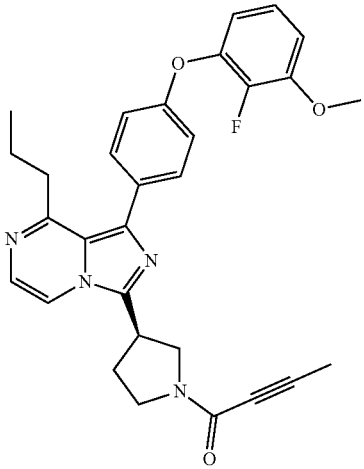 [SMILES: CC#CC(=O)N1CC[C@@H](c2nc(-c3ccc(Oc4cccc(OC)c4F)cc3)c3c(CCC)nccn23)C1] | 513.22/ 513.2 | (R)-1-(3-(1-(4-(2-fluoro-3-methoxyphenoxy)phenyl)-8-propylimidazo[1,5-a]pyrazin-3-yl)pyrrolidin-1-yl)but-2-yn-1-one |
| 111 | 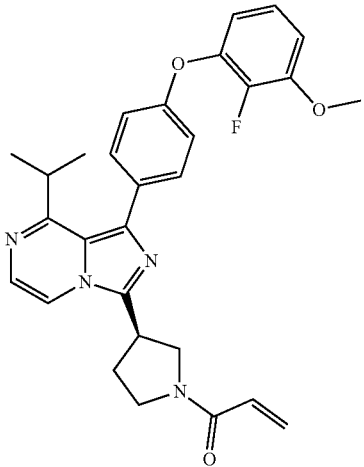 [SMILES: C=CC(=O)N1CC[C@@H](c2nc(-c3ccc(Oc4cccc(OC)c4F)cc3)c3c(C(C)C)nccn23)C1] | 501.22/ 501.2 | (R)-1-(3-(1-(4-(2-fluoro-3-methoxyphenoxy)phenyl)-8-isopropylimidazo[1,5-a]pyrazin-3-yl)pyrrolidin-1-yl)prop-2-en-1-one |
| 112 | 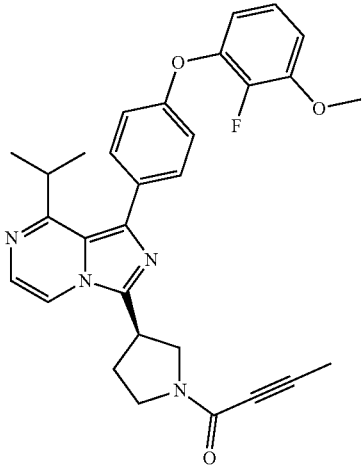 [SMILES: CC#CC(=O)N1CC[C@@H](c2nc(-c3ccc(Oc4cccc(OC)c4F)cc3)c3c(C(C)C)nccn23)C1] | 513.22/ 513.2 | (R)-1-(3-(1-(4-(2-fluoro-3-methoxyphenoxy)phenyl)-8-isopropylimidazo[1,5-a]pyrazin-3-yl)pyrrolidin-1-yl)but-2-yn-1-one |

-continued

| Entry | Structure | MS (cald.) [M + H]+/ MS (found) | name |
|---|---|---|---|
| 113 | 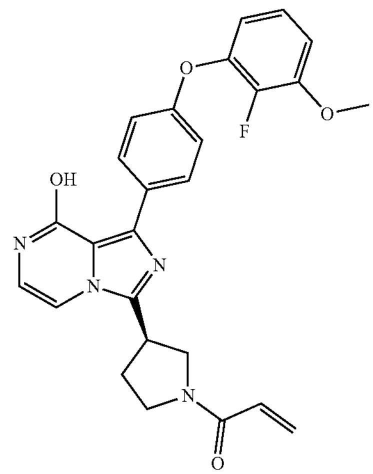 [SMILES: C=CC(=O)N1CC[C@@H](c2nc(-c3ccc(Oc4cccc(OC)c4F)cc3)c3c(O)nccn23)C1] | 475.17/ 475.2 | (R)-1-(3-(1-(4-(2-fluoro-3-methoxyphenoxy)phenyl)-8-hydroxyimidazo[1,5-a]pyrazin-3-yl)pyrrolidin-1-yl)prop-2-en-1-one |
| 114 | 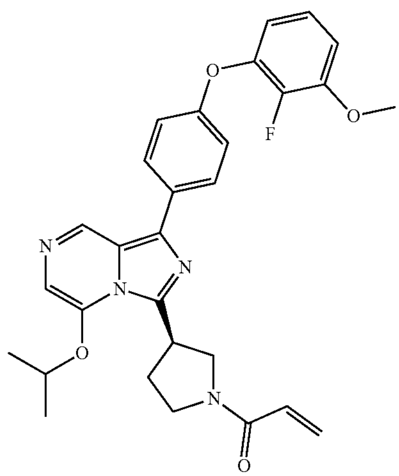 [SMILES: C=CC(=O)N1CC[C@@H](c2nc(-c3ccc(Oc4cccc(OC)c4F)cc3)c3cncc(OC(C)C)n23)C1] | 517.22/ 517.2 | (R)-1-(3-(1-(4-(2-fluoro-3-methoxyphenoxy)phenyl)-5-isopropoxyimidazo[1,5-a]pyrazin-3-yl)pyrrolidin-1-yl)prop-2-en-1-one |
| 115 | 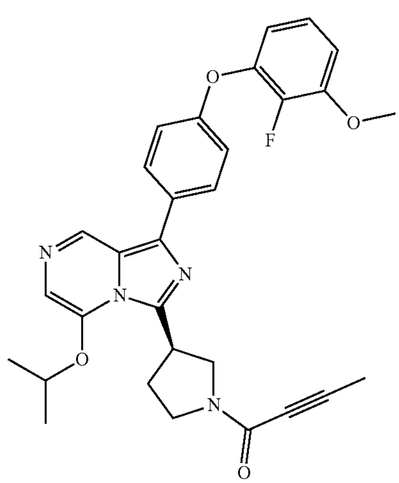 [SMILES: CC#CC(=O)N1CC[C@@H](c2nc(-c3ccc(Oc4cccc(OC)c4F)cc3)c3cncc(OC(C)C)n23)C1] | 429.22/ 429.2 | (R)-1-(3-(1-(4-(2-fluoro-3-methoxyphenoxy)phenyl)-5-isopropoxyimidazo[1,5-a]pyrazin-3-yl)pyrrolidin-1-yl)but-2-yn-1-one |

-continued

| Entry | Structure | MS (cald.) [M + H]+/ MS (found) | name |
|---|---|---|---|
| 116 | 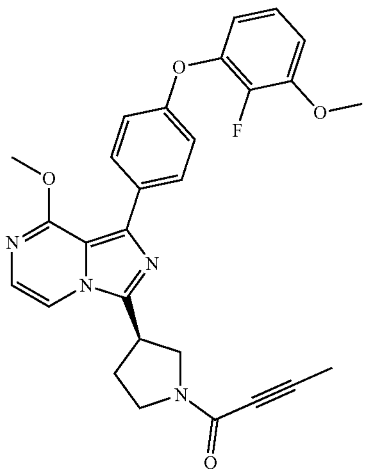 | 501.19/ 501.2 | (R)-1-(3-(1-(4-(2-fluoro-3-methoxyphenoxy)phenyl)-8-methoxyimidazo[1,5-a]pyrazin-3-yl)pyrrolidin-1-yl)but-2-yn-1-one |
| 117 | 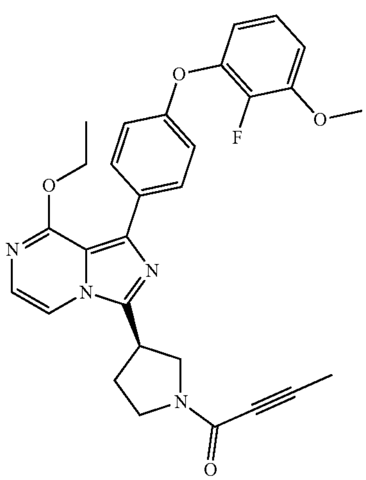 [SMILES: CC#CC(=O)N1CC[C@@H](c2nc(-c3ccc(Oc4cccc(OC)c4F)cc3)c3c(OCC)nccn23)C1] | 415.20/ 415.2 | (R)-1-(3-(8-ethoxy-1-(4-(2-fluoro-3-methoxyphenoxy)phenyl)imidazo[1,5-a]pyrazin-3-yl)pyrrolidin-1-yl)but-2-yn-1-one |
| 118 | 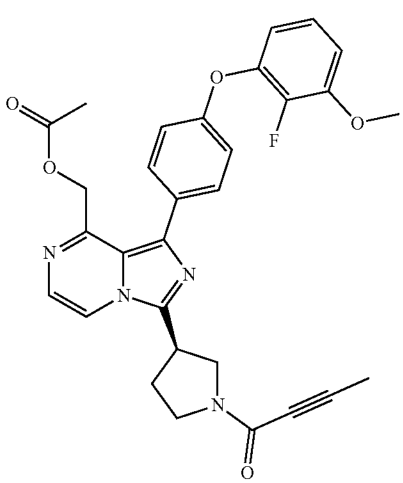 [SMILES: CC#CC(=O)N1CC[C@@H](c2nc(-c3ccc(Oc4cccc(OC)c4F)cc3)c3c(COC(C)=O)nccn23)C1] | 543.20/ 543.2 | (R)-(3-(1-(but-2-ynoyl)pyrrolidin-3-yl)-1-(4-(2-fluoro-3-methoxyphenoxy)phenyl)imidazo[1,5-a]pyrazin-8-yl)methyl acetate |

| Entry | Structure | MS (cald.) [M + H]+/ MS (found) | name |
|---|---|---|---|
| 119 | 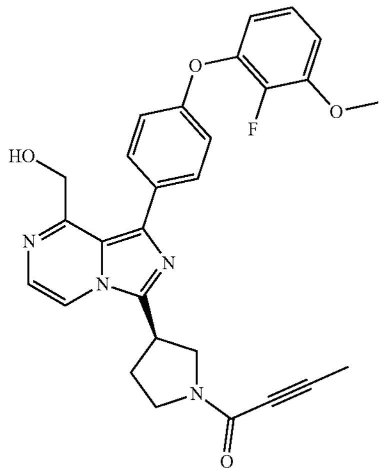 [SMILES: CC#CC(=O)N1CC[C@@H](c2nc(-c3ccc(Oc4cccc(OC)c4F)cc3)c3c(CO)nccn23)C1] | 501.19/ 501.2 | (R)-1-(3-(1-(4-(2-fluoro-3-methoxyphenoxy)phenyl)-8-(hydroxymethyl)imidazo[1,5-a]pyrazin-3-yl)pyrrolidin-1-yl)but-2-yn-1-one |
| 120 | 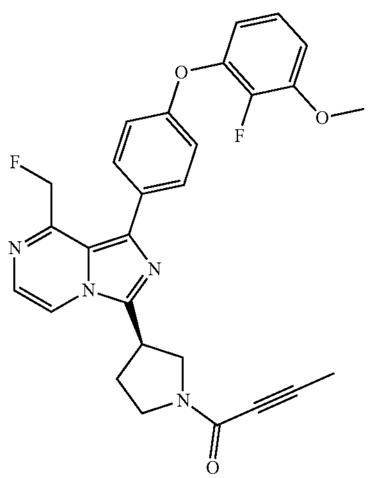 [SMILES: CC#CC(=O)N1CC[C@@H](c2nc(-c3ccc(Oc4cccc(OC)c4F)cc3)c3c(CF)nccn23)C1] | 503.18/ 503.2 | (R)-1-(3-(1-(4-(2-fluoro-3-methoxyphenoxy)phenyl)-8-(fluoromethyl)imidazo[1,5-a]pyrazin-3-yl)pyrrolidin-1-yl)but-2-yn-1-one |
| 121 | 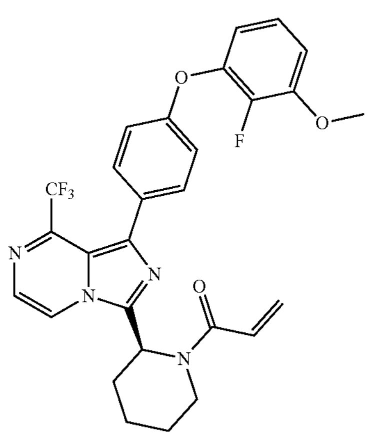 [SMILES: C=CC(=O)N1CCCC[C@H]1c1nc(-c2ccc(Oc3cccc(OC)c3F)cc2)c2c(C(F)(F)F)nccn12] | 541.18/ 541.2 | (S)-1-(2-(1-(4-(2-fluoro-3-methoxyphenoxy)phenyl)-8-(trifluoromethyl)imidazo[1,5-a]pyrazin-3-yl)piperidin-1-yl)prop-2-en-1-one |

-continued

| Entry | Structure | MS (cald.) [M + H]+/ MS (found) | name |
|---|---|---|---|
| 122 | 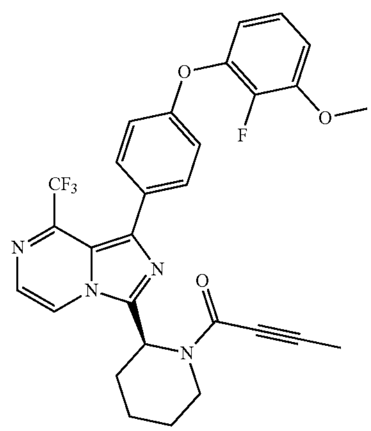 [SMILES: CC#CC(=O)N1CCCC[C@H]1c1nc(-c2ccc(Oc3cccc(OC)c3F)cc2)c2c(C(F)(F)F)nccn12] | 553.18/ 553.2 | (S)-1-(2-(1-(4-(2-fluoro-3-methoxyphenoxy)phenyl)-8-(trifluoromethyl)imidazo[1,5-a]pyrazin-3-yl)piperidin-1-yl)but-2-yn-1-one |
| 123 | 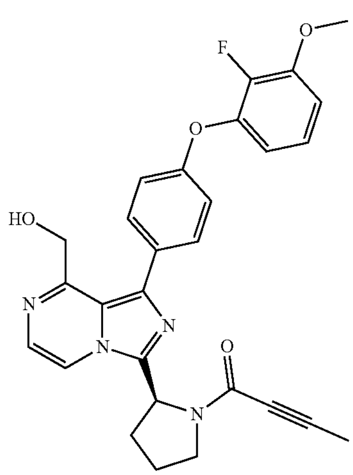 [SMILES: CC#CC(=O)N1CCC[C@H]1c1nc(-c2ccc(Oc3cccc(OC)c3F)cc2)c2c(CO)nccn12] | 501.19/ 501.2 | (S)-1-(2-(1-(4-(2-fluoro-3-methoxyphenoxy)phenyl)-8-(hydroxymethyl)imidazo[1,5-a]pyrazin-3-yl)pyrrolidin-1-yl)but-2-yn-1-one |

Example 124
(S)-1-(2-(1-(4-((2,3-Difluorobenzyl)oxy)phenyl)imidazo[1,5-a]pyrazin-3-yl)pyrrolidin-1-yl)prop-2-en-1-one (124)
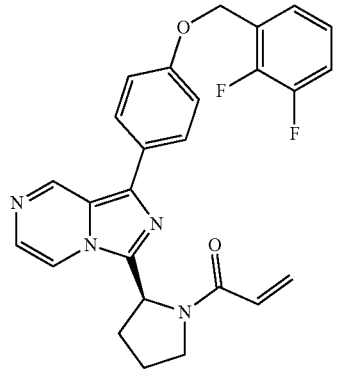 [SMILES: C=CC(=O)N1CCC[C@H]1c1nc(-c2ccc(OCc3cccc(F)c3F)cc2)c2cnccn12]
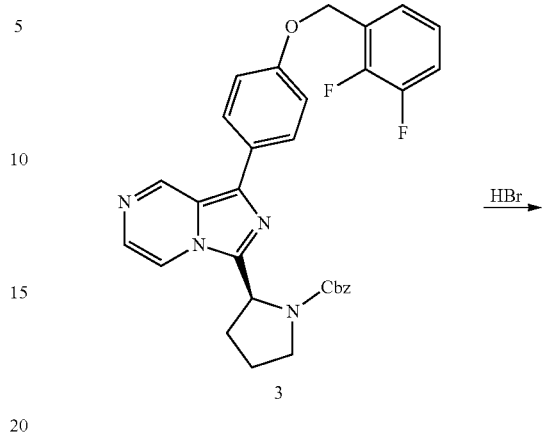
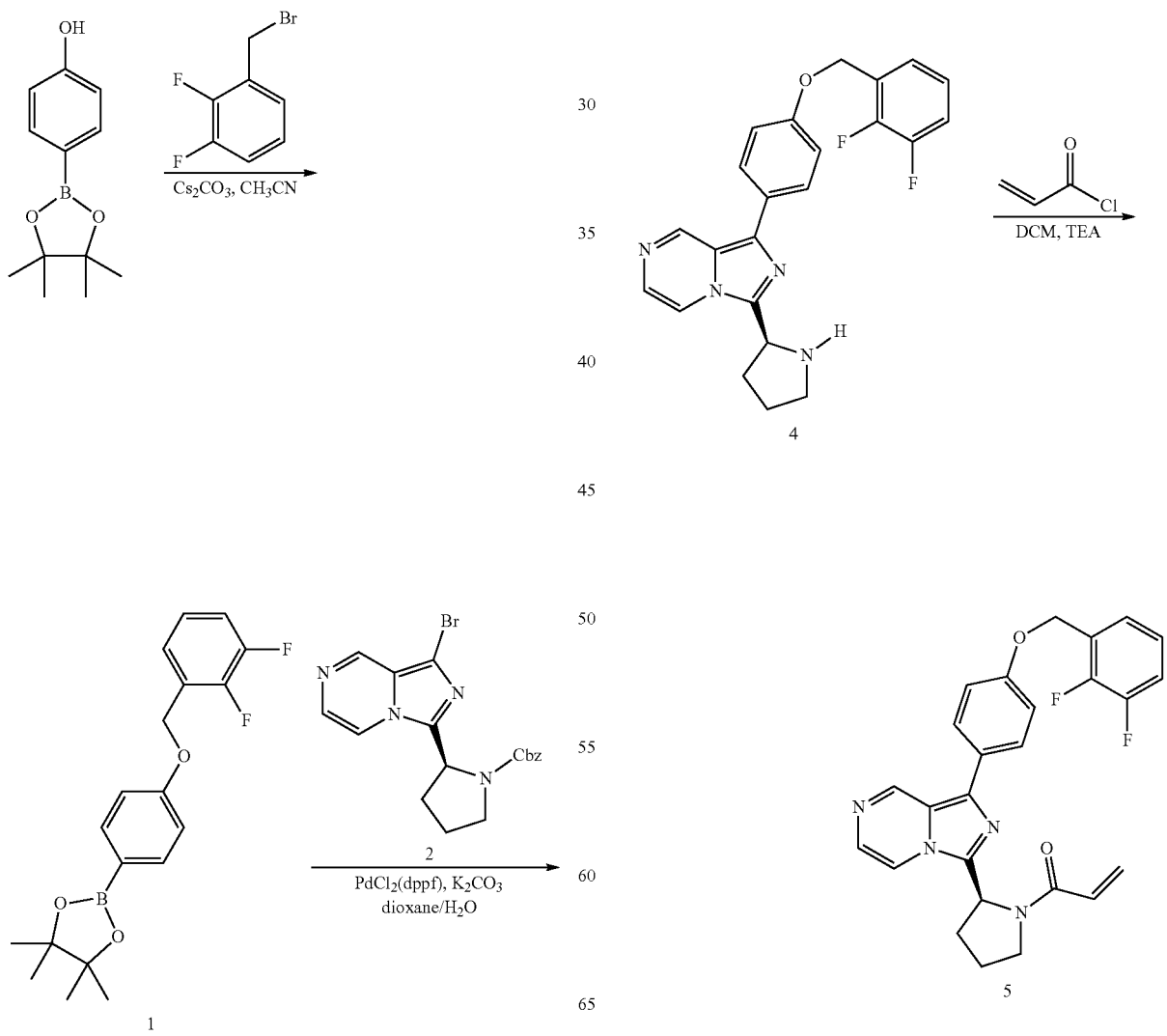

Step 1: 2-(4-((2,3-Difluorobenzyl)oxy)phenyl)-4,4,5,5-tetramethyl-1,32-dioxaborolane (1)

A mixture of 4-(4,4,5,5-tetramethyl-1,3,2-dioxaborolan-2-yl)phenol (440 mg, 2 mmol, 1.0 eq), 1-(bromomethyl)-2,3-difluorobenzene (414 mg, 2 mmol, 1.0 eq) and Cesium carbonate (975 mg, 3 mmol, 1.5 eq) in acetonitrile (15.0 mL) was stirred at rt for 5 h. The solution was concentrated, and water was added. The mixture was extracted with EA. The organic layer was washed with sodium bicarbonate, water and brine. The solution was dried over $Na_2SO_4$, filtered and concentrated to give crude product 1 (835 mg).

Step 2: (S)-Benzyl-2-(1-(4-((2,3-difluorobenzyl)oxy)phenyl)imidazo[1,5-a]pyrazin-3-yl)pyrrolidine-1-carboxylate (3)

A mixture of 1 (100 mg, 0.25 mmol, 1.0 eq), 2 (130 mg, 0.375 mmol, 1.5 eq), $PdCl_2$(dppf) (18 mg, 0.025 mmol, 0.1 eq), and potassium carbonate (69 mg, 0.5 mmol, 2.0 eq) in dioxane (5.0 mL) and water (1.0 mL) was stirred under reflex overnight. The mixture was allowed to cool to room temperature. Water was added and the mixture was extracted with EA. The organic layer was washed with water and brine. The solution was dried over anhydrous $Na_2SO_4$, filtered and concentrated. The residue was purified by silica gel column chromatography (DCM/MeOH=100:1) to afford the desired product 3 (100 mg, yield 74.1%).
$^1$H NMR (400 MHz, $CDCl_3$): δ 9.08 (d, J=33.8 Hz, 1H), 7.83 (s, 2H), 7.60-7.39 (m, 2H), 7.32 (s, 4H), 7.10 (s, 6H), 6.89 (s, 1H), 5.45-4.71 (m, 6H), 3.92-3.51 (m, 2H), 2.78-2.22 (m, 3H), 2.11 (d, J=36.8 Hz, 1H). LCMS: m/z=541 [M+H]$^+$.

Step 3: (S)-1-(4-((2,3-Difluorobenzyl)oxy)phenyl)-3-(pyrrolidin-2-yl)imidazo[1,5-a]pyrazine (4)

A solution of 3 (100 mg, 0.19 mmol, 1.0 eq) in DCM (2.0 mL) was mixed with 33% HBr/acetic acid (2 mL). The mixture was stirred at room temperature (22° C.) for 2 h. Water was added and the mixture was extracted with DCM. The pH of aqueous phase was adjusted to 8 with 2.0 M sodium hydroxide. The mixture was extracted with DCM, and the organic layer was washed with water and brine. The solution was dried over $Na_2SO_4$, filtered and concentrated to give 4 (58 mg, yield 75.2%).
LCMS: m/z=407 [M+H]$^+$.

Step 4: (S)-1-(2-(1-(4-((2,3-Difluorobenzyl)oxy)phenyl)imidazo[1,5-a]pyrazin-3-yl)pyrrolidin-1-yl)prop-2-en-1-one (5)

To a solution of 4 (29 mg, 0.07 mmol, 1.0 eq) and TEA (14 mg, 0.14 mmol, 2.0 eq) in DCM (2.0 mL), was added acryloyl chloride (6.3 mg, 0.07 mmol, 1.0 eq). The mixture was stirred at 15° C. for 20 min. The mixture was diluted with water and extracted with DCM. The organic layer was washed with water and brine. It was dried over $Na_2SO4$, filtered and concentrated. The residue was purified with prep-TLC to give 5 (23.0 mg, yield 71.9%).
$^1$H NMR (400 MHz, $CDCl_3$): δ 9.11 (s, 1H), 8.33 (d, J=4.2 Hz, 1H), 7.82 (d, J=8.5 Hz, 2H), 7.55 (d, J=4.9 Hz, 1H), 7.30 (d, J=6.9 Hz, 1H), 7.21-7.00 (m, 4H), 6.45 (dd, J=16.8, 10.2 Hz, 1H), 6.39-6.24 (m, 1H), 5.68 (d, J=10.1 Hz, 1H), 5.61-5.43 (m, 1H), 5.21 (s, 2H), 3.90 (dd, J=13.3, 8.9 Hz, 1H), 3.74 (dd, J=17.0, 7.9 Hz, 1H), 2.84 (dd, J=19.4, 8.0 Hz, 1H), 2.56 (d, J=4.5 Hz, 1H), 2.31 (td, J=16.2, 8.1 Hz, 1H), 2.26-2.08 (m, 1H). LCMS: m/z=461 [M+H]$^+$.

Example 125

(S)-1-(2-(1-(4-((2-fluorophenoxy)methyl)phenyl)imidazo[1,5-a]pyrazin-3-yl)pyrrolidin-1-yl)prop-2-en-1-one (125)

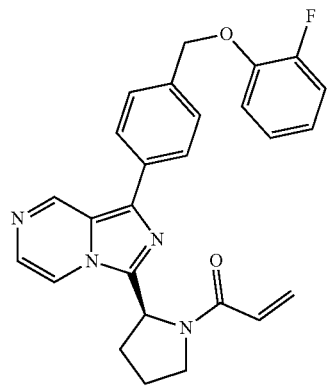 [SMILES: C=CC(=O)N1CCC[C@H]1c1nc(-c2ccc(COc3ccccc3F)cc2)c2cnccn12]

Scheme 8

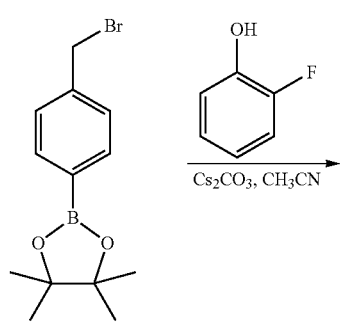

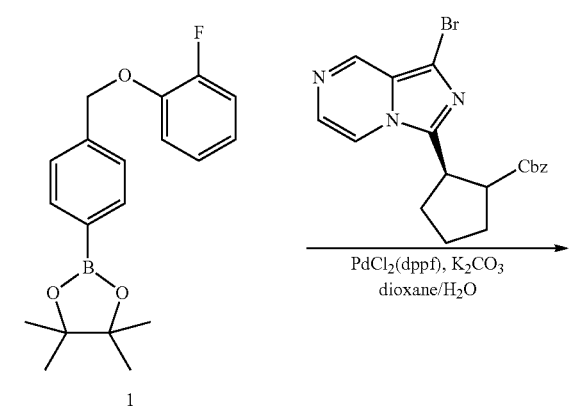

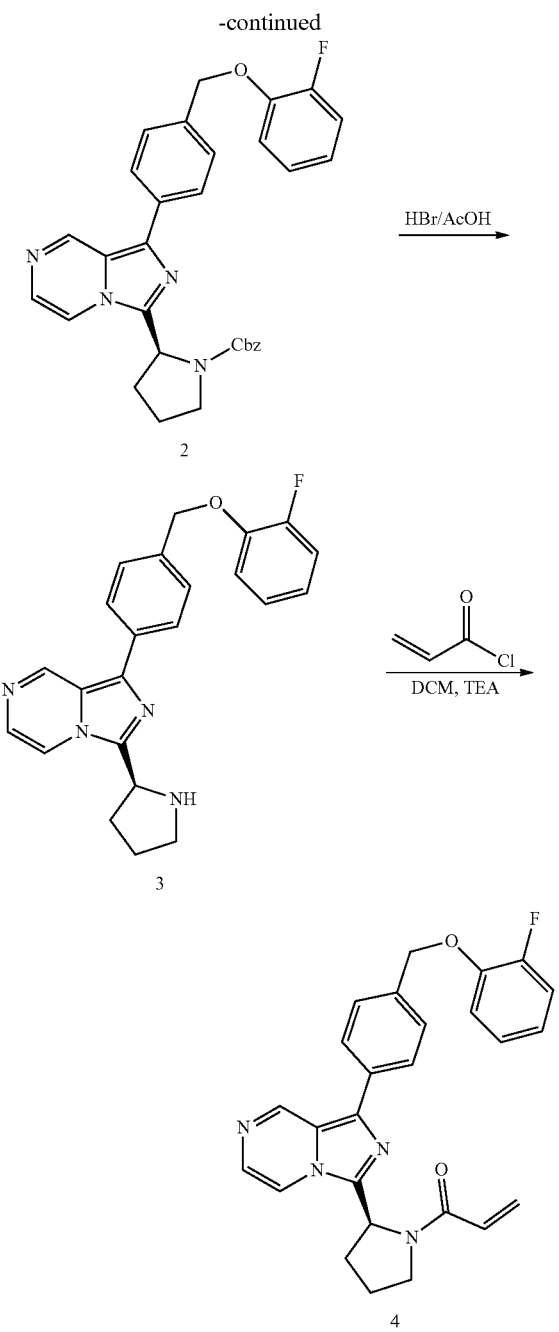

¹H NMR (400 MHz, CDCl₃): δ 7.81 (d, J=7.2 Hz, 2H), 7.43 (d, J=7.2 Hz, 2H), 7.11-7.06 (m, 1H), 6.99-6.88 (m, 3H), 5.16 (s, 2H), 1.34 (s, 12H).

Step 2: (S)-benzyl 2-(1-(4-((2-fluorophenoxy)methyl)phenyl)imidazo[1,5-a]pyrazin-3-yl)pyrrolidine-1-carboxylate (2)

A mixture of compound 1 (148 mg, 0.45 mmol, 1.5 eq), (S)-benzyl 2-(1-bromoimidazo[1,5-a]pyrazin-3-yl)pyrrolidine-1-carboxylate (120 mg, 0.30 mmol, 1.0 eq), PdCl₂(dppf) (22 mg), and potassium carbonate (83 mg, 0.60 mmol, 2.0 eq) in dioxane (10 mL) and water (2.0 mL) was stirred under reflux for 3 h. The mixture was allowed to cool to room temperature. Water was added and the mixture was extracted with EA. The combined organic layers were washed with water and brine. The solution was dried over anhydrous sodium sulfate. The solvent was removed in vacuum and the residue was purified by silica gel column chromatography (PE/EA=2:1-1:2) to afford the desired product 2 (110 mg, yield 72%).

¹H NMR (400 MHz, CDCl₃): δ 9.18-9.09 (m, 1H), 8.25 (s, 0.5H), 7.91 (s, 2H), 7.66-7.46 (m, 4H), 7.33-7.26 (m, 3H), 7.25-7.02 (m, 4H), 6.98-6.90 (m, 2H), 5.33-5.21 (m, 3H), 5.20-4.81 (m, 2H), 3.78-3.67 (m, 2H), 2.54-2.35 (m, 3H), 2.08-2.07 (m, 1H). LCMS: m/z=509 [M+H]⁺.

Step 3: (S)-1-(4-((2-Fluorophenoxy)methyl)phenyl)-3-(pyrrolidin-2-yl)imidazo[1,5-a]pyrazine (3)

A solution of compound 2 (107 mg, 0.20 mmol, 1.0 eq) in DCM (2.0 mL) was mixed with 33% HBr/acetic acid (2.0 mL). The mixture was stirred at room temperature (22° C.) for 1 h. Water was added and the mixture was extracted with DCM. The pH of the aqueous phase was adjusted to 8 with ammonium hydroxide. The mixture was extracted with DCM, and the organic layer was washed with water and brine. The solution was dried over Na₂SO₄, filtered and concentrated to give 3 (65 mg), which was used into next reaction without further purification. LCMS: m/z=375 [M+H]⁺.

Step 4: (S)-1-(2-(1-(4-((2-Fluorophenoxy)methyl)phenyl)imidazo[1,5-a]pyrazin-3-yl)pyrrolidin-1-yl)prop-2-en-1-one (4)

To a solution of compound 3 (32 mg, 0.084 mmol, 1.0 eq) and TEA (0.02 mL) in DCM (5.0 mL), was added acryloyl chloride (7.6 mg, 0.084 mmol, 1.0 eq). The mixture was stirred at 15° C. for 30 min. The mixture was quenched with methanol (2.0 mL) and the solvent was removed in vacuo. The residue was purified with prep-TLC to give 4 (10.4 mg, yield 28%).

¹H NMR (400 MHz, CDCl₃): δ 9.17 (s, 1H), 8.36 (d, J=4.0 Hz, 1H), 7.90 (d, J=8.0 Hz, 2H), 7.59-7.53 (m, 3H), 7.12-7.01 (m, 3H), 6.90-6.62 (m, 1H), 6.48-6.42 (m, 1H), 6.33-6.29 (m, 1H), 5.69-5.66 (m, 1H), 5.56-5.53 (m, 1H), 5.20 (s, 2H), 3.90-3.88 (m, 1H), 3.74-3.72 (m, 1H), 2.91-2.82 (m, 1H), 2.64-2.58 (m, 1H), 2.38-2.25 (m, 1H), 2.20-2.16 (m, 1H). LCMS: m/z=429 [M+H]⁺.

Step 1: 2-(4-((2-Fluorophenoxy)methyl)phenyl)-4,4,5,5-tetramethyl-1,3,2-dioxaborolane (1)

A suspension of 2-(4-(bromomethyl)phenyl)-4,4,5,5-tetramethyl-1,3,2-dioxaborolane (1.0 g, 3.37 mmol, 1.0 eq), 2-fluorophenol (415 mg, 3.70 mmol, 1.1 eq) and Cesium carbonate (1.43 g, 4.38 mmol, 1.3 eq) in acetonitrile (20 mL) was stirred at rt for 5 h. The mixture was mixed with water (50 mL) and extracted with EA. The combined organic layers were washed with sodium bicarbonate, water, and brine. The solution was dried over Na₂SO₄, filtered and concentrated to give crude product 1 (1.3 g), which was used into next reaction without further purification.

Examples 126 to 163 were prepared following the procedures described above for Examples 124 and 125:

| Entry | structure | MS (cald.) [M + H]+/ MS (found) | name |
|---|---|---|---|
| 126 | 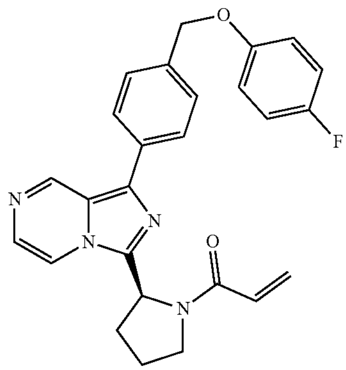 [SMILES: C=CC(=O)N1CCC[C@H]1c1nc(-c2ccc(COc3ccc(F)cc3)cc2)c2cnccn12] | 443.18/ 443.2 | (S)-1-(2-(1-(4-((4-fluorophenoxy)methyl)phenyl)imidazo[1,5-a]pyrazin-3-yl)pyrrolidin-1-yl)prop-2-en-1-one |
| 127 | 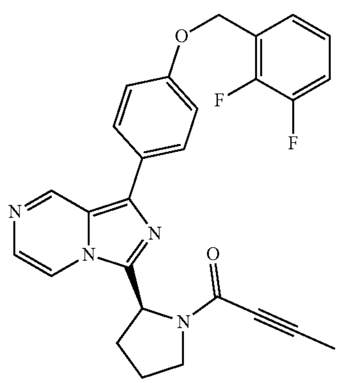 [SMILES: CC#CC(=O)N1CCC[C@H]1c1nc(-c2ccc(OCc3cccc(F)c3F)cc2)c2cnccn12] | 473.17/ 473.2 | (S)-1-(2-(1-(4-((2,3-difluorobenzyl)oxy)phenyl)imidazo[1,5-a]pyrazin-3-yl)pyrrolidin-1-yl)but-2-yn-1-one |
| 128 | 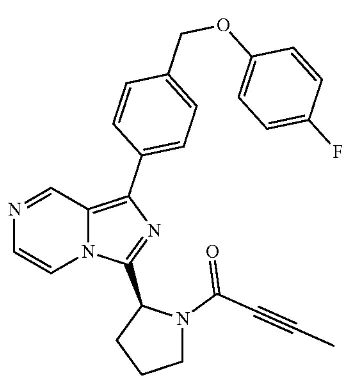 [SMILES: CC#CC(=O)N1CCC[C@H]1c1nc(-c2ccc(COc3ccc(F)cc3)cc2)c2cnccn12] | 455.18/ 455.2 | (S)-1-(2-(1-(4-((4-fluorophenoxy)methyl)phenyl)imidazo[1,5-a]pyrazin-3-yl)pyrrolidin-1-yl)but-2-yn-1-one |
| 129 | 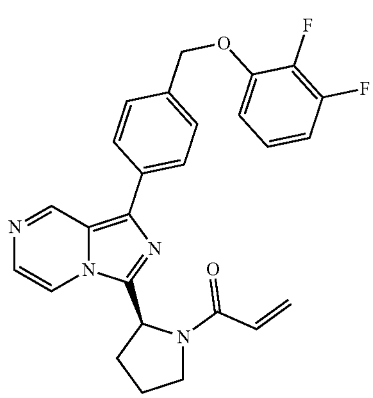 [SMILES: C=CC(=O)N1CCC[C@H]1c1nc(-c2ccc(COc3cccc(F)c3F)cc2)c2cnccn12] | 461.17/ 461.2 | (S)-1-(2-(1-(4-((2,3-difluorophenoxy)methyl)phenyl)imidazo[1,5-a]pyrazin-3-yl)pyrrolidin-1-yl)prop-2-en-1-one |

|Entry|structure|MS (cald.) [M + H]⁺/ MS (found)|name|
|---|---|---|---|
|130| 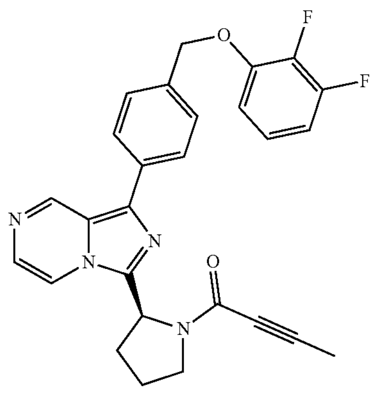 [SMILES: CC#CC(=O)N1CCC[C@H]1c1nc(-c2ccc(COc3cccc(F)c3F)cc2)c2cnccn12] |473.17/ 473.2|(S)-1-(2-(1-(4-((2,3-difluorophenoxy)methyl)phenyl)imidazo[1,5-a]pyrazin-3-yl)pyrrolidin-1-yl)but-2-yn-1-one|
|131| 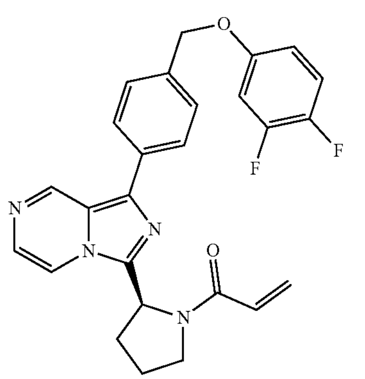 [SMILES: C=CC(=O)N1CCC[C@H]1c1nc(-c2ccc(COc3ccc(F)c(F)c3)cc2)c2cnccn12] |461.17/ 461.2|(S)-1-(2-(1-(4-((3,4-difluorophenoxy)methyl)phenyl)imidazo[1,5-a]pyrazin-3-yl)pyrrolidin-1-yl)prop-2-en-1-one|
|132| 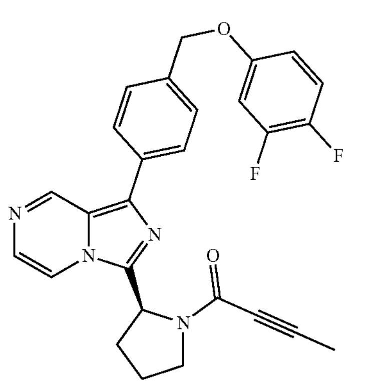 [SMILES: CC#CC(=O)N1CCC[C@H]1c1nc(-c2ccc(COc3ccc(F)c(F)c3)cc2)c2cnccn12] |473.17/ 473.2|(S)-1-(2-(1-(4-((3,4-difluorophenoxy)methyl)phenyl)imidazo[1,5-a]pyrazin-3-yl)pyrrolidin-1-yl)but-2-yn-1-one|

| Entry | structure | MS (cald.) [M + H]+/ MS (found) | name |
|---|---|---|---|
| 133 | 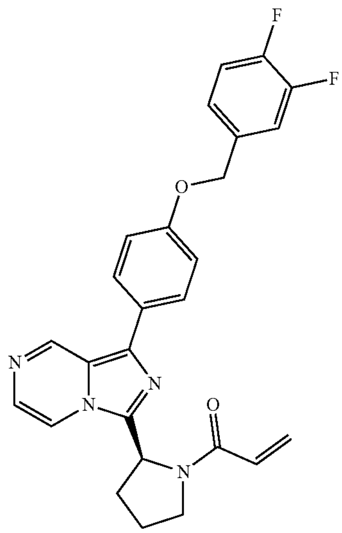 [SMILES: C=CC(=O)N1CCC[C@H]1c1nc(-c2ccc(OCc3ccc(F)c(F)c3)cc2)c2cnccn12] | 461.17/ 461.2 | (S)-1-(2-(1-(4-((3,4-difluorobenzyl)oxy)phenyl)imidazo[1,5-a]pyrazin-3-yl)pyrrolidin-1-yl)prop-2-en-1-one |
| 134 | 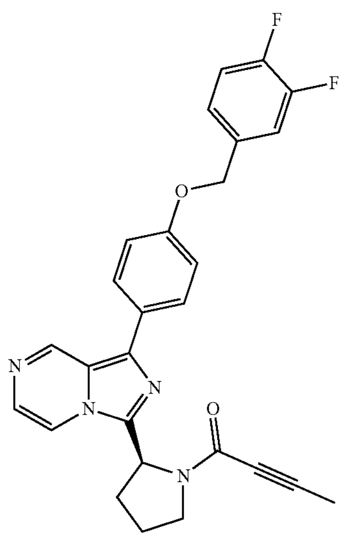 [SMILES: CC#CC(=O)N1CCC[C@H]1c1nc(-c2ccc(OCc3ccc(F)c(F)c3)cc2)c2cnccn12] | 473.17/ 473.2 | (S)-1-(2-(1-(4-((3,4-difluorobenzyl)oxy)phenyl)imidazo[1,5-a]pyrazin-3-yl)pyrrolidin-1-yl)but-2-yn-1-one |
| 135 | 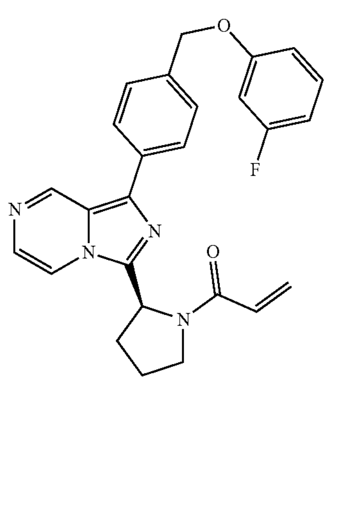 [SMILES: C=CC(=O)N1CCC[C@H]1c1nc(-c2ccc(COc3cccc(F)c3)cc2)c2cnccn12] | 443.18/ 443.2 | (S)-1-(2-(1-(4-((3-fluorobenzyl)oxy)phenyl)imidazo[1,5-a]pyrazin-3-yl)pyrrolidin-1-yl)prop-2-en-1-one |

-continued

| Entry | structure | MS (cald.) [M + H]+/ MS (found) | name |
|---|---|---|---|
| 136 | 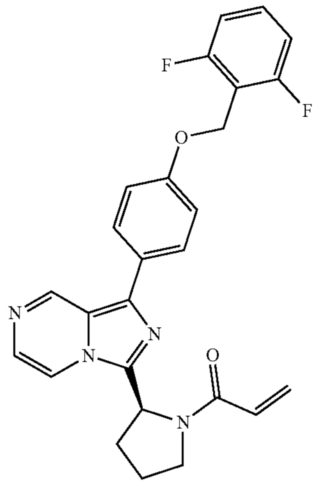 [SMILES: C=CC(=O)N1CCC[C@H]1c1nc(-c2ccc(OCc3c(F)cccc3F)cc2)c2cnccn12] | 461.17/ 461.2 | (S)-1-(2-(1-(4-((2,6-difluorobenzyl)oxy)phenyl)imidazo[1,5-a]pyrazin-3-yl)pyrrolidin-1-yl)prop-2-en-1-one |
| 137 | 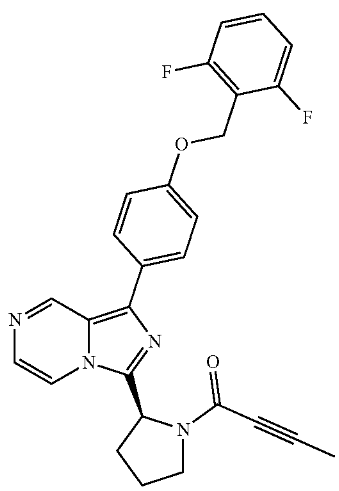 [SMILES: CC#CC(=O)N1CCC[C@H]1c1nc(-c2ccc(OCc3c(F)cccc3F)cc2)c2cnccn12] | 473.17/ 473.2 | (S)-1-(2-(1-(4-((2,6-difluorobenzyl)oxy)phenyl)imidazo[1,5-a]pyrazin-3-yl)pyrrolidin-1-yl)but-2-yn-1-one |
| 138 | 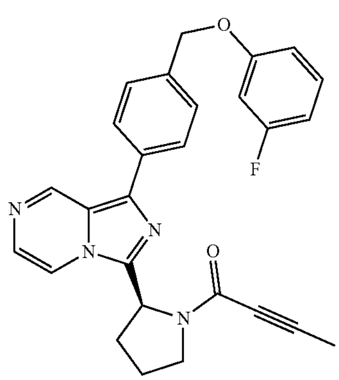 [SMILES: CC#CC(=O)N1CCC[C@H]1c1nc(-c2ccc(COc3cccc(F)c3)cc2)c2cnccn12] | 455.18/ 455.2 | (S)-1-(2-(1-(4-((3-fluorobenzyl)oxy)phenyl)imidazo[1,5-a]pyrazin-3-yl)pyrrolidin-1-yl)but-2-yn-1-one |

US 11,974,999 B2
-continued
| Entry | structure | MS (cald.) [M + H]+/ MS (found) | name |
|---|---|---|---|
| 139 | 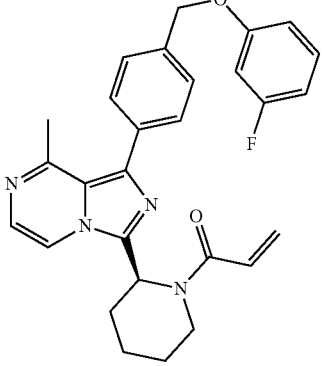 | 471.21/ 471.2 | (S)-1-(2-(1-(4-((3-fluorobenzyl)oxy)phenyl)-8-methylimidazo[1,5-a]pyrazin-3-yl)piperidin-1-yl)prop-2-en-1-one |
| 140 | 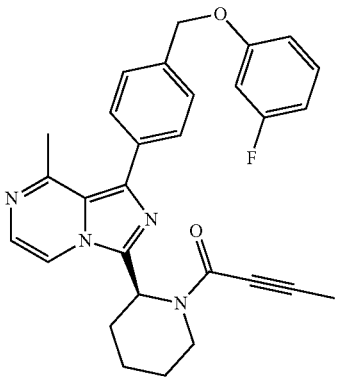 [SMILES: CC#CC(=O)N1CCCC[C@H]1c1nc(-c2ccc(COc3cccc(F)c3)cc2)c2c(C)nccn12] | 483.21/ 483.2 | (S)-1-(2-(1-(4-((3-fluorobenzyl)oxy)phenyl)-8-methylimidazo[1,5-a]pyrazin-3-yl)piperidin-1-yl)but-2-yn-1-one |
| 141 | 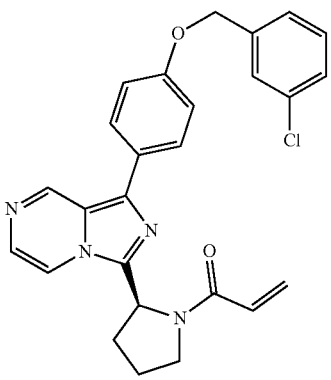 [SMILES: C=CC(=O)N1CCC[C@H]1c1nc(-c2ccc(OCc3cccc(Cl)c3)cc2)c2cnccn12] | 459.15/ 459.2 | (S)-1-(2-(1-(4-((3-chlorobenzyl)oxy)phenyl)imidazo[1,5-a]pyrazin-3-yl)pyrrolidin-1-yl)prop-2-en-1-one |
| 142 | 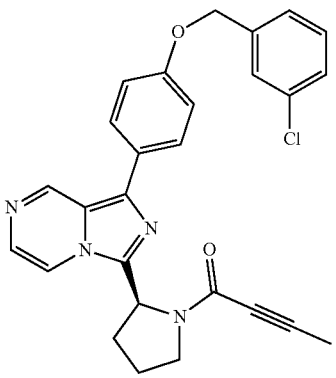 [SMILES: CC#CC(=O)N1CCC[C@H]1c1nc(-c2ccc(OCc3cccc(Cl)c3)cc2)c2cnccn12] | 471.15/ 471.2 | (S)-1-(2-(1-(4-((3-chlorobenzyl)oxy)phenyl)imidazo[1,5-a]pyrazin-3-yl)pyrrolidin-1-yl)but-2-yn-1-one |

-continued

| Entry | structure | MS (cald.) [M + H]+/ MS (found) | name |
|---|---|---|---|
| 143 | 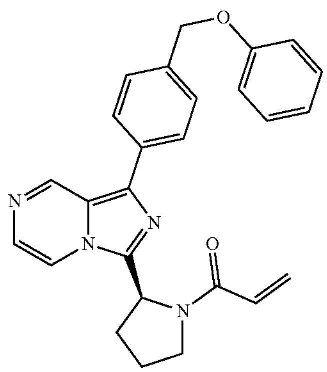 [SMILES: C=CC(=O)N1CCC[C@H]1c1nc(-c2ccc(COc3ccccc3)cc2)c2cnccn12] | 425.19/ 425.2 | (S)-1-(2-(1-(4-(phenoxymethyl)phenyl)imidazo[1,5-a]pyrazin-3-yl)pyrrolidin-1-yl)prop-2-en-1-one |
| 144 | 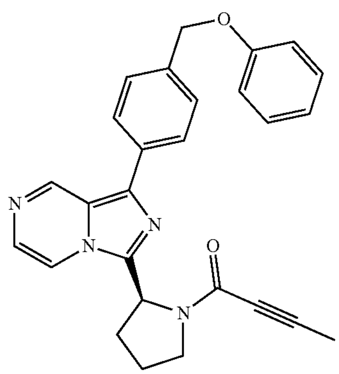 [SMILES: CC#CC(=O)N1CCC[C@H]1c1nc(-c2ccc(COc3ccccc3)cc2)c2cnccn12] | 437.19/ 437.2 | (S)-1-(2-(1-(4-(phenoxymethyl)phenyl)imidazo[1,5-a]pyrazin-3-yl)pyrrolidin-1-yl)but-2-yn-1-one |
| 145 | 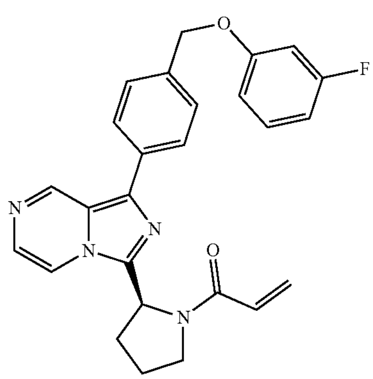 [SMILES: C=CC(=O)N1CCC[C@H]1c1nc(-c2ccc(COc3cccc(F)c3)cc2)c2cnccn12] | 443.18/ 443.2 | (S)-1-(2-(1-(4-((3-fluorophenoxy)methyl)phenyl)imidazo[1,5-a]pyrazin-3-yl)pyrrolidin-1-yl)prop-2-en-1-one |
| 146 | 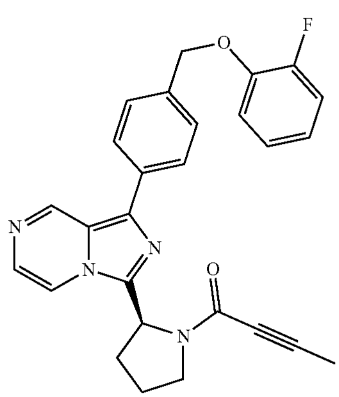 [SMILES: CC#CC(=O)N1CCC[C@H]1c1nc(-c2ccc(COc3ccccc3F)cc2)c2cnccn12] | 455.18/ 455.2 | (S)-1-(2-(1-(4-((2-fluorophenoxy)methyl)phenyl)imidazo[1,5-a]pyrazin-3-yl)pyrrolidin-1-yl)but-2-yn-1-one |

-continued

| Entry | structure | MS (cald.) [M + H]+/ MS (found) | name |
|---|---|---|---|
| 147 | 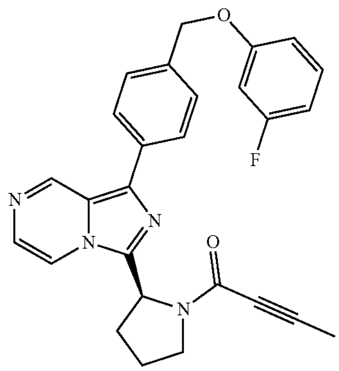 [SMILES: CC#CC(=O)N1CCC[C@H]1c1nc(-c2ccc(COc3cccc(F)c3)cc2)c2cnccn12] | 455.18/ 455.2 | (S)-1-(2-(1-(4-((3-fluorophenoxy)methyl)phenyl)imidazo[1,5-a]pyrazin-3-yl)pyrrolidin-1-yl)but-2-yn-1-one |
| 148 | 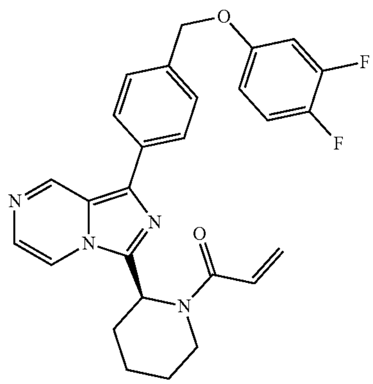 [SMILES: C=CC(=O)N1CCCC[C@H]1c1nc(-c2ccc(COc3ccc(F)c(F)c3)cc2)c2cnccn12] | 475.19/ 475.2 | (S)-1-(2-(1-(4-((3,4-difluorophenoxy)methyl)phenyl)imidazo[1,5-a]pyrazin-3-yl)piperidin-1-yl)prop-2-en-1-one |
| 149 | 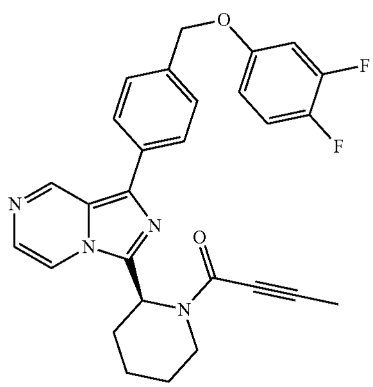 [SMILES: CC#CC(=O)N1CCCC[C@H]1c1nc(-c2ccc(COc3ccc(F)c(F)c3)cc2)c2cnccn12] | 487.19/ 487.2 | (S)-1-(2-(1-(4-((3,4-difluorophenoxy)methyl)phenyl)imidazo[1,5-a]pyrazin-3-yl)piperidin-1-yl)but-2-yn-1-one |
| 150 | 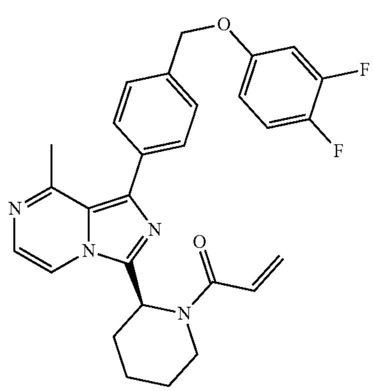 [SMILES: C=CC(=O)N1CCCC[C@H]1c1nc(-c2ccc(COc3ccc(F)c(F)c3)cc2)c2c(C)nccn12] | 489.20/ 489.2 | (S)-1-(2-(1-(4-((3,4-difluorophenoxy)methyl)phenyl)-8-methylimidazo[1,5-a]pyrazin-3-yl)piperidin-1-yl)prop-2-en-1-one |

-continued

| Entry | structure | MS (cald.) [M + H]+/ MS (found) | name |
|---|---|---|---|
| 151 | 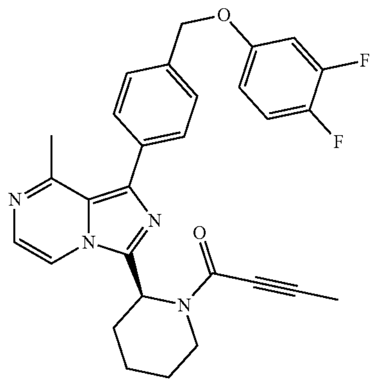 [SMILES: CC#CC(=O)N1CCCC[C@H]1c1nc(-c2ccc(COc3ccc(F)c(F)c3)cc2)c2c(C)nccn12] | 501.20/ 501.2 | (S)-1-(2-(1-(4-((3,4-difluorophenoxy)methyl)phenyl)-8-methylimidazo[1,5-a]pyrazin-3-yl)piperidin-1-yl)but-2-yn-1-one |
| 152 | 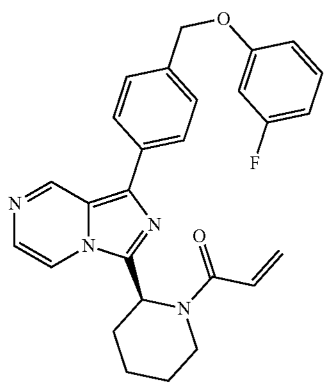 [SMILES: C=CC(=O)N1CCCC[C@H]1c1nc(-c2ccc(COc3cccc(F)c3)cc2)c2cnccn12] | 457.20/ 457.2 | (S)-1-(2-(1-(4-((3-fluorobenzyl)oxy)phenyl)imidazo[1,5-a]pyrazin-3-yl)piperidin-1-yl)prop-2-en-1-one |
| 153 | 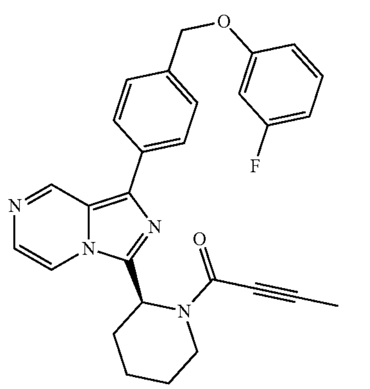 [SMILES: CC#CC(=O)N1CCCC[C@H]1c1nc(-c2ccc(COc3cccc(F)c3)cc2)c2cnccn12] | 469.20/ 469.2 | (S)-1-(2-(1-(4-((3-fluorobenzyl)oxy)phenyl)imidazo[1,5-a]pyrazin-3-yl)piperidin-1-yl)but-2-yn-1-one |
| 154 | 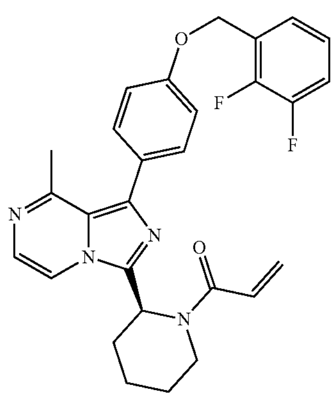 [SMILES: C=CC(=O)N1CCCC[C@H]1c1nc(-c2ccc(OCc3cccc(F)c3F)cc2)c2c(C)nccn12] | 489.20/ 489.2 | (S)-1-(2-(1-(4-((2,3-difluorobenzyl)oxy)phenyl)-8-methylimidazo[1,5-a]pyrazin-3-yl)piperidin-1-yl)prop-2-en-1-one |

-continued

| Entry | structure | MS (cald.) [M + H]+/ MS (found) | name |
|---|---|---|---|
| 155 | 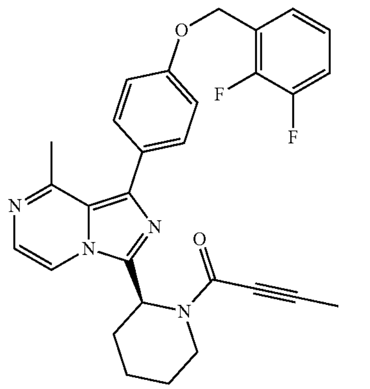 [SMILES: CC#CC(=O)N1CCCC[C@H]1c1nc(-c2ccc(OCc3cccc(F)c3F)cc2)c2c(C)nccn12] | 501.20/ 501.2 | (S)-1-(2-(1-(4-((2,3-difluorobenzyl)oxy)phenyl)-8-methylimidazo[1,5-a]pyrazin-3-yl)piperidin-1-yl)but-2-yn-1-one |
| 156 | 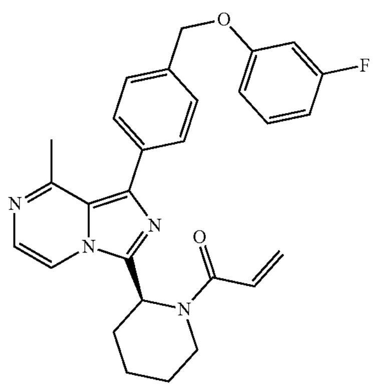 [SMILES: C=CC(=O)N1CCCC[C@H]1c1nc(-c2ccc(COc3cccc(F)c3)cc2)c2c(C)nccn12] | 471.21/ 471.2 | (S)-1-(2-(1-(4-((3-fluorophenoxy)methyl)phenyl)-8-methylimidazo[1,5-a]pyrazin-3-yl)piperidin-1-yl)prop-2-en-1-one |
| 157 | 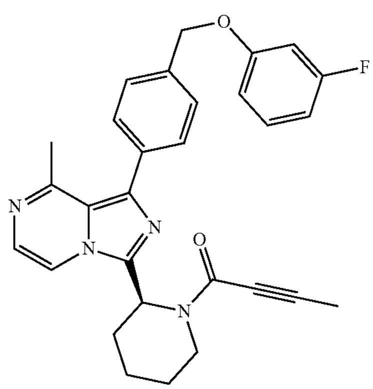 [SMILES: CC#CC(=O)N1CCCC[C@H]1c1nc(-c2ccc(COc3cccc(F)c3)cc2)c2c(C)nccn12] | 483.21/ 483.2 | (S)-1-(2-(1-(4-((3-fluorophenoxy)methyl)phenyl)-8-methylimidazo[1,5-a]pyrazin-3-yl)piperidin-1-yl)but-2-yn-1-one |
| 158 | 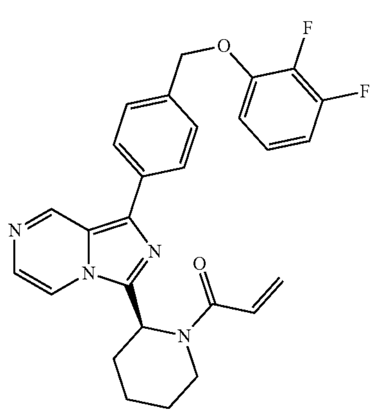 [SMILES: C=CC(=O)N1CCCC[C@H]1c1nc(-c2ccc(COc3cccc(F)c3F)cc2)c2cnccn12] | 475.19/ 475.2 | (S)-1-(2-(1-(4-((2,3-difluorophenoxy)methyl)phenyl)imidazo[1,5-a]pyrazin-3-yl)piperidin-1-yl)prop-2-en-1-one |

-continued

| Entry | structure | MS (cald.) [M + H]+/ MS (found) | name |
|---|---|---|---|
| 159 | 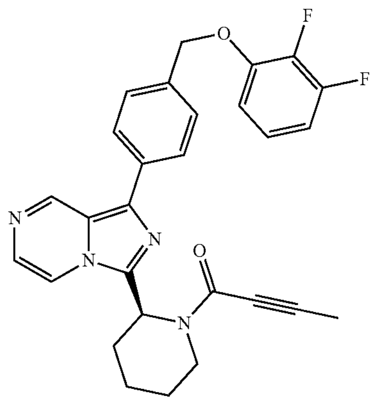 [SMILES: CC#CC(=O)N1CCCC[C@H]1c1nc(-c2ccc(COc3cccc(F)c3F)cc2)c2cnccn12] | 487.19/ 487.2 | (S)-1-(2-(1-(4-((2,3-difluorophenoxy)methyl)phenyl)imidazo[1,5-a]pyrazin-3-yl)piperidin-1-yl)but-2-yn-1-one |
| 160 | 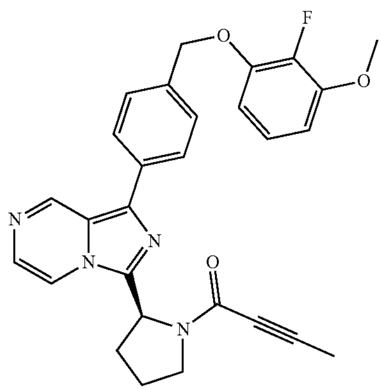 [SMILES: CC#CC(=O)N1CCC[C@H]1c1nc(-c2ccc(COc3cccc(OC)c3F)cc2)c2cnccn12] | 485.19/ 485.2 | (S)-1-(2-(1-(4-((2-fluoro-3-methoxyphenoxy)methyl)phenyl)imidazo[1,5-a]pyrazin-3-yl)pyrrolidin-1-yl)but-2-yn-1-one |
| 161 | 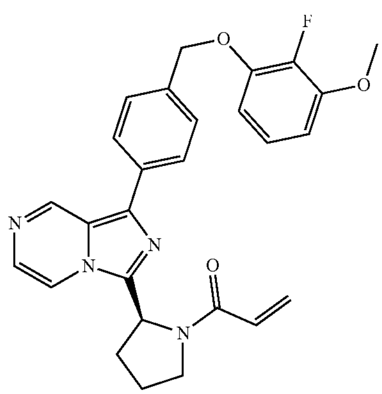 [SMILES: C=CC(=O)N1CCC[C@H]1c1nc(-c2ccc(COc3cccc(OC)c3F)cc2)c2cnccn12] | 473.19/ 473.2 | (S)-1-(2-(1-(4-((2-fluoro-3-methoxyphenoxy)methyl)phenyl)imidazo[1,5-a]pyrazin-3-yl)pyrrolidin-1-yl)prop-2-en-1-one |
| 162 | 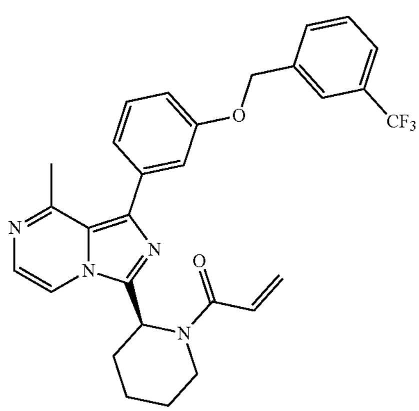 [SMILES: C=CC(=O)N1CCCC[C@H]1c1nc(-c2cccc(OCc3cccc(C(F)(F)F)c3)c2)c2c(C)nccn12] | 521.21/ 521.2 | (S)-1-(2-(8-methyl-1-(3-((3-(trifluoromethyl)benzyl)oxy)phenyl)imidazo[1,5-a]pyrazin-3-yl)piperidin-1-yl)prop-2-en-1-one |

| Entry | structure | MS (cald.) [M + H]⁺/ MS (found) | name |
|---|---|---|---|
| 163 | 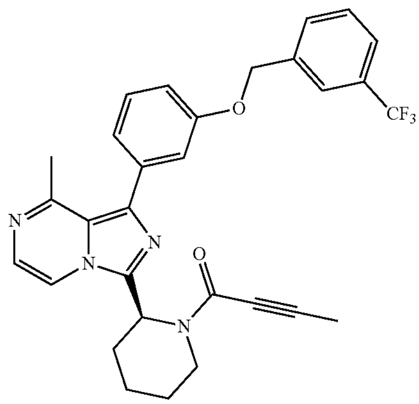 [SMILES: CC#CC(=O)N1CCCC[C@H]1c1nc(-c2cccc(OCc3cccc(C(F)(F)F)c3)c2)c2c(C)nccn12] | 533.21/ 533.2 | (S)-1-(2-(8-methyl-1-(3-((3-(trifluoromethyl)benzyl)oxy)phenyl)imidazo[1,5-a]pyrazin-3-yl)piperidin-1-yl)but-2-yn-1-one |
Example 164
(S)-4-(3-(1-(But-2-ynoyl)pyrrolidin-2-yl)imidazo[1,5-a]pyrazin-1-yl)-N-(2-fluoro-3-methoxyphenyl)benzamide (164)
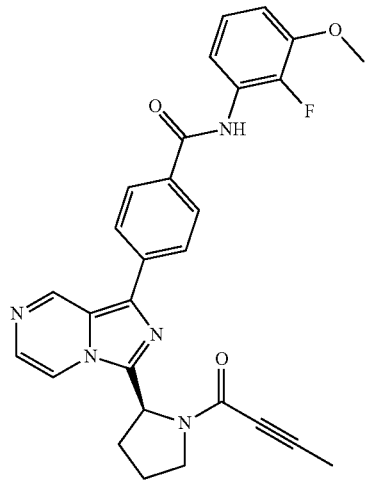 [SMILES: CC#CC(=O)N1CCC[C@H]1c1nc(-c2ccc(C(=O)Nc3cccc(OC)c3F)cc2)c2cnccn12]
Scheme 9
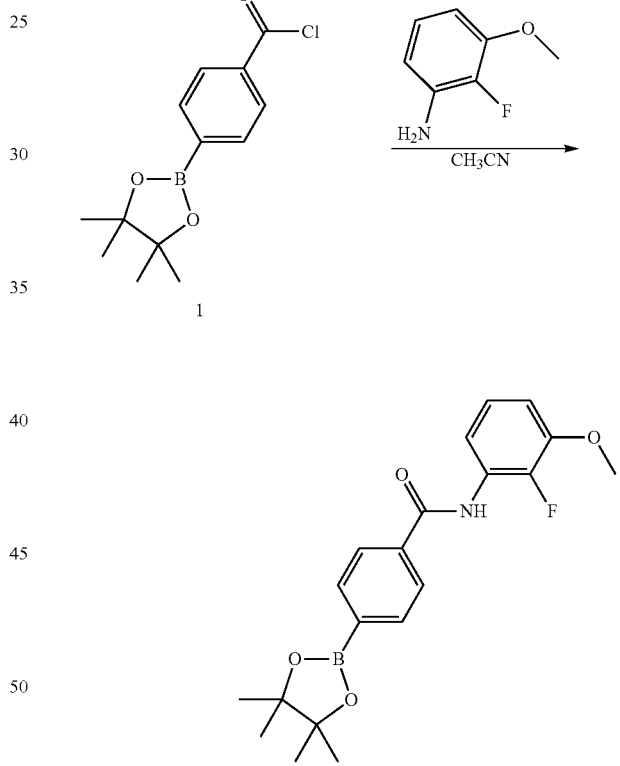
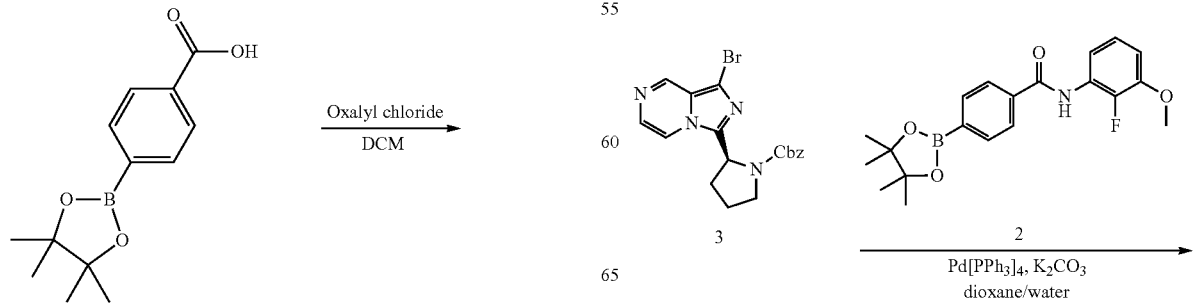

181

-continued

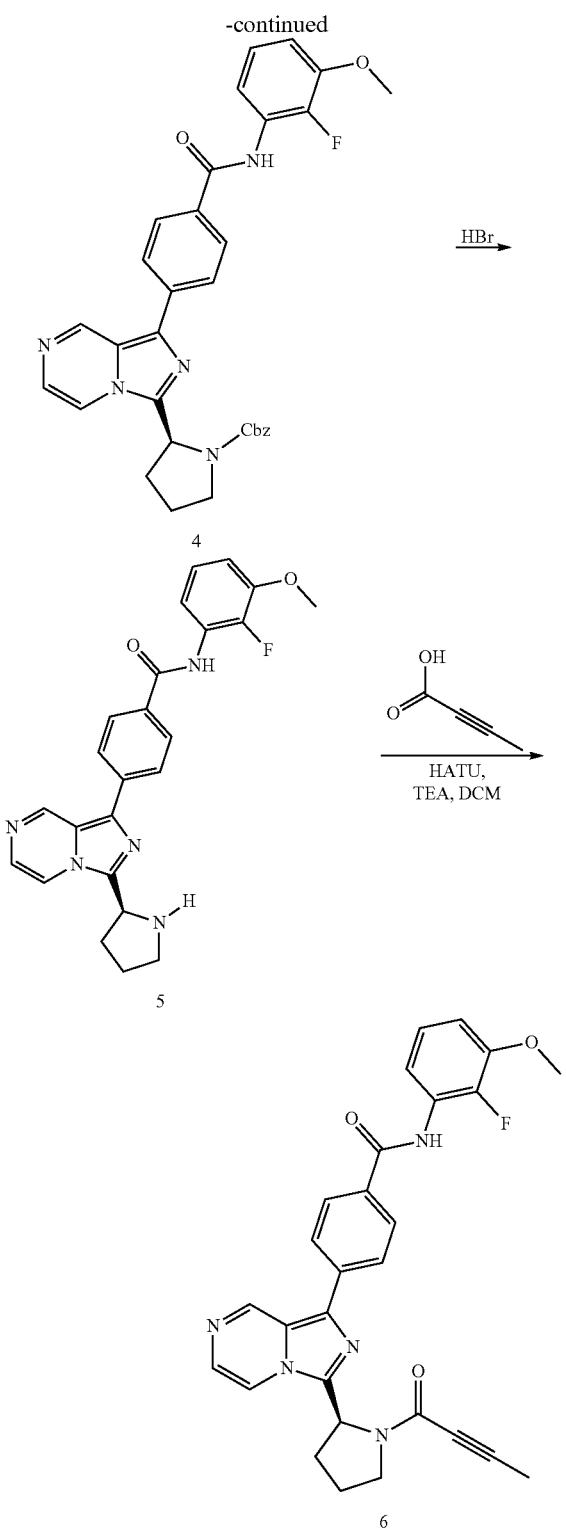

Step 1: 4-(4,4,5,5-Tetramethyl-1,3,2-dioxaborolan-2-yl)benzoyl chloride (1)

To a solution of 4-(4,4,5,5-tetramethyl-1,3,2-dioxaborolan-2-yl)benzoic acid (1.0 g, 4.03 mmol, 1.0 eq) and 2 drops of DMF in DCM (20 mL), was added oxalyl chloride (1.0 mL, 10.08 mmol, 2.5 eq) slowly for 40 min. The mixture was stirred at room temperature for 4 h. The solution was concentrated to give the desired product 1 (1.2 g), which was used into next reaction without further purification.

Step 2: N-(2-Fluoro-3-methoxyphenyl)-4-(4,4,5,5-tetramethyl-1,3-dioxolan-2-yl)benzamide (2)

To a solution of compound 1 (697 mg, 2.61 mmol, 1.0 eq) in CH$_3$CN (10.0 mL), was added 2-fluoro-3-methoxyaniline (406 mg, 2.88 mmol, 1.1 eq) in CH$_3$CN (10.0 mL). The mixture was stirred at rt for 14 h. The volume of reaction mixture was reduced into ⅓, and 3% citric acid solution (50 mL) was added. The mixture was extracted with DCM, and the organic layer was washed with 3% citric acid solution and brine. The solution was dried over Na$_2$SO$_4$, filtered and concentrated to give the desired product 2 as a white solid (0.93 g, yield 61.8%), which was used into next reaction without further purification.

Step 3: (S)-Benzyl-2-(1-(4-((2-fluoro-3-methoxyphenyl)carbamoyl)phenyl)imidazo[1,5-a]pyrazin-3-yl)pyrrolidine-1-carboxylate (4)

A mixture of compound 2 (352 mg, 0.95 mmol, 2.0 eq), compound 3 (190 mg, 0.475 mmol, 1.0 eq), Pd[PPh$_3$]$_4$ (40 mg), and Cesium carbonate (361 mg, 0.95 mmol, 2.0 eq) in dioxane (7.0 mL) and water (1.0 mL) was stirred under reflux for 5 h. The mixture was allowed to cool to room temperature, and water was added. It was extracted with EA. The combined organic layers were washed water and brine. The solution was dried over anhydrous Na$_2$SO$_4$, filtered and concentrated. The residue was purified by silica gel column chromatography (DCM/MeOH=100:1) to give the desired product 4 (340 mg). LCMS: m/z=566 [M+H]$^+$.

Step 4: (S)—N-(2-Fluoro-3-methoxyphenyl)-4-(3-(pyrrolidin-2-yl)imidazo[1,5-a]pyrazin-1-yl)benzamide (5)

A solution of compound 4 (340 mg) was in DCM (10.0 mL) was mixed with 33% HBr/acetic acid (2.0 mL), and the mixture was stirred at room temperature (20° C.) for 2 h. Water was added and the mixture was extracted with DCM. The pH of the aqueous phase was adjusted to 8 with 2.0 M sodium hydroxide. The mixture was extracted with DCM, and the combined organic layers were washed with water and brine. The solution was dried over Na$_2$SO$_4$, filtered and concentrated to give the desired product 5 (140 mg, yield 68.4%).

$^1$H NMR (400 MHz, CDCl$_3$): δ 9.27 (s, 1H), 8.16-8.02 (m, 7H), 7.57 (d, J=4.8 Hz, 1H), 7.15-7.10 (m, 1H), 6.80-6.76 (m, 1H), 4.69-4.65 (m, 1H), 3.93 (s, 3H), 3.24-3.22 (m, 1H), 3.10-3.07 (m, 1H), 2.32-2.27 (m, 2H), 2.04-1.96 (m, 2H). LCMS: m/z=432 [M+H]$^+$.

Step 5: (S)-4-(3-(1-(But-2-ynoyl)pyrrolidin-2-yl)imidazo[1,5-a]pyrazin-1-yl)-N-(2-fluoro-3-methoxyphenyl)benzamide (6)

To a solution of compound 5 (20 mg, 0.046 mmol, 1.0 eq) and TEA (14 mg, 0.139 mmol, 3.0 eq) in DCM (4.0 mL), were added but-2-ynoic acid (3.9 mg, 0.046 mmol, 1.0 eq) and HATU (17.6 mg 0.046 mmol, 1.0 eq). The mixture was stirred at 15° C. for 40 min. The mixture was diluted with water and it was extracted with DCM. The combined organic layers were washed with water and brine. The solution was dried over Na$_2$SO$_4$, filtered and concentrated. The residue was purified with prep-TLC to give the desired product 6 (11 mg, yield 47.7%).

$^1$H NMR (400 MHz, CDCl$_3$): δ 9.23 (s, 1H), 8.37 (d, J=4.8 Hz, 1H), 8.15 (s, 1H), 8.10-7.99 (m, 5H), 7.61 (d, J=4.8 Hz, 1H), 7.14-7.10 (m, 1H), 6.80-6.76 (m, 1H), 5.51-5.49 (m, 1H), 3.92 (s, 3H), 3.90-3.86 (m, 2H), 2.75-2.66 (m, 2H), 2.39-2.34 (m, 1H), 2.17-2.14 (m, 1H), 1.98 (s, 2.5H), 1.64 (s, 0.5H). LCMS: m/z=498 [M+H]$^+$.

Examples 165 and 215 were prepared following the procedure described for Example 164:

| Entry | Structure | MS (cald.) [M + H]+/ MS (found) | name |
|---|---|---|---|
| 165 | 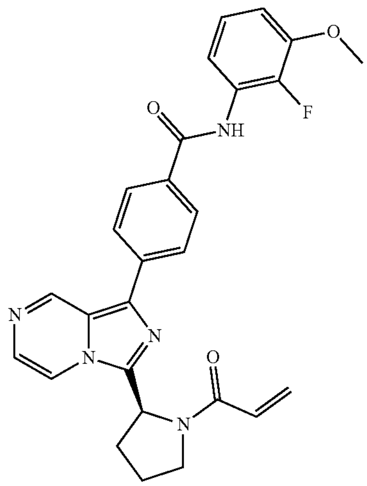 [SMILES: C=CC(=O)N1CCC[C@H]1c1nc(-c2ccc(C(=O)Nc3cccc(OC)c3F)cc2)c2cnccn12] | 486.19/ 486.2 | (S)-4-(3-(1-acryloylpyrrolidin-2-yl)imidazo[1,5-a]pyrazin-1-yl)-N-(2-fluoro-3-methoxyphenyl)benzamide |
| 166 | 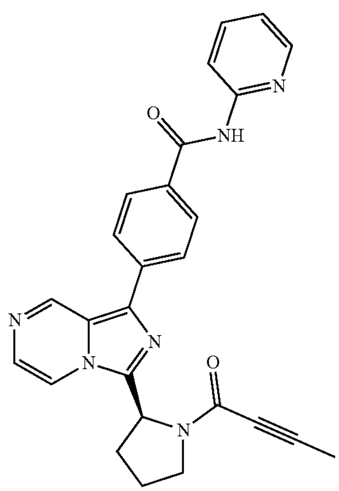 [SMILES: CC#CC(=O)N1CCC[C@H]1c1nc(-c2ccc(C(=O)Nc3ccccn3)cc2)c2cnccn12] | 451.18/ 451.2 | (S)-4-(3-(1-(but-2-ynoyl)pyrrolidin-2-yl)imidazo[1,5-a]pyrazin-1-yl)-N-(pyridin-2-yl)benzamide |
| 167 | 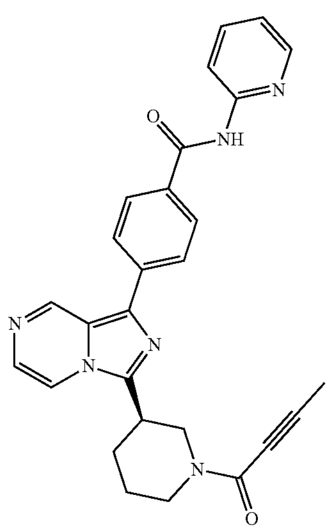 [SMILES: CC#CC(=O)N1CCC[C@@H](c2nc(-c3ccc(C(=O)Nc4ccccn4)cc3)c3cnccn23)C1] | 465.20/ 465.2 | (R)-4-(3-(1-(but-2-ynoyl)piperidin-3-yl)imidazo[1,5-a]pyrazin-1-yl)-N-(pyridin-2-yl)benzamide |

-continued

| Entry | Structure | MS (cald.) [M + H]+/ MS (found) | name |
|---|---|---|---|
| 168 | 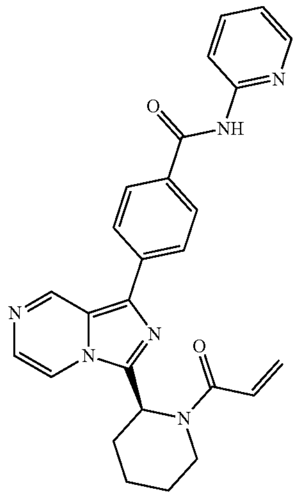 [SMILES: C=CC(=O)N1CCCC[C@H]1c1nc(-c2ccc(C(=O)Nc3ccccn3)cc2)c2cnccn12] | 453.20/ 453.2 | (S)-4-(3-(1-acryloylpiperidin-2-yl)imidazo[1,5-a]pyrazin-1-yl)-N-(pyridin-2-yl)benzamide |
| 169 | 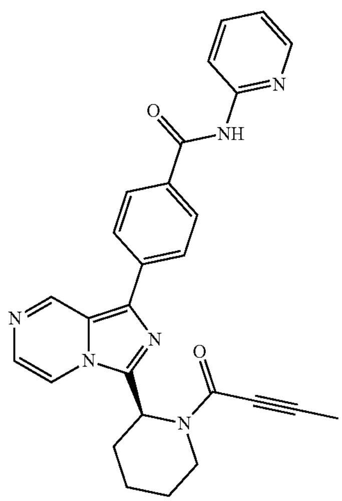 [SMILES: CC#CC(=O)N1CCCC[C@H]1c1nc(-c2ccc(C(=O)Nc3ccccn3)cc2)c2cnccn12] | 465.20/ 465.2 | (S)-4-(3-(1-(but-2-ynoyl)piperidin-2-yl)imidazo[1,5-a]pyrazin-1-yl)-N-(pyridin-2-yl)benzamide |
| 170 | 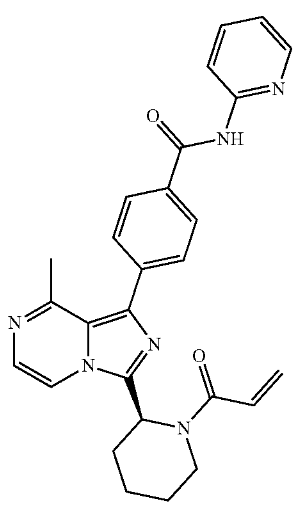 [SMILES: C=CC(=O)N1CCCC[C@H]1c1nc(-c2ccc(C(=O)Nc3ccccn3)cc2)c2c(C)nccn12] | 467.21/ 467.2 | (S)-4-(3-(1-acryloylpiperidin-2-yl)-8-methylimidazo[1,5-a]pyrazin-1-yl)-N-(pyridin-2-yl)benzamide |

-continued

| Entry | Structure | MS (cald.) [M + H]+/ MS (found) | name |
|---|---|---|---|
| 171 | 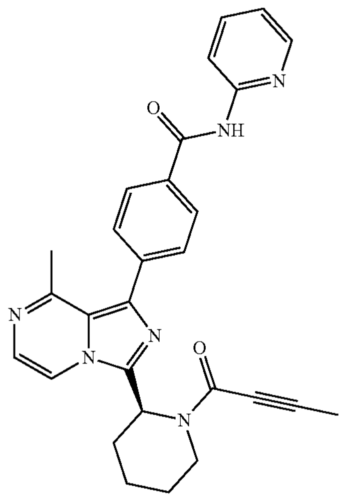 [SMILES: CC#CC(=O)N1CCCC[C@H]1c1nc(-c2ccc(C(=O)Nc3ccccn3)cc2)c2c(C)nccn12] | 479.21/ 479.2 | (S)-4-(3-(1-(but-2-ynoyl)piperidin-2-yl)-8-methylimidazo[1,5-a]pyrazin-1-yl)-N-(pyridin-2-yl)benzamide |
| 172 | 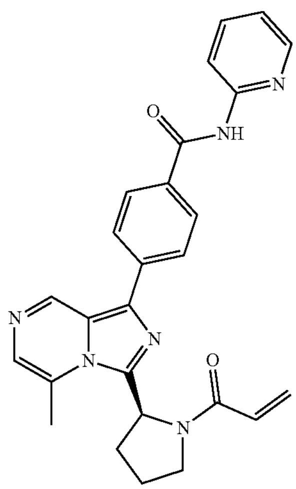 [SMILES: C=CC(=O)N1CCC[C@H]1c1nc(-c2ccc(C(=O)Nc3ccccn3)cc2)c2cncc(C)n12] | 453.20/ 453.2 | (S)-4-(3-(1-acryloylpyrrolidin-2-yl)-5-methylimidazo[1,5-a]pyrazin-1-yl)-N-(pyridin-2-yl)benzamide |
| 173 | 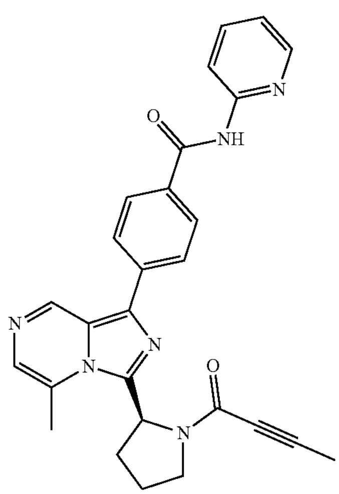 [SMILES: CC#CC(=O)N1CCC[C@H]1c1nc(-c2ccc(C(=O)Nc3ccccn3)cc2)c2cncc(C)n12] | 465.20/ 465.2 | (S)-4-(3-(1-(but-2-ynoyl)pyrrolidin-2-yl)-5-methylimidazo[1,5-a]pyrazin-1-yl)-N-(pyridin-2-yl)benzamide |

-continued

| Entry | Structure | MS (cald.) [M + H]⁺/ MS (found) | name |
| --- | --- | --- | --- |
| 174 | 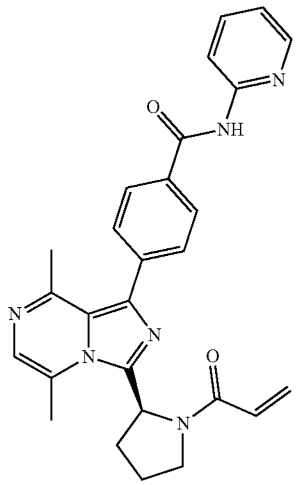 [SMILES: C=CC(=O)N1CCC[C@H]1c1nc(-c2ccc(C(=O)Nc3ccccn3)cc2)c2c(C)ncc(C)n12] | 467.21/ 467.2 | (S)-4-(3-(1-acryloylpyrrolidin-2-yl)-5,8-dimethylimidazo[1,5-a]pyrazin-l-yl)-N-(pyridin-2-yl)benzamide |
| 175 | 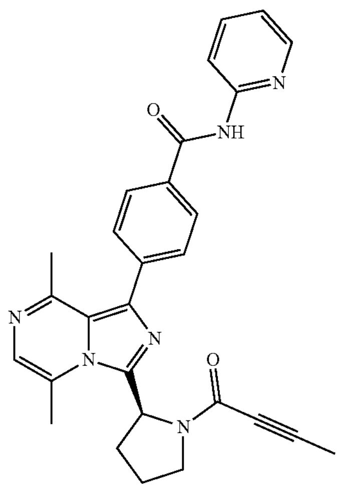 [SMILES: CC#CC(=O)N1CCC[C@H]1c1nc(-c2ccc(C(=O)Nc3ccccn3)cc2)c2c(C)ncc(C)n12] | 479.21/ 479.2 | (S)-4-(3-(1-(but-2-ynoyl)pyrrolidin-2-yl)-5,8-dimethylimidazo[1,5-a]pyrazin-1-yl)-N-(pyridin-2-yl)benzamide |
| 176 | 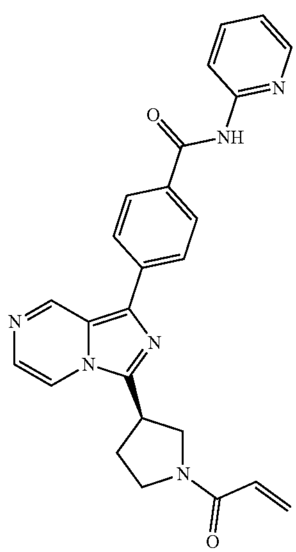 [SMILES: C=CC(=O)N1CC[C@@H](c2nc(-c3ccc(C(=O)Nc4ccccn4)cc3)c3cnccn23)C1] | 439.18/ 439.2 | (R)-4-(3-(1-acryloylpyrrolidin-3-yl)imidazo[1,5-a]pyrazin-1-yl)-N-(pyridin-2-yl)benzamide |

| Entry | Structure | MS (cald.) [M + H]+/ MS (found) | name |
|---|---|---|---|
| 177 | 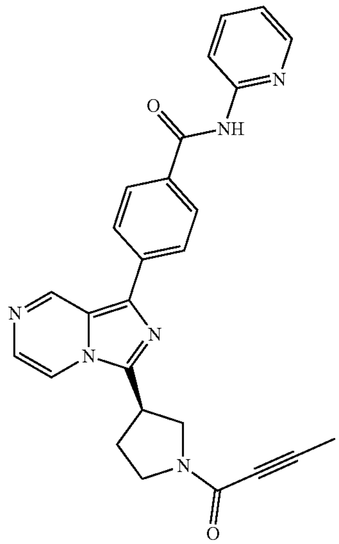 [SMILES: CC#CC(=O)N1CC[C@@H](c2nc(-c3ccc(C(=O)Nc4ccccn4)cc3)c3cnccn23)C1] | 451.18/ 451.2 | (R)-4-(3-(1-(but-2-ynoyl)pyrrolidin-3-yl)imidazo[1,5-a]pyrazin-1-yl)-N-(pyridin-2-yl)benzamide |
| 178 | 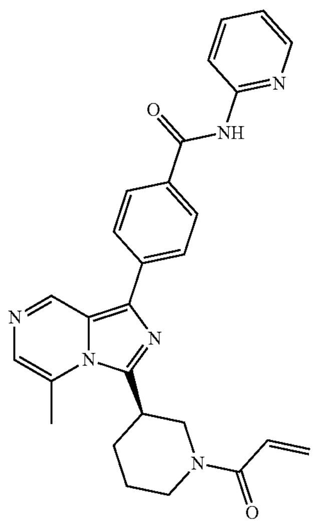 [SMILES: C=CC(=O)N1CCC[C@@H](c2nc(-c3ccc(C(=O)Nc4ccccn4)cc3)c3cncc(C)n23)C1] | 467.21/ 467.2 | (R)-4-(3-(1-acryloylpiperidin-3-yl)-5-methylimidazo[1,5-a]pyrazin-1-yl)-N-(pyridin-2-yl)benzamide |
| 179 | 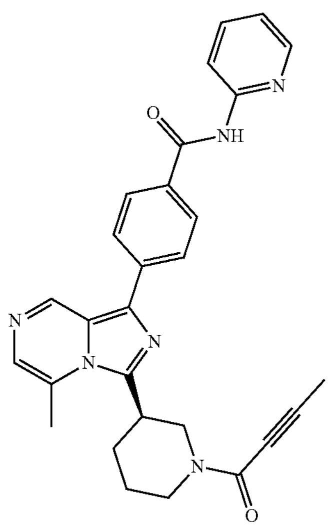 [SMILES: CC#CC(=O)N1CCC[C@@H](c2nc(-c3ccc(C(=O)Nc4ccccn4)cc3)c3cncc(C)n23)C1] | 479.21/ 479.2 | (R)-4-(3-(1-(but-2-ynoyl)piperidin-3-yl)-5-methylimidazo[1,5-a]pyrazin-1-yl)-N-(pyridin-2-yl)benzamide |

-continued
| Entry | Structure | MS (cald.) [M + H]+/MS (found) | name |
|---|---|---|---|
| 180 | 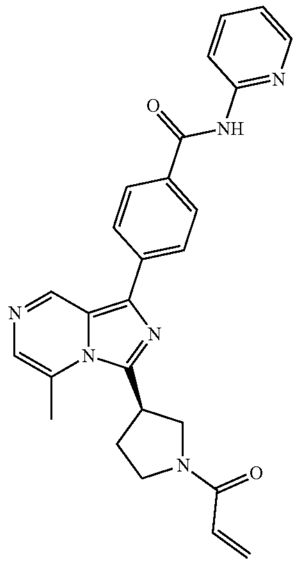 [SMILES: C=CC(=O)N1CC[C@@H](c2nc(-c3ccc(C(=O)Nc4ccccn4)cc3)c3cncc(C)n23)C1] | 453.20/453.2 | (R)-4-(3-(1-acryloylpyrrolidin-3-yl)-5-methylimidazo[1,5-a]pyrazin-1-yl)-N-(pyridin-2-yl)benzamide |
| 181 | 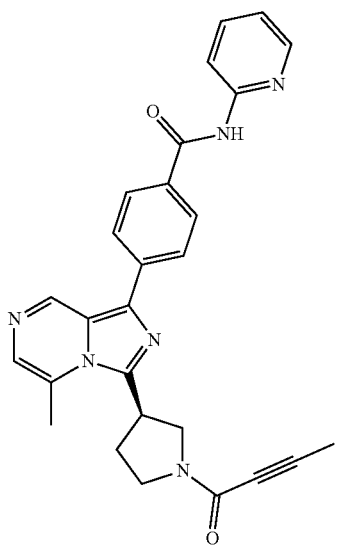 [SMILES: CC#CC(=O)N1CC[C@@H](c2nc(-c3ccc(C(=O)Nc4ccccn4)cc3)c3cncc(C)n23)C1] | 465.20/465.2 | (R)-4-(3-(1-(but-2-ynoyl)pyrrolidin-3-yl)-5-methylimidazo[1,5-a]pyrazin-1-yl)-N-(pyridin-2-yl)benzamide |

-continued
| Entry | Structure | MS (cald.) [M + H]+/ MS (found) | name |
|---|---|---|---|
| 182 | 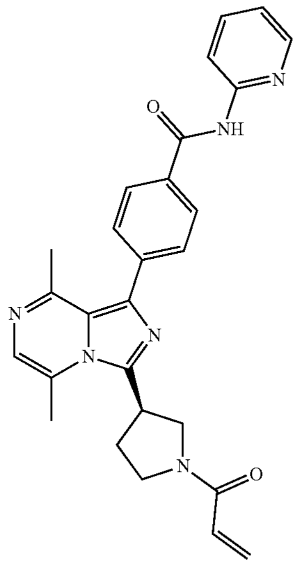 [SMILES: C=CC(=O)N1CC[C@@H](c2nc(-c3ccc(C(=O)Nc4ccccn4)cc3)c3c(C)ncc(C)n23)C1] | 467.20/ 467.2 | (R)-4-(3-(1-acryloylpyrrolidin-3-yl)-5,8-dimethylimidazo[1,5-a]pyrazin-1-yl)-N-(pyridin-2-yl)benzamide |
| 183 | 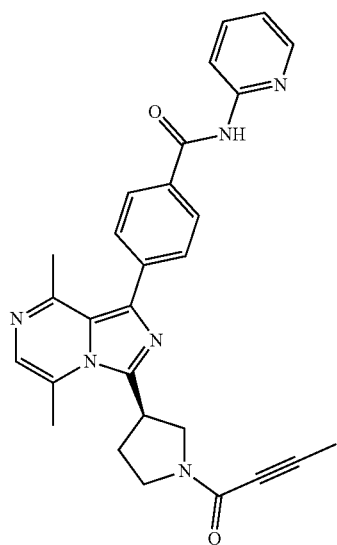 [SMILES: CC#CC(=O)N1CC[C@@H](c2nc(-c3ccc(C(=O)Nc4ccccn4)cc3)c3c(C)ncc(C)n23)C1] | 479.20/ 479.2 | (R)-4-(3-(1-(but-2-ynoyl)pyrrolidin-3-yl)-5,8-dimethylimidazo[1,5-a]pyrazin-1-yl)-N-(pyridin-2-yl)benzamide |

| Entry | Structure | MS (cald.) [M + H]+/ MS (found) | name |
|---|---|---|---|
| 184 | 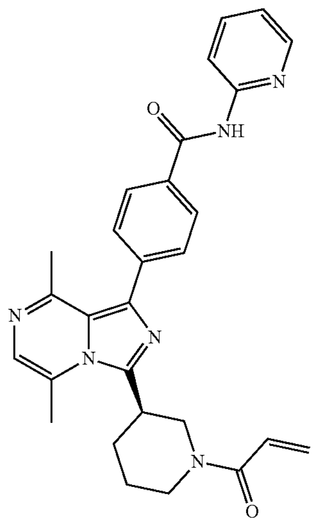 [SMILES: C=CC(=O)N1CCC[C@@H](c2nc(-c3ccc(C(=O)Nc4ccccn4)cc3)c3c(C)ncc(C)n23)C1] | 481.20/ 481.2 | (R)-4-(3-(1-acryloylpiperidin-3-yl)-5,8-dimethylimidazo[1,5-a]pyrazin-1-yl)-N-(pyridin-2-yl)benzamide |
| 185 | 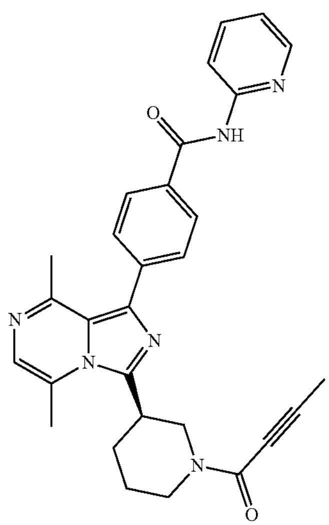 [SMILES: CC#CC(=O)N1CCC[C@@H](c2nc(-c3ccc(C(=O)Nc4ccccn4)cc3)c3c(C)ncc(C)n23)C1] | 493.20/ 493.2 | (R)-4-(3-(1-(but-2-ynoyl)piperidin-3-yl)-5,8-dimethylimidazo[1,5-a]pyrazin-1-yl)-N-(pyridin-2-yl)benzamide |
| 186 | 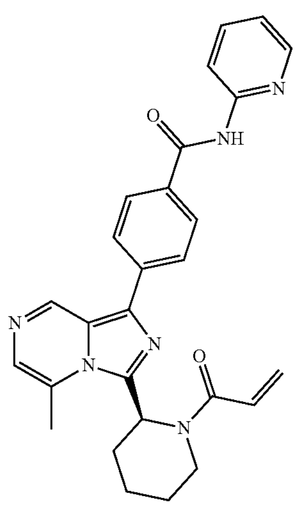 [SMILES: C=CC(=O)N1CCCC[C@H]1c1nc(-c2ccc(C(=O)Nc3ccccn3)cc2)c2cncc(C)n12] | 467.20/ 467.2 | (S)-4-(3-(1-acryloylpiperidin-2-yl)-5-methylimidazo[1,5-a]pyrazin-1-yl)-N-(pyridin-2-yl)benzamide |

-continued

| Entry | Structure | MS (cald.) [M + H]+/ MS (found) | name |
|---|---|---|---|
| 187 | 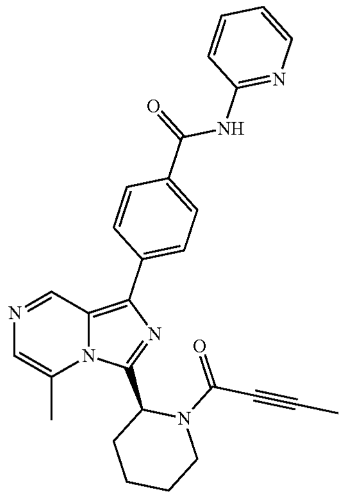 [SMILES: CC#CC(=O)N1CCCC[C@H]1c1nc(-c2ccc(C(=O)Nc3ccccn3)cc2)c2cncc(C)n12] | 479.20/ 479.2 | (S)-4-(3-(1-(but-2-ynoyl)piperidin-2-yl)-5-methylimidazo[1,5-a]pyrazin-1-yl)-N-(pyridin-2-yl)benzamide |
| 188 | 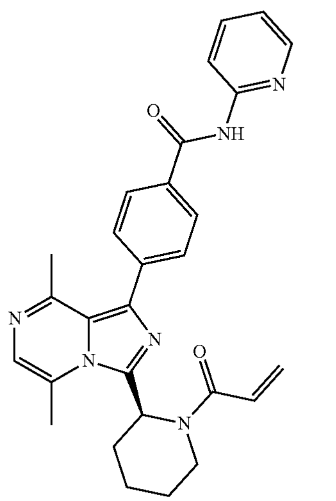 [SMILES: C=CC(=O)N1CCCC[C@H]1c1nc(-c2ccc(C(=O)Nc3ccccn3)cc2)c2c(C)ncc(C)n12] | 481.20/ 481.2 | (S)-4-(3-(1-acryloylpiperidin-2-yl)-5,8-dimethylimidazo[1,5-a]pyrazin-1-yl)-N-(pyridin-2-yl)benzamide |
| 189 | 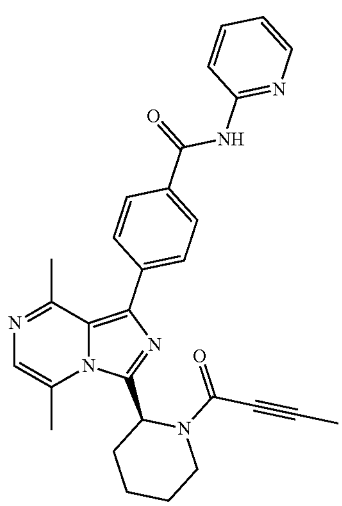 [SMILES: CC#CC(=O)N1CCCC[C@H]1c1nc(-c2ccc(C(=O)Nc3ccccn3)cc2)c2c(C)ncc(C)n12] | 493.20/ 493.2 | (S)-4-(3-(1-(but-2-ynoyl)piperidin-2-yl)-5,8-dimethylimidazo[1,5-a]pyrazin-1-yl)-N-(pyridin-2-yl)benzamide |

-continued

| Entry | Structure | MS (cald.) [M + H]+/ MS (found) | name |
|---|---|---|---|
| 190 | 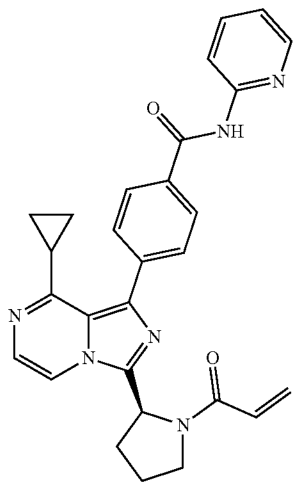 [SMILES: C=CC(=O)N1CCC[C@H]1c1nc(-c2ccc(C(=O)Nc3ccccn3)cc2)c2c(C3CC3)nccn12] | 479.21/ 479.2 | (S)-4-(3-(1-acryloylpyrrolidin-2-yl)-8-cyclopropylimidazo[1,5-a]pyrazin-1-yl)-N-(pyridin-2-yl)benzamide |
| 191 | 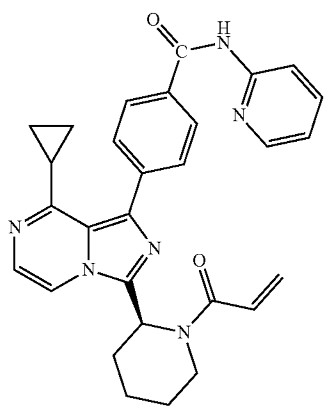 [SMILES: C=CC(=O)N1CCCC[C@H]1c1nc(-c2ccc(C(=O)Nc3ccccn3)cc2)c2c(C3CC3)nccn12] | 493.23/ 493.2 | (S)-4-(3-(1-acryloylpiperidin-2-yl)-8-cyclopropylimidazo[1,5-a]pyrazin-1-yl)-N-(pyridin-2-yl)benzamide |
| 192 | 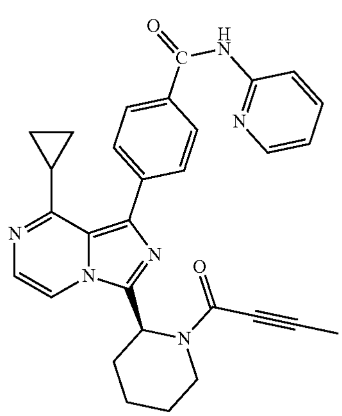 [SMILES: CC#CC(=O)N1CCCC[C@H]1c1nc(-c2ccc(C(=O)Nc3ccccn3)cc2)c2c(C3CC3)nccn12] | 505.23/ 505.2 | (S)-4-(3-(1-(but-2-ynoyl)piperidin-2-yl)-8-cyclopropylimidazo[1,5-a]pyrazin-1-yl)-N-(pyridin-2-yl)benzamide |

| Entry | Structure | MS (cald.) [M + H]+/ MS (found) | name |
|---|---|---|---|
| 193 | 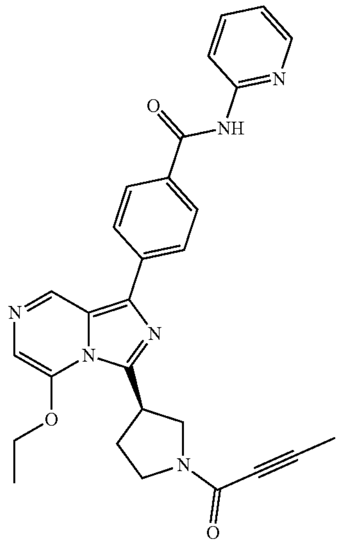 [SMILES: CC#CC(=O)N1CC[C@@H](c2nc(-c3ccc(C(=O)Nc4ccccn4)cc3)c3cncc(OCC)n23)C1] | 495.21/ 495.2 | (R)-4-(3-(1-(but-2-ynoyl)pyrrolidin-3-yl)-5-ethoxyimidazo[1,5-a]pyrazin-1-yl)-N-(pyridin-2-yl)benzamide |
| 194 | 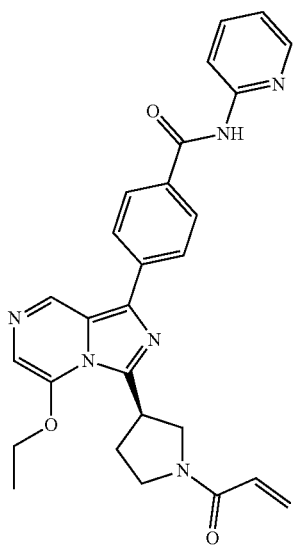 [SMILES: C=CC(=O)N1CC[C@@H](c2nc(-c3ccc(C(=O)Nc4ccccn4)cc3)c3cncc(OCC)n23)C1] | 483.21/ 483.2 | (R)-4-(3-(1-acryloylpyrrolidin-3-yl)-5-ethoxyimidazo[1,5-a]pyrazin-1-yl)-N-(pyridin-2-yl)benzamide |

-continued
| Entry | Structure | MS (cald.) [M + H]+/ MS (found) | name |
|---|---|---|---|
| 195 | 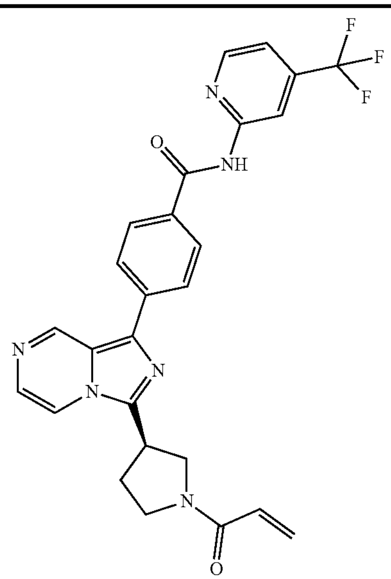 | 507.17/ 507.2 | (R)-4-(3-(1-acryloylpyrrolidin-3-yl)imidazo[1,5-a]pyrazin-1-yl)-N-(4-(trifluoromethyl)pyridin-2-yl)benzamide |
| 196 | 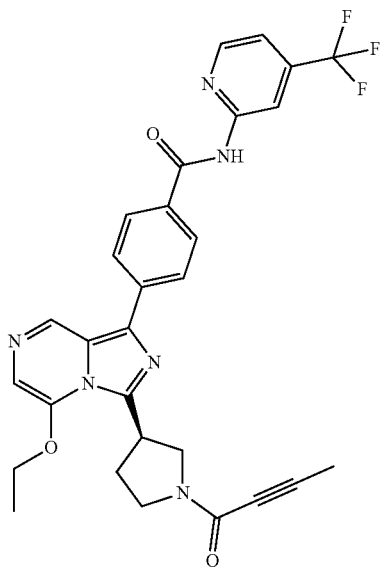 [SMILES: CC#CC(=O)N1CC[C@@H](c2nc(-c3ccc(C(=O)Nc4cc(C(F)(F)F)ccn4)cc3)c3cncc(OCC)n23)C1] | 563.19/ 563.2 | (R)-4-(3-(1-(but-2-ynoyl)pyrrolidin-3-yl)-5-ethoxyimidazo[1,5-a]pyrazin-1-yl)-N-(4-(trifluoromethyl)pyridin-2-yl)benzamide |

| Entry | Structure | MS (cald.) [M + H]+/ MS (found) | name |
|---|---|---|---|
| 197 | 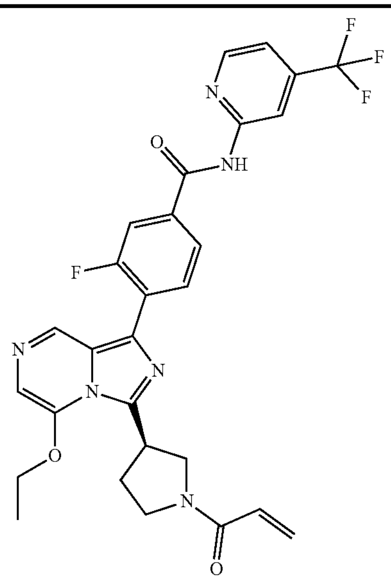 | 569.18/ 569.2 | (R)-4-(3-(1-acryloylpyrrolidin-3-yl)-5-ethoxyimidazo[1,5-a]pyrazin-1-yl)-3-fluoro-N-(4-(trifluoromethyl)pyridin-2-yl)benzamide |
| 198 | 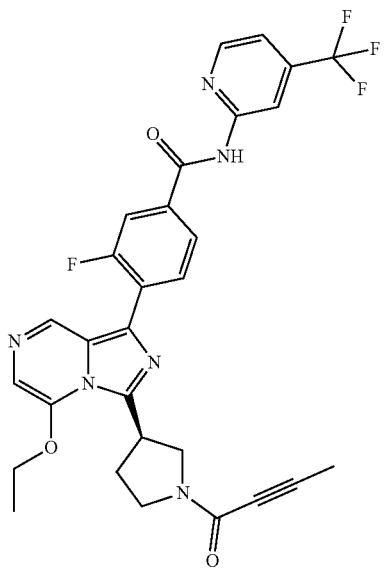 [SMILES: CC#CC(=O)N1CC[C@@H](c2nc(-c3ccc(C(=O)Nc4cc(C(F)(F)F)ccn4)cc3F)c3cncc(OCC)n23)C1] | 581.18/ 581.2 | (R)-4-(3-(1-(but-2-ynoyl)pyrrolidin-3-yl)-5-ethoxyimidazo[1,5-a]pyrazin-1-yl)-3-fluoro-N-(4-(trifluoromethyl)pyridin-2-yl)benzamide |

| Entry | Structure | MS (cald.) [M + H]+/ MS (found) | name |
|---|---|---|---|
| 199 | 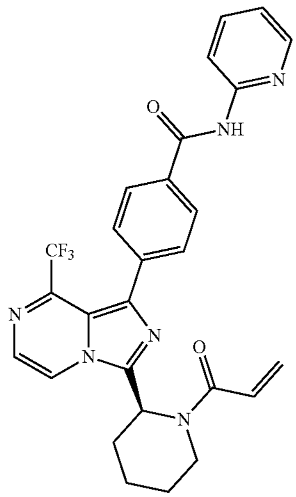 [SMILES: C=CC(=O)N1CCCC[C@H]1c1nc(-c2ccc(C(=O)Nc3ccccn3)cc2)c2c(C(F)(F)F)nccn12] | 521.18/ 521.2 | (S)-4-(3-(1-acryloylpiperidin-2-yl)-8-(trifluoromethyl)imidazo[1,5-a]pyrazin-1-yl)-N-(pyridin-2-yl)benzamide |
| 200 | 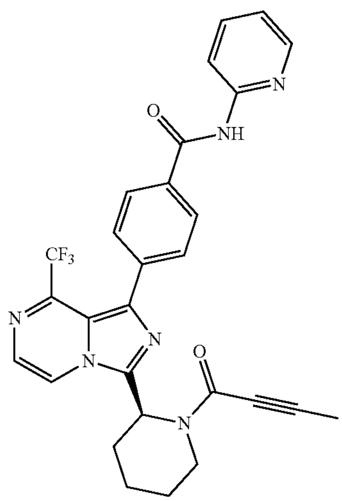 [SMILES: CC#CC(=O)N1CCCC[C@H]1c1nc(-c2ccc(C(=O)Nc3ccccn3)cc2)c2c(C(F)(F)F)nccn12] | 533.18/ 533.2 | (S)-4-(3-(1-(but-2-ynoyl)piperidin-2-yl)-8-(trifluoromethyl)imidazo[1,5-a]pyrazin-1-yl)-N-(pyridin-2-yl)benzamide |
| 201 | 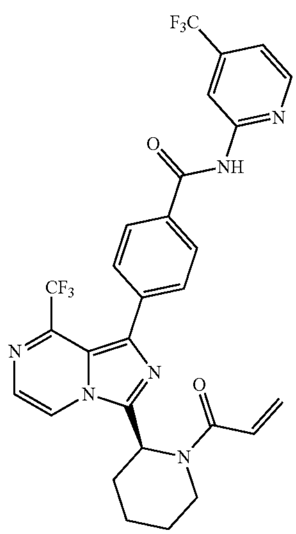 [SMILES: C=CC(=O)N1CCCC[C@H]1c1nc(-c2ccc(C(=O)Nc3cc(C(F)(F)F)ccn3)cc2)c2c(C(F)(F)F)nccn12] | 589.17/ 589.2 | (S)-4-(3-(1-acryloylpiperidin-2-yl)-8-(trifluoromethyl)imidazo[1,5-a]pyrazin-1-yl)-N-(4-(trifluoromethyl)pyridin-2-yl)benzamide |

| Entry | Structure | MS (cald.) [M + H]+/ MS (found) | name |
| --- | --- | --- | --- |
| 202 | 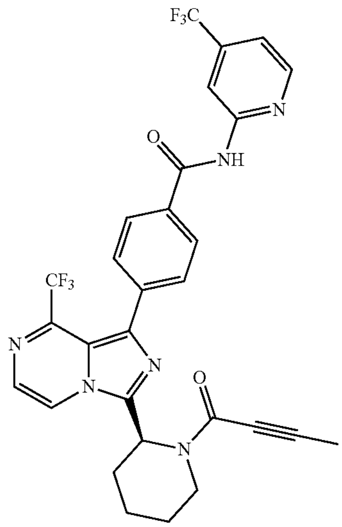 [SMILES: CC#CC(=O)N1CCCC[C@H]1c1nc(-c2ccc(C(=O)Nc3cc(C(F)(F)F)ccn3)cc2)c2c(C(F)(F)F)nccn12] | 601.17/ 601.2 | (S)-4-(3-(1-(but-2-ynoyl)piperidin-2-yl)-8-(trifluoromethyl)imidazo[1,5-a]pyrazin-1-yl)-N-(4-(trifluoromethyl)pyridin-2-yl)benzamide |
| 203 | 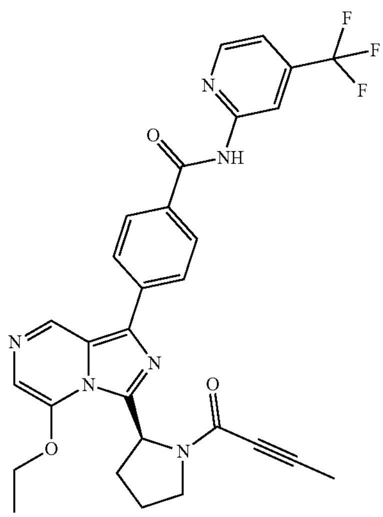 [SMILES: CC#CC(=O)N1CCC[C@H]1c1nc(-c2ccc(C(=O)Nc3cc(C(F)(F)F)ccn3)cc2)c2cncc(OCC)n12] | 563.19/ 563.2 | (S)-4-(3-(1-(but-2-ynoyl)pyrrolidin-2-yl)-5-ethoxyimidazo[1,5-a]pyrazin-1-yl)-N-(4-(trifluoromethyl)pyridin-2-yl)benzamide |
| 204 | 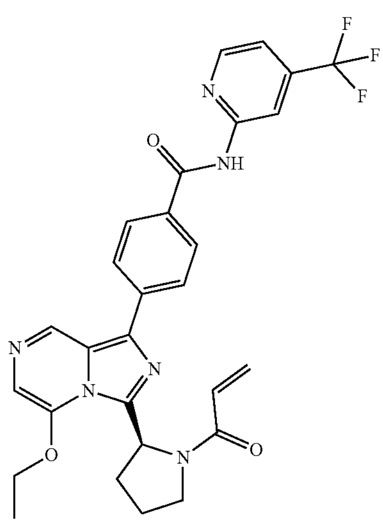 [SMILES: C=CC(=O)N1CCC[C@H]1c1nc(-c2ccc(C(=O)Nc3cc(C(F)(F)F)ccn3)cc2)c2cncc(OCC)n12] | 551.19/ 551.2 | (S)-4-(3-(1-acryloylpyrrolidin-2-yl)-5-ethoxyimidazo[1,5-a]pyrazin-1-yl)-N-(4-(trifluoromethyl)pyridin-2-yl)benzamide |

-continued

| Entry | Structure | MS (cald.) [M + H]+/ MS (found) | name |
|---|---|---|---|
| 205 | 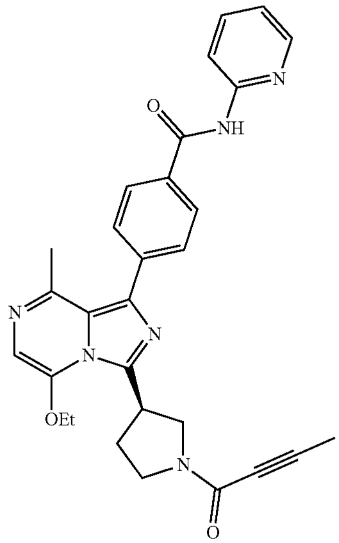 [SMILES: CC#CC(=O)N1CC[C@@H](c2nc(-c3ccc(C(=O)Nc4ccccn4)cc3)c3c(C)ncc(OCC)n23)C1] | 509.22/ 509.2 | (R)-4-(3-(1-(but-2-ynoyl)pyrrolidin-3-yl)-5-ethoxy-8-methylimidazo[1,5-a]pyrazin-1-yl)-N-(pyridin-2-yl)benzamide |
| 206 | 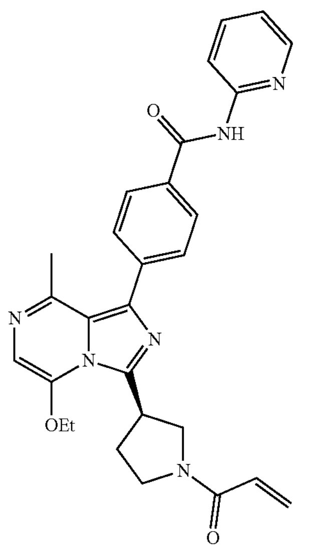 [SMILES: C=CC(=O)N1CC[C@@H](c2nc(-c3ccc(C(=O)Nc4ccccn4)cc3)c3c(C)ncc(OCC)n23)C1] | 497.22/ 497.2 | (R)-4-(3-(1-acryloylpyrrolidin-3-yl)-5-ethoxy-8-methylimidazo[1,5-a]pyrazin-1-yl)-N-(pyridin-2-yl)benzamide |
| 207 | 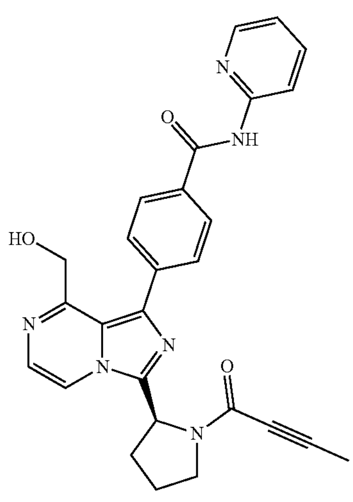 [SMILES: CC#CC(=O)N1CCC[C@H]1c1nc(-c2ccc(C(=O)Nc3ccccn3)cc2)c2c(CO)nccn12] | 481.19/ 481.2 | (S)-4-(3-(1-(but-2-ynoyl)pyrrolidin-2-yl)-8-(hydroxymethyl)imidazo[1,5-a]pyrazin-1-yl)-N-(pyridin-2-yl)benzamide |

| Entry | Structure | MS (cald.) [M + H]+/ MS (found) | name |
|---|---|---|---|
| 208 | 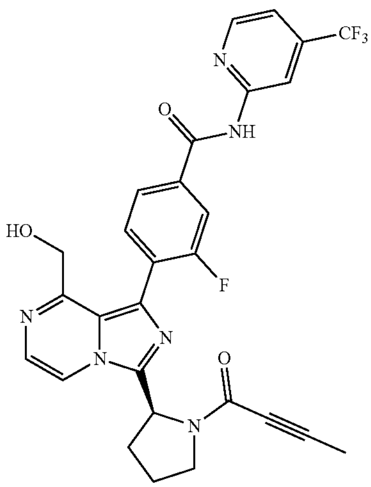 [SMILES: CC#CC(=O)N1CCC[C@H]1c1nc(-c2ccc(C(=O)Nc3cc(C(F)(F)F)ccn3)cc2F)c2c(CO)nccn12] | 567.17/ 567.2 | (S)-4-(3-(1-(but-2-ynoyl)pyrrolidin-2-yl)-8-(hydroxymethyl)imidazo[1,5-a]pyrazin-1-yl)-3-fluoro-N-(4-(trifluoromethyl)pyridin-2-yl)benzamide |
| 209 | 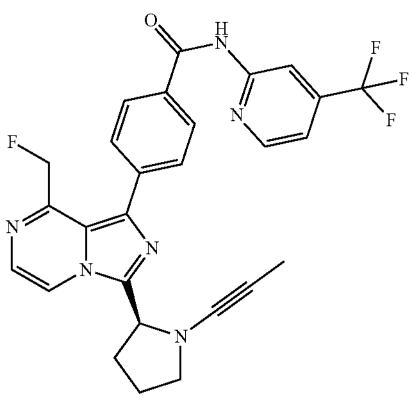 [SMILES: CC#CN1CCC[C@H]1c1nc(-c2ccc(C(=O)Nc3cc(C(F)(F)F)ccn3)cc2)c2c(CF)nccn12] | 523.18/ 523.2 | (S)-4-(8-(fluoromethyl)-3-(1-(prop-1-yn-1-yl)pyrrolidin-2-yl)imidazo[1,5-a]pyrazin-1-yl)-N-(4-(trifluoromethyl)pyridin-2-yl)benzamide |
| 210 | 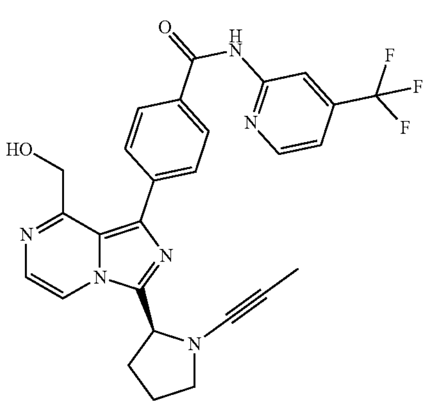 [SMILES: CC#CN1CCC[C@H]1c1nc(-c2ccc(C(=O)Nc3cc(C(F)(F)F)ccn3)cc2)c2c(CO)nccn12] | 521.18/ 521.2 | (S)-4-(8-(hydroxymethyl)-3-(1-(prop-1-yn-1-yl)pyrrolidin-2-yl)imidazo[1,5-a]pyrazin-1-yl)-N-(4-(trifluoromethyl)pyridin-2-yl)benzamide |

| Entry | Structure | MS (cald.) [M + H]+/ MS (found) | name |
|---|---|---|---|
| 211 | 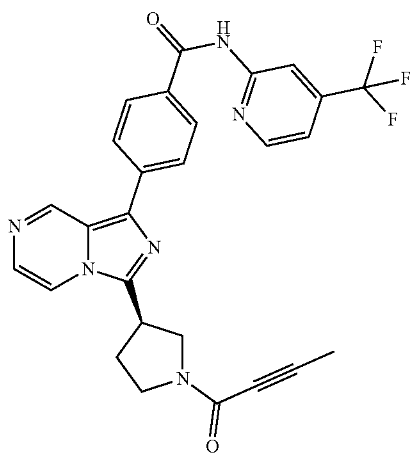 [SMILES: CC#CC(=O)N1CC[C@@H](c2nc(-c3ccc(C(=O)Nc4cc(C(F)(F)F)ccn4)cc3)c3cnccn23)C1] | 519.17/ 519.2 | (R)-4-(3-(1-(but-2-ynoyl)pyrrolidin-3-yl)imidazo[1,5-a]pyrazin-1-yl)-N-(4-(trifluoromethyl)pyridin-2-yl)benzamide |
| 212 | 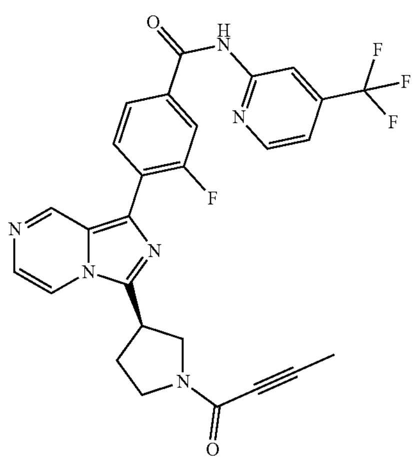 [SMILES: CC#CC(=O)N1CC[C@@H](c2nc(-c3ccc(C(=O)Nc4cc(C(F)(F)F)ccn4)cc3F)c3cnccn23)C1] | 537.16/ 537.2 | (R)-4-(3-(1-(but-2-ynoyl)pyrrolidin-3-yl)imidazo[1,5-a]pyrazin-1-yl)-3-fluoro-N-(4-(trifluoromethyl)pyridin-2-yl)benzamide |

Example 213

(6R)-6-(1-(4-(2-fluoro-3-methoxyphenoxy)phenyl)imidazo[1,5-a]pyrazin-3-yl)hexahydroindolizin-3(2H)-one (213)

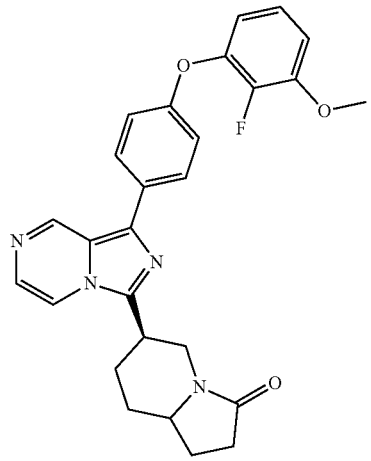 [SMILES: COc1cccc(Oc2ccc(-c3nc([C@@H]4CCC5CCC(=O)N5C4)n4ccncc34)cc2)c1F]

Scheme 10

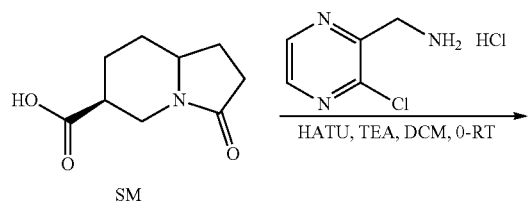

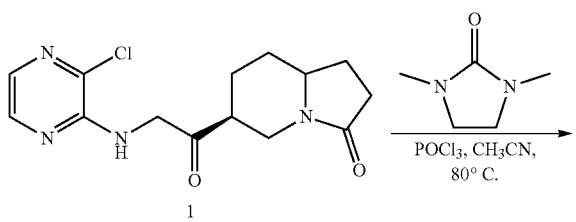

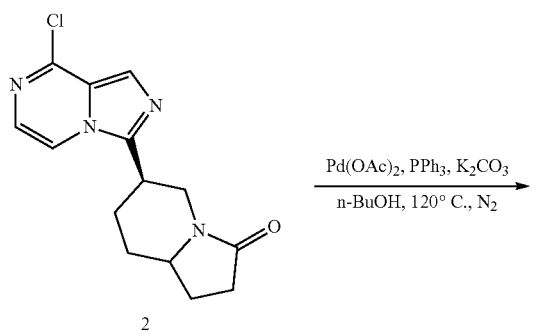

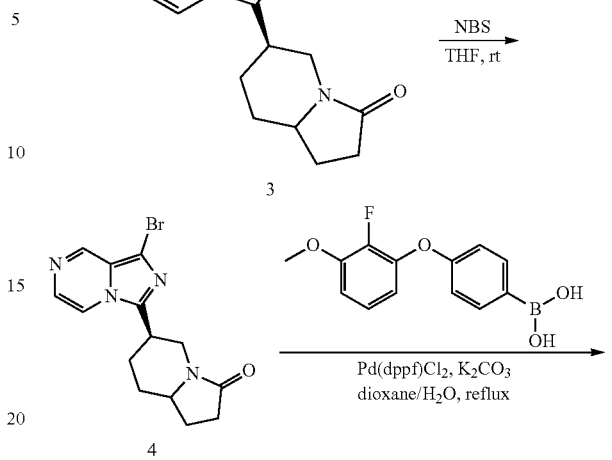

Step 1: 6-((3-Chloropyrazin-2-yl)glycyl)hexahydroindolizin-3(2H)-one (1)

A mixture of SM (1.4 g, crude, 7.8 mmol), (3-chloropyrazin-2-yl)methanamine hydrochloride (1.4 g, 7.8 mmol), HATU (2.7 mg, 7.8 mmol) and TEA (3.2 mg, 31.2 mmol) in DCM (30 mL) was stirred at 25° C. overnight. The mixture was quenched with $H_2O$ (60 mL) and it was extracted with DCM (25 mL×3). The combined organic layers were dried over anhydrous sodium sulfate, filtered and concentrated to give a crude product. The crude product was purified by prep-TLC to give 1 (1.3 g, 50%). LCMS: m/z=309 [M+H]$^+$.

Step 2: 6-(8-Chloroimidazo[1,5-a]pyrazin-3-yl)hexahydroindolizin-3(2H)-one (2)

To a solution of compound 1 (700 mg, 2.3 mmol) in acetonitrile (15 ml) and 1,3-dimethyl-2-imidazolidinone (777 mg, 6.8 mmol) at 0° C., POCl$_3$ (1.4 g, 9.1 mmol) was added dropwise while the temperature remained around 15° C. Then the reaction mixture was refluxed at 80° C. overnight. The solvent was removed and water (150 mL) was added. The pH of aqueous layer was adjusted to 8-9 and the mixture was extracted with ethyl acetate (40 mL×3). The combined organic layers were washed with brine, dried over sodium sulfate, and filtered. The solvent was removed under vacuum. The residue was purified using prep-TLC to give 2 (130 mg, 20%). LCMS: m/z=291 [M+H]+.

Step 3: 6-(Imidazo[1,5-a]pyrazin-3-yl)hexahydroindolizin-3(2H)-one (3)

The mixture of 1 (93 mg, 0.32 mmol), triphenylphosphine (13 mg, 0.05 mmol), Pd(OAc)$_2$ (7 mg, 0.03 mmol) and potassium carbonate (88 mg, 0.64 mmol) in n-butanol (5.0 mL) was stirred at 130° C. for 2 h under N2 atmosphere. The reaction mixture was concentrated and the residue was purified by prep-TLC to give 3 (50 mg, 61%).

$^1$H NMR (400 MHz, CDCl$_3$): δ 8.94 (s, 1H), 7.76 (d, J=4.0 Hz, 2H), 7.54 (d, J=3.6 Hz, 1H), 4.38 (d, J=12.0 Hz, 1H), 3.67-3.59 (m, 1H), 3.14-2.96 (m, 2H), 2.47 (t, J=7.6 Hz, 2H), 2.35-2.27 (m, 1H), 2.23-2.15 (m, 2H), 2.14-2.07 (m, 2H), 1.77-1.64 (m, 1H), 1.50-1.35 (m, 1H), 1.29-1.21 (m, 1H). LCMS: m/z=257 [M+H]+.

Step 4: 6-(8-Bromoimidazo[1,5-a]pyrazin-3-yl) hexahydroindolizin-3(2H)-one (4)

To a solution of 3 (45 mg, 0.176 mmol) in THF (10.0 mL) was added NBS (31 mg, 0.176 mmol). The solution was stirred at rt for 2 h. The solvent was removed in vacuum and the residue was purified by prep-TLC to give 4 (46 mg, 78%).

$^1$H NMR (400 MHz, CDCl$_3$): δ 8.87 (s, 1H), 7.69 (d, J=4.0 Hz, 1H), 7.60 (d, J=3.6 Hz, 1H), 4.46-4.29 (m, 1H), 3.65-3.52 (m, 1H), 3.08-2.93 (m, 2H), 2.47 (t, J=8.0 Hz, 2H), 2.36-2.27 (m, 1H), 2.20-2.13 (m, 2H), 2.12-2.06 (s, 1H), 1.75-1.65 (m, 1H), 1.52-1.33 (m, 1H). LCMS: m/z=334/336 [M+H]+.

Step 5: 6-(1-(4-(2-Fluoro-3-methoxyphenoxy)phenyl)imidazo[1,5-a]pyrazin-3-yl)hexahydroindolizin-3(2H)-one (5)

A mixture of 4 (40 mg, 0.12 mmol), (4-(2-fluoro-3-methoxyphenoxy)phenyl)boronic acid (63 mg, 0.24 mmol), PdCl$_2$(dppf) (9 mg), and potassium carbonate (33 mg, 0.012 mmol) in dioxane (5.0 mL) and water (1.0 mL) was stirred under reflux for 3 h. The mixture was concentrated and the residue was purified by prep-TLC to give 5 (29 mg, 51%).

$^1$H NMR (400 MHz, CDCl$_3$): δ 9.16 (s, 1H), 7.84 (d, J=8.4 Hz, 2H), 7.68 (d, J=4.0 Hz, 1H), 7.54 (s, 1H), 7.12 (d, J=8.4 Hz, 2H), 7.03 (t, J=7.6, 2.0 Hz, 1H), 6.84-6.76 (m, 1H), 6.73-6.67 (m, 1H), 4.49-4.38 (m, 1H), 3.94 (s, 3H), 3.70-3.60 (m, 1H), 3.61-3.05 (m, 2H), 2.48 (t, J=8.4 Hz, 2H), 2.37-2.26 (m, 1H), 2.25-2.19 (m, Hz, 2H), 2.14-2.08 (m, 1H), 1.76-1.67 (m, 1H), 1.50-1.39 (m, 1H). LCMS: m/z=473 [M+H]+.

Example 214

7-(1-(4-(2-fluoro-3-methoxyphenoxy)phenyl)imidazo[1,5-a]pyrazin-3-yl)-2-methyloctahydro-1H-pyrido[1,2-c]pyrimidin-1-one (214)

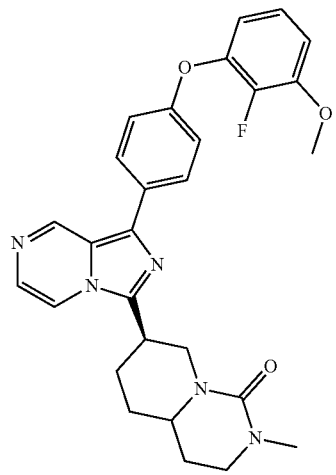 [SMILES: COc1cccc(Oc2ccc(-c3nc([C@@H]4CCC5CCN(C)C(=O)N5C4)n4ccncc34)cc2)c1F]

Scheme 11

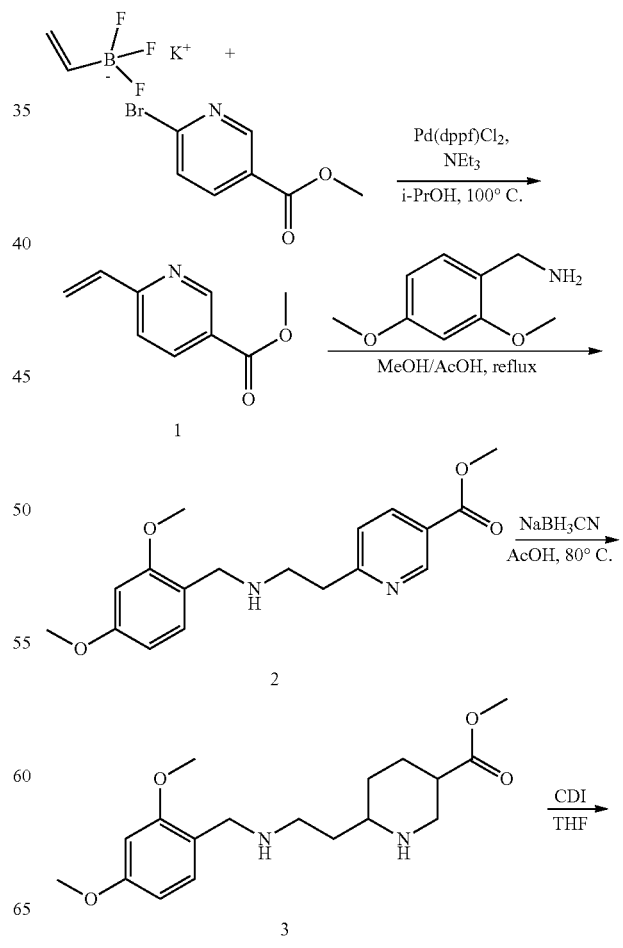

-continued

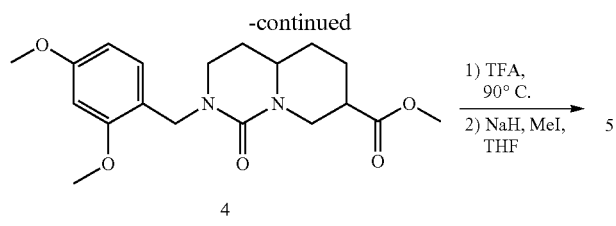

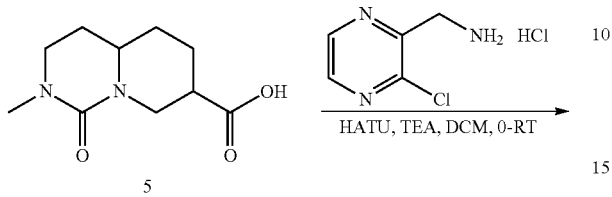

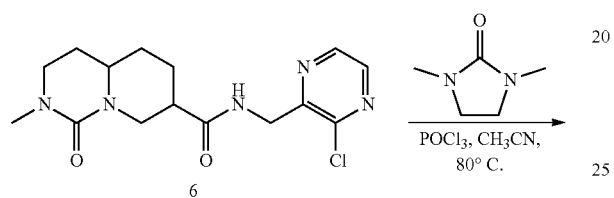

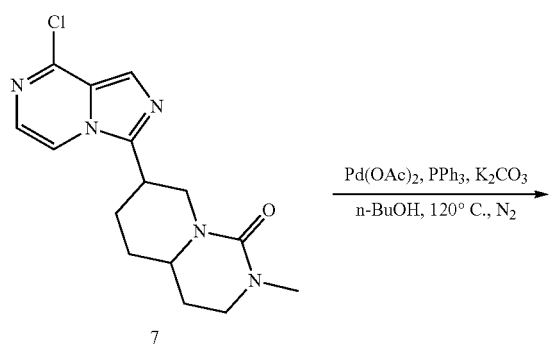

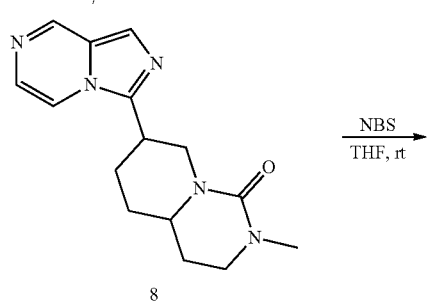

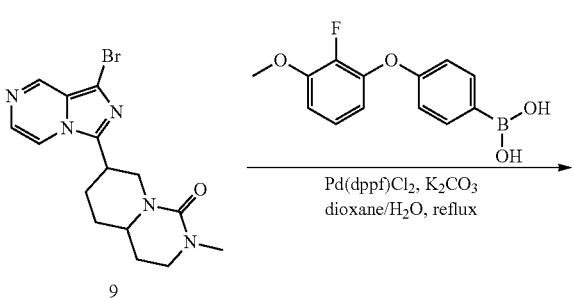

-continued

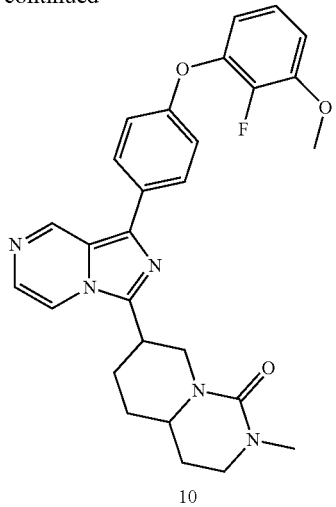

Step 1: Methyl 6-vinylnicotinate (1)

To a solution of methyl 6-bromonicotinate (10 g, 46.5 mmol) in i-PrOH (100 mL) were added potassium vinyltrifluoroborate (12.4 g, 93 mmol), Et$_3$N (14.1 g, 140 mmol), and Pd(dppf)Cl$_2$-DCM (1.1 g). The mixture was stirred at 100° C. for 2 h under nitrogen. The reaction was complete monitored by TLC. The mixture was concentrated and the residue was purified by column chromatography on silica gel eluted with PE/EA=15/1 to give methyl 6-vinylnicotinate 1 (7.2 g, 95%).

$^1$H NMR (400 MHz, CDCl$_3$): δ 9.15 (d, J=1.56 Hz, 1H), 8.23 (dd, J=8.22, 2.35 Hz, 1H), 7.39 (d, J=8.22 Hz, 1H), 6.85 (dd, J=17.41, 10.76 Hz, 1H), 6.36 (d, J=20.0 Hz, 1H), 5.55 (d, J=12.0 Hz, 1H), 3.94 (s, 3H).

Step 2: Methyl 6-(2-((2,4-dimethoxybenzyl)amino)ethyl)nicotinate (2)

To a solution of methyl 6-vinylnicotinate 1 (2.0 g, 12.3 mmol) in MeOH (15 mL) were added (2,4-dimethoxyphenyl)methanamine (4.08 g, 24.5 mmol) and AcOH (15 mL). The mixture was heated to reflux overnight. The mixture was concentrated, basified with aq. NaHCO$_3$ and extracted with EA. The organic layer was dried and concentrated. The residue was purified by column chromatography on silica gel eluted with PE/EA=3/1 to give methyl 6-(2-((2,4-dimethoxybenzyl)amino)ethyl)nicotinate 2 (2.6 g, 64%).

$^1$H NMR (400 MHz, CDCl$_3$): δ 9.11 (d, J=1.56 Hz, 1H), 8.18 (dd, J=8.22, 2.35 Hz, 1H), 7.26 (d, J=8.22 Hz, 1H), 7.09 (dd, J=17.41, 10.76 Hz, 1H), 6.41 (m, 2H), 3.94 (s, 3H), 3.78 (s, 3H), 3.76 (s, 3H), 3.74 (s, 2H), 3.05-3.00 (m, 4H). LCMS: m/z=331 [M+H]$^+$.

Step 3: Methyl 6-(2-((2,4-dimethoxybenzyl)amino)ethyl)piperidine-3-carboxylate (3)

To a solution of compound 2 (2.5 g, 7.6 mmol) in AcOH (40 mL) was added NaBH$_3$CN (1.9 g, 30.3 mmol). The mixture was stirred at room temperature for 1 h, and then heated to 70° C. overnight. The solvent was evaporated and the residue was dissolved in MeOH. The solution was alkalified with NaHCO$_3$ solution. The solvent was removed and the mixture was extracted with DCM. The organic layer was dried over sodium sulfate and concentrated. The residue was purified by column chromatography on silica gel eluted with DCM/MeOH=20/1 to give methyl 6-(2-((2,4-dimethoxybenzyl)amino)ethyl)piperidine-3-carboxylate 3 (1.2 g). LCMS: m/z=337 [M+H]$^+$.

Step 4: Methyl 2-(2,4-dimethoxybenzyl)-1-oxooctahydro-1H-pyrido[1,2-c]pyrimidine-7-carboxylate (4)

To a solution of compound 3 (1.5 g, crude, 1.0 eq) in THF (20 mL) was added CDI (1.45 g, 2.0 eq). The reaction mixture was stirred at 70° C. overnight, and then it was allowed to cool to room temperature. Water was added and the mixture was extracted with EA. The combined organic layers were washed with water and brine. The solution was dried over anhydrous Na$_2$SO$_4$, filtered and concentrated. The residue was purified by silica gel column chromatography (DCM/MeOH=100:1) to afford the desired product 4 (400 mg, yield 25%).
$^1$H NMR (400 MHz, CDCl$_3$): δ 7.19 (m, 1H), 6.46-6.44 (m, 2H), 4.80 (d, J=12.8 Hz, 1H), 4.55-4.41 (m, 2H), 3.79 (s, 6H), 3.67 (s, 3H), 3.21-3.18 (m, 3H), 2.64-2.58 (m, 1H), 2.49-2.43 (m, 1H), 2.12-2.00 (m, 2H), 1.96-1.70 (m, 2H), 1.68-1.66 (m, 1H), 1.58-1.57 (m, 1H). LCMS: m/z=363 [M+H]$^+$.

Step 5: 2-Methyl-1-oxooctahydro-1H-pyrido[1,2-c]pyrimidine-7-carboxylic acid (5)

A solution of compound 4 (400 mg, 1.06 mmol) in TFA (5.0 mL) was stirred at 90° C. for 2 h. The solvent was removed and the residue was suspended in dry THF (20 mL), followed by addition of NaH (220 mg, 5.5 mmol) in an ice water bath. The mixture was stirred at room temperature for 30 min and then MeI (776 mg, 5.5 mmol) was added dropwise. The reaction was stirred at room temperature overnight and quenched with water. The pH of the mixture was adjusted to 2 with concentrated hydrochloric acid and the mixture was extracted with ethyl acetate. The organic layer was washed with water and brine. The solution was dried over Na$_2$SO$_4$, filtered and concentrated. The crude product 5 (160 mg) was used for next step without purification.
$^1$H NMR (400 MHz, CDCl$_3$): δ 8.04 (br, 2H), 4.70-4.67 (m, 1H), 3.25-3.19 (m, 3H), 2.91 (s, 3H), 2.63-2.61 (m, 1H), 2.44-2.42 (m, 1H), 2.16-2.08 (m, 3H), 1.79-1.76 (m, 2H), 1.62-1.51 (m, 1H), 1.35-1.26 (m, 1H). LCMS: m/z=213 [M+H]$^+$.

Step 6: N-((3-Chloropyrazin-2-yl)methyl)-2-methyl-1-oxooctahydro-1H-pyrido[1,2-c]pyrimidine-7-carboxamide (6)

A mixture of compound 5 (270 mg, 1.28 mmol), (3-chloropyrazin-2-yl)methanamine hydrochloride (277 mg, 1.54 mmol), HATU (632 mg, 1.66 mmol) and TEA (518 mg, 5.12 mmol) in DCM (13 mL) was stirred at 25° C. overnight. The mixture was quenched with H$_2$O (40 mL) and extracted with DCM (15 mL×3). The combined organic layers were dried over anhydrous sodium sulfate, filtered and concentrated. The residue was purified by prep-TLC to give 6 (130 mg, 30%).
$^1$H NMR (400 MHz, CDCl$_3$): δ 8.45 (s, 1H), 8.32 (s, 1H), 7.06 (s, 2H), 4.74-4.69 (m, 3H), 3.23-3.22 (m, 3H), 2.93 (s, 3H), 2.74-2.71 (m, 1H), 2.53-2.40 (m, 1H), 2.13-2.02 (m, 2H), 1.81-1.77 (m, 2H). LCMS: m/z=338 [M+H]$^+$.

Step 7: 7-(8-Chloroimidazo[1,5-a]pyrazin-3-yl)-2-methyloctahydro-1H-pyrido[1,2-c]pyrimidin-1-one (7)

To a solution of compound 6 (130 mg, 0.38 mmol), and 1,3-dimethyl-2-imidazolidinone (130 mg, 1.14 mmol) in acetonitrile (10 ml) at 0° C., POCl$_3$ (236 mg, 1.54 mmol) was added dropwise while the temperature remained around 5° C. The reaction mixture was refluxed at 80° C. overnight. The reaction mixture was concentrated and water (15 mL) was added. The pH of aqueous layer was adjusted to 8-9 and the mixture was extracted with ethyl acetate (20 mL×3). The combined organic layers were washed with brine, dried over sodium sulfate, and filtered. The solvent was removed. The residue was purified using prep-TLC to give 7 (60 mg, 49%).
$^1$H NMR (400 MHz, CDCl$_3$): δ 7.87 (d, J=4.8 Hz, 1H), 7.78 (s, 1H), 7.34 (d, J=4.8 Hz, 1H), 4.76-4.75 (m, 1H), 3.46-3.42 (m, 1H), 3.39-3.30 (m, 2H), 3.14-3.10 (m, 1H), 2.97 (s, 3H), 2.74-2.68 (m, 1H), 2.24-2.20 (m, 3H), 1.95-1.91 (m, 1H), 1.88-1.83 (m, 1H), 1.57-1.52 (m, 1H). LCMS: m/z=320 [M+H]$^+$.

Step 8: 7-(Imidazo[1,5-a]pyrazin-3-yl)-2-methyloctahydro-1H-pyrido[1,2-c]pyrimidin-1-one (8)

A mixture of compound 7 (60 mg, 0.19 mmol), triphenylphosphine (10 mg, 0.04 mmol), Pd(OAc)$_2$ (4.2 mg, 0.02 mmol) and potassium carbonate (39 mg, 0.29 mmol) in n-butanol (5.0 mL) was stirred at 130° C. for 2 hours under N2 atmosphere. The mixture was concentrated and the residue was purified by prep-TLC to give 8 (20 mg, 37%).
$^1$H NMR (400 MHz, CDCl$_3$): δ 8.92 (s, 1H), 7.87 (d, J=4.8 Hz, 1H), 7.73 (s, 1H), 7.52 (d, J=4.8 Hz, 1H), 4.79-4.78 (m, 1H), 3.42-3.40 (m, 1H), 3.39-3.27 (m, 2H), 3.13-3.09 (m, 1H), 2.97 (s, 3H), 2.74-2.71 (m, 1H), 2.22-2.20 (m, 3H), 1.95-1.91 (m, 1H), 1.88-1.83 (m, 1H), 1.57-1.52 (m, 1H).
LCMS: m/z=286 [M+H]$^+$.

Step 9: 7-(J-Bromoimidazo[1,5-a]pyrazin-3-yl)-2-methyloctahydro-1H-pyrido[1,2-c]pyrimidin-1-one (9)

To a solution of compound 8 (20 mg, 0.063 mmol, 1.0 eq) in THF (5.0 mL), was added NBS (11 mg, 0.063 mmol, 1.0 eq). The solution was stirred at rt for 30 min. The solvent was removed and the residue was purified by prep-TLC to give 9 (12 mg, 52%).
$^1$H NMR (400 MHz, CDCl$_3$): δ 8.84 (s, 1H), 7.83 (d, J=4.4 Hz, 1H), 7.56 (d, J=4.8 Hz, 1H), 4.74-4.71 (m, 1H), 3.48-3.47 (m, 1H), 3.39-3.27 (m, 2H), 3.13-3.09 (m, 1H), 2.97 (s, 3H), 2.75 (s, 1H), 2.69-2.66 (m, 1H), 2.25-2.19 (m, 3H), 1.93-1.87 (m, 3H), 1.57-1.52 (m, 1H). LCMS: m/z=363/365 [M+H]$^+$.

Step 10: 7-(1-(4-(2-Fluoro-3-methoxyphenoxy)phenyl)imidazo[1,5-a]pyrazin-3-yl)-2-methyloctahydro-1H-pyrido[1,2-c]pyrimidin-1-one (10)

A mixture of compound 9 (15 mg, 0.04 mmol, 1.0 eq), (4-(2-fluoro-3-methoxyphenoxy)phenyl)boronic acid (16 mg, 0.062 mmol, 1.5 eq), PdCl$_2$(dppf) (3.0 mg), and potassium carbonate (11 mg, 0.08 mmol, 2.0 eq) in dioxane (5.0 mL) and water (0.5 mL) was stirred under reflux for 2 h. The mixture was concentrated and the residue was purified by prep-TLC to give 10 (6.0 mg, 30%).

¹H NMR (400 MHz, CDCl₃): δ 9.14 (s, 1H), 7.86-7.81 (m, 3H), 7.52-750 (m, 2H), 7.12-7.10 (m, 2H), 7.02-7.00 (m, 1H), 6.81-6.77 (m, 1H), 6.70-6.67 (m, 1H), 4.81-4.78 (m, 1H), 3.93 (s, 3H), 3.41-3.40 (m, 1H), 3.30-3.27 (m, 2H), 3.12-3.09 (m, 1H), 2.98 (s, 3H), 2.82-2.79 (m, 1H), 2.28-2.19 (m, 2H), 1.93-1.87 (m, 2H), 1.57-1.52 (m, 1H). LCMS: m/z=502 [M+H]⁺.

Examples 215 and 216 were prepared following the procedure described for Example 213 and 214:

| Entry | Structure | MS (cald.) [M + H]⁺/ MS (found) | name |
|---|---|---|---|
| 215 | 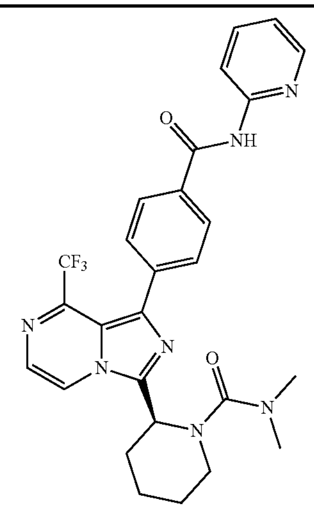 | 538.21/ 538.2 | (S)-N,N-dimethyl-2-(1-(4-(pyridin-2-ylcarbamoyl)phenyl)-8-(trifluoromethyl)imidazo[1,5-a]pyrazin-3-yl)piperidine-1-carboxamide |
| 216 | 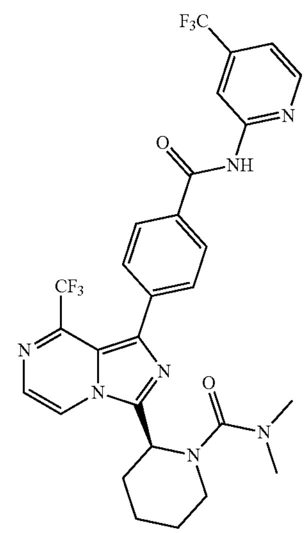 [SMILES: CN(C)C(=O)N1CCCC[C@H]1c1nc(-c2ccc(C(=O)Nc3cc(C(F)(F)F)ccn3)cc2)c2c(C(F)(F)F)nccn12] | 606.20/ 606.2 | (S)-N,N-dimethyl-2-(8-(trifluoromethyl)-1-(4-((4-(trifluoromethyl)pyridin-2-yl)carbamoyl)phenyl)imidazo[1,5-a]pyrazin-3-yl)piperidine-1-carboxamide |

Btk Kinase Assay and Other Kinases Assay

Btk kinase activity was determined using a homogenous time resolved fluorescence (HTRF) methodology. Measurements were performed in a reaction volume of 15 μL using 384-well assay plates. Kinase enzyme, inhibitor, ATP and 1 μM peptide substrate were incubated in a reaction buffer compose of Hepes 50 mM (pH7.0), NaN3 0.02%, BSA 0.01%, Orthocanadate 0.1 mM. After one hour, the kinase reaction was quenched by the addition of Ep-labeled antibody and XL-665 in 1× Detection buffer containing 60 mM EDTA (Cisbio), and the mixture was allowed to incubate for one hour. The HTRF signal was measured on a multimode plate reader (EnVision® Multilabel Reader, Perkin Elmer) with an excitation wavelength ($\lambda_{Ex}$) of 330 nm and detection wavelengths ($\lambda_{Em}$) of 615 and 665 nm. Activity was determined by the ratio of the fluorescence at 665 nm to that at 615 nm. For each compound, enzyme activity as measured at various concentrations of compound, Negative control reactions were performed in the absence of inhibitor in two replicates and eight no enzyme controls were used to determine baseline fluorescence levels. IC₅₀s were obtained according to the equation:

$$Y=100/(1+10^{((\text{Log IC50}-X)*\text{HillSlope})}).$$

For BTK assay, [ATP]=80 μM, BTK=3.4 nM.

For LYN assay, [ATP]=20 μM, LYN=0.12 nM. For LCK assay, [ATP]=20 μM, LCK=0.2 nM. For BLK assay, [ATP]= 20 μM, BLK=0.6 nM.

Example 217

The following Table shows the activity of selected compounds of this invention in the BTK inhibition assay. The compound numbers correspond to the compound numbers in previous Tables. Compounds having an activity designated as "A" provided an $IC_{50} \leq 10$ nM; Compounds having an activity designated as "B" provided an $IC_{50}$ 10-100 nM; Compounds having an activity designated as "C" provided an $IC_{50}$ 100-1000 nM; Compounds having an activity designated as "D" provided an $IC_{50}$ 1000-10000 nM; Compounds having an activity designated as "E" provided an $IC_{50} \geq 10000$ nM.

| Compound # | BTK Inhibition |
|---|---|
| 1 | A |
| 2 | B |
| 3 | D |
| 4 | C |
| 5 | B |
| 6 | A |
| 7 | B |
| 8 | C |
| 9 | B |
| 10 | B |
| 11 | B |
| 12 | B |
| 13 | B |
| 14 | D |
| 15 | E |
| 16 | A |
| 17 | C |
| 18 | C |
| 19 | C |
| 20 | A |
| 21 | C |
| 22 | A |
| 23 | B |
| 24 | D |
| 25 | B |
| 26 | B |
| 27 | A |
| 28 | A |
| 29 | A |
| 30 | A |
| 31 | C |
| 32 | D |
| 33 | D |
| 34 | B |
| 35 | D |
| 36 | B |
| 37 | D |
| 38 | E |
| 39 | C |
| 40 | A |
| 41 | B |
| 42 | B |
| 43 | B |
| 44 | C |
| 45 | B |
| 46 | C |
| 47 | C |
| 48 | A |
| 49 | B |
| 50 | B |
| 51 | C |
| 52 | C |
| 53 | C |
| 54 | C |
| 55 | A |
| 56 | B |
| 57 | B |
| 58 | B |
| 59 | C |
| 60 | B |
| 61 | A |
| 62 | A |
| 63 | C |
| 64 | A |
| 65 | B |
| 66 | D |
| 67 | D |
| 68 | A |
| 69 | A |
| 70 | B |
| 71 | C |
| 72 | B |
| 73 | B |
| 74 | A |
| 75 | B |
| 76 | B |
| 77 | C |
| 78 | B |
| 79 | C |
| 80 | B |
| 81 | C |
| 82 | A |
| 83 | B |
| 84 | A |
| 85 | A |
| 86 | A |
| 87 | E |
| 88 | B |
| 89 | A |
| 90 | B |
| 91 | C |
| 92 | A |
| 93 | A |
| 94 | A |
| 95 | A |
| 96 | A |
| 97 | A |
| 98 | A |
| 99 | B |
| 100 | A |
| 101 | B |
| 102 | E |
| 103 | B |
| 104 | A |
| 105 | A |
| 106 | A |
| 107 | B |
| 108 | E |
| 109 | C |
| 110 | D |
| 111 | D |
| 112 | E |
| 113 | C |
| 114 | B |
| 115 | C |
| 116 | E |
| 117 | E |
| 118 | C |
| 119 | B |
| 120 | B |
| 121 | D |
| 122 | E |
| 123 | C |
| 124 | B |
| 125 | B |
| 126 | B |
| 127 | D |

BTK Inhibition Data

| Compound # | BTK Inhibition |
|---|---|
| 128 | D |
| 129 | C |
| 130 | D |
| 131 | C |
| 132 | D |
| 133 | C |
| 134 | D |
| 135 | B |
| 136 | B |
| 137 | D |
| 138 | D |
| 139 | B |
| 140 | C |
| 141 | B |
| 142 | D |
| 143 | B |
| 144 | D |
| 145 | B |
| 146 | D |
| 147 | D |
| 148 | C |
| 149 | D |
| 150 | B |
| 151 | C |
| 152 | C |
| 153 | D |
| 154 | B |
| 155 | C |
| 156 | B |
| 157 | C |
| 158 | C |
| 159 | D |
| 160 | D |
| 161 | B |
| 162 | D |
| 163 | D |
| 164 | D |
| 165 | C |
| 166 | D |
| 167 | D |
| 168 | B |
| 169 | C |
| 170 | A |
| 171 | B |
| 172 | B |
| 173 | D |
| 174 | A |
| 175 | C |
| 176 | B |
| 177 | C |
| 178 | C |
| 179 | D |
| 180 | C |
| 181 | D |
| 182 | B |
| 183 | C |
| 184 | A |
| 185 | C |
| 186 | C |
| 187 | D |
| 188 | B |
| 189 | C |
| 190 | E |
| 191 | E |
| 192 | E |
| 193 | C |
| 194 | A |
| 195 | B |
| 196 | C |
| 197 | A |
| 198 | B |
| 199 | E |
| 200 | E |
| 201 | D |
| 202 | E |
| 203 | C |
| 204 | A |
| 205 | B |
| 206 | A |
| 207 | C |
| 208 | C |
| 209 | C |
| 210 | C |
| 211 | B |
| 212 | B |
| 213 | C |
| 214 | C |
| 215 | E |
| 216 | E |

Example 218

The following Table shows the activity of selected compounds of this invention in the BTK, TEC, BLK, LYN, LCK inhibition assay. The compound numbers correspond to the compound numbers in previous Tables. Compounds having an activity designated as "A" provided an $IC_{50} \leq 10$ nM; Compounds having an activity designated as "B" provided an $IC_{50}$ 10-100 nM; Compounds having an activity designated as "C" provided an $IC_{50}$ 100-1000 nM; Compounds having an activity designated as "D" provided an $IC_{50}$ 1000-10000 nM; Compounds having an activity designated as "E" provided an $IC_{50} \geq 10000$ nM; N/A is not available.

TABLE 2

| Compound | BTK $IC_{50}$ | TEC $IC_{50}$ | LYN $IC_{50}$ | LCK $IC_{50}$ | EGFR $IC_{50}$ | ITK $IC_{50}$ |
|---|---|---|---|---|---|---|
| 1 | A | C | E | E | C | D |
| 5 | B | C | E | E | C | E |
| 16 | A | C | E | E | D | D |
| 20 | A | C | E | E | D | D |
| 27 | A | C | E | E | C | D |
| 30 | A | C | E | E | D | D |
| 136 | B | C | E | E | D | D |

Calcium FluxAssay

Calcium flux fluorescence-based assays were performed in aFDSS7000EX (Hamamatsu Photonics) fluorometric imaging plate reader according to manufacturer instructions. Compounds to be assayed were dissolved in DMSO, diluted to appropriate concentrations in $Ca^{2+}$ buffer ranging from 0 to 10 μM (at a dilution factor of 0.1), added 5 μl (6×) to each well (the final DMSO concentration was 0.1% in each well). Then 12.5 μL 2× dye loading solution (Fluo-4 NW Calcium Assay Kits, Invitrogen) was added per well of a 384-well plate. Afterwards, actively growing Ramos cells (ATCC) in RPM1640 medium supplemented with 10% FBS (Invitrogen) were washed and re-plated in assay buffer (from Fluo-4 NW Calcium Assay Kits, Invitrogen) to approximately $6.4 \times 10^6$/ml (80000 cells/12.5 μL in 384-well plates). The plates were incubated at 37° C. for 30 minutes, then at room temperature for an additional 30 minutes. The plates were now ready to be used in an experiment. Immediately after the transfer and a 10-s recording of baseline fluorescence, the compound treated cells were stimulated with a goat anti-human IgM antibody (10 μg/ml; Jackson Immuno Research) and read in a FDSS for 240 seconds. Difference between the signal and that at baseline, designated adjusted relative fluorescence unit, was calculated by using a custom Excel (Microsoft, Redmond, Wash.) template to determine IgM-induced calcium influx and its inhibition by compounds. The table below show the result. Compounds having an activity designated as "A" provided an IC 50≤10 nM; Compounds having an activity designated as "B" provided an $IC_{50}$ 10-100 nM; Compounds having an activity designated as "C" provided an $IC_{50}$ 100-1000 nM.

TABLE 3

| Compound | Ramos Ca Flux (nM) |
|---|---|
| Example 1 | N/A |
| Example 30 | N/A |

Btk Occupancy in Cellular Assays

For PCI-33380 labeling of human B cells, $10^6$ Jeko-1 cells were pre-incubated with compound for 1.5 h before labeling. Then cells were treated with PCI-33380 at 5 µM for 1 h. Washed, lysed in Ripa buffer containing sample reducing agent, and analyzed by SDS/PAGE and fluorescent gel scanning using a Typhoon scanner 9500 (GE Healthcare) (Ex, 532 nm; Em, 555 nm). The gel was then blotted and total Btk levels detected by standard Western blot with Btk antibody (CST).

By using the fluorescently tagged derivative PCI-33380, we found that 100 nM of Compound 1 and 30, 50 nM of Compound 6, 25 nM of Compound 27, 25 nM of compound 206 were sufficient to fully occupy the active site of Btk in human mantle cell lymphoma cell lines Jeko-1 cells in culture.

Btk Occupancy In Vivo

For analysis of Btk occupancy in Babc/L mice following oral dosing of compounds after 4 hours. Isolating peripheral blood mononuclear cells (PBMCs) with mouse peripheral blood separation kit (Hao Yang Biological Manufacture CO., LTD, Tianjin) were collected from Babc/L mice (1 ml blood from two mice). Spleens were processed to splenocytes followed by 5 min incubation in red blood cell lysing buffer (from mouse peripheral blood separation kit). PBMCs or splenocytes were then PCI-33380-labeled and lysates analyzed by fluorescent gel scanning as described in cellular assays. Compound 1 and 30 were achieved full occupancy at 5 mg/kg single oral dose in all Babc/L mice. Compound 5 and 27 were achieved full occupancy at 10 mg/kg single oral dose in all Babc/L mice.

What is claimed is:

1. A compound of Formula (I) having the following structure:

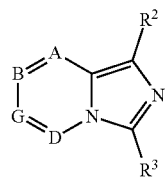

(I)

wherein:
A and D is $CR^1$, G is CH, and B is N;
$R^1$ is hydrogen, —COOCH$_3$, —CH$_2$OH, —CH$_2$OCOCH$_3$, $C_{1-6}$alkyl, $C_{1-6}$cycloalkyl, $C_{1-4}$alkoxy, —O—$C_{1-4}$alkoxy, $C_{1-6}$alkyl substituted with one to five fluorines, $C_{1-4}$alkoxy substituted with one to five fluorines, $C_{1-4}$alkoxy substituted with OH, $C_{1-4}$alkoxy substituted with OCH$_3$, NH$_2$ or N(CH$_3$)$_2$, or

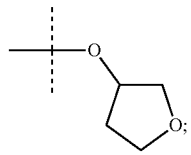

$R^2$ is

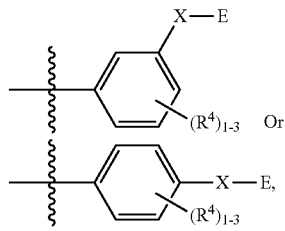

X is O, OCR$^a$R$^b$, CR$^a$R$^b$O, S(O), S(O)$_2$, CR$^a$R$^b$, NR$^c$ (C=O), C=ONR$^c$ or a bond; and E is a heteroaryl substituted with one to three R$^5$ substituents;

R$^4$ and R$^5$ are each independently selected from the group consisting of hydrogen, halogen, hydroxy, cyano, OCF$_3$, OCF$_2$H, C$_{1-6}$ alkyl, optionally substituted with one to five fluorines, C$_{3-6}$ cycloalkyl, optionally substituted with one to five fluorines, C$_{1-4}$alkoxy, optionally substituted with one to five fluorines, C$_{1-4}$ alkylthio, optionally substituted with one to five fluorines, C$_{1-4}$ alkylsulfonyl, optionally substituted with one to five fluorines, carboxy, C$_{1-4}$ alkyloxycarbonyl, and C$_{1-4}$ alkylcarbonyl;

R$^a$ and R$^b$ are each independently hydrogen, fluorine, or C$_{1-3}$ alkyl, optionally substituted with one to five fluorines;

R$^c$ is hydrogen or C$_{1-3}$ alkyl, optionally substituted with one to five fluorines; and R$^3$ is a selected from the group consisting of:

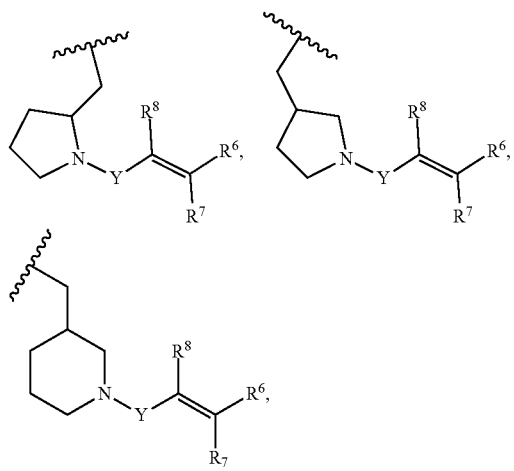

-continued

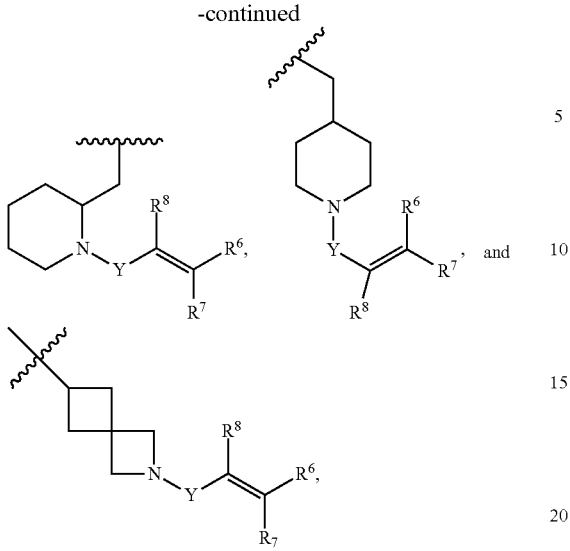

Y is C(=O), OC(=O), NHC(=O), S=O, S(=O)$_2$, or NHS(=O)$_2$;

R$^6$, R$^7$, R$^8$ are each independently hydrogen, halogen, CN, C$_{1-4}$ alkyl, C$_{1-6}$ alkoxyalkyl, C$_{1-8}$ alkylaminoalkyl, or C$_{1-4}$ alkylphenyl; and R$^7$ and R$^8$ are optionally taken together form a bond, a tautomer thereof, or a pharmaceutical acceptable solvate thereof.

2. A pharmaceutical composition comprising a therapeutically effective amount of the compound of claim 1, and a pharmaceutically acceptable excipient.

3. A compound of Formula (I) having the following structure:

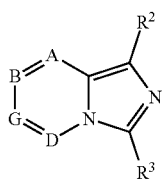
(I)

wherein:

A and D is CR$^1$, G is CH, and B is N;

R$^1$ is hydrogen, —COOCH$_3$, —CH$_2$OH, —CH$_2$OCOCH$_3$, C$_{1-6}$alkyl, C$_{1-6}$cycloalkyl, C$_{1-4}$alkoxy, —O—C$_{1-4}$alkoxy, C$_{1-6}$alkyl substituted with one to five fluorines, C$_{1-4}$alkoxy substituted with one to five fluorines, C$_{1-4}$alkoxy substituted with OH, C$_{1-4}$alkoxy substituted with OCH$_3$, NH$_2$ or N(CH$_3$)$_2$, or

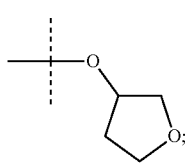

R$^2$ is

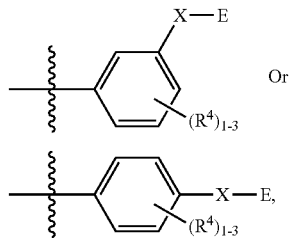

X is O, OCR$^a$R$^b$, CR$^a$R$^b$O, S(O), S(O)$_2$, CR$^a$R$^b$, NR$^c$(C=O), C=ONR$^c$ or a bond; and E is a heteroaryl substituted with one to three R$^5$ substituents;

R$^4$ and R$^5$ are each independently selected from the group consisting of hydrogen, halogen, hydroxy, cyano, OCF$_3$, OCF$_2$H, C$_{1-6}$ alkyl, optionally substituted with one to five fluorines, C$_{3-6}$ cycloalkyl, optionally substituted with one to five fluorines, C$_{1-4}$alkoxy, optionally substituted with one to five fluorines, C$_{1-4}$ alkylthio, optionally substituted with one to five fluorines, C$_{1-4}$ alkylsulfonyl, optionally substituted with one to five fluorines, carboxy, C$_{1-4}$ alkyloxycarbonyl, and C$_{1-4}$ alkylcarbonyl;

R$^a$ and R$^b$ are each independently hydrogen, fluorine, or C$_{1-3}$ alkyl, optionally substituted with one to five fluorines;

R$^c$ is hydrogen or C$_{1-3}$ alkyl, optionally substituted with one to five fluorines; and R$^3$ is selected from the group consisting of:

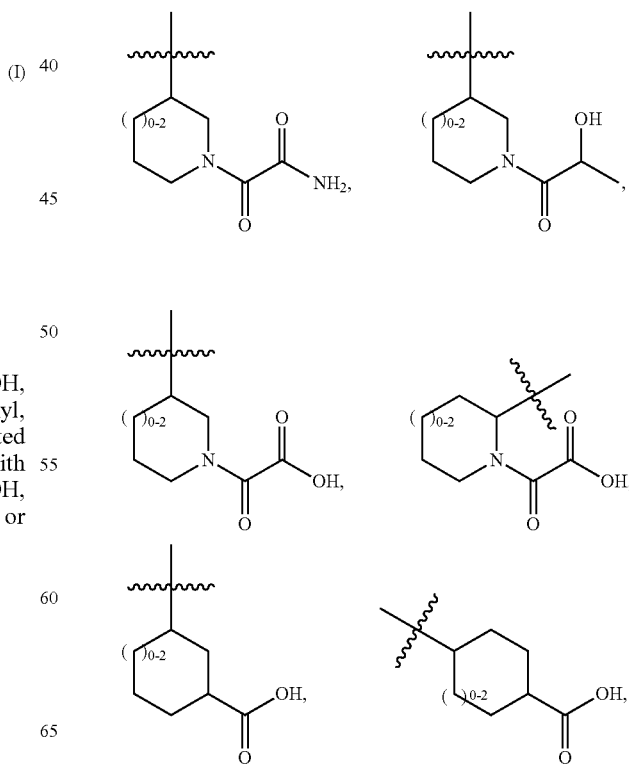

-continued
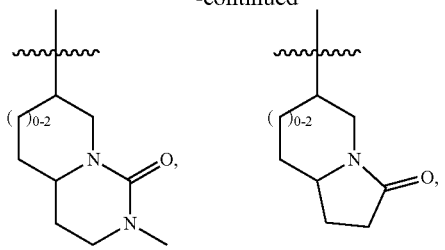
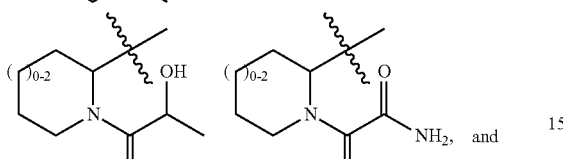
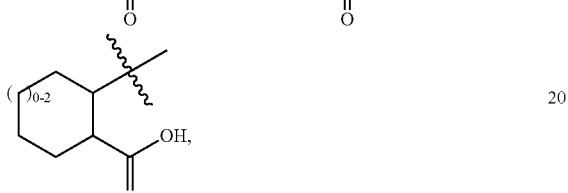
a tautomer thereof, or a pharmaceutical acceptable solvate thereof.
4. A pharmaceutical composition comprising a therapeutically effective amount of the compound of claim 3, and a pharmaceutically acceptable excipient.
* * * * *